US012624350B2

(12) United States Patent
Srivatsan et al.

(10) Patent No.: US 12,624,350 B2
(45) Date of Patent: May 12, 2026

(54) HIGH-THROUGHPUT SINGLE-NUCLEI AND SINGLE-CELL LIBRARIES AND METHODS OF MAKING AND OF USING

(71) Applicants: ILLUMINA, INC., San Diego, CA (US); UNIVERSITY OF WASHINGTON, Seattle, WA (US)

(72) Inventors: Sanjay Srivatsan, Seattle, WA (US); Jose McFaline-Figueroa, Seattle, WA (US); Vijay Ramani, Seattle, WA (US); Junyue Cao, Seattle, WA (US); Gregory Booth, Seattle, WA (US); Jay Shendure, Seattle, WA (US); Cole Trapnell, Seattle, WA (US); Frank J. Steemers, San Diego, CA (US)

(73) Assignees: ILLUMINA, INC., San Diego, CA (US); UNIVERSITY OF WASHINGTON, Seattle, WA (US)

( * ) Notice: Subject to any disclaimer, the term of this patent is extended or adjusted under 35 U.S.C. 154(b) by 1120 days.

(21) Appl. No.: 17/276,667

(22) PCT Filed: Mar. 2, 2020

(86) PCT No.: PCT/US2020/020637
§ 371 (c)(1),
(2) Date: Mar. 16, 2021

(87) PCT Pub. No.: WO2020/180778
PCT Pub. Date: Sep. 10, 2020

(65) Prior Publication Data
US 2022/0033805 A1     Feb. 3, 2022

Related U.S. Application Data

(60) Provisional application No. 62/812,853, filed on Mar. 1, 2019.

(51) Int. Cl.
*C12N 15/10*     (2006.01)

(52) U.S. Cl.
CPC .............................. *C12N 15/1065* (2013.01)

(58) Field of Classification Search
CPC .................................................. C12N 15/1065
See application file for complete search history.

(56) References Cited

U.S. PATENT DOCUMENTS

| | | | |
|---|---|---|---|
| 10,900,065 B2 | 1/2021 | Seelig et al. | |
| 11,168,355 B2 | 11/2021 | Seelig et al. | |
| 11,427,856 B2 | 8/2022 | Seelig et al. | |
| 2014/0228223 A1 | 8/2014 | Gnirke et al. | |
| 2015/0051088 A1 | 2/2015 | Kim | |
| 2018/0023119 A1* | 1/2018 | Adey ................... | C12Q 1/6869 |
| | | | 506/16 |
| 2018/0251825 A1 | 9/2018 | Stoeckius et al. | |
| 2019/0040382 A1 | 2/2019 | Steemers et al. | |
| 2019/0316182 A1* | 10/2019 | Edelman ............. | C12Q 1/6804 |

FOREIGN PATENT DOCUMENTS

| | | |
|---|---|---|
| JP | 2012-523569 A | 10/2012 |
| RU | 2016107196 A1 | 9/2017 |
| RU | 2017116989 A1 | 11/2018 |
| WO | WO 2010/118235 A1 | 10/2010 |
| WO | WO 2017/075294 A1 | 5/2017 |

OTHER PUBLICATIONS

Stoeckius, M., Zheng, S., Houck-Loomis, B. et al. Cell Hashing with barcoded antibodies enables multiplexing and doublet detection for single cell genomics. Genome Biology 19, 224 (2018).*
Cao J, Packer JS, Ramani V, Cusanovich DA, Huynh C, Daza R, Qiu X, Lee C, Furlan SN, Steemers FJ, Adey A, Waterston RH, Trapnell C, Shendure J. Comprehensive single-cell transcriptional profiling of a multicellular organism. Science. Aug. 18, 2017;357(6352):661-667 (2017).*
Rosenberg et al (Single-cell profiling of the developing mouse brain and spinal cord with split-pool barcoding, Science, 360, 176-182 (Year: 2018).*
Dongju et al (Multiplexed single-cell RNA-seq via transient barcoding for drug screening, BioRxiv, 359851, doi: https://doi.org/10.1101/359851 (Year: 2018).*
Cambridge dictionary, https://dictionary.cambridge.org/us/dictionary/english/absorption (Year: 2015).*
Athanasiadou et al., "A complete statistical model for calibration of RNA-seq counts using external spike-ins and maximum likelihood theory," PLOS Computational Biology, Mar. 2019, vol. 15, No. 3, pp. 1-26.

(Continued)

*Primary Examiner* — Juliet C Switzer
*Assistant Examiner* — Brian Ellis Young
(74) *Attorney, Agent, or Firm* — Mueting Raasch Group

(57) ABSTRACT

Provided herein are methods for preparing a sequencing library that includes nucleic acids from a plurality of single cells. In one embodiment, the method includes nuclear or cellular hashing which permits increased sample throughput and increased doublet detection at high collision rates. In one embodiment, the method includes normalization hashing which aids in estimating and removing technical noise in cell to cell variation and increases sensitivity and specificity.

18 Claims, 113 Drawing Sheets

Specification includes a Sequence Listing.

(56)            References Cited

OTHER PUBLICATIONS

Berlin et al., "Assembling large genomes with single-molecule sequencing and locality-sensitive hashing", *Nature Biotechnology*, 2015, 33:6, 623-634.

Birnbaum, "Power in Numbers: Single-Cell RNA-seq Strategies to Dissect Complex Tissues", *Annu Rev Genet.*, 2018, 23:52, 203-221.

Cao et al., "Comprehensive single-cell transcriptional profiling of a multicellular organism," Science, Aug. 2017, vol. 357, No. 6352, pp. 661-667.

Cusanovich et al., "Multiplex Single Cell Profiling of Chromatin Accessibility by Combinatorial Cellular Indexing," Author Manuscript, Science, May 2015, vol. 348, No. 6237, pp. 910-914.

Datlinger et al., "Pooled CRISPR screening with single-cell transcriptome readout," Author Manuscript, Nature Methods, Mar. 2017, vol. 14, No. 3, pp. 297-301.

Dixit et al., "Perturb-Seq: Dissecting Molecular Circuits with Scalable Single-Cell RNA Profiling of Pooled Genetic Screens," Cell, Dec. 2016, vol. 167, Issue 7, pp. 1853-1866.

Goldstein et al., "Massively parallel nanowell-based single-cell gene expression profiling", *BMC Genomics*, 2017, 18:519, 2-10.

International Search Report and Written Opinion for PCT/US2020/020637 dated Jun. 17, 2020, 14 pages.

International Preliminary Report on Patentability for PCT/US2020/020637 dated Aug. 25, 2021, 6 pages.

Jaitin et al., "Dissecting Immune Circuits by Linking CRISPR-Pooled Screens with Single-Cell RNA-Seq," Cell, Dec. 2016, vol. 167, Issue 7, pp. 1883-1896.

Kelland, L R, "Flavopiridol, the first cyclin-dependent kinase inhibitor to enter the clinic: current status," Expert Opinion on Investigational Drugs, Dec. 2000, vol. 9, No. 12, pp. 2903-2911.

Lu et al., "Transcriptional signature of flavopiridol-induced tumor cell death," Molecular Cancer Therapeutics, Jul. 2004, vol. 3, No. 7, pp. 861-872.

Srivatsan et al., "Massively multiplex chemical transcriptomics at single-cell resolution", *Science*, 2020, 367, 45-51.

Stoeckius et al., "Simultaneous epitope and transcriptome measurement in single cells", *Nature Methods*, 2017, 14:9, 865-871.

Stoeckius et al., "Cell Hashing with barcoded antibodies enables multiplexing and doublet detection for single cell genomics", *Genome Biology*, 2018, 19:224, 1-12.

Takahashi et al., "A decade of transcription factor-mediated reprogramming to pluripotency," Nature Reviews, Mar. 2016, vol. 17, No. 3, pp. 183-193.

Tung et al., "Batch effects and the effective design of single-cell gene expression studies", *Scientific Reports*, 2017, 7:39921.

Lutzmayer S., et al., "Novel Small RNA Spike-in Oligonucleotides Enable Absolute Normalization of Small RNA-Seq Data", Scientific Reports, Jul. 19, 2017, vol. 7, No. 5913, pp. 1-6, Abstract; p. 1 last para.; Fig. 1a.

* cited by examiner

*Fig. 1*

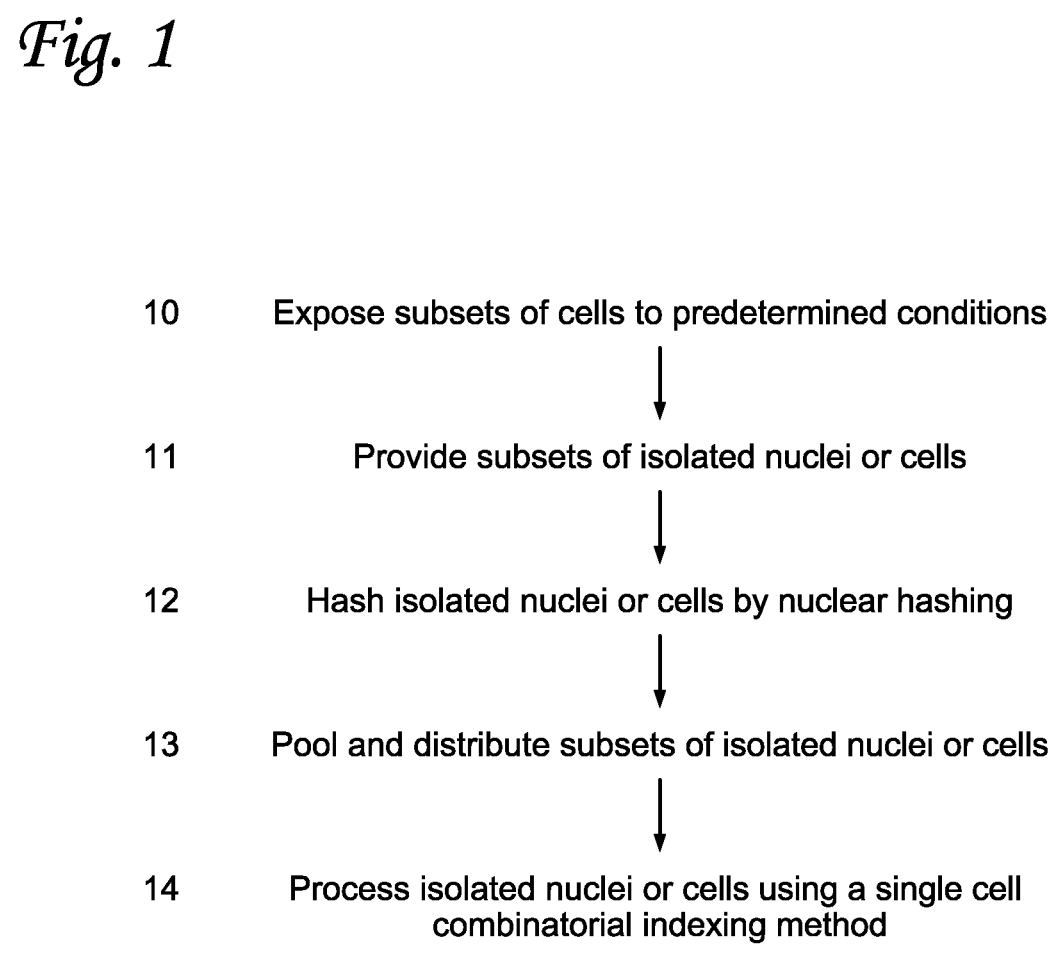

10     Expose subsets of cells to predetermined conditions

↓

11     Provide subsets of isolated nuclei or cells

↓

12     Hash isolated nuclei or cells by nuclear hashing

↓

13     Pool and distribute subsets of isolated nuclei or cells

↓

14     Process isolated nuclei or cells using a single cell combinatorial indexing method

*Fig. 2*

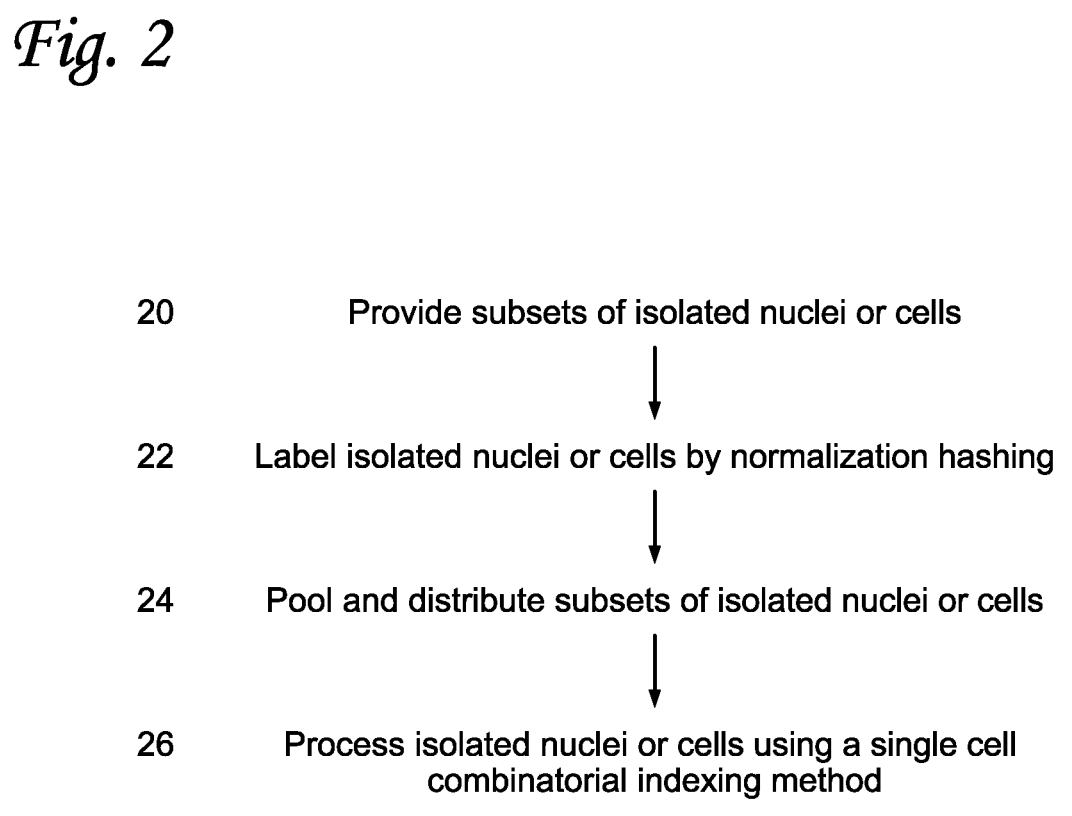

20          Provide subsets of isolated nuclei or cells $\downarrow$

22          Label isolated nuclei or cells by normalization hashing $\downarrow$ 24          Pool and distribute subsets of isolated nuclei or cells $\downarrow$ 26          Process isolated nuclei or cells using a single cell combinatorial indexing method

| 30 | Index nuclei by reverse transcription |
| 31 | Pool and distribute indexed nuclei |
| 32 | Index nuclei by ligation |
| 33 | Pool and distribute dual-indexed nuclei |
| 34 | Second strand synthesis |
| 35 | Tagmentation |
| 36 | Index nuclei by amplification |
| 37 | Immobilize library and sequence |

*Fig. 4A*
A
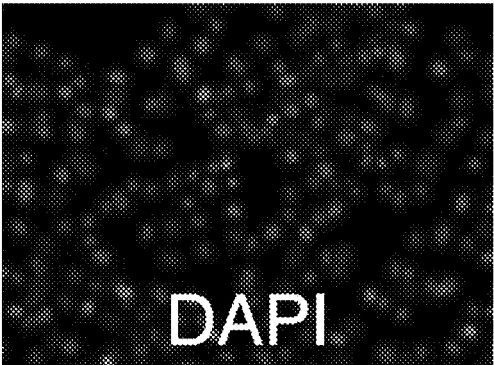

*Fig. 5A*
A
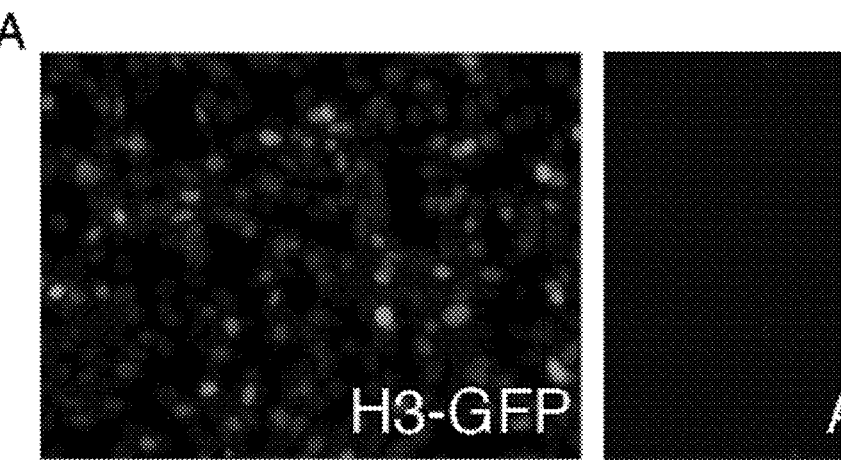
*Fig. 5B*
B
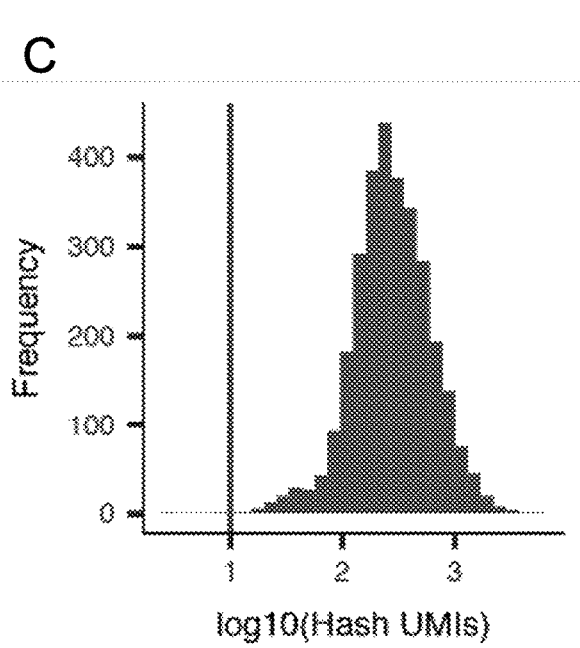
*Fig. 5C*
*Fig. 5D*
C
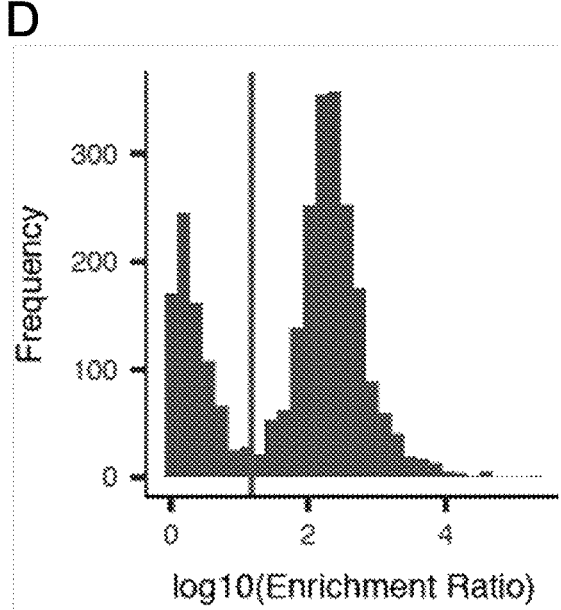
D

E

F

*Fig. 7H*  H
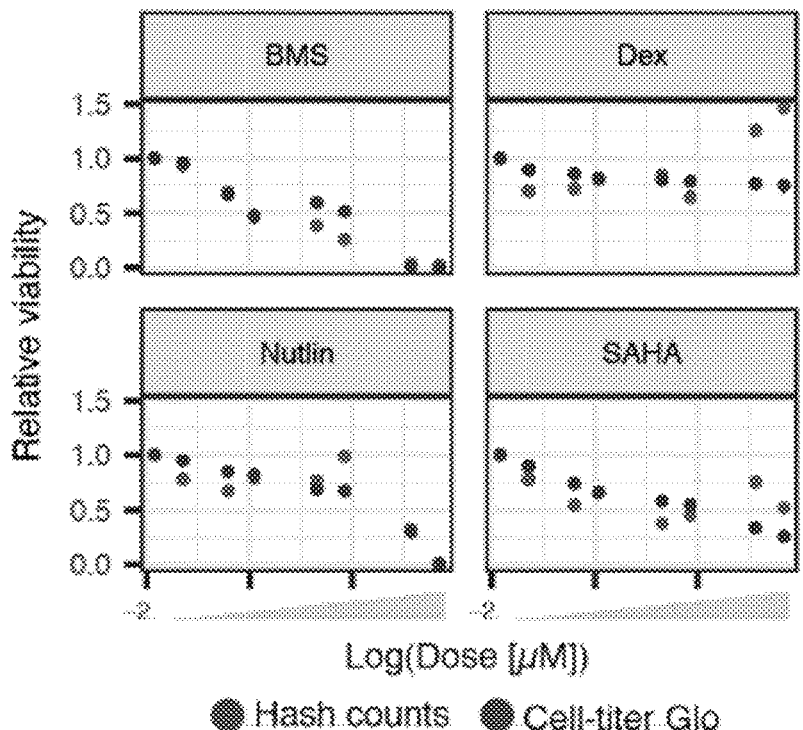
*Fig. 7I*  I
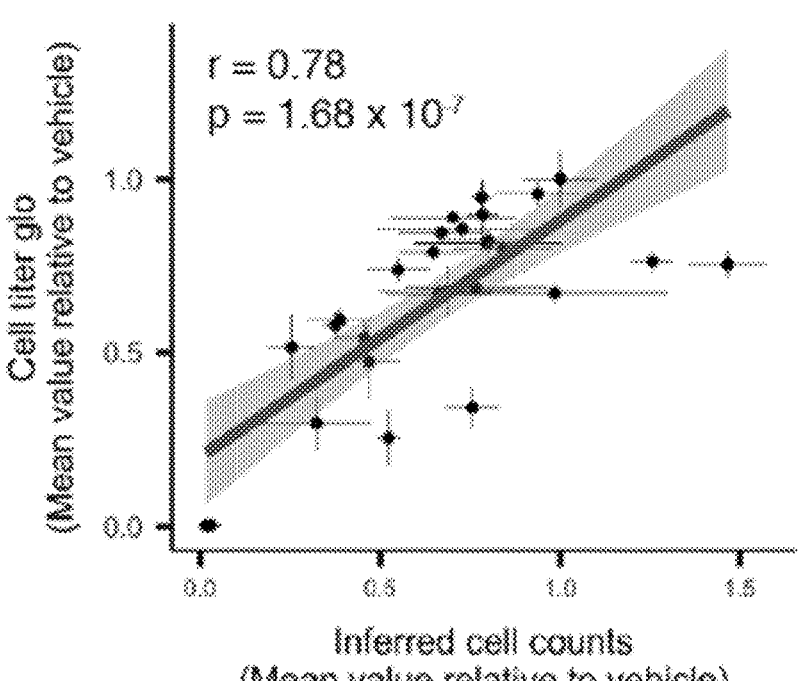

*Fig. 9B*
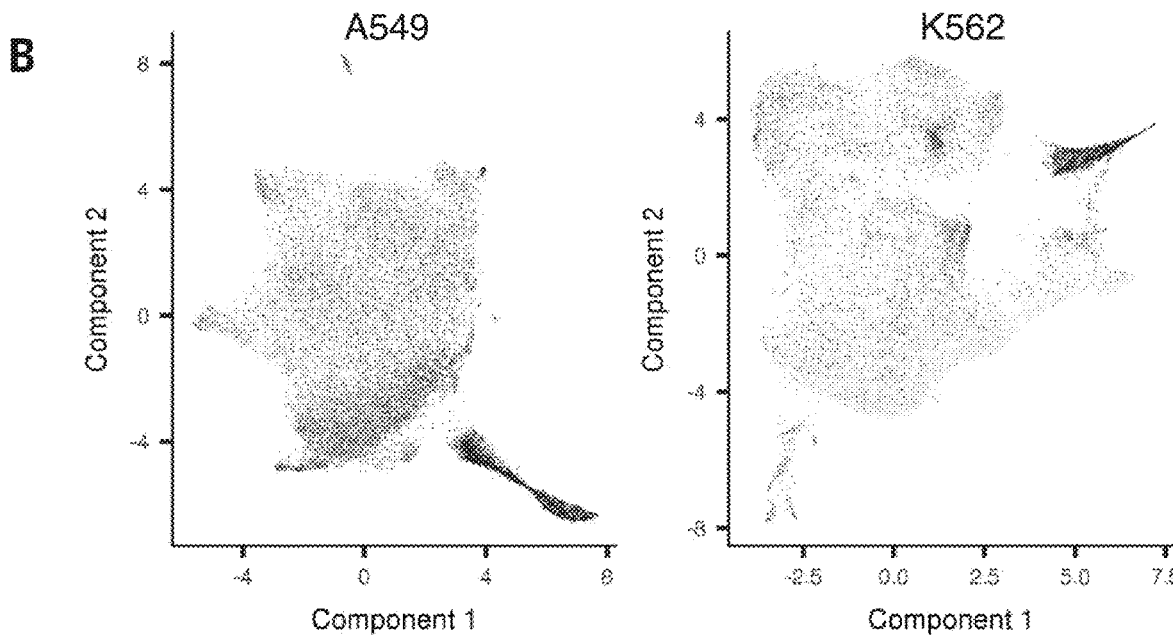
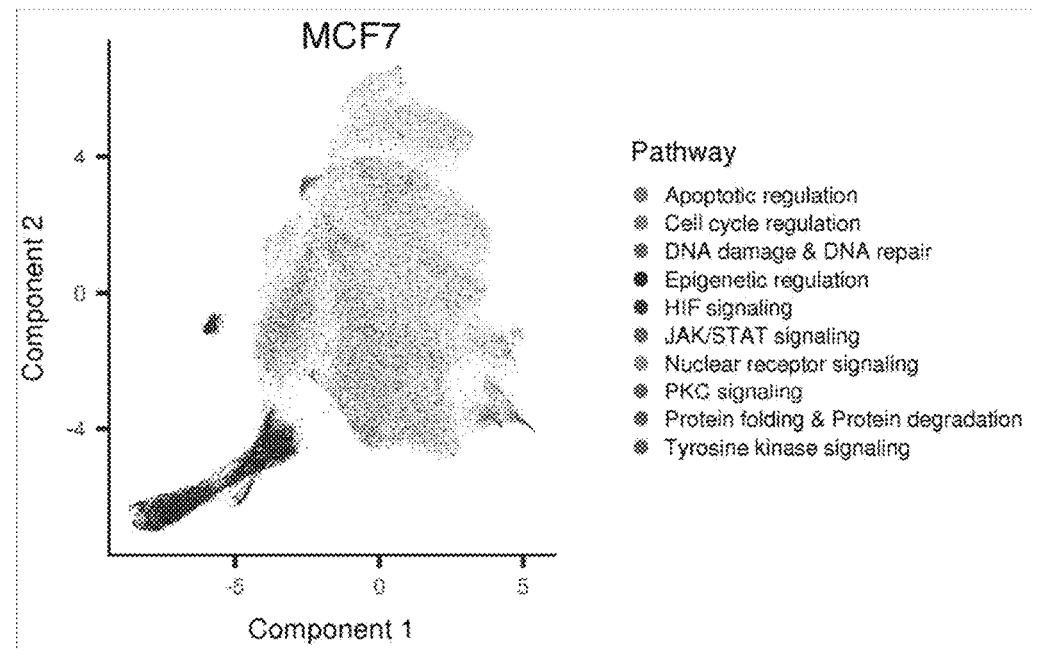
Pathway
- Apoptotic regulation
- Cell cycle regulation
- DNA damage & DNA repair
- Epigenetic regulation
- HIF signaling
- JAK/STAT signaling
- Nuclear receptor signaling
- PKC signaling
- Protein folding & Protein degradation
- Tyrosine kinase signaling

*Fig. 10A*
A
52 Plate Oligos
768 Unique Well Oligos
39,936 Barcode Combinations
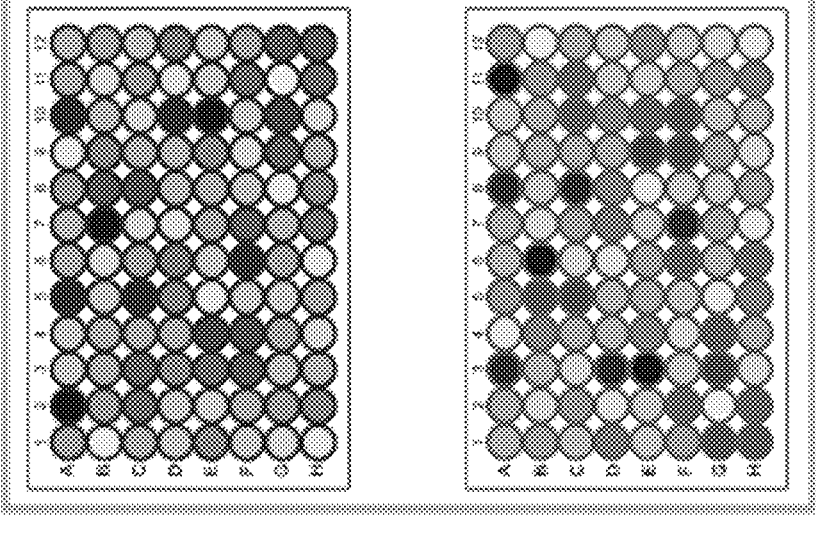
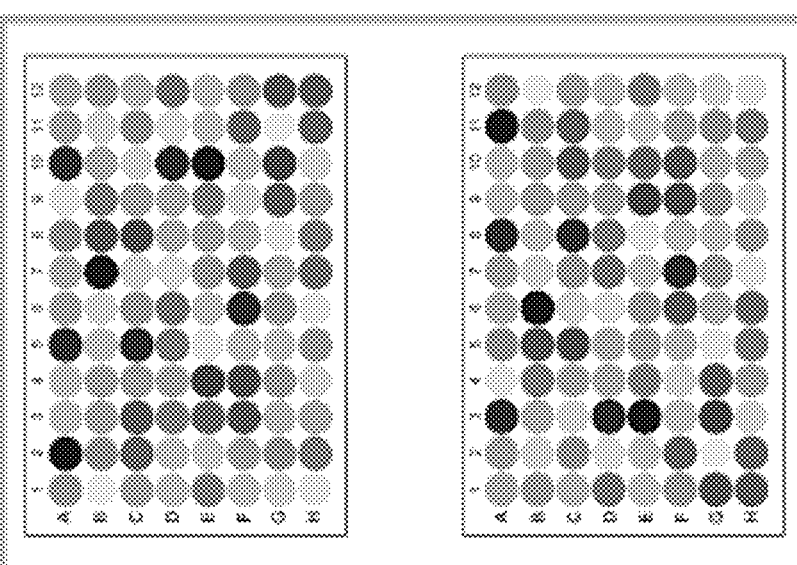

B      Possible Hash Oligo Pairings

C      Observed Hash Oligo Pairings

*Fig. 17A*
A A549
*Fig. 17B*
B K562
*Fig. 17C*
C MCF7
0 Proliferation Index 4

*Fig. 17D*     D
A549
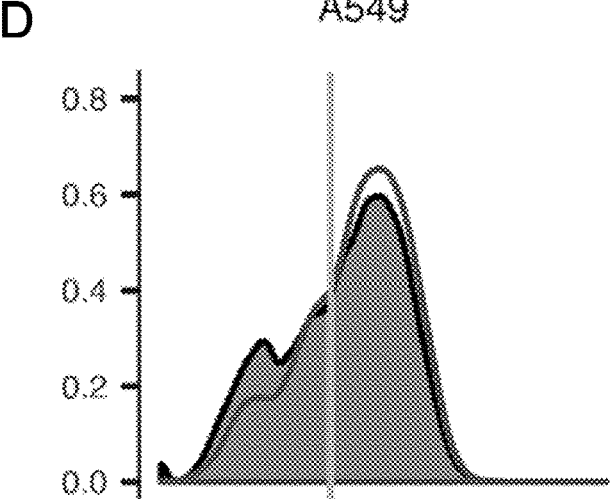
*Fig. 17E*     E
K562
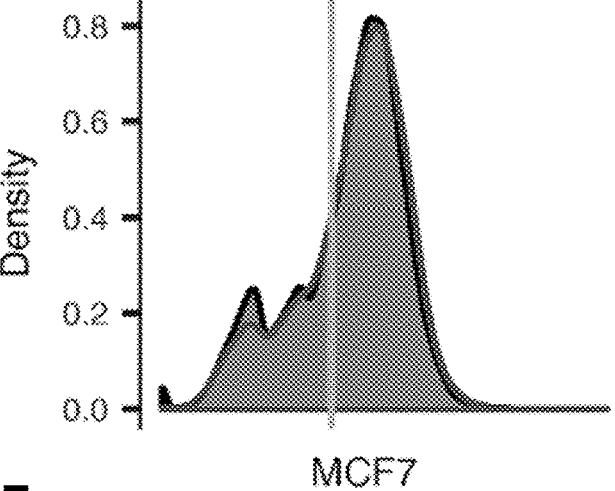
*Fig. 17F*     F
MCF7
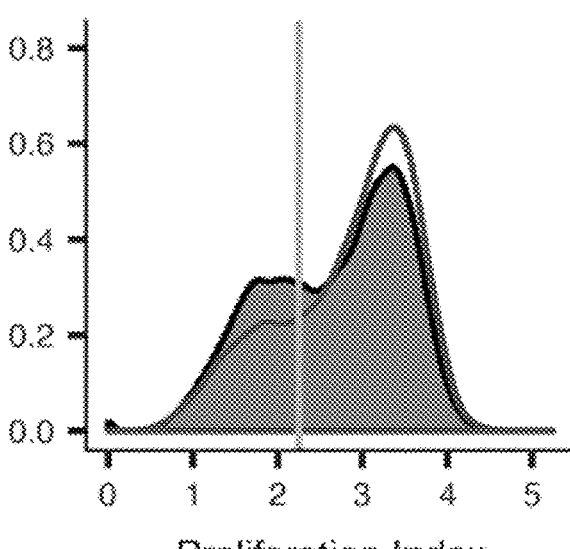
Proliferation Index Percentage of low proliferation index
cells per drug-dose combination

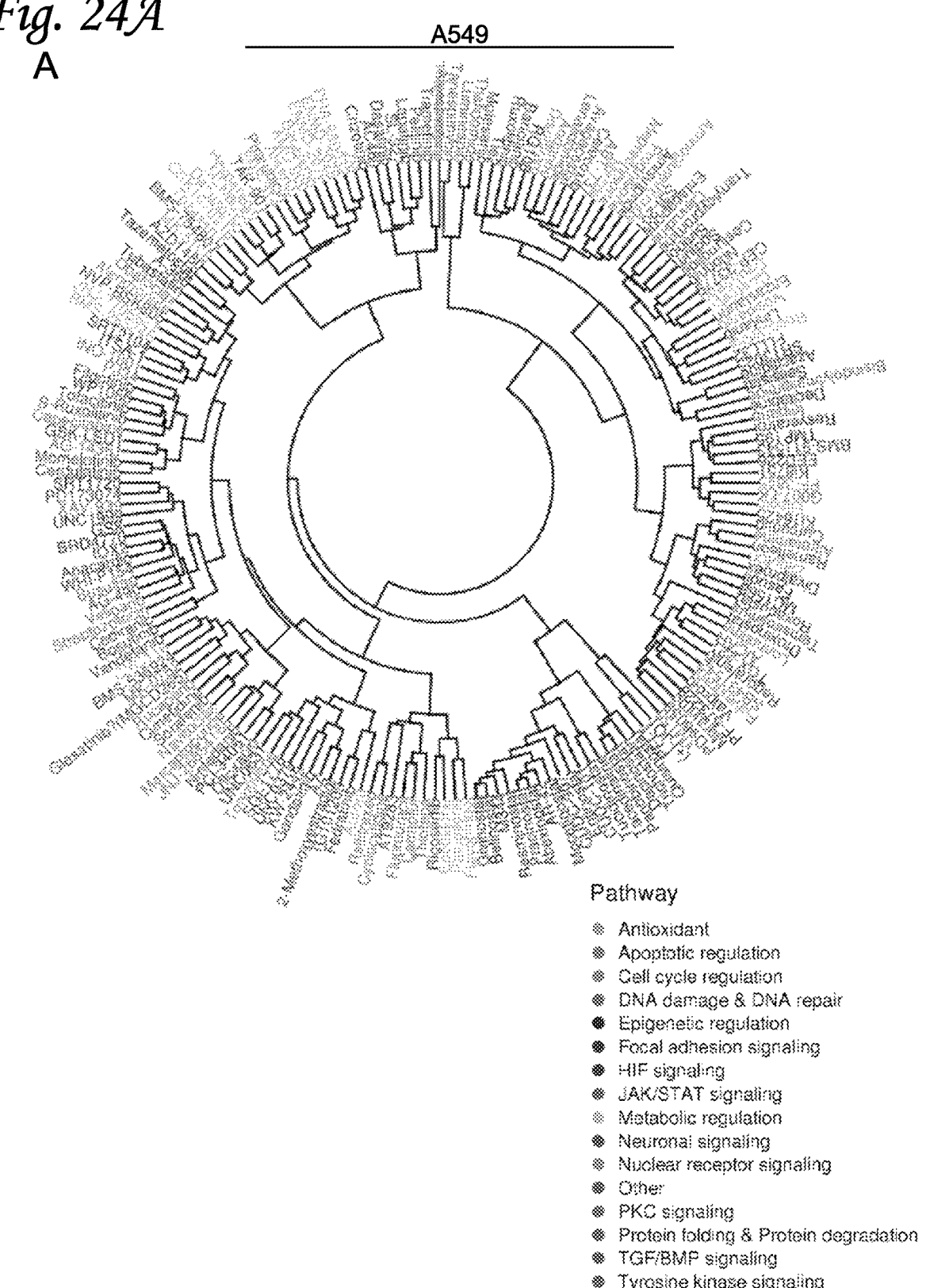

A549

Pathway

- Antioxidant
- Apoptotic regulation
- Cell cycle regulation
- DNA damage & DNA repair
- Epigenetic regulation
- Focal adhesion signaling
- HIF signaling
- JAK/STAT signaling
- Metabolic regulation
- Neuronal signaling
- Nuclear receptor signaling
- Other
- PKC signaling
- Protein folding & Protein degradation
- TGF/BMP signaling
- Tyrosine kinase signaling
- Vehicle

*Fig. 24B*
B

K562

Pathway
- Antioxidant
- Apoptotic regulation
- Cell cycle regulation
- DNA damage & DNA repair
- Epigenetic regulation
- Focal adhesion signaling
- HIF signaling
- JAK/STAT signaling
- Metabolic regulation
- Neuronal signaling
- Nuclear receptor signaling
- Other
- PKC signaling
- Protein folding & Protein degradation
- TGF/BMP signaling
- Tyrosine kinase signaling
- Vehicle

*Fig. 24C*
C

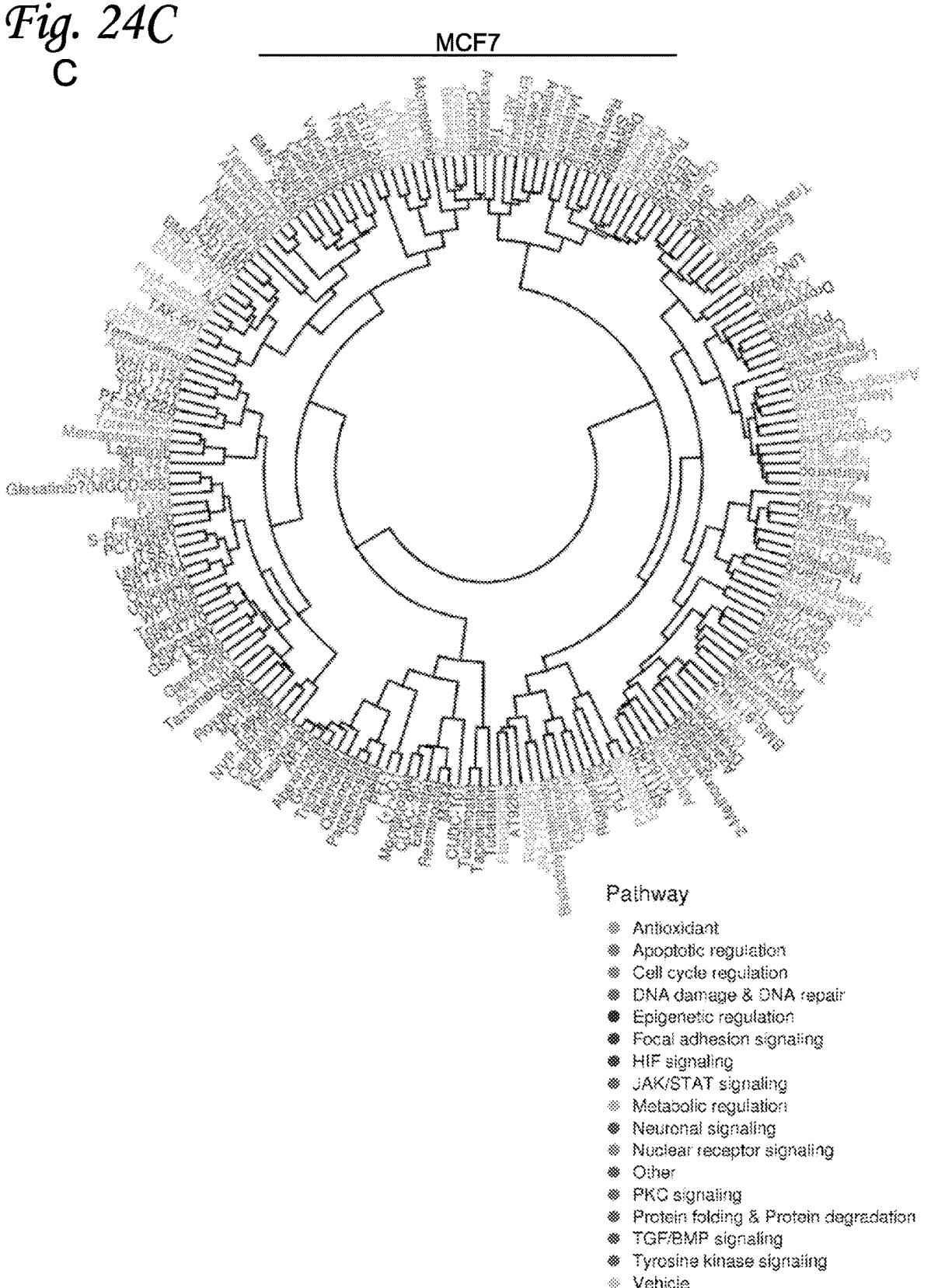

MCF7

Pathway
- Antioxidant
- Apoptotic regulation
- Cell cycle regulation
- DNA damage & DNA repair
- Epigenetic regulation
- Focal adhesion signaling
- HIF signaling
- JAK/STAT signaling
- Metabolic regulation
- Neuronal signaling
- Nuclear receptor signaling
- Other
- PKC signaling
- Protein folding & Protein degradation
- TGF/BMP signaling
- Tyrosine kinase signaling
- Vehicle

*Fig. 25*

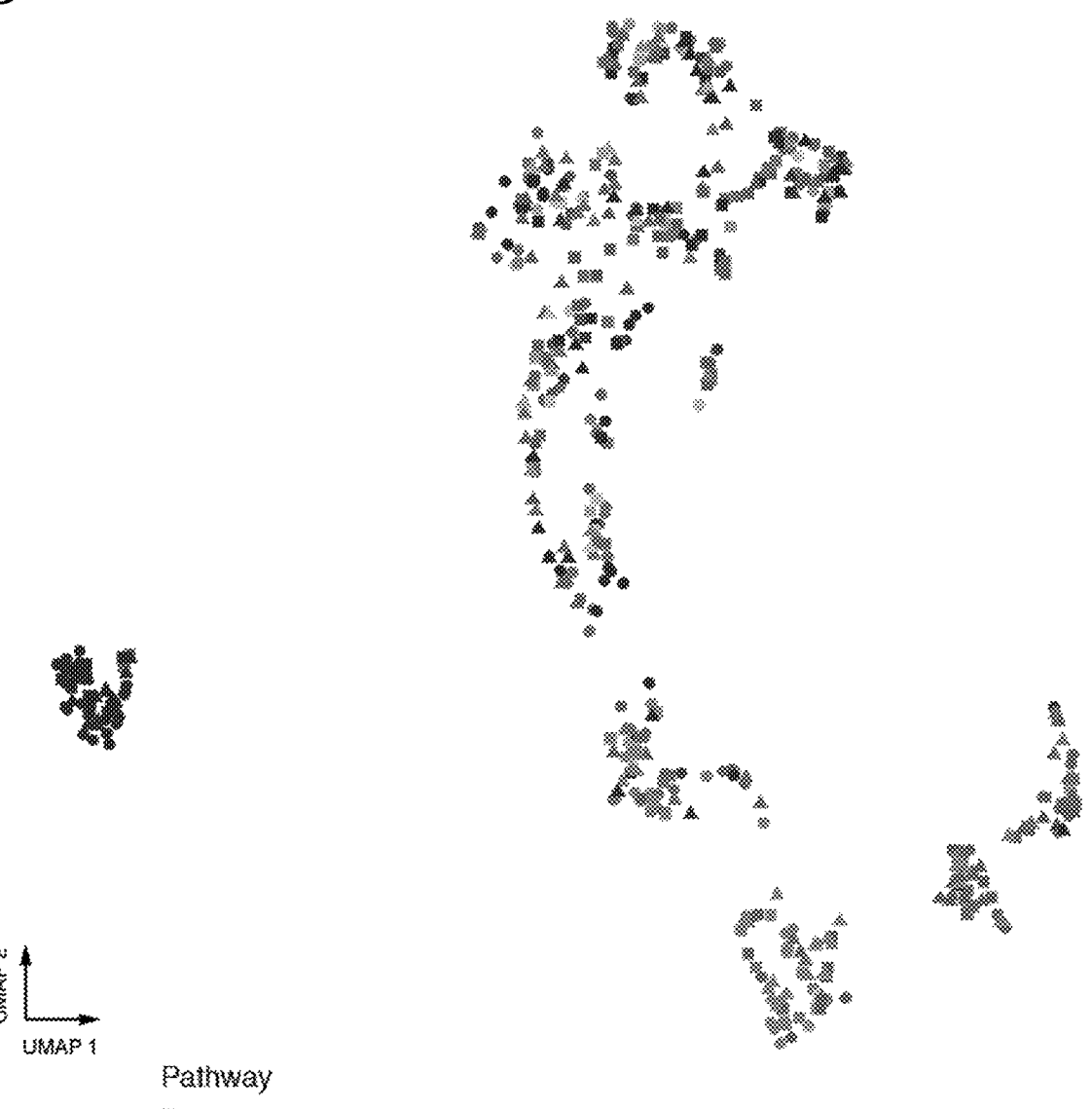

Pathway

Antioxidant
Apoptotic regulation
Cell cycle regulation
DNA damage & DNA repair
Epigenetic regulation
Focal adhesion signaling
HIF signaling
JAK/STAT signaling
Metabolic regulation
Neuronal signaling
Nuclear receptor signaling
Other
PKC signaling
Protein folding & Protein degradation
TGF/BMP signaling
Tyrosine kinase signaling

■  MCF7

●  A549

▲  K562

E

Fulvestrant

F

Trametinib

A

B

*Fig. 28C*
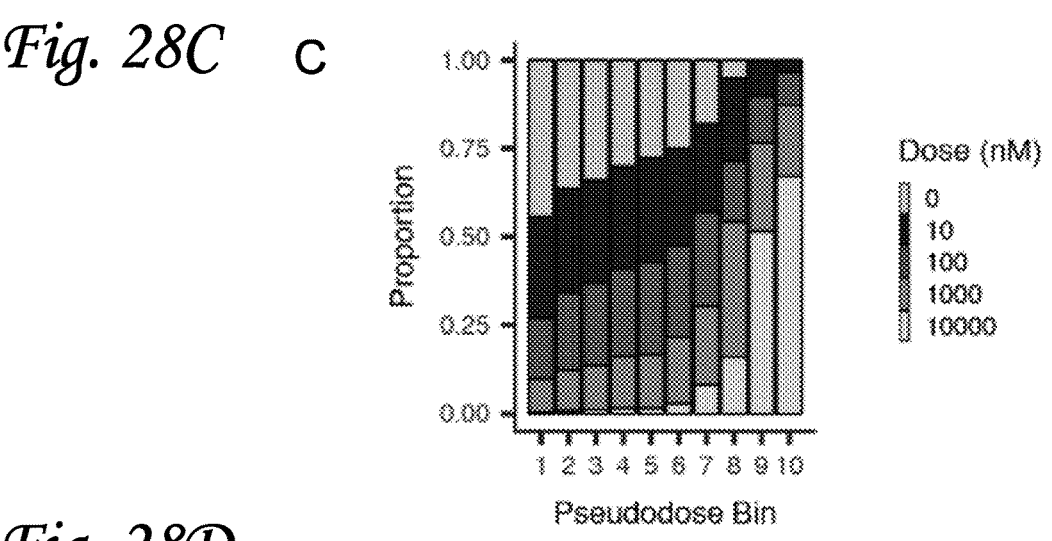
*Fig. 28D*
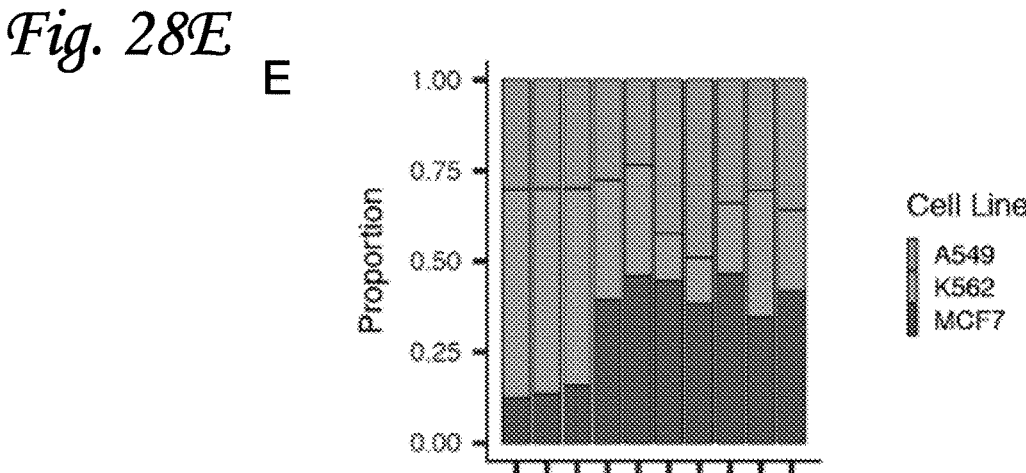
*Fig. 28E*

A

B

C

72/113

Replacement Sheet

A

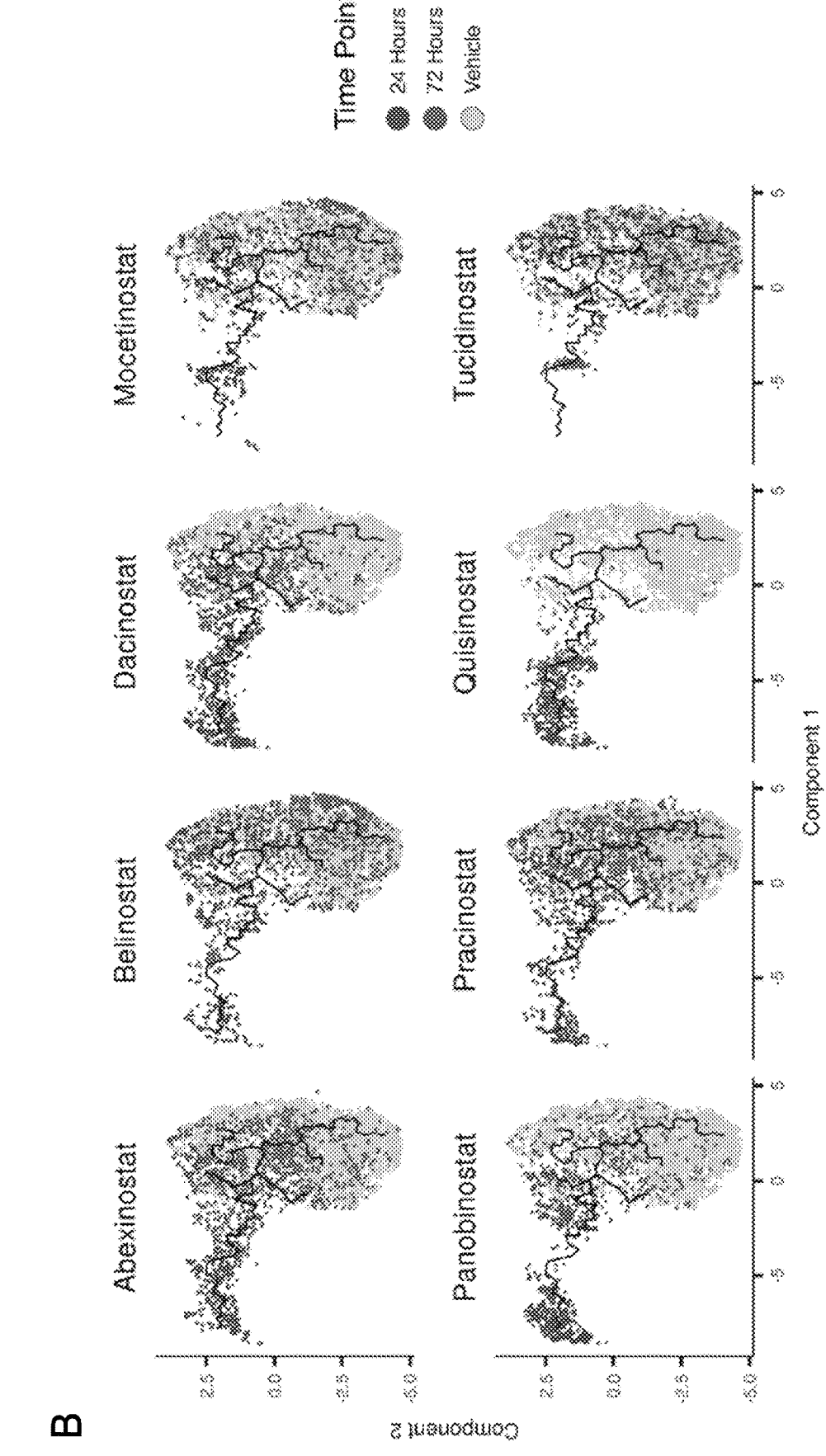

*Fig. 37A*
A
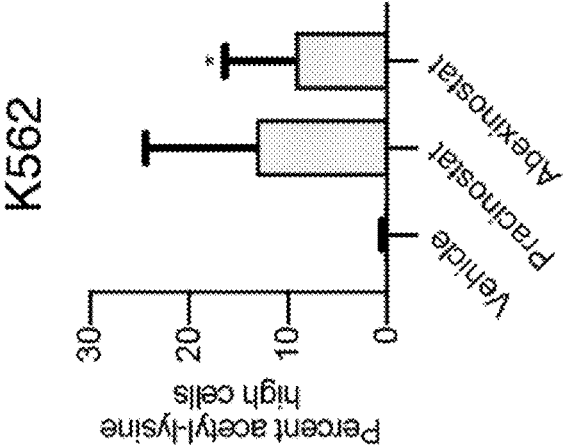
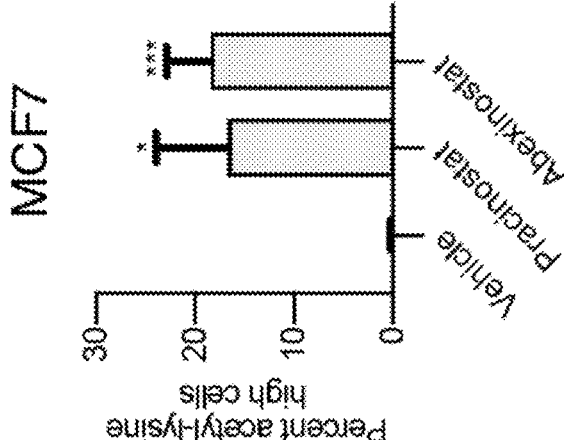
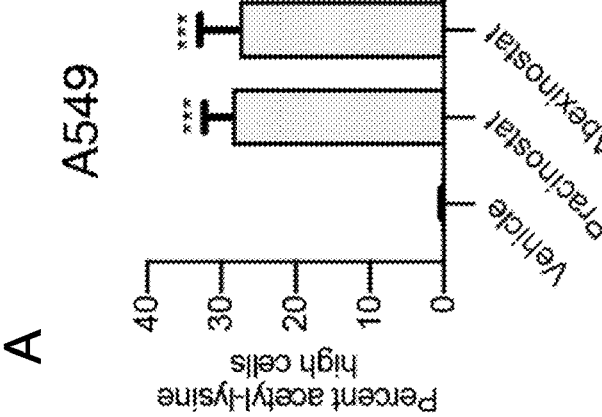

Overlap of HDACi
pseudodose DEGs

K

L

*Fig. 39M*

*Fig. 40A*    A
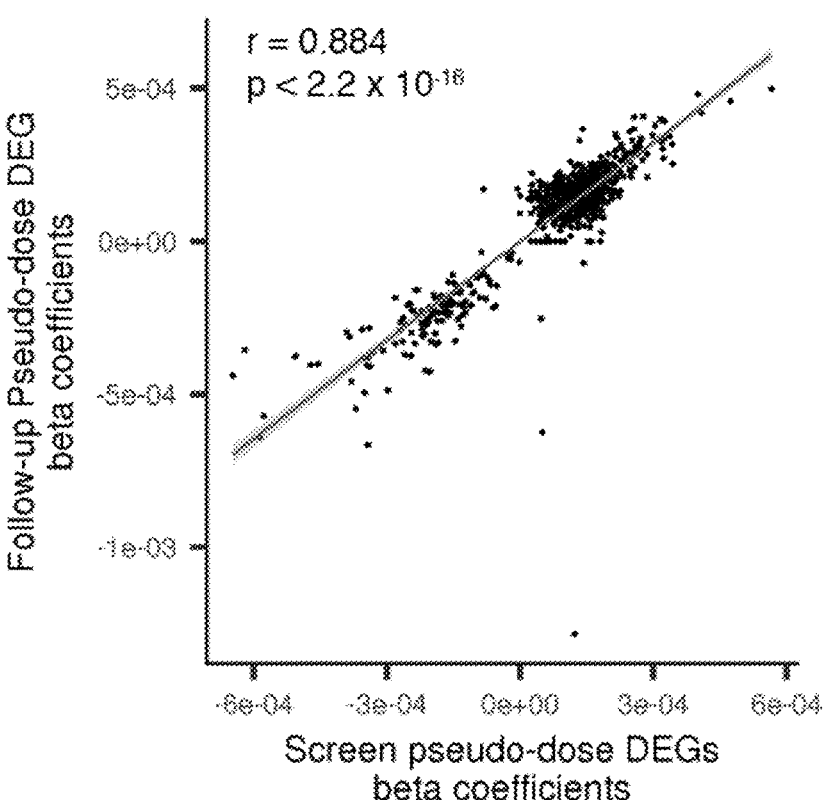
*Fig. 40B*
B
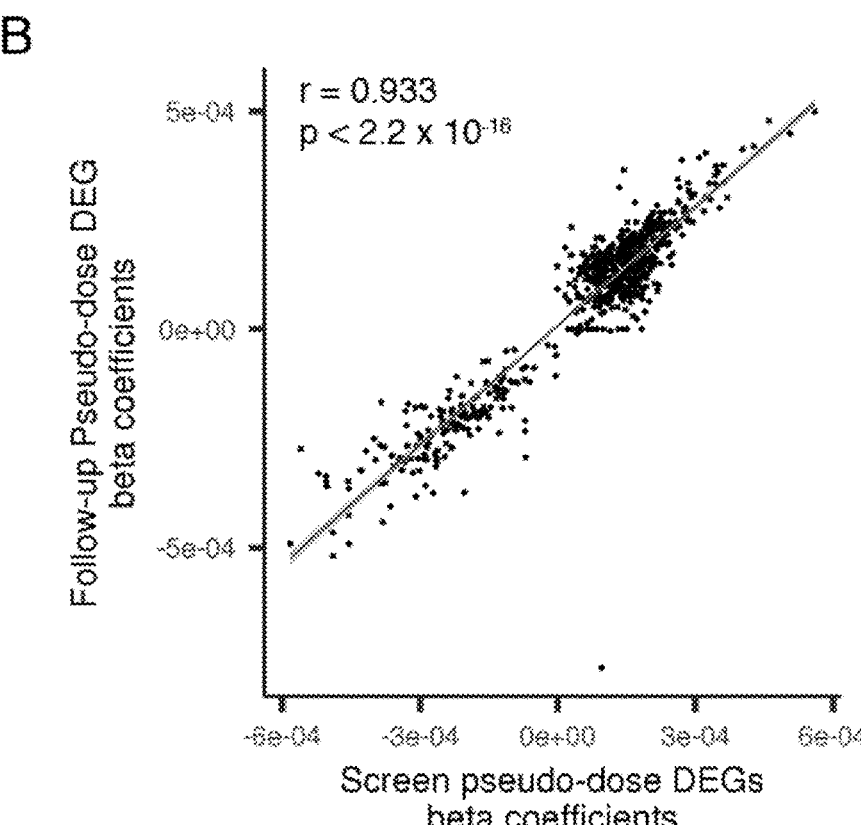

A

E

A

B

C

D

HIGH-THROUGHPUT SINGLE-NUCLEI AND SINGLE-CELL LIBRARIES AND METHODS OF MAKING AND OF USING

CROSS-REFERENCE TO RELATED APPLICATIONS

This application claims the benefit of U.S. Provisional Application Ser. No. 62/812,853, filed Mar. 1, 2019, which is incorporated by reference herein in its entirety.

This application is the § 371 U.S. National Stage of International Application No. PCT/US2020/020637, filed 2 Mar. 2020, which claims the benefit of U.S. Provisional Application Ser. No. 62/812,853, filed Mar. 1, 2019, which are incorporated by reference herein in their entireties its entirety.

GOVERNMENT FUNDING

This invention was made with government support under Grant Nos. HG007811, HD088158, and R01 HG006283, awarded by the National Institutes of Health, and Grant No. DGE1258485, awarded by the National Science Foundation. The government has certain rights in the invention.

FIELD

Embodiments of the present disclosure relate to sequencing nucleic acids. In particular, embodiments of the methods and compositions provided herein relate to producing indexed single-nuclei and single-cell libraries using hashing oligos and/or normalization oligos and obtaining sequence data therefrom.

SEQUENCE LISTING

This application contains a Sequence Listing electronically submitted via EFS-Web to the United States Patent and Trademark Office as an ASCII text file entitled "IP-1815-PCT_ST25.txt" having a size of 4 kilobytes and created on Feb. 28, 2020. The information contained in the Sequence Listing is incorporated by reference herein.

BACKGROUND

High-throughput screens (HTSs) are a cornerstone of the pharmaceutical drug discovery pipeline (J. R. Broach, J. Thorner, Nature 384 (Suppl), 14-16 (1996), Pereira, J. A. Williams, Br. J. Pharmacol. 152, 53-61 (2007)). However, conventional HTSs have at least two major limitations. First, the readout of most are restricted to gross cellular phenotypes, e.g., proliferation (D. Shum et al., J. Enzyme Inhib. Med. Chem. 23, 931-945 (2008), C. Yu et al., Nat. Biotechnol. 34, 419-423 (2016)), morphology (Z. E. Perlman et al., Science 306, 1194-1198 (2004), Y. Futamura et al., Chem. Biol. 19, 1620-1630 (2012)), or a highly specific molecular readout (J. Kang et al., Nat. Biotechnol. 34, 70-77 (2016), K. L. Huss, P. E. Blonigen, R. M. Campbell, J. Biomol. Screen. 12, 578-584 (2007)). Subtle changes in cell state or gene expression that might otherwise provide mechanistic insights or reveal off-target effects are routinely missed.

Second, even when HTSs are performed in conjunction with more comprehensive molecular phenotyping such as transcriptional profiling (C. Ye et al., Nat. Commun. 9, 4307 (2018), E. C. Bush et al., Nat. Commun. 8, 105 (2017), A. Subramanian et al., Cell 171, 1437-1452.e17 (2017), J. Lamb et al., Science 313, 1929-1935 (2006)), a limitation of bulk assays is that even cells ostensibly of the same "type" can exhibit heterogeneous responses (M. B. Elowitz, A. J. Levine, E. D. Siggia, P. S. Swain, Science 297, 1183-1186 (2002), C. Trapnell, Genome Res. 25, 1491-1498 (2015)). Such cellular heterogeneity can be highly relevant in vivo. For example, it remains largely unknown whether the rare subpopulations of cells that survive chemotherapeutics are doing so on the basis of their genetic background, epigenetic state, or some other aspect (S. M. Shaffer et al., Nature 546, 431-435 (2017), S. L. Spencer, S. Gaudet, J. G. Albeck, J. M. Burke, P. K. Sorger, Nature 459, 428-432 (2009)). Moreover, the sparsity and levels of technical noise often make it difficult to extract biologically meaningful information.

In principle, single-cell transcriptome sequencing (scRNA-seq) represents a form of high-content molecular phenotyping that could enable HTSs to overcome both limitations. However, the per-sample and per-cell costs of most scRNA-seq technologies remain high, precluding even modestly sized screens. Recently, several groups have developed "cellular hashing" methods, in which cells from different samples are molecularly labeled and mixed before scRNA-seq. However, current hashing approaches require relatively expensive reagents (e.g., antibodies (M. Stoeckius et al., Genome Biol. 19, 224 (2018)) or chemically modified DNA oligos (J. Gehring, J. H. Park, S. Chen, M. Thomson, L. Pachter, bioRxiv 315333 [Preprint] 5 May 2018. doi.org/10.1101/315333, C. S. McGinnis et al., Nat. Methods 16, 619-626 (2019)), use cell-type-dependent protocols (D. Shin, W. Lee, J. H. Lee, D. Bang, Sci. Adv. 5, eaav2249 (2019)), and/or use scRNA-seq platforms with a high per-cell cost.

SUMMARY OF THE APPLICATION

High cell count single-cell and single-nuclei sequencing with Single-cell Combinatorial Indexed Sequencing (sci-) methods has shown its efficacy in separation of populations within cells and complex tissues via transcriptomes, chromatin-accessibility, mutational differences, and other differences. One method described herein, nuclear hashing or cellular hashing, uses hashing oligos to increase sample throughput and increases doublet detection at high collision rates. Another method described herein, normalization hashing, uses normalization oligos as a standard to aid in estimating and removing technical noise in cell to cell variation and to increase sensitivity and specificity.

Provided herein are methods for preparing a sequencing library. In one embodiment, the library includes nucleic acids from a plurality of single nuclei or single cells, and the method includes providing a plurality of cells in a first plurality of compartments, and contacting nuclei isolated from the cells of each compartment or the cells of each compartment with a hashing oligo to generate hashed nuclei or hashed cells. In one embodiment, at least one copy of the hashing oligo is associated with isolated nuclei or cells. In one embodiment, the hashing oligo includes a hashing index. In one embodiment, the hashing index in each compartment includes an index sequence that is different from index sequences in the other compartments. The association between the hashing oligo and the isolated nuclei or cells can be non-specific, such by absorption. The method can further include combining the hashed nuclei or hashed cells of different compartments to generate pooled hashed nuclei or pooled hashed cells. In one embodiment, the method can further include exposing the plurality of cells of each compartment to a predetermined condition. The exposure to a predetermined condition can be at any point in the method, and in one embodiment occurs before the contacting.

In one embodiment, the method can optionally include processing the pooled hashed cells or pooled hashed nuclei using a single-cell combinatorial indexing method to result in a sequencing library including nucleic acids from the plurality of single nuclei. Examples of single-cell combinatorial indexing methods that can be used include, but are not limited to, single-nuclei transcriptome sequencing, single-cell transcriptome sequencing, single-cell transcriptome and transposon-accessible chromatin sequencing, whole genome sequencing of single nuclei, single nuclei sequencing of transposon accessible chromatin, sci-HiC, DRUG-seq, sci-CAR, sci-MET, sci-Crop, sci-perturb, or sci-Crispr.

Also provided by the disclosure is a method for normalizing a sequencing library. In one embodiment, the sequencing library includes nucleic acids from a plurality of single nuclei or single cells. In one embodiment, the method includes providing a first plurality of compartments including isolated nuclei or cells, and contacting the isolated nuclei or cells of each compartment with populations of normalizing oligos, wherein members of each population of normalization oligos are associated with isolated nuclei or cells. In one embodiment, the contacting occurs before the isolated nuclei or cells are distributed to compartments. The normalizing oligos can be associated with isolated nuclei or cells prior to compartmentalization or after compartmentalization. The association between the normalization oligos and the isolated nuclei or cells can be non-specific, such by absorption. The method can further include combining the labeled nuclei or labeled cells of different compartments to generate pooled labeled nuclei or pooled labeled cells. In one embodiment, the method can further include exposing the plurality of cells of each compartment to a predetermined condition. The exposure to a predetermined condition can be at any point in the method, and in one embodiment occurs before the contacting.

Definitions

Terms used herein will be understood to take on their ordinary meaning in the relevant art unless specified otherwise. Several terms used herein and their meanings are set forth below.

As used herein, the terms "organism" and "subject," are used interchangeably and refer to microbes (e.g., prokaryotic or eukaryotic), animals, and plants. An example of an animal is a mammal, such as a human.

As used herein, the term "cell type" is intended to identify cells based on morphology, phenotype, developmental origin or other known or recognizable distinguishing cellular characteristic. A variety of different cell types can be obtained from a single organism (or from the same species of organism). Exemplary cell types include, but are not limited to, gametes (including female gametes, e.g., ova or egg cells, and male gametes, e.g., sperm), ovary epithelial, ovary fibroblast, testicular, urinary bladder, pancreatic epithelial, pancreatic alpha, immune cells, B cells, T cells, natural killer cells, dendritic cells, cancer cells, eukaryotic cells, stem cells, blood cells, muscle cells, fat cells, skin cells, nerve cells, bone cells, pancreatic cells, endothelial cells, pancreatic beta, pancreatic endothelial, bone marrow lymphoblast, bone marrow B lymphoblast, bone marrow macrophage, bone marrow erythroblast, bone marrow dendritic, bone marrow adipocyte, bone marrow osteocyte, bone marrow chondrocyte, promyeloblast, bone marrow megakaryoblast, bladder, brain B lymphocyte, brain glial, neuron, brain astrocyte, neuroectoderm, brain macrophage, brain microglia, brain epithelial, cortical neuron, brain fibroblast, breast epithelial, colon epithelial, colon B lymphocyte, mammary epithelial, mammary myoepithelial, mammary fibroblast, colon enterocyte, cervix epithelial, breast duct epithelial, tongue epithelial, tonsil dendritic, tonsil B lymphocyte, peripheral blood lymphoblast, peripheral blood T lymphoblast, peripheral blood cutaneous T lymphocyte, peripheral blood natural killer, peripheral blood B lymphoblast, peripheral blood monocyte, peripheral blood myeloblast, peripheral blood monoblast, peripheral blood promyeloblast, peripheral blood macrophage, peripheral blood basophil, liver endothelial, liver mast, liver epithelial, liver B lymphocyte, spleen endothelial, spleen epithelial, spleen B lymphocyte, liver hepatocyte, liver, fibroblast, lung epithelial, bronchus epithelial, lung fibroblast, lung B lymphocyte, lung Schwann, lung squamous, lung macrophage, lung osteoblast, neuroendocrine, lung alveolar, stomach epithelial, and stomach fibroblast.

As used herein, the term "tissue" is intended to mean a collection or aggregation of cells that act together to perform one or more specific functions in an organism. The cells can optionally be morphologically similar. Exemplary tissues include, but are not limited to, embryonic, epididymidis, eye, muscle, skin, tendon, vein, artery, blood, heart, spleen, lymph node, bone, bone marrow, lung, bronchi, trachea, gut, small intestine, large intestine, colon, rectum, salivary gland, tongue, gall bladder, appendix, liver, pancreas, brain, stomach, skin, kidney, ureter, bladder, urethra, gonad, testicle, ovary, uterus, fallopian tube, thymus, pituitary, thyroid, adrenal, or parathyroid. Tissue can be derived from any of a variety of organs of a human or other organism. A tissue can be a healthy tissue or an unhealthy tissue. Examples of unhealthy tissues include, but are not limited to, malignancies in reproductive tissue, lung, breast, colorectum, prostate, nasopharynx, stomach, testes, skin, nervous system, bone, ovary, liver, hematologic tissues, pancreas, uterus, kidney, lymphoid tissues, etc. The malignancies may be of a variety of histological subtypes, for example, carcinoma, adenocarcinoma, sarcoma, fibroadenocarcinoma, neuroendocrine, or undifferentiated.

As used herein, the term "compartment" is intended to mean an area or volume that separates or isolates something from other things. Exemplary compartments include, but are not limited to, vials, tubes, wells, droplets, boluses, beads, vessels, surface features, or areas or volumes separated by physical forces such as fluid flow, magnetism, electrical current or the like. In one embodiment, a compartment is a well of a multi-well plate, such as a 96- or 384-well plate. As used herein, a droplet may include a hydrogel bead, which is a bead for encapsulating one or more nuclei or cell, and includes a hydrogel composition. In some embodiments, the droplet is a homogeneous droplet of hydrogel material or is a hollow droplet having a polymer hydrogel shell. Whether homogenous or hollow, a droplet may be capable of encapsulating one or more nuclei or cells.

As used herein, a "transposome complex" refers to an integration enzyme and a nucleic acid including an integration recognition site. A "transposome complex" is a functional complex formed by a transposase and a transposase recognition site that is capable of catalyzing a transposition reaction (see, for instance, Gunderson et al., WO 2016/130704). Examples of integration enzymes include, but are not limited to, an integrase or a transposase. Examples of integration recognition sites include, but are not limited to, a transposase recognition site.

As used herein, the term "nucleic acid" is intended to be consistent with its use in the art and includes naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of adenine, uracil, cytosine or guanine. Useful non-native bases that can be included in a nucleic acid are known in the art. Examples of non-native bases include a locked nucleic acid (LNA), a bridged nucleic acid (BNA), and pseudo-complementary bases (Trilink Biotechnologies, San Diego, California). LNA and BNA bases can be incorporated into a DNA oligonucleotide and increase oligonucleotide hybridization strength and specificity. LNA and BNA bases and the uses of such bases are known to the person skilled in the art and are routine.

As used herein, the term "target," when used in reference to a nucleic acid, is intended as a semantic identifier for the nucleic acid in the context of a method or composition set forth herein and does not necessarily limit the structure or function of the nucleic acid beyond what is otherwise explicitly indicated. A target nucleic acid may be essentially any nucleic acid of known or unknown sequence. It may be, for example, a fragment of genomic DNA (e.g., chromosomal DNA), extra-chromosomal DNA such as a plasmid, cell-free DNA, RNA (e.g., mRNA), proteins (e.g. cellular or cell surface proteins), or cDNA. Sequencing may result in determination of the sequence of the whole, or a part of the target molecule. The targets can be derived from a primary nucleic acid sample, such as a nucleus. In one embodiment, the targets can be processed into templates suitable for amplification by the placement of universal sequences at the end or ends of each target fragment. The targets can also be obtained from a primary RNA sample by reverse transcription into cDNA. In one embodiment, target is used in reference to a subset of DNA, RNA, or proteins present in the cell. Targeted sequencing uses selection and isolation of genes or regions or proteins of interest, typically by either PCR amplification (e.g. region-specific primers) or hybridization-based capture method or antibodies. Targeted enrichment can occur at various stages of the method. For instance, a targeted RNA representation can be obtained using target specific primers in the reverse transcription step or hybridization-based enrichment of a subset out of a more complex library. An example is exome sequencing or the L1000 assay (Subramanian et al., 2017, Cell, 171; 1437-1452). Targeted sequencing can include any of the enrichment processes known to one of ordinary skill in the art.

As used herein, the term "universal," when used to describe a nucleotide sequence, refers to a region of sequence that is common to two or more nucleic acid molecules or samples where the molecules also have regions of sequence that differ from each other. A universal sequence that is present in different members of a collection of molecules can allow capture of multiple different nucleic acids using a population of universal capture nucleic acids, e.g., capture oligonucleotides that are complementary to a portion of the universal sequence, e.g., a universal capture sequence. Non-limiting examples of universal capture sequences include sequences that are identical to or complementary to P5 and P7 primers. Similarly, a universal sequence present in different members of a collection of molecules can allow the replication (e.g., sequencing) or amplification of multiple different nucleic acids using a population of universal primers that are complementary to a portion of the universal sequence, e.g., a universal anchor sequence. In one embodiment universal anchor sequences are used as a site to which a universal primer (e.g., a sequencing primer for read 1 or read 2) anneals for sequencing. A capture oligonucleotide or a universal primer therefore includes a sequence that can hybridize specifically to a universal sequence.

The terms "P5" and "P7" may be used when referring to a universal capture sequence or a capture oligonucleotide. The terms "P5'" (P5 prime) and "P7'" (P7 prime) refer to the complement of P5 and P7, respectively. It will be understood that any suitable universal capture sequence or a capture oligonucleotide can be used in the methods presented herein, and that the use of P5 and P7 are exemplary embodiments only. Uses of capture oligonucleotides such as P5 and P7 or their complements on flowcells are known in the art, as exemplified by the disclosures of WO 2007/010251, WO 2006/064199, WO 2005/065814, WO 2015/106941, WO 1998/044151, and WO 2000/018957. For example, any suitable forward amplification primer, whether immobilized or in solution, can be useful in the methods presented herein for hybridization to a complementary sequence and amplification of a sequence. Similarly, any suitable reverse amplification primer, whether immobilized or in solution, can be useful in the methods presented herein for hybridization to a complementary sequence and amplification of a sequence. One of skill in the art will understand how to design and use primer sequences that are suitable for capture and/or amplification of nucleic acids as presented herein.

As used herein, the term "primer" and its derivatives refer generally to any nucleic acid that can hybridize to a target sequence of interest. Typically, the primer functions as a substrate onto which nucleotides can be polymerized by a polymerase or to which nucleotides can be ligated; in some embodiments, however, the primer can become incorporated into the synthesized nucleic acid strand and provide a site to which another primer can hybridize to prime synthesis of a new strand that is complementary to the synthesized nucleic acid molecule. The primer can include any combination of nucleotides or analogs thereof. In some embodiments, the primer is a single-stranded oligonucleotide or polynucleotide. The terms "polynucleotide" and "oligonucleotide" are used interchangeably herein to refer to a polymeric form of nucleotides of any length, and may include ribonucleotides, deoxyribonucleotides, analogs thereof, or mixtures thereof. The terms should be understood to include, as equivalents, analogs of either DNA, RNA, cDNA, or antibody-oligo conjugates made from nucleotide analogs and to be applicable to single stranded (such as sense or antisense) and double stranded polynucleotides. The term as used herein also encompasses cDNA, that is complementary or copy DNA produced from a RNA template, for example by the action of reverse transcriptase. This term refers only to the primary structure of the molecule. Thus, the term includes triple-, double- and single-stranded deoxyribonucleic acid ("DNA"), as well as triple-, double- and single-stranded ribonucleic acid ("RNA").

As used herein, the term "adapter" and its derivatives, e.g., universal adapter, refers generally to any linear oligo- nucleotide which can be attached to a nucleic acid molecule of the disclosure. In some embodiments, the adapter is substantially non-complementary to the 3' end or the 5' end of any target sequence present in the sample. In some embodiments, suitable adapter lengths are in the range of about 10-100 nucleotides, about 12-60 nucleotides, or about 15-50 nucleotides in length. Generally, the adapter can include any combination of nucleotides and/or nucleic acids. In some aspects, the adapter can include one or more cleavable groups at one or more locations. In another aspect, the adapter can include a sequence that is substantially identical, or substantially complementary, to at least a por- tion of a primer, for example a universal primer. In some embodiments, the adapter can include a barcode (also referred to herein as a tag or index) to assist with down- stream error correction, identification, or sequencing. The terms "adaptor" and "adapter" are used interchangeably.

As used herein, the term "each," when used in reference to a collection of items, is intended to identify an individual item in the collection but does not necessarily refer to every item in the collection unless the context clearly dictates otherwise.

As used herein, the term "transport" refers to movement of a molecule through a fluid. The term can include passive transport such as movement of molecules along their con- centration gradient (e.g. passive diffusion). The term can also include active transport whereby molecules can move along their concentration gradient or against their concen- tration gradient. Thus, transport can include applying energy to move one or more molecules in a desired direction or to a desired location such as an amplification site.

As used herein, "amplify", "amplifying" or "amplification reaction" and their derivatives, refer generally to any action or process whereby at least a portion of a nucleic acid molecule is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. Amplification optionally includes linear or exponential replication of a nucleic acid molecule. In some embodiments, such amplification can be performed using isothermal conditions; in other embodi- ments, such amplification can include thermocycling. In some embodiments, the amplification is a multiplex ampli- fication that includes the simultaneous amplification of a plurality of target sequences in a single amplification reac- tion. In some embodiments, "amplification" includes ampli- fication of at least some portion of DNA and RNA based nucleic acids alone, or in combination. The amplification reaction can include any of the amplification processes known to one of ordinary skill in the art. In some embodi- ments, the amplification reaction includes polymerase chain reaction (PCR).

As used herein, "amplification conditions" and its deriva- tives, generally refers to conditions suitable for amplifying one or more nucleic acid sequences. Such amplification can be linear or exponential. In some embodiments, the ampli- fication conditions can include isothermal conditions or alternatively can include thermocycling conditions, or a combination of isothermal and thermocycling conditions. In some embodiments, the conditions suitable for amplifying one or more nucleic acid sequences include polymerase chain reaction (PCR) conditions. Typically, the amplification conditions refer to a reaction mixture that is sufficient to amplify nucleic acids such as one or more target sequences flanked by a universal sequence, or to amplify an amplified target sequence ligated to one or more adapters. Generally, the amplification conditions include a catalyst for amplifi- cation or for nucleic acid synthesis, for example a poly- merase; a primer that possesses some degree of complemen- tarity to the nucleic acid to be amplified; and nucleotides, such as deoxyribonucleotide triphosphates (dNTPs) to pro- mote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodi- ments, amplification conditions include a plurality of cycles where the steps of annealing, extending and separating are repeated. Typically, the amplification conditions include cations such as Mg' or Mn' and can also include various modifiers of ionic strength.

As used herein, "re-amplification" and their derivatives refer generally to any process whereby at least a portion of an amplified nucleic acid molecule is further amplified via any suitable amplification process (referred to in some embodiments as a "secondary" amplification), thereby pro- ducing a reamplified nucleic acid molecule. The secondary amplification need not be identical to the original amplifi- cation process whereby the amplified nucleic acid molecule was produced; nor need the reamplified nucleic acid mol- ecule be completely identical or completely complementary to the amplified nucleic acid molecule; all that is required is that the reamplified nucleic acid molecule include at least a portion of the amplified nucleic acid molecule or its comple- ment. For example, the re-amplification can involve the use of different amplification conditions and/or different prim- ers, including different target-specific primers than the pri- mary amplification.

As used herein, the term "polymerase chain reaction" ("PCR") refers to the method of Mullis U.S. Pat. Nos. 4,683,195 and 4,683,202, which describe a method for increasing the concentration of a segment of a polynucle- otide of interest in a mixture of genomic DNA without cloning or purification. This process for amplifying the polynucleotide of interest consists of introducing a large excess of two oligonucleotide primers to the DNA mixture containing the desired polynucleotide of interest, followed by a series of thermal cycling in the presence of a DNA polymerase. The two primers are complementary to their respective strands of the double stranded polynucleotide of interest. The mixture is denatured at a higher temperature first and the primers are then annealed to complementary sequences within the polynucleotide of interest molecule. Following annealing, the primers are extended with a poly- merase to form a new pair of complementary strands. The steps of denaturation, primer annealing and polymerase extension can be repeated many times (referred to as ther- mocycling) to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as PCR. Because the desired amplified segments of the polynucleotide of interest become the predominant nucleic acid sequences (in terms of concentration) in the mixture, they are said to be "PCR amplified". In a modification to the method discussed above, the target nucleic acid molecules can be PCR amplified using a plurality of different primer pairs, in some cases, one or more primer pairs per target nucleic acid molecule of interest, thereby forming a multiplex PCR reaction.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher. It is also possible to detect the amplified target sequences by several different methodologies (e.g., gel electrophoresis followed by densitometry, quantitation with a bioanalyzer or quantitative PCR, hybridization with a labeled probe; incorporation of biotinylated primers followed by avidin-enzyme conjugate detection; incorporation of $^{32}$P-labeled deoxynucleotide triphosphates into the amplified target sequence).

As used herein, "amplified target sequences" and its derivatives, refers generally to a nucleic acid sequence produced by the amplifying the target sequences using target-specific primers and the methods provided herein. The amplified target sequences may be either of the same sense (i.e. the positive strand) or antisense (i.e., the negative strand) with respect to the target sequences.

As used herein, the terms "ligating", "ligation" and their derivatives refer generally to the process for covalently linking two or more molecules together, for example covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, the ligation can include forming a covalent bond between a 5' phosphate group of one nucleic acid and a 3' hydroxyl group of a second nucleic acid thereby forming a ligated nucleic acid molecule. Generally, for the purposes of this disclosure, an amplified target sequence can be ligated to an adapter to generate an adapter-ligated amplified target sequence.

As used herein, "ligase" and its derivatives, refers generally to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but are not limited to, T4 DNA ligase, T4 RNA ligase, and *E. coli* DNA ligase.

As used herein, "ligation conditions" and its derivatives, generally refers to conditions suitable for ligating two molecules to each other. In some embodiments, the ligation conditions are suitable for sealing nicks or gaps between nucleic acids. As used herein, the term nick or gap is consistent with the use of the term in the art. Typically, a nick or gap can be ligated in the presence of an enzyme, such as ligase at an appropriate temperature and pH. In some embodiments, T4 DNA ligase can join a nick between nucleic acids at a temperature of about 70-72° C.

The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "amplification site" refers to a site in or on an array where one or more amplicons can be generated. An amplification site can be further configured to contain, hold or attach at least one amplicon that is generated at the site.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "capacity," when used in reference to a site and nucleic acid material, means the maximum amount of nucleic acid material that can occupy the site. For example, the term can refer to the total number of nucleic acid molecules that can occupy the site in a particular condition. Other measures can be used as well including, for example, the total mass of nucleic acid material or the total number of copies of a particular nucleotide sequence that can occupy the site in a particular condition. Typically, the capacity of a site for a target nucleic acid will be substantially equivalent to the capacity of the site for amplicons of the target nucleic acid.

As used herein, the term "capture agent" refers to a material, chemical, molecule, or moiety thereof that is capable of attaching, retaining or binding to a target molecule (e.g., a target nucleic acid). Exemplary capture agents include, without limitation, a capture nucleic acid (also referred to herein as a capture oligonucleotide) that is complementary to at least a portion of a target nucleic acid, a member of a receptor-ligand binding pair (e.g. avidin, streptavidin, biotin, lectin, carbohydrate, nucleic acid binding protein, epitope, antibody, etc.) capable of binding to a target nucleic acid (or linking moiety attached thereto), or a chemical reagent capable of forming a covalent bond with a target nucleic acid (or linking moiety attached thereto).

As used herein, the term "reporter moiety" can refer to any identifiable tag, label, indices, barcodes, or group that enables to determine the composition, identity, and/or the source of an analyte that is investigated. In some embodiments, a reporter moiety may include an antibody that specifically binds to a protein. In some embodiments, the antibody may include a detectable label. In some embodiments, the reporter can include an antibody or affinity reagent labeled with a nucleic acid tag. The nucleic acid tag can be detectable, for example, via a proximity ligation assay (PLA) or proximity extension assay (PEA) or sequencing-based readout (Shahi et al. Scientific Reports volume 7, Article number: 44447, 2017) or CITE-seq (Stoeckius et at Nature Methods 14:865-868, 2017).

As used herein, the term "clonal population" refers to a population of nucleic acids that is homogeneous with respect to a particular nucleotide sequence. The homogenous sequence is typically at least 10 nucleotides long, but can be even longer including for example, at least 50, 100, 250, 500 or 1000 nucleotides long. A clonal population can be derived from a single target nucleic acid or template nucleic acid. Typically, all of the nucleic acids in a clonal population will have the same nucleotide sequence. It will be understood that a small number of mutations (e.g. due to amplification artifacts) can occur in a clonal population without departing from clonality.

As used herein, "providing" in the context of a composition, an article, a nucleic acid, or a nucleus means making the composition, article, nucleic acid, or nucleus, purchasing the composition, article, nucleic acid, or nucleus, or otherwise obtaining the compound, composition, article, or nucleus.

As used herein, an "index" (also referred to as an "index region," "index adaptor," "tag," or a "barcode") refers to a unique nucleic acid tag that can be used to identify a sample or source of the nucleic acid material. When nucleic acid samples are derived from multiple sources, the nucleic acids in each nucleic acid sample can be tagged with different nucleic acid tags such that the source of the sample can be identified. Any suitable index or set of indexes can be used, as known in the art and as exemplified by the disclosures of U.S. Pat. No. 8,053,192, PCT Publication No. WO 05/068656, and U.S. Pat. Publication No. 2013/0274117. In some embodiments, an index can include a six-base Index 1 (i7) sequence, an eight-base Index 1 (i7) sequence, an eight-base Index 2 (i5e) sequence, a ten-base Index 1 (i7) sequence, or a ten-base Index 2 (i5) sequence from Illumina, Inc. (San Diego, California).

As used herein, the term "unique molecular identifier" or "UMI" refers to a molecular tag, either random, non-random, or semi-random, that may be attached to a nucleic acid molecule. When incorporated into a nucleic acid molecule, a UMI can be used to correct for subsequent amplification bias by directly counting unique molecular identifiers (UMIs) that are sequenced after amplification.

The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

BRIEF DESCRIPTION OF THE FIGURES

The following detailed description of illustrative embodiments of the present disclosure may be best understood when read in conjunction with the following drawings.

FIG. 1 shows a general block diagram of a general illustrative method for one embodiment of nuclear or cellular hashing according to the present disclosure.

FIG. 2 shows a general block diagram of a general illustrative method for one embodiment of normalization hashing according to the present disclosure.

FIG. 18 shows single cell measurements enable estimation of proliferation status and viability across drug-dose combinations. Heatmap depicting estimates of relative proliferation rate, the percentage of cells exhibiting low proliferation index, and the estimated viability for each compound (row) at each dose (column) pair.

FIG. 24 shows clustergrams of the correlation of compound-driven molecular signatures. Clustergrams depicting the Pearson correlation of beta-coefficients across dosedependent differentially expressed genes for every pairwise combination of compounds screened for A549 (A), K562 (B) and MCF7 (C) cells. Compounds names are colored by the pathway targeted.

FIG. 25 shows UMAP embedding of drugs based on their dose-dependent effects on each gene's expression. Each drug was provided to UMAP as a vector of the effect estimates (see Methods) for all genes. Point shape corresponds to cell type and color corresponds to compound class.

Heatmap of pairwise distances between two cell types (columns) for a given drug (rows) in PCA reduced dimensional space. Hierarchically clustered to visualize cell type-specific responses to each drug. B) Insets of highlighted portions of the heatmap with pathway annotation shown to the left. Specific compounds highlighted with a red arrow are shown to the right (C-E) as UMAP embeddings. F) Trametinib treated cell lines are highlighted to illustrate colocalization of A549 and K562. Colored points correspond to labeled compound and all other drugs are shown in gray. Shape encodes the cell line from which each effect profile was captured (squares: MCF7; triangles: K562; circle: A549).

FIG. 27 shows HDAC inhibitor trajectory captures cellular heterogeneity in drug response and biochemical affinity. (A) MNN alignment and UMAP embedding of transcriptional profiles of cells treated with one of 17 HDAC inhibitors. Pseudodose root is displayed as a red dot. (B) Ridge plots displaying the distribution of cells along pseudodose by dose shown for three HDAC inhibitors with varying biochemical affinities. (C) Relationship between TC50 and average log 10(IC50) from in vitro measurements. Asterisks indicate compounds with a solubility <200 mM (in DMSO) that were not included in the fit.

Figure 28A:
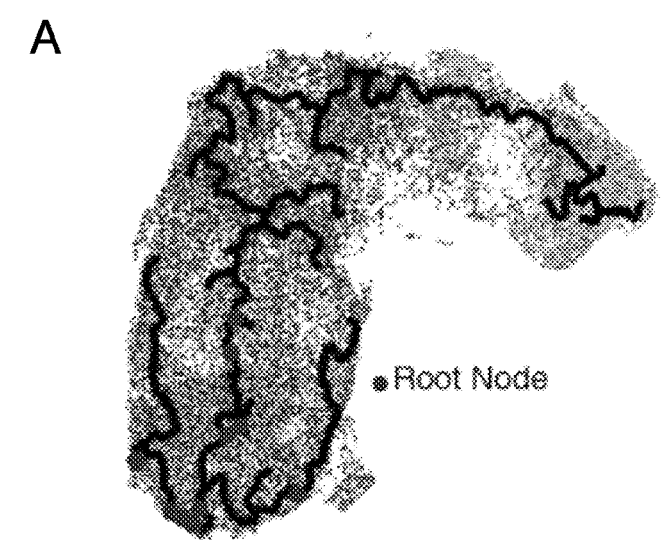
Figure 28B:
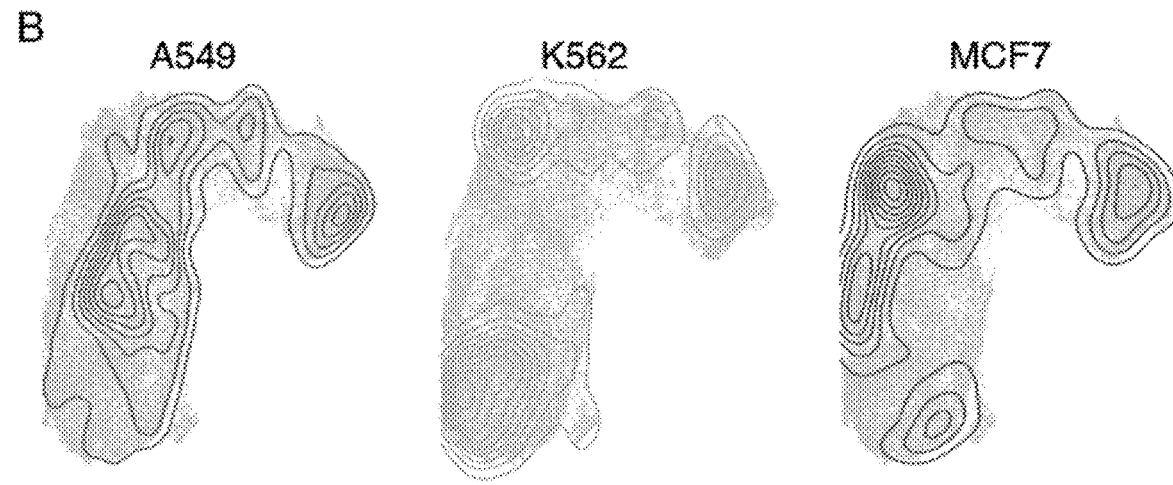

FIG. 28 shows HDAC inhibitor-treated cell types align and enable joint pseudodose trajectory reconstruction. A) UMAP embedding highlighting the reconstructed pseudodose trajectory over the mutual nearest neighbor-aligned HDAC inhibitor and vehicle treated cells. Root nodes (red points) were chosen as nodes in the principal graph that had over 50% of their nearest neighbors annotated as vehicle treated cells. B) Distribution of each cell line within the embedding. C) Barplot displaying the fraction of each pseudodose bin occupied by cells treated at each dose. D) Barplot displaying the fraction of each pseudodose bin occupied by cells treated with each compound. E) Proportion within each pseudodose bin corresponding to each cell line.

Figure 29A:
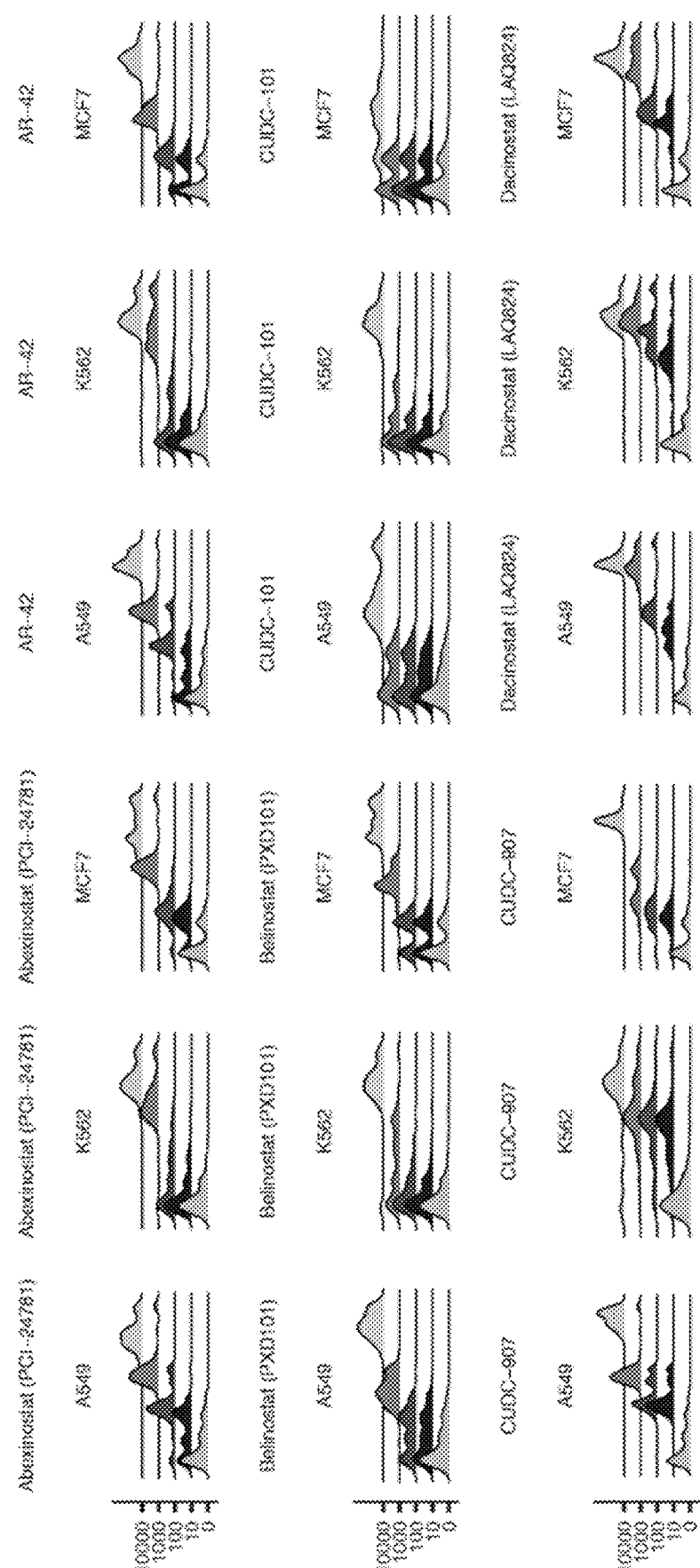
Figure 29B:
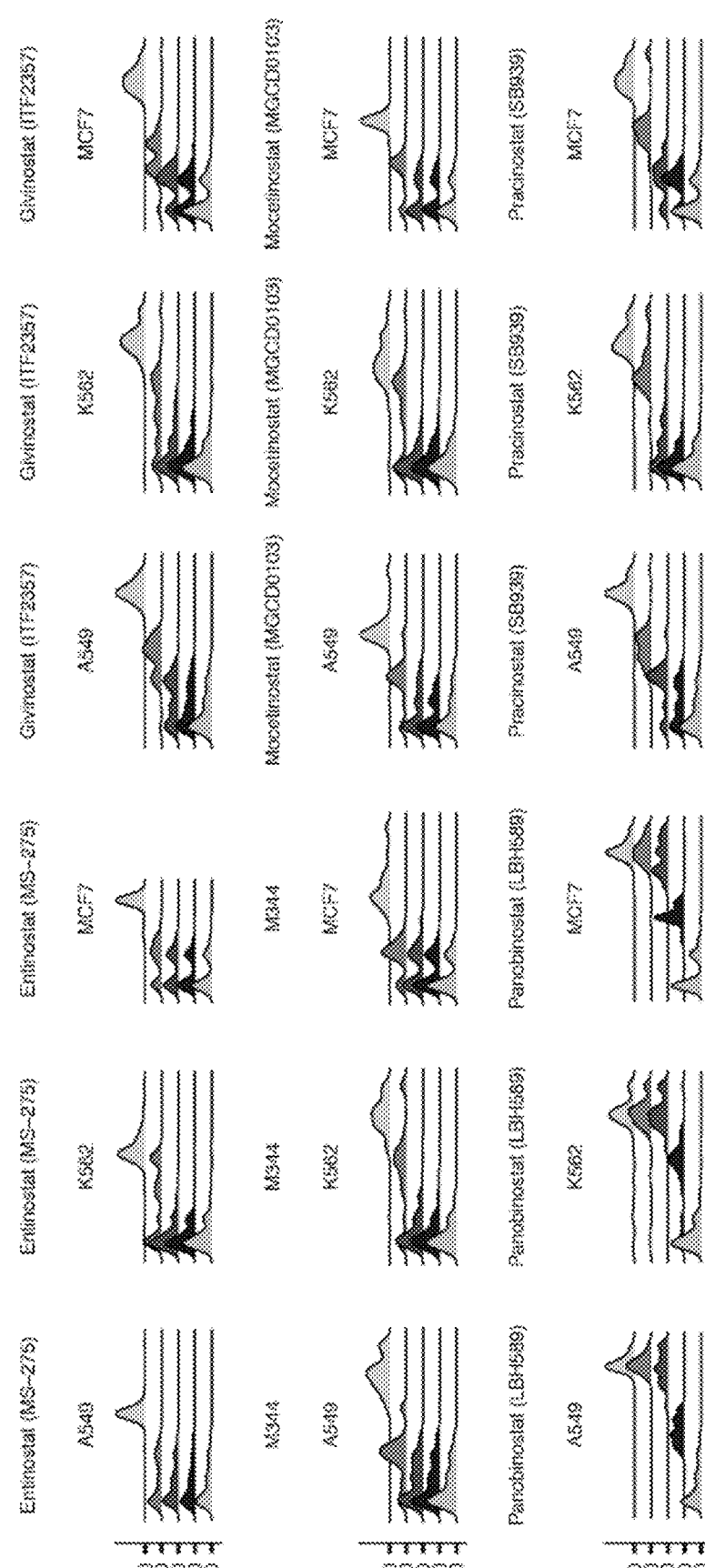
Figure 29C:
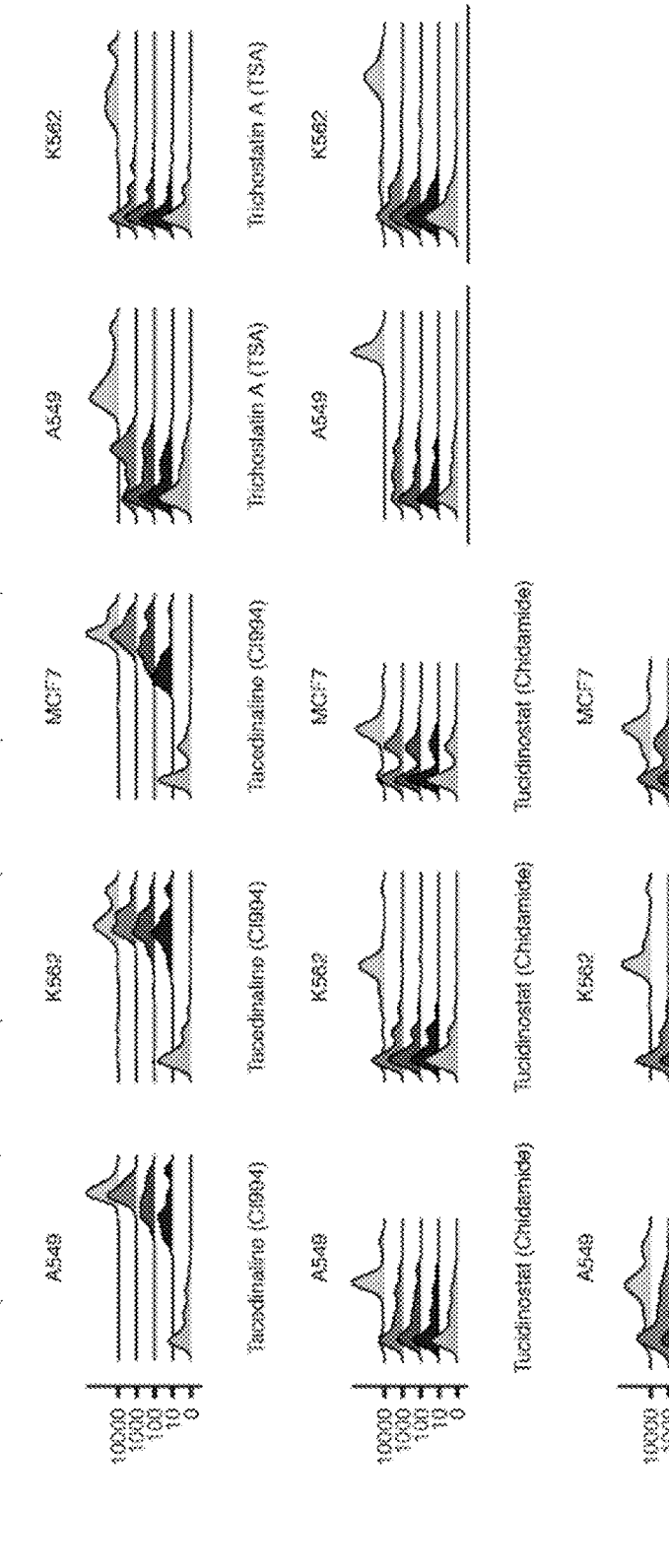

FIG. 29 shows ridge plots display the distribution of cells along pseudodose for each HDAC inhibitor and dose combination for compounds that localized to the HDAC trajectory.

Figures 30A, 30B, 30C:
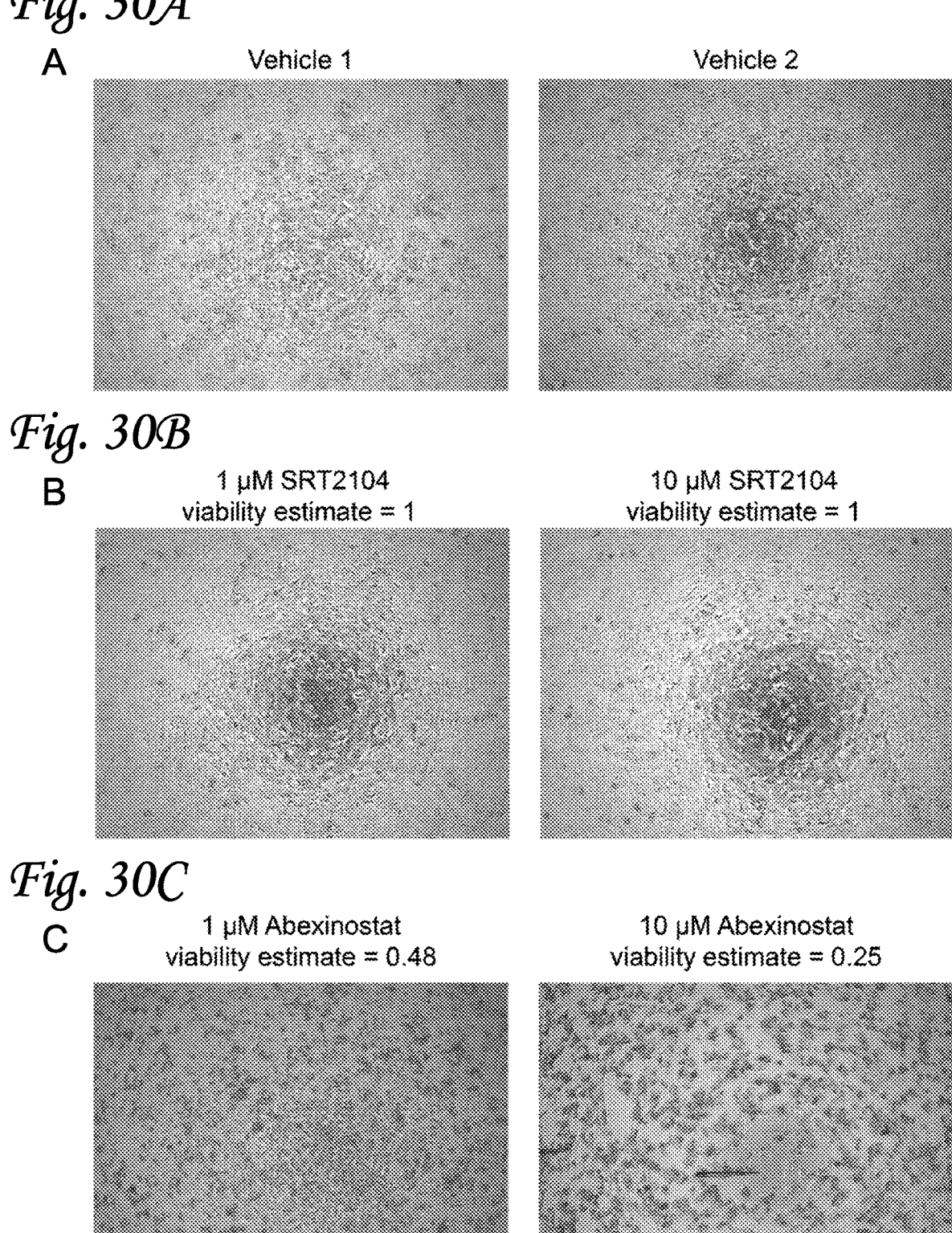
Figure 31A:
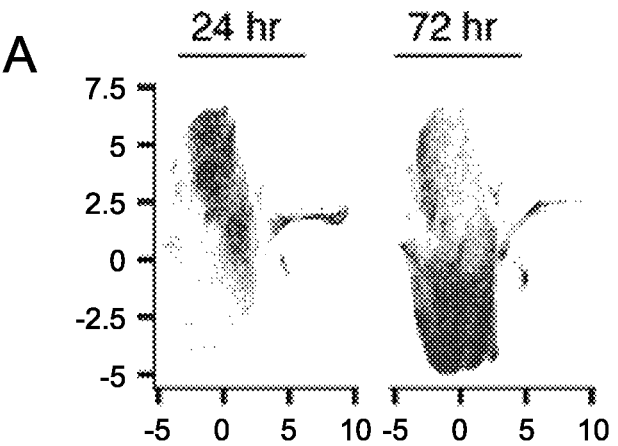
Figure 31B:
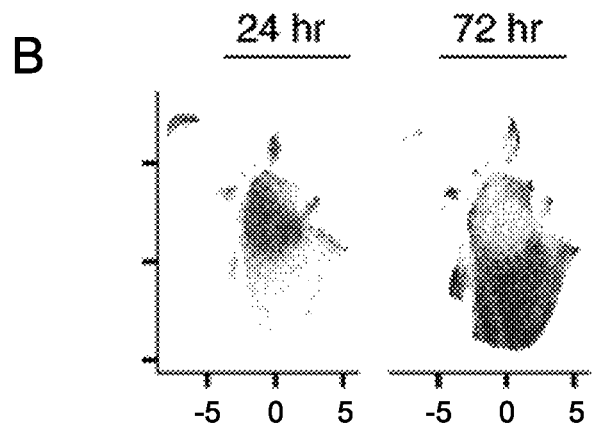
Figure 31C:
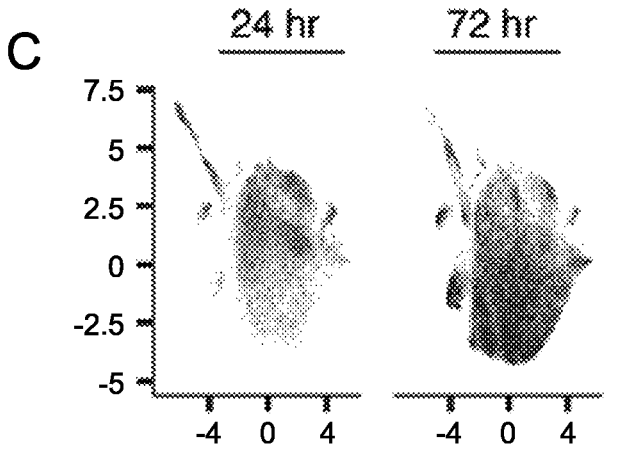
Figure 31D:
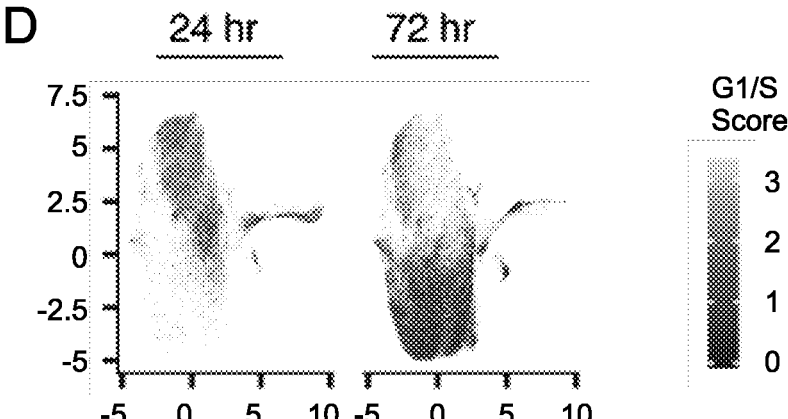
Figure 31E:
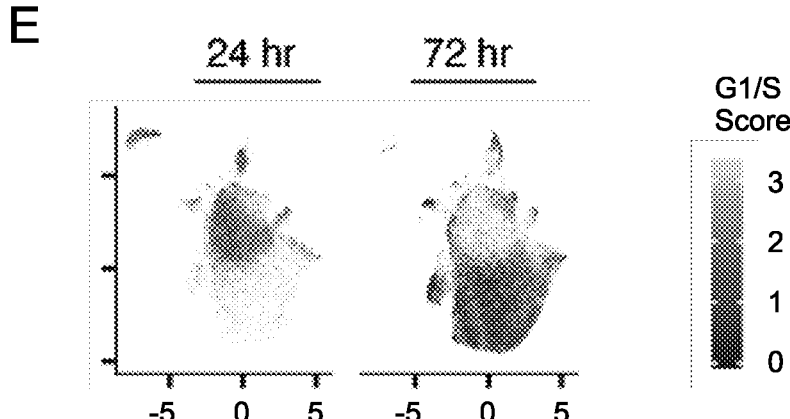
Figure 31F:
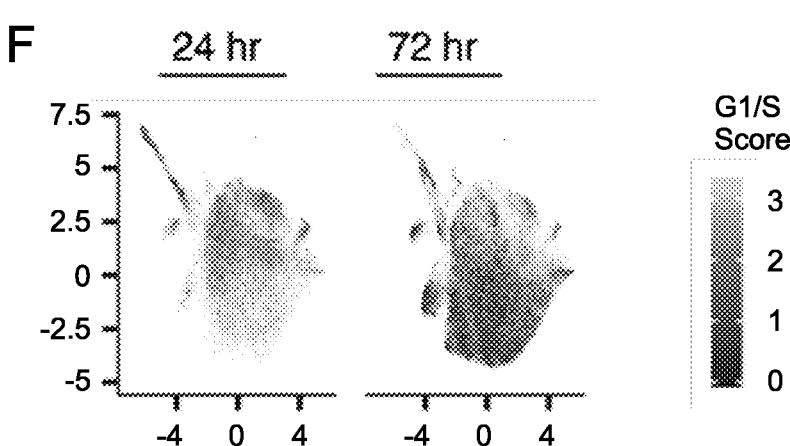
Figure 31G:
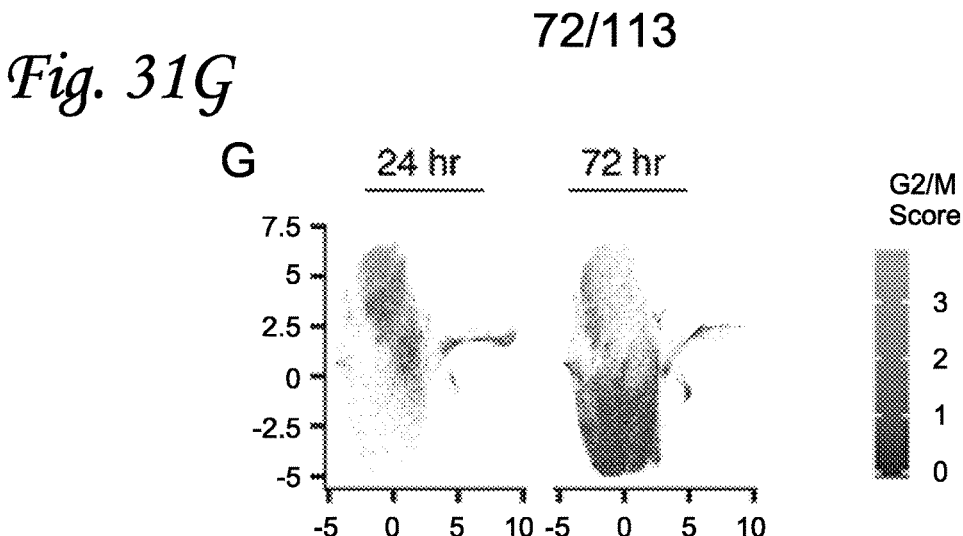
Figure 31H:
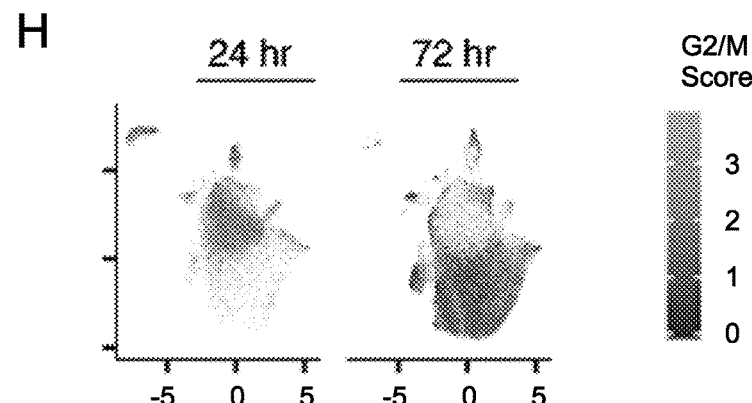
Figure 31I:
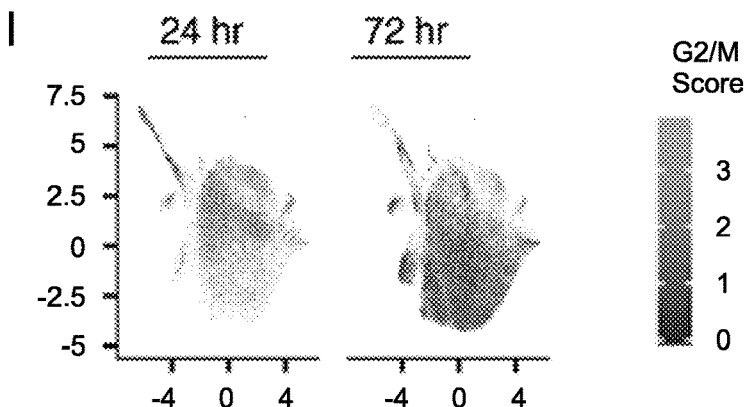
Figure 31J:
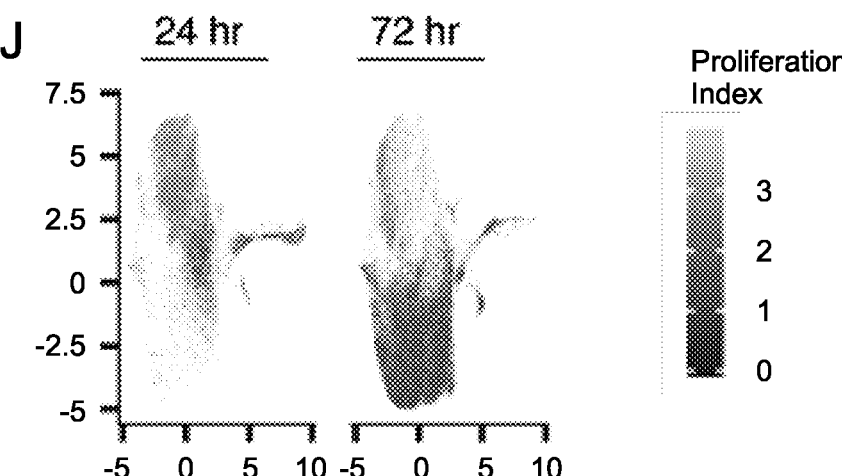
Figure 31K:
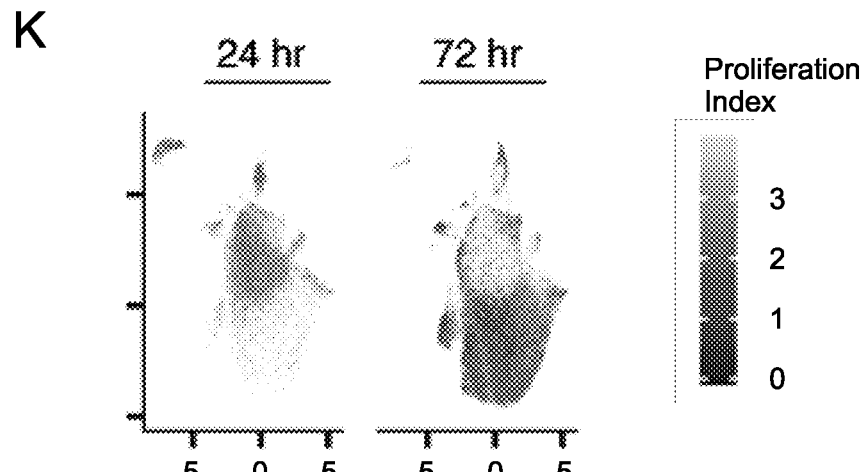
Figure 31L:
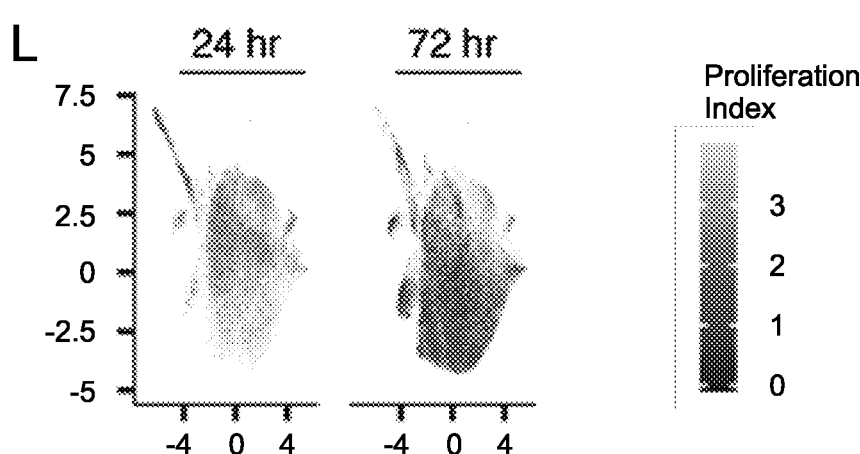
Figure 31M:
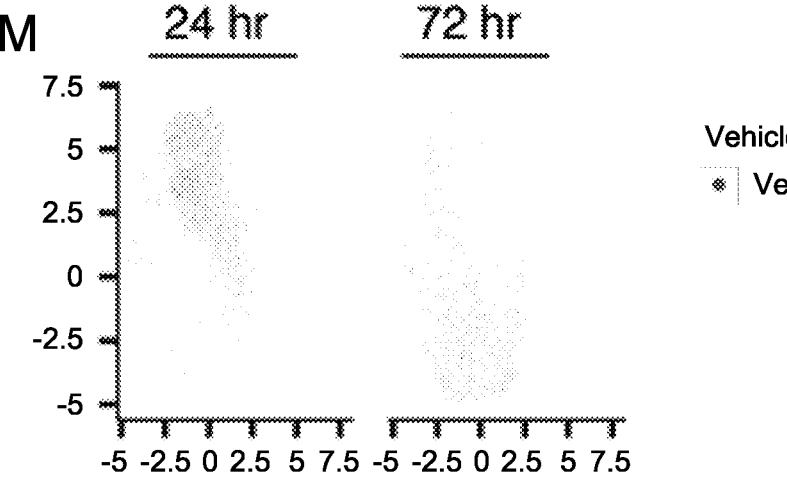
Figure 31N:
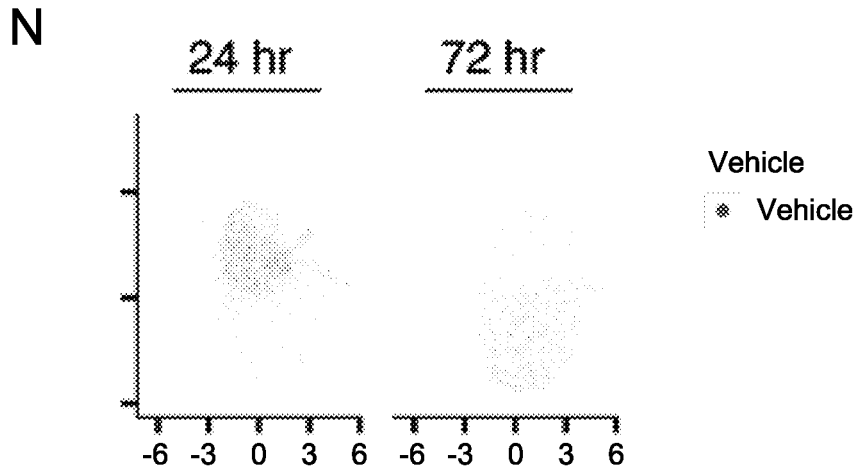
Figure 31O:
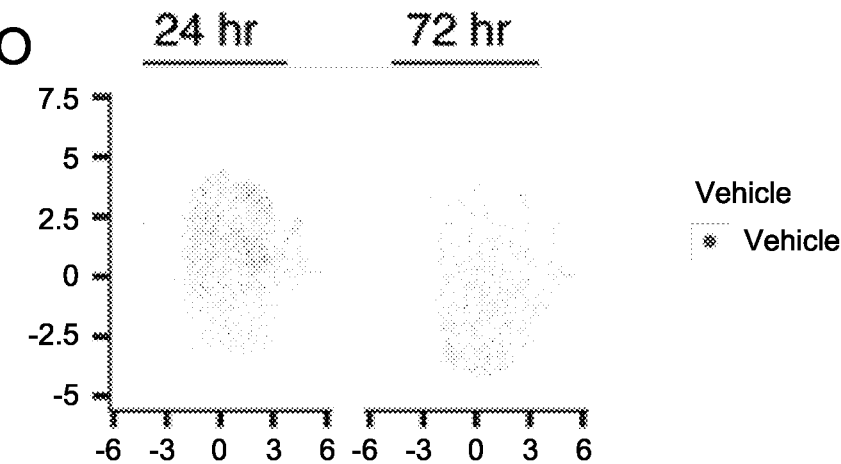
Figure 31P:
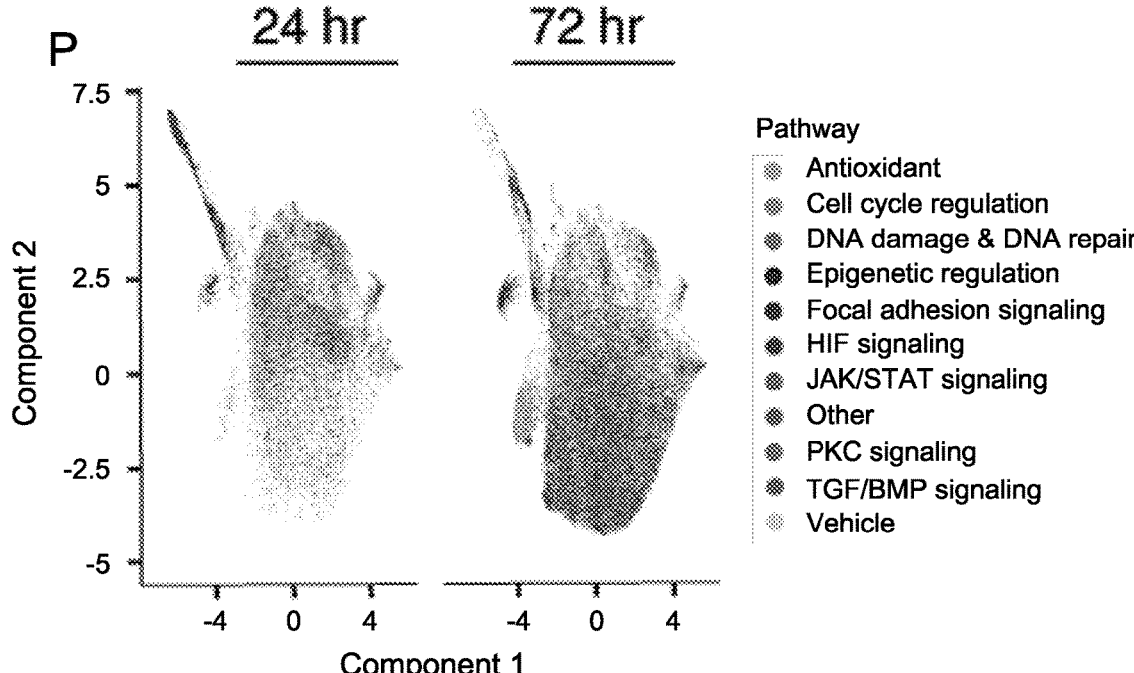
Figure 31Q:
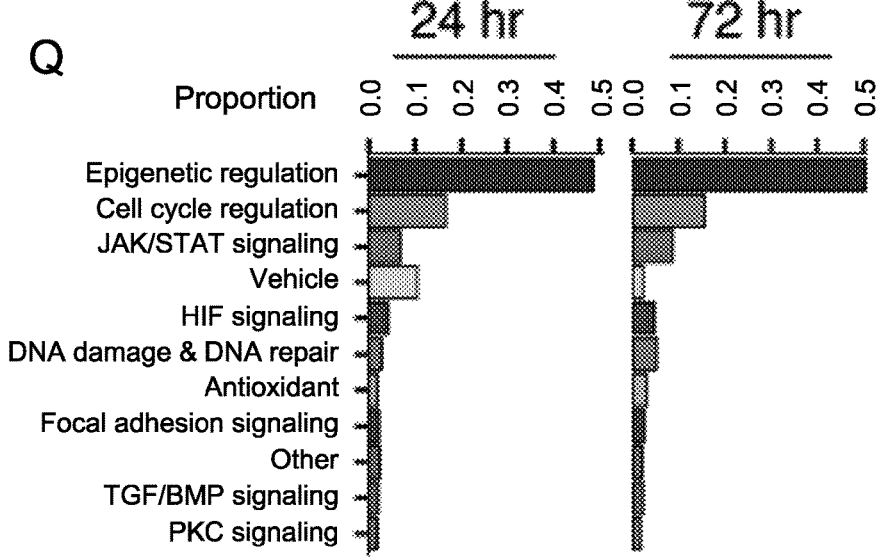
Figure 31R:
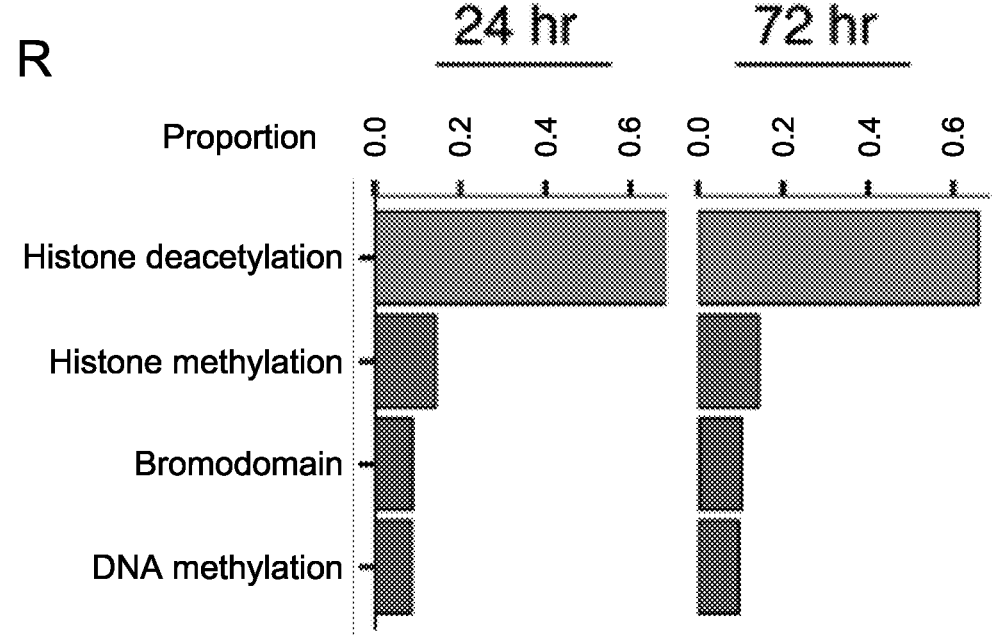
Figure 31S:
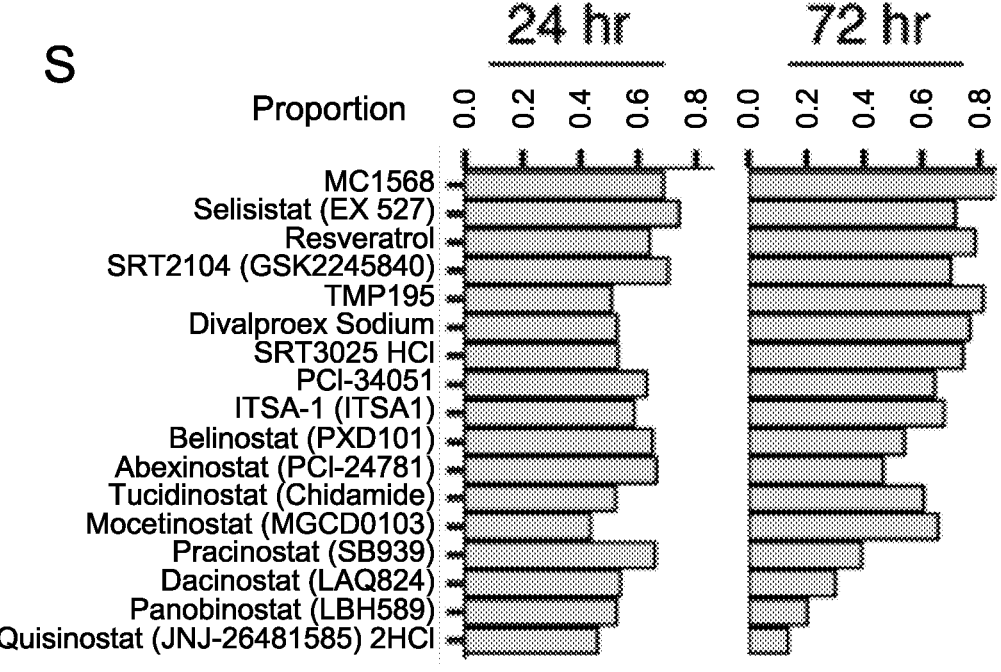

FIG. 30 shows contact inhibition of cell proliferation 72 hours post drug exposure. Representative brightfield images of A549 cells exposed to vehicle (A) or the specified dose of the SIRT1 activator SRT2104 (B) or the HDAC inhibitor Abexinostat (C). Viability estimates as determined by recovered cell counts for each drug/dose combination normalized to cell counts of vehicle control wells.

FIG. 31 shows aligning A549 cells at 24 and 72 hours after treatment reveals time-dependent responses to diverse small molecules. (A-C) UMAP embedding of A549 cells at 24 and 72 hours post treatment in the absence of a correction for differences in viability and proliferation (A), after linear transformation of the data to account for changes in proliferation index and viability (B) and after mutual nearest neighbor based alignment of data after linear transformation (C). Cells are colored by the time point at which they were collected. (D-F) UMAP embeddings as in panels A-C with cells colored by the aggregated normalized expression score of G1/S marker genes. (G-I) UMAP embeddings as in panels A-C with cells colored by the aggregated normalized expression score of G2/M marker genes. (J-L) UMAP embeddings as in panels A-C with cells colored by proliferation index. (M-O) UMAP embeddings as in panels AC only visualizing cells treated with vehicle control. (P) UMAP embeddings from panel C with cells colored as to the pathway targeted by the treatment to which they were exposed. (Q) Proportion of cells broken up by pathway targeted. Note that only a subset of our 188 compounds across a limited number of pathways were tested at 72 hours. (R) Proportion of cells broken up by the activity targeted by treatment with epigenetic regulation compounds. (S) Proportion of cells broken up by HDAC compound.

Figure 32A:
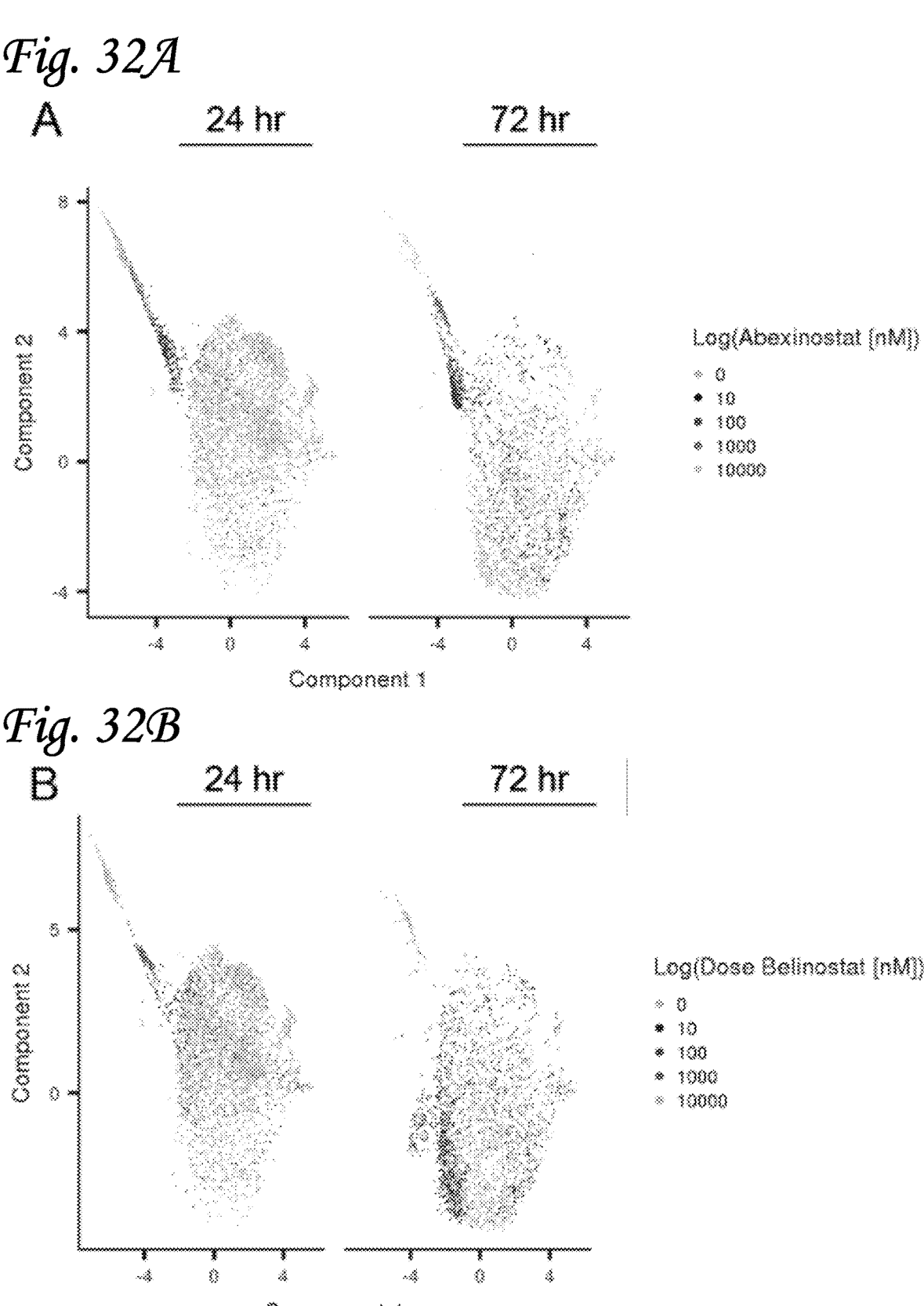
Figures 32C, 32D:
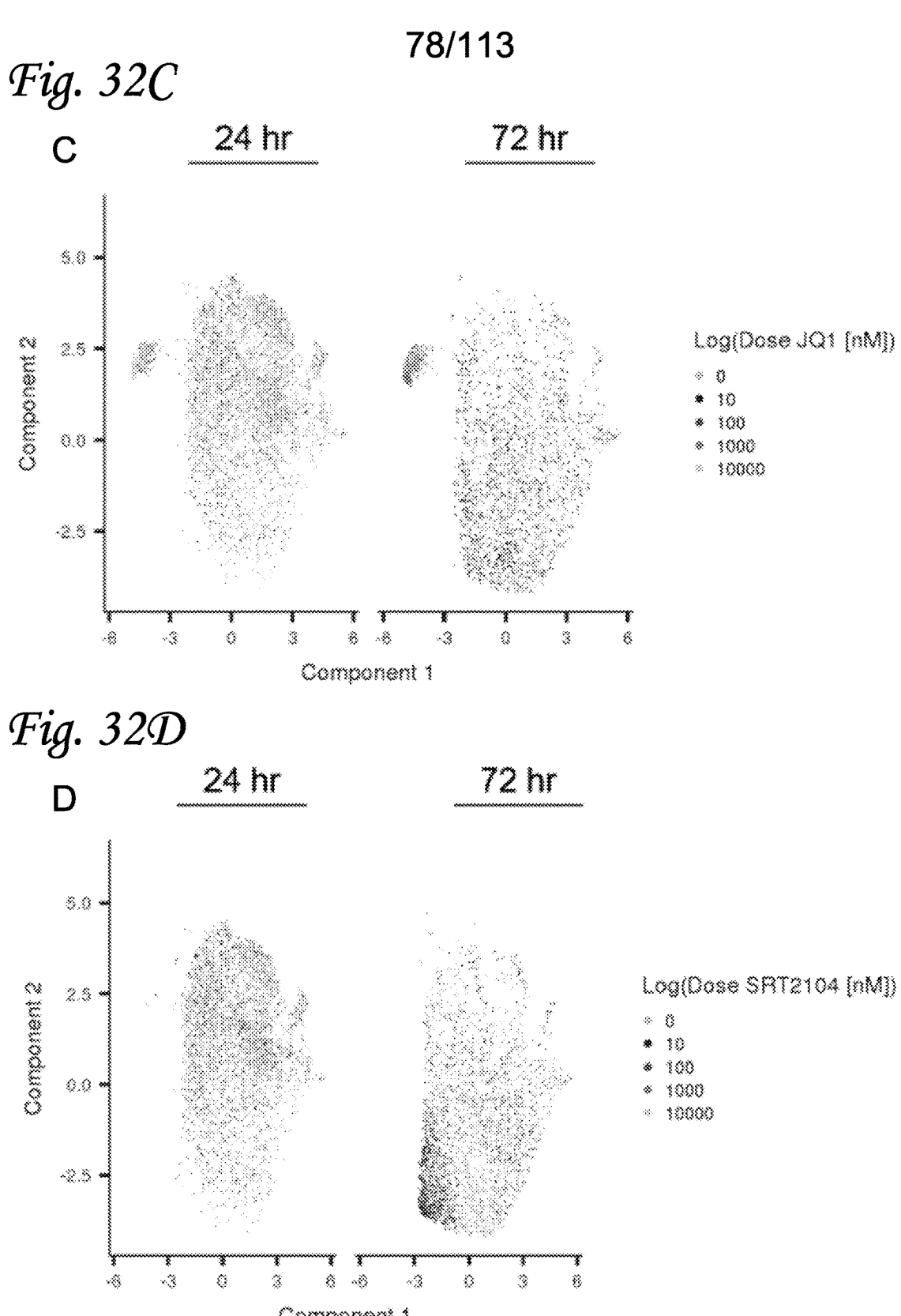

FIG. 32 shows bromodomain inhibition, sirtuin activation, and histone deacetylase inhibition induce characteristic transcriptomic responses. (A-D) UMAP embedding of MNN aligned A549 cells 24 and 72 hours after treatment with the pan-HDAC inhibitors abexinostat (A) or belinostat (B), the bromodomain inhibitor JQ1 (C), and the SIRT1 activator SRT2104 (D). Cells are colored by the dose to which each cell was exposed.

Figure 33A:
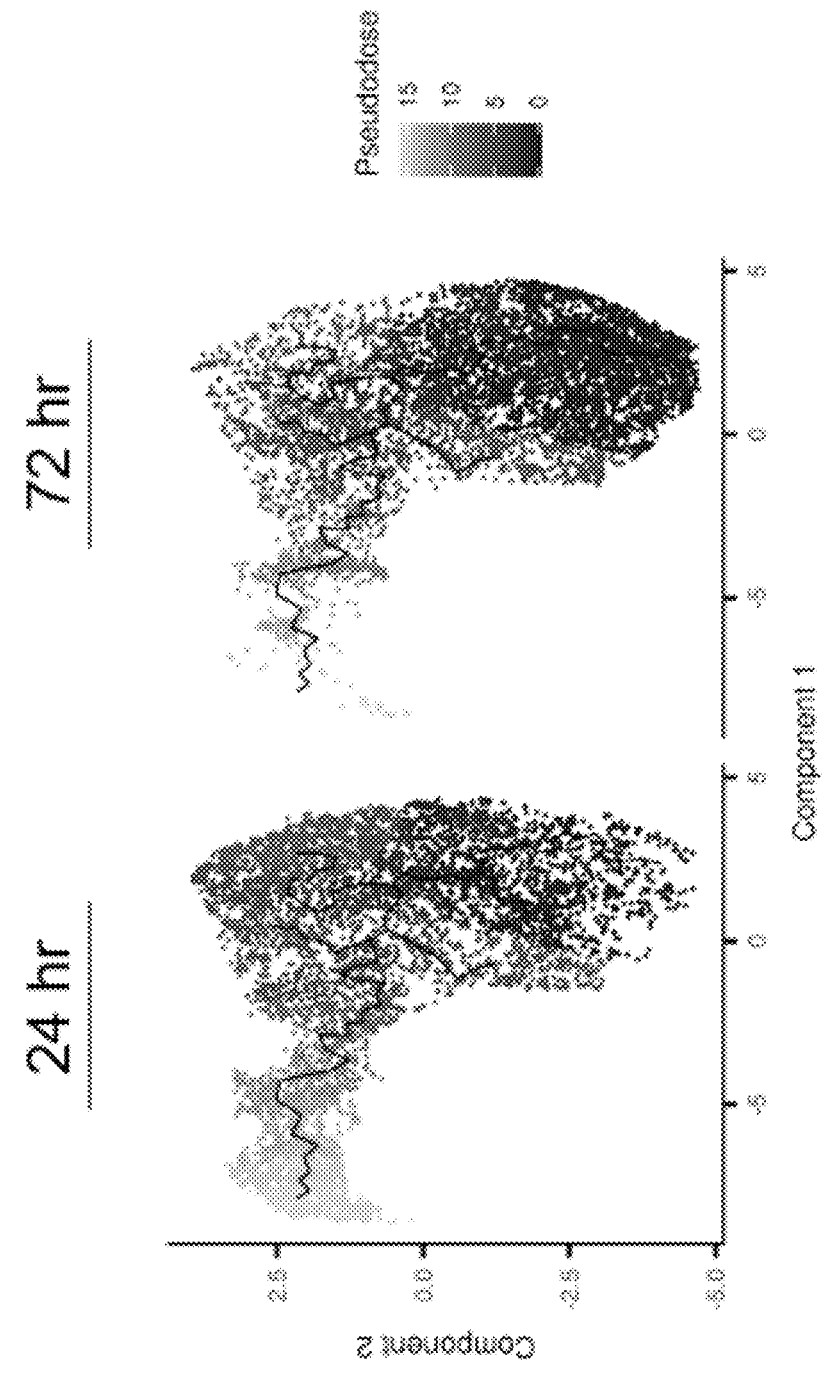
Figure 33C:
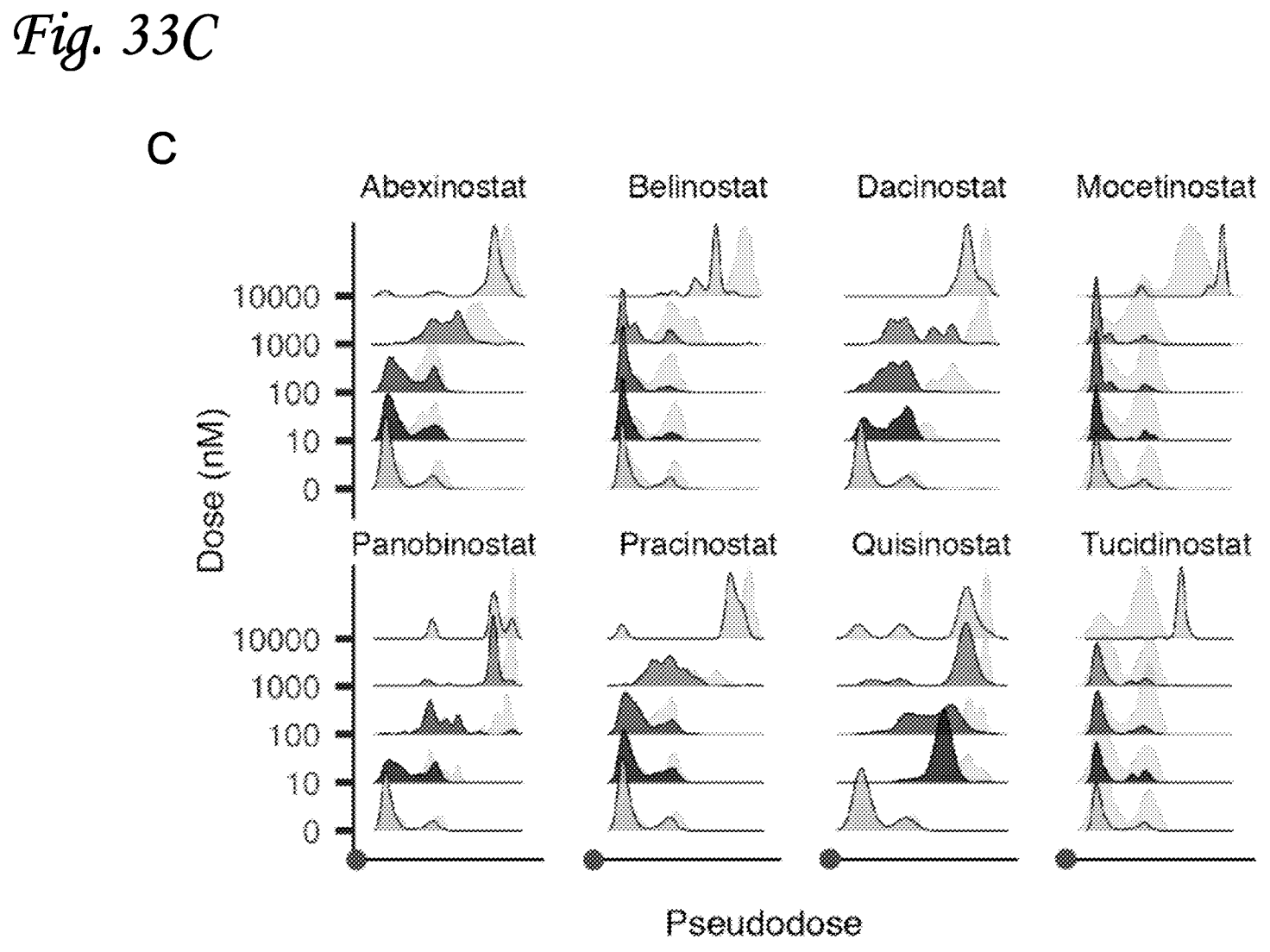

FIG. 33 shows the heterogeneous response to the majority of HDAC inhibitors does not appear to be driven by cellular asynchrony. A) Aligned UMAP embeddings of cells exposed to vehicle HDAC inhibitors for 24 or 72 hours. Cells are colored by their progression along pseudodose. B) Aligned UMAP embeddings of cells exposed to vehicle (grey cells) or the labeled HDAC inhibitor for 24 (red cells) or 72 (blue cells) hours. C) Ridge plots displaying the density of HDAC inhibitor-exposed A549 cells along an aligned pseudodose trajectory. Results are displayed for the 8 HDAC inhibitors that were assayed at both 24 and 72 hours. Gray and color filled lines denote cells exposed with inhibitors for 24 or 72 hours, respectively.

Figure 34A:
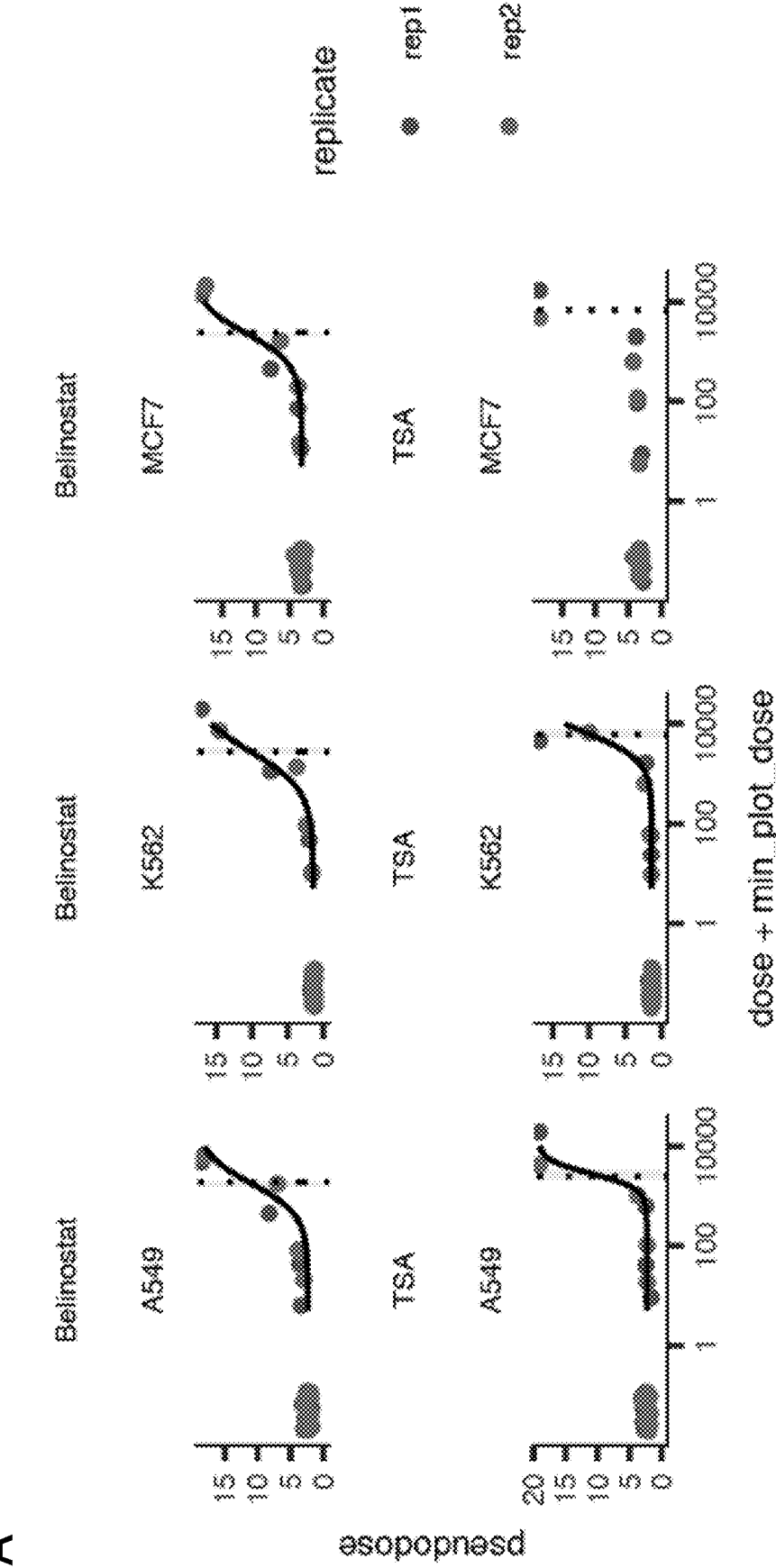
Figure 34B:
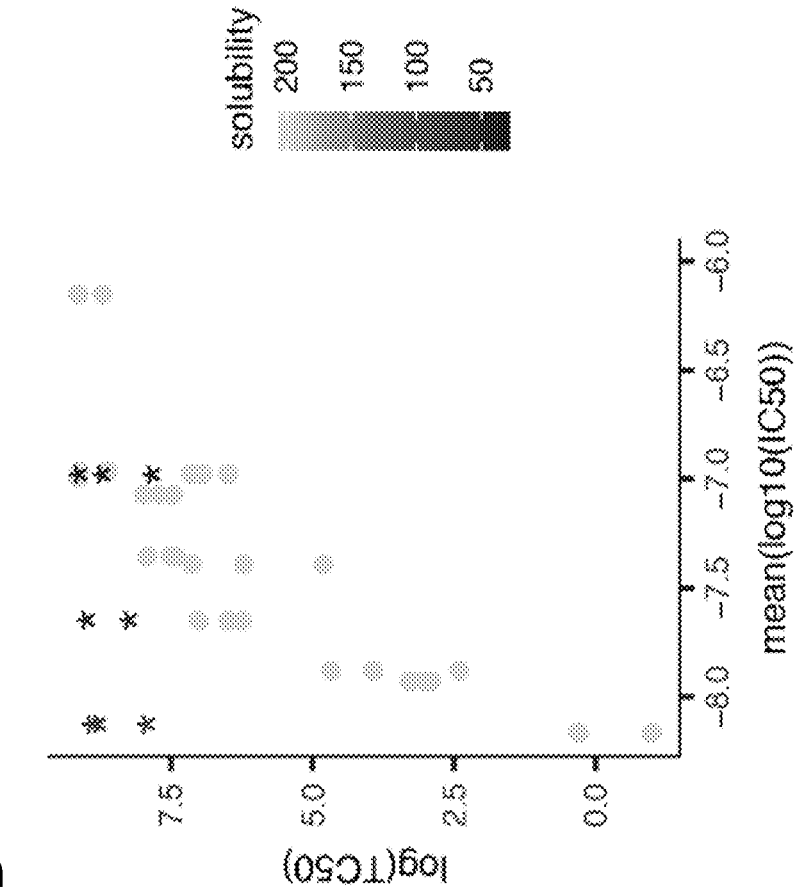
Figure 34C:
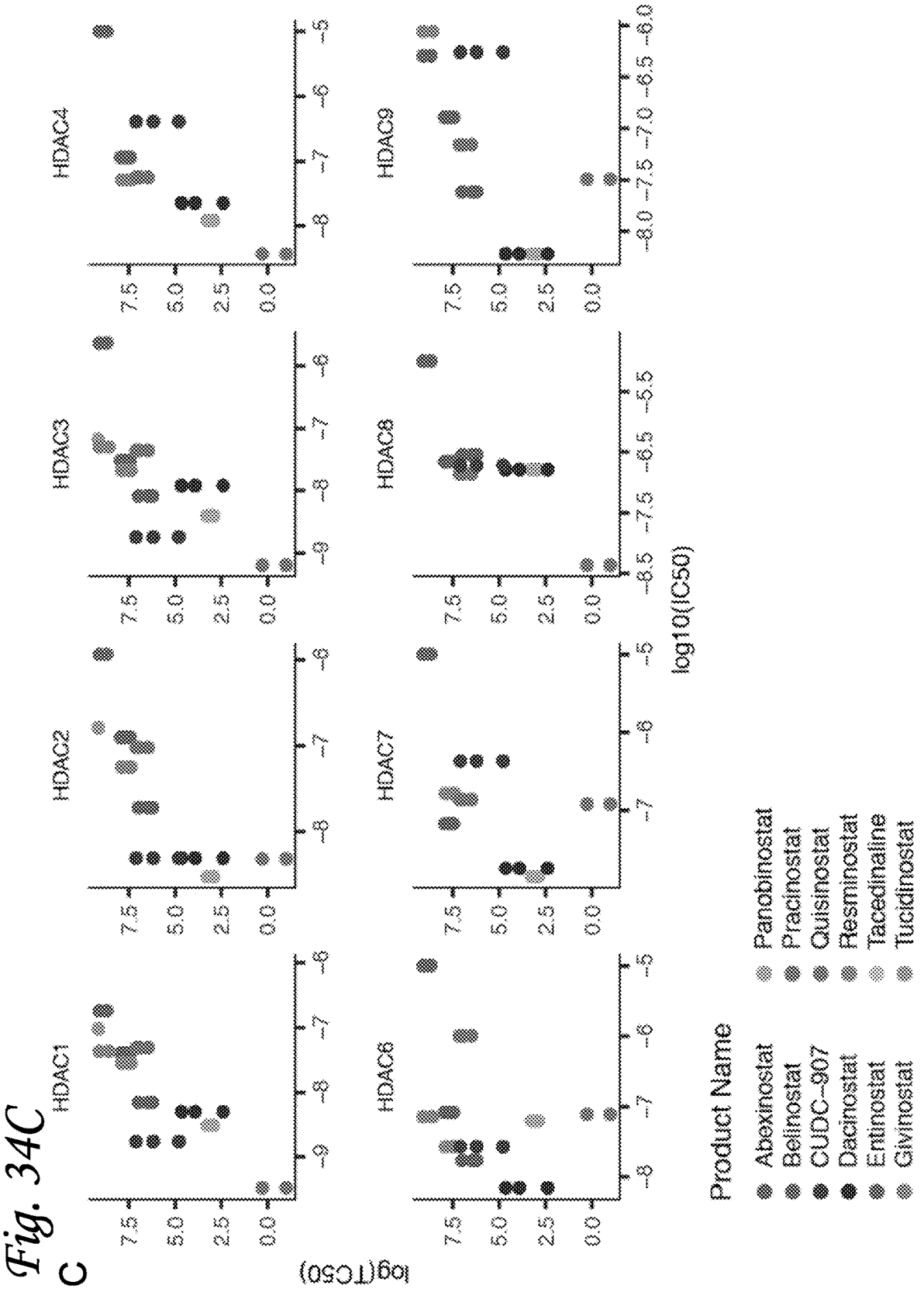

FIG. 34 shows transcriptional trajectory of HDAC inhibitor-treated cells corresponds to in vitro IC50 measurements. A) Pseudodose response curves were fit for each compound and each cell line using the drc R package. The mean position of each dose along the pseudodose trajectory was used as the response. Two illustrative examples for belinostat (top) and trichostatin A (TSA) (below) are shown. Dotted vertical lines illustrate the transcriptional EC50 (TC50) for each compound in each cell line. Shaded gray area denotes the 95% confidence intervals for each TC50 estimate. B) Plot displaying aggregate in vitro measured mean of log 10(IC50 [M]) versus log(TC50) colored by solubility supplied by Selleckchem Chemicals. Points displayed as (*) were not used for fits. C) log 10(IC50 [M]) versus log(TC50) for each HDAC isoform. Each point is colored by the HDAC inhibitor used.

Figure 35A:
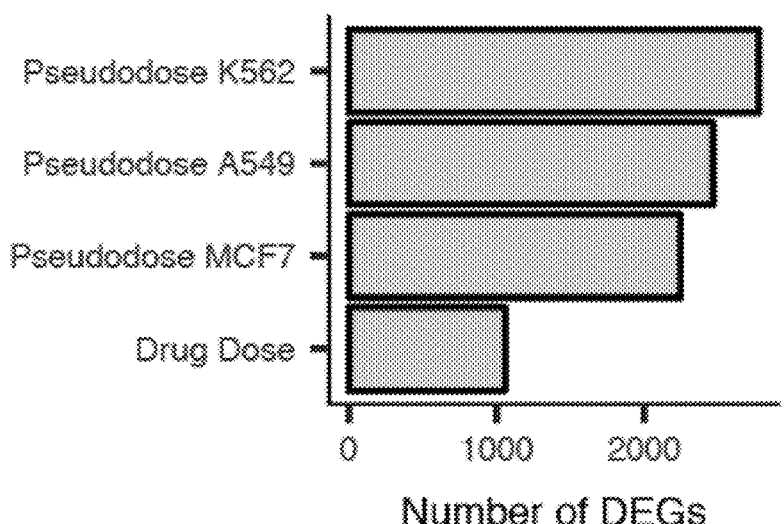
Figure 35B:
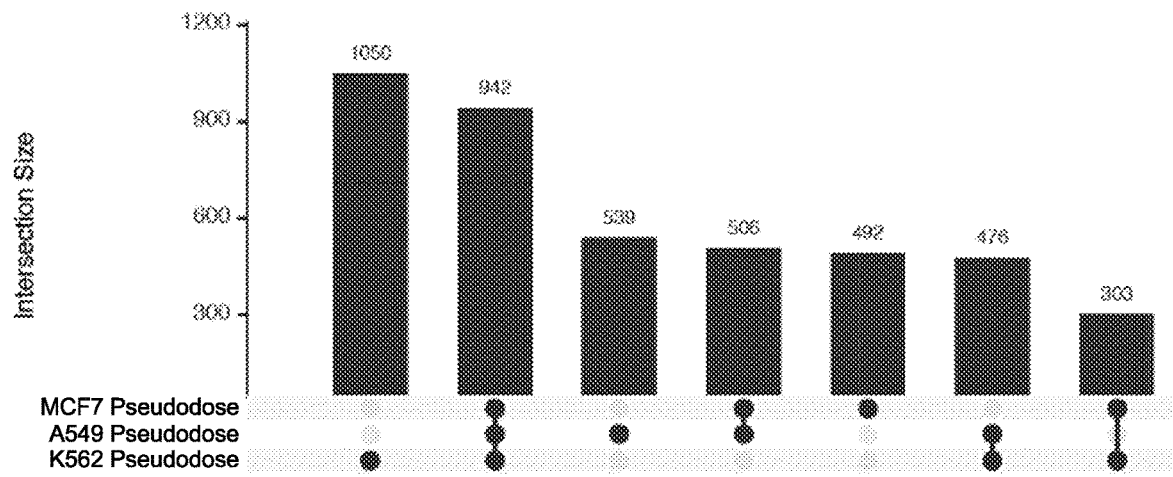

FIG. 35 shows linear models identify pseudodose-dependent modules of proliferation and metabolism. A) Barplot of the total number of significant dose-dependent and pseudodose-dependent DEGs (FDR<0.05). B) Upset plot displaying the intersections of significant pseudodose-dependent DEGs between the three cell types. C) Pseudodose heatmap depicting 4,308 genes that varied significantly as a function of pseudodose. Each row corresponds to the expected expression for a gene in the three cell lines as fit by the model described in the 'Differential expression analysis' section of the Methods. Genes (rows) were scaled and standardized within each cell line before joining the three matrices and performing hierarchical clustering. Clusters from hierarchical clustering were then used as an input into GSAhyper using the Hallmarks geneset collection. Select genes and genesets characterizing each cluster are shown (right).

FIG. 36 shows HDAC inhibitor treatment induces cell cycle arrest in all three cell lines. A) Percentage of cells expressing RNA for AURKA and CDKN1A across pseudodose bins. Black bars denote the bootstrapped 95% confidence interval. B) Boxplots depicting the percentage of cells in the low proliferation fraction in at a given drug dose across pseudodose bins. C) DNA content analysis of the three cell lines upon treatment with DMSO (top) or 10 μM abexinostat (bottom). D) Quantification of flow cytometry data depicting the number of cells in each DNA content category.

Figure 37B:
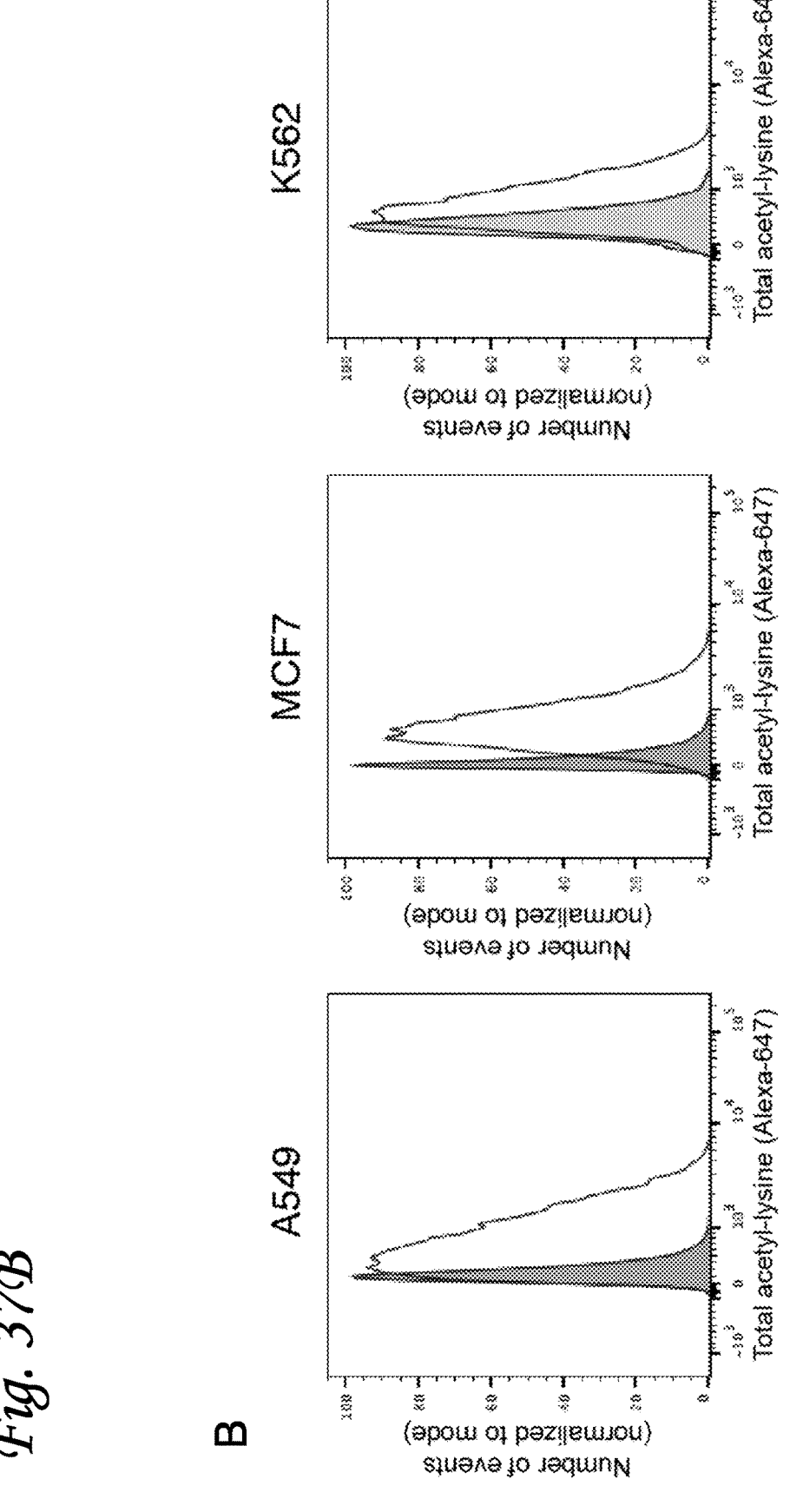

FIG. 37 shows HDAC inhibitor exposure leads to sequestration of acetate in the form of acetylated lysines. A) Quantification of flow cytometry measurements of total cellular acetylated lysines in A549 (left panel), MCF7 (middle panel) and K562 (right panel) cells exposed to 10 μM pracinostat, 10 μM p abexinostat or vehicle control. Error bars denote standard deviation of the mean (Wilcoxon rank sum test, n=3 culture replicates, * p<0.05, *** p<0.005). B) Representative flow cytometry histograms for the experiment quantified in panel A. Blue shaded regions and red lines correspond to DMSO vehicle control and 10 μM abexinostat, respectively.

FIG. 38 shows HDAC inhibitors shared transcriptional response indicative of acetyl-CoA deprivation. (A) Heatmap of row-centered and z-scaled gene expression depicting the up-regulation of pseudodose-dependent genes involved in cellular carbon metabolism. (B) Diagram of the roles of genes from (A) in cytoplasmic acetyl-CoA regulation. Red circles indicate acetyl groups. Enzymes are shown in gray. Transporters are shown in green (FA, fatty acid; Ac-CoA, acetyl-CoA; C, citrate).

FIG. 39 shows supplementation with acetyl-CoA precursors decrease, while inhibition of enzymes that replenish acetyl-coA pools exacerbate, progression along the HDAC inhibitor pseudodose trajectory. A-D) UMAP embeddings of A549 (panels A and B) and MCF7 (panels C and D) single cell transcriptomes after exposure to the HDAC inhibitors pracinostat or abexinostat, in the presence or absence of acetyl-CoA precursors or inhibitors to enzymes that replenish acetyl-CoA pools. UMAP were constructed from cells from all conditions in the experiment. Cells are colored by pseudodose bin (panels A and C) or dose (panels B and D). E) Venn diagram of the overlap of differentially expressed genes across trajectories between or original HDACi trajectory vs. A549 or MCF7 HDACi trajectories from this new experiment. F,H) Boxplots of pseudodose estimates for select conditions of cells exposed to 1 or 10 μM pracinostat with or without co-treatment with acetyl-coA precursors for A549 (panel H) or MCF7 (panel L) cells. Values are normalized to vehicle treated cells. Wilcoxon rank sum test. G,I) Boxplots of pseudodose estimates for select conditions of cells exposed to vehicle and pracinostat with or without co-treatment with acetyl-coA precursors for A549 (panel I) or MCF7 (panel M) cells. Values were normalized to vehicle treated cells. Wilcoxon rank sum test. J,L) Heatmaps depicting the fraction of cells per pseudodose bin for cells exposed to various acetyl-coA precursors in pracinostat-exposed A549 (F) or MCF7 (J) cell. K,M) Heatmaps depicting the fraction of cells per pseudodose bin for cells exposed to various inhibitors targeting enzymes that replenish acetyl-coA pools in pracinostat-exposed A549 (panel G) and MCF7 (panel K) cells.

Figure 40C:
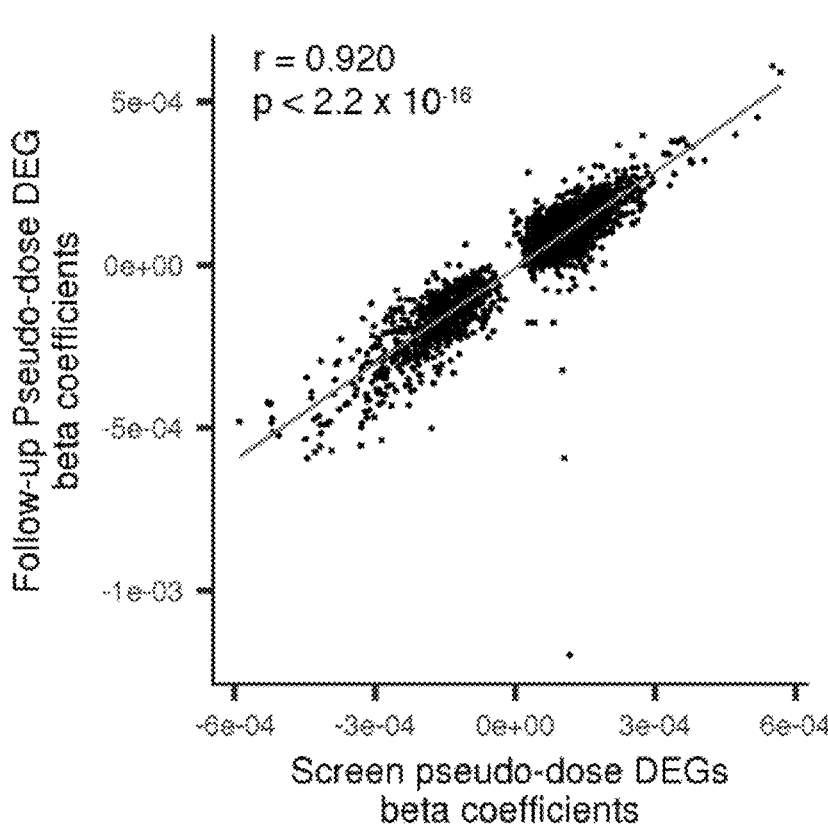
Figure 40D:
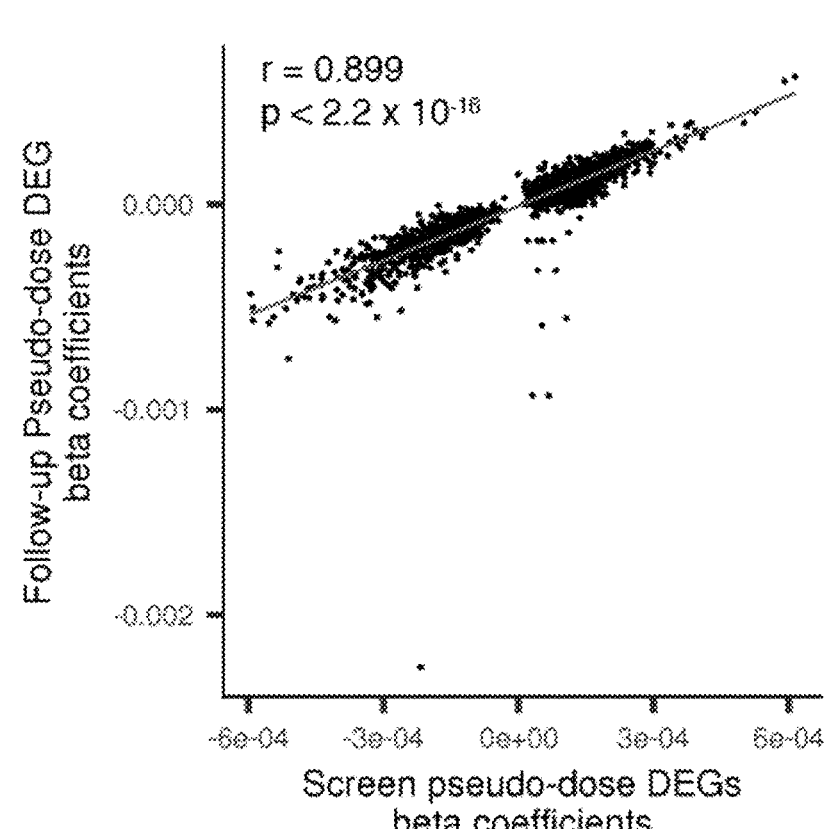

FIG. 40 shows correlation of effect sizes between differentially expressed genes post-HDAC inhibition from original screen vs. new experiment. A-B) Correlation of effect size estimates (beta coefficients) for differentially expressed genes between vehicle control and 10 μM abexinostat (panel A) or 10 μM pracinostat (panel B) for A549 cells. C-D) Correlation of effect size estimates (beta coefficients) for differentially expressed genes between vehicle control and 10 μM abexinostat (panel C) or 10 μM pracinostat (panel D)

for MCF7 cells. X-axes correspond to large-scale sci-Plex experiment. Y-axes correspond to targeted follow-up sci-Plex experiment.

FIG. 41 shows multiplexed, single-cell ATAC-seq co-assays nuclear labels (hashes) and accessible chromatin through combinatorial indexing approach. A. Cells from individual samples are grown and treated in separate wells. Within treatment wells, cells are lysed and nuclei are isolated. Well-specific single-stranded DNA oligo labels are added to each well and fixation traps the labels within nuclei. Nuclei from all samples are then pooled for downstream combinatorial indexing steps. B. Schematic of how combinatorial indexing adds the same molecular indexes to labels and accessible DNA within a nucleus. C. Recovered labels correctly identify cells from samples containing only mouse (NIH-3T3) or only human (A549) cells in barnyard mixture experiments. D. Nuclei containing multiple labels represent doublets. E. Distribution of the number of label UMIs recovered per cell. Red line represents a cutoff requirement for including a cell in downstream analysis. F. Distribution of label enrichment ratios per cell. A cell's enrichment ratio reflects the count of the most abundant label divided by the counts of the second most abundant label within a nucleus. Cells below the red line (enrichment ratio <5) were called doublets.

FIG. 42 shows labeling strategy enables pairing chromatin profiles from single cells to treatment groups. A. Experimental design. B. Uniform Manifold Approximation and Projection (UMAP) representation of all recovered cells colored by treatment, as determined by labels. Note that the distance between two cells indicates the extent of difference in accessible chromatin landscape. C. Dose response curves for each drug, fit to the number of cells recovered from each treatment dose. D. UMAP representation of cells from each drug treatment group colored by dose as determined by labels. E. Browser tracks showing pseudo-bulk ATAC profiles from cells treated with increasing dosage of SAHA.

FIG. 43 shows a ladder of hash oligos can be captured by nuclei and serve as external standards in sci-RNA-seq experiments. (A) An experimental overview of the hash ladder method. Nuclei are isolated from cells, fixed with a ladder of hash oligos, then processed with sci-RNA-seq. (B) Boxplot of hash oligo UMI counts per cell, each hash oligo spiked in at different abundance. (C) Scatter plot of expected and observed hash ladder UMI counts, demonstrating a cell with low (left) and high (right) hash capture efficiency.

FIG. 44 shows hash ladder expands our ability to detect global reduction in transcript levels caused by flavopiridol. (A) Overview of the experiment. HEK293T cells were treated with flavopiridol for different periods of time and labeled with a ladder of hash oligos and additional hash oligo for multiplexing prior to sci-RNA-seq preparation. (B) Boxplot showing total RNA UMI counts for cells treated with flavopiridol at different time points. (C) Barplot showing number of differentially expressed genes in response to flavopiridol using conventional and hash ladder normalization approaches. (D) Violin plot showing the ratio of effect size estimates of common differentially expressed genes computed with hash ladder vs. conventional normalization.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Applications

Many applications and fields of use can be envisioned using the methods described herein. For example, the high-throughput single-nuclei and single-cell methods can be used for drug discovery. Measurements of transcriptional diversity of single cells induced by an agent or genetic perturbation can be used for drug screening. In one application, genome editing is used for the classification of variants of genes and the genome (Findlay, Nature, 2018 562(7726):217-222). In another application, the methods can be used for understanding health and disease, science, medical, diagnostics, biomedical research, clinical applications, or biomarker discovery.

Exposure of Cells to Predetermined Conditions

The method provided herein can be used to produce sequencing libraries from a plurality of single cells. In one embodiment, the method includes exposing cells to different predetermined conditions. The method includes exposing subsets of cells to different predetermined conditions (FIG. 1, block 10). Different conditions can include, for instance, different culture conditions (e.g., different media, different environmental conditions), different doses of an agent, different agents, or combinations of agents. Agents are described herein. The nuclei or cells of each subset of cells and/or sample or samples are tagged using nuclear hashing, pooled, and analyzed by massively multiplex single nuclei or single cell sequencing methods. Essentially any single-nuclei or single-cell sequencing method can be used including, but not limited to, single-nuclei transcriptome sequencing (U.S. Prov. Pat. App. No. 62/680,259 and Gunderson et al. (WO2016/130704)), whole genome sequencing of single nuclei (U.S. Pat. Appl. Pub. No. US 2018/0023119), or single nuclei sequencing of transposon accessible chromatin (U.S. Pat. No. 10,059,989), sci-HiC (Ramani et al., Nature Methods, 2017, 14:263-266), DRUG-seq (Ye et al., Nature Commun., 9, article number 4307), or any combination of analytes from DNA, RNA and proteins, for example sci-CAR (Cao et al., Science, 2018, 361(6409):1380-1385). The nuclear hashing is used to demultiplex and identify individual cells or nuclei from different conditions.

The cells can be from any organism, and from any cell type or any tissue of the organism. Typically, the cells are distributed into a first plurality of compartments. In one embodiment, a compartment is a well of a multi-well device, such as a 96-well, a 384-well plate, or a 1536-well plate, where the cells in a compartment are referred to as a subset of cells. In one embodiment, the cells in a subset are genetically homogeneous, and in another embodiment the cells in a subset are genetically heterogeneous. The number of cells can vary and can be dependent on the practical limitations of equipment (e.g., the size of the wells of a multi-well plate, number of indexes) used in other steps of the method as described herein. In one embodiment, the number of cells in a subset can be no greater than 100,000,000, no greater than 10,000,000, no greater than 1,000,000, no greater than 100,000, no greater than 45,000, no greater than 35,000, no greater than 25,000, no greater than 15,000, no greater than 5,000, no greater than 1,000, no greater than 500, or no greater than 50.

In one embodiment, each subset of cells is exposed to an agent or perturbation. An agent can be essentially anything that causes a change to a cell. For example, an agent can alter the transcriptome of a cell, alter the chromatin structure of a cell, alter the activity of a protein in the cell, alter the DNA of a cell, or alter the DNA editing of a cell. Examples of agents include, but are not limited to, a compound such as a protein (including an antibody), a non-ribosomal protein, a polyketide, an organic molecule (including an organic molecule of 900 Daltons or less), an inorganic molecule, an RNA or RNAi molecule, a carbohydrate, a glycoprotein, a nucleic acid, or a combination thereof. In one embodiment, an agent causes a genetic perturbation, for instance a DNA editing protein such as CRISPR or Talen. In one embodiment, an agent is a drug, such as a therapeutic drug. In one embodiment, the cell can be a wild-type cell, and in another embodiment, the cell can be genetically modified to include a genetic perturbation, for instance, gene knock-in, gene knock-out, or over-expression (Szlachta et al., Nat Commun., 2018, 9:4275). In one embodiment, cells are modified by introducing a genetic perturbation, exposed to an agent, and any resulting changes in, for instance, transcription of genome organization can be identified in single cells (Datlinger et al., Nature Methods, 2017, 14(3):297-30 [sci-Crop]; Adhemar et al., Cell, 2016, 167:1883-1896 [sci-Crispr]; and Dixit et al., Cell, 2016, 167(7):1853-1866) [sci-Perturb]. Optionally, in those embodiments using a guide RNA to target a genetic perturbation the method can further include identifying and confirming the actual edit to the genome.

Subsets of cells can be exposed to the same agent, but different variables can be altered across the compartments of a multi-well device, permitting multiple variables to be tested in a single experiment. For instance, different dosages, different duration of exposure, and different cell types can be tested in a single plate. In one embodiment, the cells can express a protein having a known activity, and the effect of an agent on the activity evaluated under different conditions. The nuclear hashing used to label the nuclei permits later identification of the nucleic acids originating from a specific subset of nuclei or cells, e.g., from one well of a multi-well plate.

Cellular and Nuclear Hashing

In the production of sequencing libraries from a plurality of cells or plurality of single nuclei, cells or nuclei can be contacted with a hashing oligo. The use of hashing oligos is optional, and can be used in conjunction with normalization oligos. Normalization oligos are described herein. In one embodiment, the contacting is after the cells have undergone the optional exposure to predetermined conditions. Typically, contacting with a hashing oligo occurs when the nuclei or the cells are separated in multiple compartments. In one embodiment, nuclei can be isolated (FIG. 1, block 11) and labeled (FIG. 1, block 12) with a hashing oligo. In another embodiment, the nuclei are exposed to the hashing oligo prior to isolation from cells. The inventors have determined that any disruption of cellular membrane allows labeling of nuclei with hashing oligos. Thus, nuclei can be labeled in the presence or absence of cytoplasmic material. Nuclei can be, and typically are, permeabilized in the process of labeling with hashing and/or normalization oligos, for instance, nuclei can be permeabilized before, during, or after labeling of nuclei with hashing oligos and/or with normalization oligos. Methods for permeabilizing membranes are known in the art. In another embodiment, cells are contacted with a hashing oligo.

Nuclei isolation is accomplished by incubating the cells in cell lysis buffer for at least 1 to 20 minutes, such as 5, 10, or 15 minutes. Optionally, the cells can be exposed to an external force to aid in lysis, such as movement through a pipette. An example of a cell lysis buffer includes 10 mM Tris-HCl, pH 7.4, 10 mM NaCl, 3 mM MgCl2, 0.1% IGEPAL CA-630, and 1% SUPERase In RNase Inhibitor. The skilled person will recognize these levels of the components can be altered somewhat without reducing the usefulness of the cell lysis buffer for isolating nuclei. The skilled person will recognize that RNASe inhibitors, BSA, and/or surfactants can be useful in buffers used for the isolation of nuclei, and that other additives can be added to the buffer for other downstream single-cell combinatorial indexing applications.

In one embodiment, the cells or nuclei are processed using any sci-seq method to measure an analyte or analytes from a cell including, but not limited to, DNA, RNA, protein, or a combination thereof.

In one embodiment, nuclei are isolated from individual cells that are adherent or in suspension. Methods for isolating nuclei from individual cells are known to the person of ordinary skill in the art. In one embodiment, nuclei are isolated from cells present in a tissue. The method for obtaining isolated nuclei typically includes preparing the tissue and isolating the nuclei from the prepared tissue. In one embodiment all steps are done on ice.

Tissue preparation can include snap freezing the tissue in liquid nitrogen, and then subjecting the tissue to either mincing or a blunt force to reduce the size of the tissue to pieces of 1 mm or less in diameter. Optionally, cold proteases and/or other enzymes for breaking down cell-cell connections can be used. Mincing can be accomplished with a blade to cut the tissue to small pieces. Applying a blunt force can be accomplished by smashing the tissue with a hammer or similar object, and the resulting composition of smashed tissue is referred to as a powder.

Conventional tissue nuclei extraction techniques normally incubate tissues with tissue specific enzyme (e.g., trypsin) at high temperature (e.g., 37° C.) for 30 minutes to several hours, and then lyse the cells with cell lysis buffer for nuclei extraction. The nuclei isolation method described herein and in U.S. Prov. Pat. App. No. 62/680,259 has several advantages: (1) No artificial enzymes are introduced, and all steps are done on ice. This reduces potential perturbation to cell states (e.g., transcriptome state, chromatin state, or methylation state). (2) This has been validated across most tissue types including brain, lung, kidney, spleen, heart, cerebellum, and disease samples such as tumor tissues. Compared with conventional tissue nuclei extraction techniques that use different enzymes for different tissue types, the new technique can potentially reduce bias when comparing cell states from different tissues. (3) The method also reduces cost and increases efficiency by removing the enzyme treatment step. (4) Compared with other nuclei extraction techniques (e.g., Dounce tissue grinder), the technique is more robust for different tissue types (e.g., the Dounce method needs optimizing Dounce cycles for different tissues) and enables processing large pieces of samples in high throughput (e.g., the Dounce method is limited to the size of the grinder).

Optionally, the isolated nuclei can be nucleosome-free or can be subjected to conditions that deplete the nuclei of nucleosomes, generating nucleosome-depleted nuclei (see, for instance, U.S. Pat. Appl. Pub. No. US 2018/0023119). Nucleosome-depleted nuclei can be useful for whole genome single nuclei sequencing.

The lysis buffer can include the hashing oligo used for nuclear hashing (FIG. 1, block 12). Alternatively, the hashing oligo can be absent from the lysis buffer but present in a subsequent step as deemed appropriate by the person of ordinary skill.

A hashing oligo includes a single stranded or double stranded nucleic acid sequence that includes DNA, RNA, or a combination thereof. A hashing oligo can be DNAse resistant or RNAse resistant. A hashing oligo can include nucleic acid components such as, but not limited to, an index, a UMI, and a universal sequence, in any combination. A hashing oligo can also include other non-nucleic acid components, including protein, such as antibody. In one embodiment, the hashing oligo includes a 5' region, a subset-specific index sequence, and a 3' end sequence. The 5' region may be a 5' PCR handle or universal sequence that can be used in a subsequent step for amplification of, and addition of specific nucleotides to, hashing oligos. A 5' PCR handle can include a nucleotide sequence that is identical to or the complement of a universal capture sequence. The 3' end sequence can be any series of nucleotides useful in a downstream step. For instance, when downstream steps include production of a transcriptome library, the 3' end sequence can include a polyadenylated sequence. In another embodiment, the hashing oligo includes a nucleic acid sequence that can be used in a subsequent ligation step, amplification step, primer extension step, or a combination thereof, to add a subset-specific index sequence and other nucleotides useful in subsequent steps of the method, such as a 5' region and/or a polyadenylated 3' end. Any further manipulation of a hashing oligo to add a subset-specific index sequence and any other element can be done prior to a pooling step described herein. In one embodiment, the hashing oligos can be added before, during, or after the cell lysis step or agent exposure. In one embodiment, the hashing oligo can be added without a cell lysis step.

An index sequence, also referred to as a tag or barcode, is useful as a marker characteristic of the compartment in which a particular target nucleic acid was present. Accordingly, an index is a nucleic acid sequence tag which is attached to each of the target nucleic acids present in a particular compartment, and the presence of the index is indicative of, or is used to identify, the compartment in which a population of nuclei or cells were present at this stage of the method. The subset-specific index sequence of a hashing oligo is indicative of which nucleic acids are from a subset of cells exposed to a specific predetermined condition, and allows those nucleic acids to be distinguished from nucleic acids that are from subsets of cells exposed to other specific predetermined conditions.

An index sequence (e.g., the subset-specific index sequence of a hashing oligo, the population-identifying index sequence of a normalization oligo, or another index) used herein can be any suitable sequence of any suitable number of nucleotides in length, e.g., 1, 2, 3, 4, 5, 6, 7, 8, 9, 10, 11, 12, 13, 14, 15, 16, 17, 18, 19, 20, or more. A four nucleotide tag gives a possibility of multiplexing 256 samples, and a six base tag enables 4096 samples to be processed. An index or barcode can be introduced through many different methods including, but not limited to, direct inclusion with the oligo, ligation, extension, adsorption, and specific or non-specific interactions of an oligo or oligos, or amplification.

The hashing oligo binds to the nuclei or cells of a compartment and is optionally fixed to the nuclei or cells. The binding can be specific or non-specific. A hashing oligo that specifically binds a cell or nucleus can include an optional domain that mediates the specific binding. Examples of domains include a ligand of a receptor on the surface of a nucleus or a cell, an antibody or antibody fragment, an aptamer, or a specific oligo sequence. The inventors have determined that a hashing oligo will non-specifically bind to a nucleus in an amount that is sufficient for demultiplexing later in the method. Thus, in one embodiment the hashing oligo non-specifically binds to the nuclei or cells of a compartment. In one embodiment, non-specific binding is by absorption. In one embodiment, the hashing oligo can be added any at any step before pooling. In one embodiment, the hashing oligo is a mixture of one or more oligos with each oligo having a unique barcode or unique sequence. The hashing oligo can contain a barcode or a sequence for barcode introduction at a later stage after binding. In one embodiment, a combination of uniquely barcoded hashing oligos can be a signature for a specific experimental condition, agent, sample, or perturbation.

The unique hashing oligo present in each subset is fixed to the nuclei or cells of that subset by exposure to a cross-linking compound. A useful example of a cross-linking compound includes, but is not limited to, paraformaldehyde, formalin, or methanol. Other useful examples are described in Hermanson (Bioconjugate Techniques, 3rd Edition, 2013). The paraformaldehyde can be at a concentration of 1% to 8%, such as 5%. Treatment of nuclei with paraformaldehyde can include adding paraformaldehyde to a suspension of nuclei and incubating at 0° C. In some embodiments, the hashing oligo is not cross-linked but remains bound.

Manipulation of the nuclei or cells, including pooling and distributing steps described herein, can include the use of a nuclei buffer. An example of a nuclei buffer includes 10 mM Tris-HCl, pH 7.4, 10 mM NaCl, 3 mM MgCl2, 1% SUPERase In RNase Inhibitor (20 U/μL, Ambion) and 1% BSA (20 mg/ml, NEB). The skilled person will recognize these levels of the components can be altered somewhat without reducing the usefulness of the nuclei buffer in which to suspend nuclei.

Isolated fixed nuclei or cells can be used immediately or aliquoted and flash frozen in liquid nitrogen for later use. When prepared for use after freezing, thawed nuclei can be permeabilized, for instance with 0.2% tritonX-100 for 3 minutes on ice, and briefly sonicated to reduce nuclei clumping.

The method further includes pooling the subsets of nuclei or cells followed by distribution of the pooled nuclei or cells into a second plurality of compartments (FIG. 1, block 13). The number of nuclei or cells present in a subset, and therefore in each compartment, can be at least 1. The number of nuclei or cells in a subset is not intended to be limiting, and can number in the billions. In one embodiment, the number present in a subset is no greater than 100,000,000, no greater than 10,000,000, no greater than 1,000,000, no greater than 100,000, no greater than 10,000, no greater than 4,000, no greater than 3,000, no greater than 2,000, or no greater than 1,000. In one embodiment, the number of nuclei present in a subset can be 1 to 1,000, 1,000 to 10,000, 10,000 to 100,000, or 100,000 to 1,000,000, or 1,000,000 to 10,000,000, or 10,000,000 to 100,000,000. In one embodiment, each compartment can be a well of a multi-well plate, such as a 96- or 384-well plate. In one embodiment, each compartment can be a droplet. Methods for distributing nuclei into subsets are known to the person skilled in the art and are routine. While fluorescence-activated cell sorting (FACS) cytometry can be used, use of simple dilution can also be used. In one embodiment, FACS cytometry is not used.

The number of compartments in the first distribution step (FIG. 1, block 13) can depend on the format used. For instance, the number of compartments can be from 2 to 96 compartments (when a 96-well plate is used), from 2 to 384 compartments (when a 384-well plate is used). In one embodiment, multiple plates can be used. For instance, the compartments from at least 2, at least 3, at least 4, etc., 96-well plates can be used, or the compartments from at least 2, at least 3, at least 4, etc., 384-well plates can be used. When the type of compartment used is a droplet that contains two or more nuclei or cells, any number of droplets can be used, such as at least 10,000, at least 100,000, at least 1,000,000, or at least 10,000,000 droplets.

After the nuclei or cells are labeled with a hashing oligo, pooled, and distributed into subsets, different procedures can be used to ultimately produce libraries of different nucleic acids in the nuclei or cells and sequence the nuclei acids (FIG. 1, block 14). In one embodiment libraries of transcriptomes of single nuclei are produced as described in detail herein (see Example 1), and another embodiment libraries of accessible chromatin of single nuclei are produced as described in detail herein (see Example 2); however, the procedure used after labeling nuclei with a hashing oligo is not intended to be limiting. For instance, libraries made using single-cell combinatorial indexing methods, e.g., libraries of whole cell single nuclei, libraries of transposon accessible chromatin, or libraries of whole cell single nuclei to determine methylation status, can be produced using nuclei or cells that have been hashed as described herein.

Normalization Hashing

In the production of sequencing libraries from a plurality of cells or plurality of single nuclei, cells or nuclei can be contacted with populations of normalization oligos. The use of normalization oligos is optional, and can be used in conjunction with cell or nuclear hashing as described herein. The contacting with normalization oligos can be before or after the cells have undergone the optional exposure to predetermined conditions. Contacting with populations of normalization oligo can occur when the nuclei or the cells are in bulk prior to being separated into multiple compartments. Alternatively, nuclei can be isolated and separated in multiple compartments (FIG. 2, block 20) and labeled (FIG. 2, block 22) with populations of normalization oligos. In another embodiment, the nuclei are exposed to the normalization oligos prior to isolation from cells. Similar to hashing oligos, any disruption of cellular membrane allows labeling of nuclei with normalization oligos. Thus, nuclei can be labeled in the presence or absence of cytoplasmic material. Nuclei can be, and typically are, permeabilized in the process of labeling with normalization oligos, for instance, nuclei can be permeabilized before, during, or after labeling of nuclei with normalization oligos. Methods for permeabilizing membranes are known in the art. In another embodiment, cells are contacted with normalization oligos.

Methods for nuclei isolation, tissue preparation and nuclei extraction, etc., described herein for cellular and nuclear hashing can be used for normalization hashing. The lysis buffer can include the populations of normalization oligos used for normalization hashing (FIG. 2, block 22). Alternatively, the normalization oligos can be absent from the lysis buffer but present in a subsequent step as deemed appropriate by the person of ordinary skill. The skilled person will understand that, if both hashing oligos and normalization oligos are used, cells or nuclei can be exposed to hashing oligos and normalization oligos at the same time or at different times during the method.

Normalization hashing serves a different purpose than cellular or nuclear hashing. Hashing oligos are typically used to label multiple subsets of cells or nuclei, where the cells or nuclei in each subset are labeled with a single unique oligo. The identity of the unique hashing oligo associated with a cell or nucleus is captured during sequencing of the library resulting from the cell or nucleus, allowing later identification of the nucleic acids of a library originating from a specific subset of nuclei or cells, e.g., from one well of a multi-well plate. In contrast, normalization hashing can be used as a method of standardization, such as a method for standardizing a sequencing library. In normalization hashing cells or nuclei, in bulk or subsets, are exposed to a composition of normalization oligos, where the composition includes multiple populations of normalization oligos. The identity of the populations of normalization oligos associated with a cell or nucleus is captured and counted during sequencing of the library resulting from the cell or nucleus, and the counts can be used as an external standard for removing technical noise in the cell-to-cell change of a variable such as gene expression. Thus, normalization oligos can be used as a standard to evaluate the sensitivity and quantitative accuracy of a sequencing library. This type of standard can assess the impact of technical variables, benchmark bioinformatic tools, and improve the accurate analysis of a sample.

A normalization oligo typically has the same characteristics as a hashing oligo. A normalization oligo includes a single stranded or double stranded nucleic acid sequence that includes DNA, RNA, or a combination thereof. A normalization oligo can be DNAse resistant or RNAse resistant. A normalization oligo can include nucleic acid components such as, but not limited to, an index, a UMI, and a universal sequence in any combination. A normalization oligo can also include other non-nucleic acid components, including protein, such as antibody. In one embodiment, the normalization oligo includes a 5' region, a population-specific index sequence, and a 3' end sequence. The 5' region may be a 5' PCR handle or universal sequence that can be used in a subsequent step for amplification of, and addition of specific nucleotides to, normalization oligos. A 5' PCR handle can include a nucleotide sequence that is identical to or the complement of a universal capture sequence. The 3' end sequence can be any series of nucleotides useful in a downstream step. For instance, when downstream steps include production of a transcriptome library, the 3' end sequence can include a polyadenylated sequence. In another embodiment, a normalization oligo includes a nucleic acid sequence that can be used in a subsequent ligation step, amplification step, primer extension step, or a combination thereof, to add a subset-specific index sequence and other nucleotides useful in subsequent steps of the method, such as a 5' region and/or a polyadenylated 3' end. Any further manipulation of a normalization oligo to add a subset-specific index sequence and any other element can be done prior to a pooling step described herein. In one embodiment, the normalization oligos can be added before, during, or after the cell lysis step or agent exposure. In one embodiment, the normalization oligos can be added without a cell lysis step.

A composition of normalization oligos that is exposed to multiple cells or nuclei includes multiple distinct populations of normalization oligos. The number of distinct populations can be at least 2, and there is no theoretical upper limit on the number of distinct populations that can be in a composition; however, practical considerations such as cost of making multiple normalization oligos and computational time required to analyze many different normalization oligos can limit the number of distinct populations. Without intending to be limiting, the maximum number of populations present in a composition can be 2, 4, 8, 16, 24, 32, 40, 48, 56, 64, 72, 80, 88, 96 or 100. For instance, number of populations present in a composition can be at least 2, at least 4, at least 8, at least 16, at least 24, at least 32, at least 40, at least 48, at least 56, at least 64, at least 72, at least 80, at least 88, or at least 96, and no greater than 10, no greater than 96, no greater than 88, no greater than 80, no greater than 72, no greater than 64, no greater than 56, no greater than 48, no greater than 40, no greater than 32, no greater than 24, no greater than 16, no greater than 8, of no greater than 4, in any combination.

In one embodiment, each normalization oligo of a single population includes one unique index sequence that is not present in any other population of the composition. In one embodiment, the normalization oligos of a single population are present at a concentration and other populations are at different concentrations, e.g., the concentrations of at least two of the populations are different, and in one embodiment the concentration of each population is different. Thus, a composition of normalization oligos can include multiple populations of oligos where each population includes a different index sequence and the concentration of each population is the same, or a composition of normalization oligos can include multiple populations of oligos where each population includes a different index sequence but the concentration of at least two populations is different. In those embodiments where each population includes a different index sequence but the concentration of one or more populations is different, the relationship between each index sequence and its concentration is known.

In another embodiment, each normalization oligo of a single population includes at least 2 unique index sequences that are not present in any other population of the composition. For instance, one population includes index sequences 1-4, a second population includes index sequences 5-8, and a third population includes index sequences 9-12. Thus, in one embodiment, a composition of normalization oligos can include multiple populations of oligos where each population includes a set of different index sequences and the concentration of each population is the same. In another embodiment, a composition of normalization oligos can include multiple populations of oligos where each population includes a different set of index sequences, but the concentration of other populations is different, e.g., the concentrations of at least two of the populations are different, and in one embodiment the concentration of each population is different. In those embodiments where each population includes a different set of index sequences but the concentration of one or more populations is different, the relationship between each index sequence and its concentration is known.

The concentration of the normalization oligos in a composition can vary depending in part on the efficiency of capture of the normalization oligos by the cells or nuclei. In general, capture of normalization oligos is determined by factors including, but not limited to, sample processing and sequencing depth. For mammalian cell lines, the inventors found the capture rate efficiency to be low, but still yielding useful data (Example 3). It was empirically determined that the composition of normalization oligos could be constructed so that around 6 million normalization oligos were captured per nuclei to obtain a median UMI count of 1,000-5,000. The skilled person can determine the capture rate efficiency for any cell type and concentration of normalization oligos needed in a composition to yield useful normalization data. Without intending to be limiting, a concentration of normalization oligos used is one that results in the binding of oligos to cells in an amount that is similar to the amount of the cellular analyte (e.g., DNR, RNA, protein, etc.) that is being measured. In one embodiment, the concentration of each population of a composition of normalization oligos can be selected a concentration of from at least 0.001 zeptomoles to no greater than 100 attomoles. For instance, a concentration can be at least 0.001 zeptomoles, at least 0.01 zeptomoles, at least 0.1 zeptomoles, at least 1 attomole, or at least 10 attomoles, and no greater than 100 attomoles, no greater than 10 attomoles, no greater than 1 attomole, no greater than 0.1 zeptomoles, or no greater than 0.01 zeptomoles, in any combination. In one embodiment, the concentration of the population at the lowest level and the concentration of the population at the highest level vary by 1, 2, 3, 4, 5, or 6 orders of magnitude.

The normalization oligo binds to the nuclei or cells is optionally fixed to the nuclei or cells. The binding and fixing of a hashing oligo described herein can be used for a normalization oligo. For instance, the binding of a normalization oligo can be specific or non-specific. In one embodiment, non-specific binding is by absorption. In one embodiment, a normalization oligo that specifically binds a cell or nucleus can include an optional domain that mediates the specific binding. The populations of normalization oligos can be fixed to the nuclei or cells as described herein. In some embodiments, the normalization oligo is not cross-linked but remains bound.

Manipulation of the nuclei or cells associated with hashing oligos, normalization oligos, or a combination thereof, including pooling and distributing steps described herein, can include the use of a nuclei buffer. An example of a nuclei buffer includes 10 mM Tris-HCl, pH 7.4, 10 mM NaCl, 3 mM MgCl2, 1% SUPERase In RNase Inhibitor (20 U/μL, Ambion) and 1% BSA (20 mg/ml, NEB). The skilled person will recognize these levels of the components can be altered somewhat without reducing the usefulness of the nuclei buffer in which to suspend nuclei.

In embodiments where normalization oligos were added to cells or nuclei in bulk, the method can further include distributing pooled cells or nuclei into a plurality of compartments. Alternatively, in embodiments where normalization oligos were added to cells or nuclei present in subsets (FIG. 2, block 22), the method can further include pooling the subsets of nuclei or cells followed by distribution of the pooled nuclei into a second plurality of compartments (FIG. 2, block 24). The number of nuclei or cells present in a subset, and therefore in each compartment, can be at least 1. The number of nuclei or cells in a subset is not intended to be limiting, and can number in the billions. In one embodiment, the number present in a subset is no greater than 100,000,000, no greater than 10,000,000, no greater than 1,000,000, no greater than 100,000, no greater than 10,000, no greater than 4,000, no greater than 3,000, no greater than 2,000, or no greater than 1,000. In one embodiment, the number of nuclei present in a subset can be 1 to 1,000, 1,000 to 10,000, 10,000 to 100,000, or 100,000 to 1,000,000, or 1,000,000 to 10,000,000, or 10,000,000 to 100,000,000. In one embodiment, each compartment can be a well of a multi-well plate, such as a 96- or 384-well plate. In one embodiment, each compartment can be a droplet. Methods for distributing nuclei into subsets are known to the person skilled in the art and are routine. While fluorescence-activated cell sorting (FACS) cytometry can be used, use of simple dilution can also be used. In one embodiment, FACS cytometry is not used.

The number of compartments in the first distribution step (FIG. 2, block 24) can depend on the format used. For instance, the number of compartments can be from 2 to 96 compartments (when a 96-well plate is used), from 2 to 384 compartments (when a 384-well plate is used). In one embodiment, multiple plates can be used. For instance, the compartments from at least 2, at least 3, at least 4, etc., 96-well plates can be used, or the compartments from at least 2, at least 3, at least 4, etc., 384-well plates can be used. When the type of compartment used is a droplet that contains two or more nuclei or cells, any number of droplets can be used, such as at least 10,000, at least 100,000, at least 1,000,000, or at least 10,000,000 droplets.

After the nuclei or cells are labeled with a normalization oligo, and if useful or necessary distributed into subsets, different procedures can be used to ultimately produce libraries of different nucleic acids in the nuclei or cells and sequence the nuclei acids (FIG. 2, block 26). The procedure used after labeling nuclei with normalization oligos is not intended to be limiting.

Single-Cell Combinatorial Indexing of Transcriptomes

Figure 3:
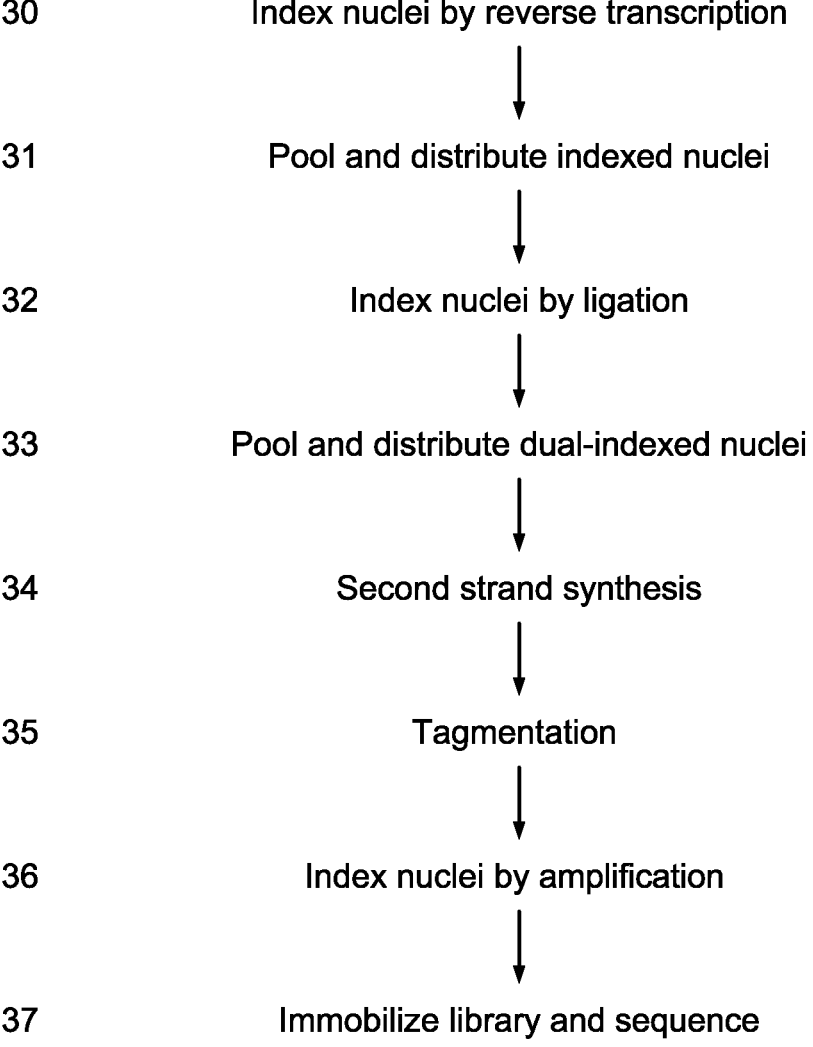
FIG. 3 shows a general block diagram of a general illustrative method for one embodiment of single-cell combinatorial indexing with nuclear hashing according to the present disclosure.

The following description of a single-cell combinatorial sequencing method is directed to seq-RNA, and is not intended to be limiting. In one embodiment the method includes indexing the mRNA nucleic acids of the distributed nuclei (FIG. 3, block 30). This step also adds an index to the oligos present, e.g., either the hashing oligos, the normalization oligos, or both. This index is distinct from the subset-specific index present on the hashing and the population-specific index present on the normalization oligos, and is referred to as a first index. Accordingly, nucleic acids derived from mRNA molecules have a first index after this step, nucleic acids derived from hashing oligos include a subset-specific index and a first index, and nucleic acids derived from normalization oligos include a population-specific index and a first index. In one embodiment, generating nuclei to include the first index includes the use of reverse transcriptase with an oligo-dT primer to add an index, a random nucleotide sequence, and a universal sequence. The random sequence is used as a unique molecular identifier (UMI) to label unique nuclei acid fragments. The random sequence can also be used to aid in removal of duplicates in downstream processing. The universal sequence serves as a complementary sequence for hybridization in the ligation step described herein. Exposing the nuclei to these components under conditions suitable for reverse transcription results in a population of indexed nuclei, where each nucleus contains two populations of indexed nucleic acid fragments. One population results from reverse transcription of the hashing oligo or normalization oligo hybridized to the oligo-dT primer, and another population results from reverse transcription of the mRNA nucleic acids hybridized to the oligo-dT primer. The indexed nucleic acid fragments can, and typically do, include on the synthesized strand the index sequence indicative of the particular compartment.

The indexed nuclei from multiple compartments can be combined (FIG. 3, block 31). For instance, the indexed nuclei from 2 to 24 compartments, from 2 to 96 compartments (when a 96-well plate is used), or from 2 to 384 compartments (when a 384-well plate is used) are combined. In one embodiment, the indexed nuclei from multiple plates are combined. For instance, the compartments from at least 2, at least 3, at least 4, etc., 96-well plates are combined, or the compartments from at least 2, at least 3, at least 4, etc., 384-well plates are combined. In one embodiment, the compartments from four 386-well plates are combined. Subsets of these combined indexed nuclei, referred to herein as pooled indexed nuclei, are then distributed into a third plurality of compartments (FIG. 3, block 31). The number of nuclei present in a subset, and therefor in each compartment, is based in part on the desire to reduce index collisions, which is the presence of two nuclei having the same index ending up in the same compartment in this step of the method. In one embodiment, the number of nuclei present in each subset is approximately equal. Methods for distributing nuclei into subsets are known to the person skilled in the art and are routine. Examples include, but are not limited to, simple dilution. In one embodiment, FACS cytometry is not used.

Distribution of nuclei into subsets is followed by incorporating into the indexed nucleic acid fragments in each compartment a second index sequence to generate dual-indexed fragments. This results in the further indexing of the indexed nucleic acid fragments (FIG. 3, block 32).

In one embodiment, the incorporation of the second index sequence includes ligating a hairpin ligation duplex to the indexed nucleic acid fragments in each compartment. The use of a hairpin ligation duplex to introduce a universal sequence, an index, or a combination thereof, to the end of a target nucleic acid fragment typically uses one end of the duplex as a primer for a subsequent amplification. In contrast, in one embodiment a hairpin ligation duplex used herein does not act as a primer. An advantage of using a hairpin ligation duplex described herein is a reduction of the self-self ligation observed with many hairpin ligation duplexes described in the art. In one embodiment, the ligation duplex includes five elements: 1) a universal sequence that is a complement of the universal sequence present on the oligo-dT primer, 2) a second index, 3) an ideoxyU, 4) a nucleotide sequence that can form a hairpin, and 5) the reverse complement of the second index. The second index sequences are unique for each compartment in which the distributed indexed nuclei were placed (FIG. 3, block 31) after the first index was added by reverse transcription.

The dual-indexed nuclei from multiple compartments can be combined (FIG. 3, block 33). For instance, the dual-indexed nuclei from 2 to 24 compartments, from 2 to 96 compartments (when a 96-well plate is used), or from 2 to 384 compartments (when a 384-well plate is used) are combined. In one embodiment, the dual-indexed nuclei from multiple plates are combined. For instance, the compartments from at least 2, at least 3, at least 4, etc., 96-well plates are combined, or the compartments from at least 2, at least 3, at least 4, etc., 384-well plates are combined. In one embodiment, the compartments from four 386-well plates are combined. Subsets of these combined dual-indexed nuclei, referred to herein as pooled dual-indexed nuclei, are then distributed into a fourth plurality of compartments (FIG. 3, block 33). The number of nuclei present in a subset, and therefor in each compartment, is based in part on the desire to reduce index collisions, which is the presence of two nuclei having the same transposase index ending up in the same compartment in this step of the method. In one embodiment, 100 to 30,000 nuclei are distributed to each well. In one embodiment, the number of nuclei in a well is at least 100, at least 500, at least 1,000, or at least 5,000. In one embodiment, the number of nuclei in a well is no greater than 30,000, no greater than 25,000, no greater than 20,000, or no greater than 15,000. In one embodiment, the number of nuclei present in a subset can be 100 to 1,000, 1,000 to 10,000, 10,000 to 20,000, or 20,000 to 30,000. In one embodiment, 2,500 nuclei are distributed to each well. In one embodiment, the number of nuclei present in each subset is approximately equal. Methods for distributing nuclei into subsets are known to the person skilled in the art and are routine. Examples include, but are not limited to, simple dilution. In one embodiment, FACS cytometry is not used.

Distribution of dual-indexed nuclei into subsets can be followed by synthesis of the second DNA strand (FIG. 3, block 34). Alternatively, synthesis of the second DNA strand can occur before distribution, e.g., in bulk.

The nuclei can then be subjected to tagmentation (FIG. 3, block 35). Each compartment containing the dual-indexed nuclei includes a transposome complex. The transposome complex can be added to each compartment before, after, or at the same time a subset of the nuclei is added to the compartment. The transposome complex, a transposase bound to a transposase recognition site, can insert the transposase recognition site into a target nucleic acid within a nucleus in a process sometimes termed "tagmentation." In some such insertion events, one strand of the transposase recognition site may be transferred into the target nucleic acid. Such a strand is referred to as a "transferred strand." In one embodiment, a transposome complex includes a dimeric transposase having two subunits, and two non-contiguous transposon sequences. In another embodiment, a transposase includes a dimeric transposase having two subunits, and a contiguous transposon sequence. In one embodiment, the 5' end of one or both strands of the transposase recognition site may be phosphorylated.

Some embodiments can include the use of a hyperactive Tn5 transposase and a Tn5-type transposase recognition site (Goryshin and Reznikoff, *J. Biol. Chem.*, 273:7367 (1998)), or MuA transposase and a Mu transposase recognition site comprising R1 and R2 end sequences (Mizuuchi, K., *Cell*, 35: 785, 1983; Savilahti, H, et al., *EMBO J.*, 14: 4893, 1995). Tn5 Mosaic End (ME) sequences can also be used as optimized by a skilled artisan.

More examples of transposition systems that can be used with certain embodiments of the compositions and methods provided herein include *Staphylococcus aureus* Tn552 (Colegio et al., *J. Bacteriol.*, 183: 2384-8, 2001; Kirby C et al., *Mol. Microbiol.*, 43: 173-86, 2002), Ty1 (Devine & Boeke, *Nucleic Acids Res.*, 22: 3765-72, 1994 and International Publication WO 95/23875), Transposon Tn7 (Craig, N L, *Science.* 271: 1512, 1996; Craig, N L, Review in: *Curr Top Microbiol Immunol.*, 204:27-48, 1996), Tn/O and IS10 (Kleckner N, et al., *Curr Top Microbiol Immunol.*, 204:49-82, 1996), Mariner transposase (Lampe D J, et al., *EMBO J.*, 15: 5470-9, 1996), Tc1 (Plasterk R H, *Curr. Topics Microbiol. Immunol.*, 204: 125-43, 1996), P Element (Gloor, G B, *Methods Mol. Biol.*, 260: 97-114, 2004), Tn3 (Ichikawa & Ohtsubo, *J Biol. Chem.* 265:18829-32, 1990), bacterial insertion sequences (Ohtsubo & Sekine, *Curr. Top. Microbiol. Immunol.* 204: 1-26, 1996), retroviruses (Brown, et al., *Proc Natl Acad Sci USA*, 86:2525-9, 1989), and retrotransposon of yeast (Boeke & Corces, *Annu Rev Microbiol.* 43:403-34, 1989). More examples include IS5, Tn10, Tn903, IS911, and engineered versions of transposase family enzymes (Zhang et al., (2009) *PLoS Genet.* 5:e1000689. Epub 2009 Oct. 16; Wilson C. et al (2007) *J. Microbiol. Methods* 71:332-5).

Other examples of integrases that may be used with the methods and compositions provided herein include retroviral integrases and integrase recognition sequences for such retroviral integrases, such as integrases from HIV-1, HIV-2, SIV, PFV-1, RSV.

Transposon sequences useful with the methods and compositions described herein are provided in U.S. Pat. Appl. Pub. No. 2012/0208705, U.S. Patent Application Pub. No.

2012/0208724 and Int. Pat. Appl. Pub. No. WO 2012/061832. In some embodiments, a transposon sequence includes a first transposase recognition site, a second transposase recognition site, and an optional index sequence present between the two transposase recognition sites.

Some transposome complexes useful herein include a transposase having two transposon sequences. In some such embodiments, the two transposon sequences are not linked to one another, in other words, the transposon sequences are non-contiguous with one another. Examples of such transposomes are known in the art (see, for instance, U.S. Patent Application Pub. No. 2010/0120098).

In some embodiments, a transposome complex includes a transposon sequence nucleic acid that binds two transposase subunits to form a "looped complex" or a "looped transposome." In one example, a transposome includes a dimeric transposase and a transposon sequence. Looped complexes can ensure that transposons are inserted into target DNA while maintaining ordering information of the original target DNA and without fragmenting the target DNA. As will be appreciated, looped structures may insert desired nucleic acid sequences, such as indexes, into a target nucleic acid, while maintaining physical connectivity of the target nucleic acid. In some embodiments, the transposon sequence of a looped transposome complex can include a fragmentation site such that the transposon sequence can be fragmented to create a transposome complex comprising two transposon sequences. Such transposome complexes are useful to ensuring that neighboring target DNA fragments, in which the transposons insert, receive code combinations that can be unambiguously assembled at a later stage of the assay.

A transposome complex can optionally include an index sequence, also referred to as a transposase index. The index sequence is present as part of the transposon sequence. Use of a transposome complex having an index results in target nucleic acid fragments that include an additional index. In one embodiment, the index sequence can be present on a transferred strand, the strand of the transposase recognition site that is transferred into the target nucleic acid.

Thus tagmentation can be used to produce nucleic acid fragments having different types of nucleotide sequences at each end. In one embodiment, the resulting nucleic acid fragments include different nucleotide sequences at each end, such as an N5 primer sequence at one end and an N7 primer at the other end, or different universal sequences at each end. Examples of useful universal sequences include, for instance, a hairpin ligation duplex and a universal sequence to which a universal primer can bind. In other embodiments, tagmentation can be used to produce nucleic acid fragments having the same type of nucleotide sequence at each end. In one embodiment, the resulting nucleic acid fragments include a nucleotide sequence at each end having a universal sequence to which a universal primer can bind, an index, or both a universal sequence and an index. A universal sequence can serve as a complementary sequence for hybridization in the amplification step described herein to introduce a third index Tagmentation of the nuclei and processing of the nucleic acid fragments can be followed by a clean-up process to enhance the purity of the molecules. Any suitable clean-up process may be used, such as electrophoresis, size exclusion chromatography, or the like. In some embodiments, solid phase reversible immobilization paramagnetic beads may be employed to separate the desired DNA molecules from, for instance, unincorporated primers, and to select nucleic acids based on size. Solid phase reversible immobilization paramagnetic beads are commercially available from Beckman Coulter (Agencourt AMPure XP), Thermofisher (MagJet), Omega Biotek (Mag-Bind), Promega Beads (Promega), and Kapa Biosystems (Kapa Pure Beads).

Removal of the ideoxyU present in the hairpin region of the hairpin ligation duplex optionally incorporated into the nucleic acid fragments can occur before, during, or after clean-up. Removal of the uracil residue can be accomplished by any available method, and in one embodiment the Uracil-Specific Excision Reagent (USER) available from NEB is used.

Tagmentation of nuclei can be followed by incorporating into the dual-indexed nucleic acid fragments in each compartment a third index sequence to generate triple-indexed fragments, where the third index sequence in each compartment is different from first and second index sequences in the compartments. This results in the further indexing of the indexed nucleic acid fragments (FIG. 3, block 36) prior to immobilizing and sequencing. The third index can be incorporated by an amplification step, such as PCR. In one embodiment, the universal sequences present at ends of the dual-indexed nucleic acid fragments (e.g., the hairpin ligation duplex-inserted nucleotides sequence at one end and the transposome complex-inserted nucleotide sequence at the other end) can be used for the binding of primers and be extended in an amplification reaction. Typically, two different primers are used. One primer hybridizes with universal sequences at the 3' end of one strand of the dual-indexed nucleic acid fragments, and a second primer hybridizes with universal sequences at the 3' end of the other strand of the dual-indexed nucleic acid fragments. Thus, the anchor sequence (e.g., the site to which a universal primer such as a sequencing primer for read 1 or read 2 anneals for sequencing) present on each primer can be different. Suitable primers can each include additional universal sequences, such as a universal capture sequence (e.g., the site to which a capture oligonucleotide hybridizes, where the capture oligonucleotide can be immobilized on a surface of a solid substrate). Because each primer includes an index, this step results in the addition of another index sequence, one at each end of the nucleic acid fragments to result in triple-indexed fragments. In one embodiment, indexed primers, such as an indexed P5 primer and an indexed P7 primer, can be used to add the third index. The triple-indexed fragments are pooled and can be subjected to a clean-up step as described herein.

The resulting triple-indexed fragments collectively provide a library of nucleic acids that can be immobilized and then sequenced. The term library, also referred to herein as a sequencing library, refers to the collection of nucleic acid fragments from single nuclei containing known universal sequences at their 3' and 5' ends. In the present embodiment, the library includes whole transcriptome nucleic acids from one or more of the isolated nuclei, and can be used to perform whole transcriptome sequencing.

Preparation of Immobilized Samples for Sequencing

The plurality of multiply indexed fragments can be prepared for sequencing. For instance, in those embodiments where transcriptome libraries of triple-indexed fragments are produced, the triple-indexed fragments are pooled and subjected to clean-up they are enriched, typically by immobilization and/or amplification, prior to sequencing (FIG. 3, block 37). Methods for attaching indexed fragments from one or more sources to a substrate are known in the art. In one embodiment, indexed fragments are enriched using a plurality of capture oligonucleotides having specificity for the indexed fragments, and the capture oligonucleotides can be immobilized on a surface of a solid substrate. For instance, capture oligonucleotides can include a first member of a universal binding pair, and wherein a second member of the binding pair is immobilized on a surface of a solid substrate. Likewise, methods for amplifying immobilized triple-indexed fragments include, but are not limited to, bridge amplification and kinetic exclusion. Methods for immobilizing and amplifying prior to sequencing are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

A pooled sample can be immobilized in preparation for sequencing. Sequencing can be performed as an array of single molecules or can be amplified prior to sequencing. The amplification can be carried out using one or more immobilized primers. The immobilized primer(s) can be, for instance, a lawn on a planar surface, or on a pool of beads. The pool of beads can be isolated into an emulsion with a single bead in each "compartment" of the emulsion. At a concentration of only one template per "compartment," only a single template is amplified on each bead.

The term "solid-phase amplification" as used herein refers to any nucleic acid amplification reaction carried out on or in association with a solid support such that all or a portion of the amplified products are immobilized on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilized on the solid support. Solid phase PCR covers systems such as emulsions, wherein one primer is anchored to a bead and the other is in free solution, and colony formation in solid phase gel matrices wherein one primer is anchored to the surface, and one is in free solution.

In some embodiments, the solid support comprises a patterned surface. A "patterned surface" refers to an arrangement of different regions in or on an exposed layer of a solid support. For example, one or more of the regions can be features where one or more amplification primers are present. The features can be separated by interstitial regions where amplification primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. Exemplary patterned surfaces that can be used in the methods and compositions set forth herein are described in U.S. Pat. Nos. 8,778,848, 8,778,849 and 9,079,148, and U.S. Pat. Appl. Pub. No. 2014/0243224.

In some embodiments, the solid support includes an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g. microwells or nanowells) on glass, silicon, plastic or other suitable solid supports with patterned, covalently-linked gel such as poly(N-(5-azidoacetamidylpentyl) acrylamide-co-acrylamide) (PAZAM, see, for example, US Pub. No. 2013/184796, WO 2016/066586, and WO 2015/002813). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However, in many embodiments the gel need not be covalently linked to the wells. For example, in some conditions silane free acrylamide (SFA, see, for example, U.S. Pat. No. 8,563,477) which is not covalently attached to any part of the structured substrate, can be used as the gel material.

In particular embodiments, a structured substrate can be made by patterning a solid support material with wells (e.g. microwells or nanowells), coating the patterned support with a gel material (e.g. PAZAM, SFA, or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of triple-index fragments can then be contacted with the polished substrate such that individual triple-index fragments will seed individual wells via interactions with primers attached to the gel material; however, the target nucleic acids will not occupy the interstitial regions due to absence or inactivity of the gel material. Amplification of the triple-index fragments will be confined to the wells since absence or inactivity of gel in the interstitial regions prevents outward migration of the growing nucleic acid colony. The process can be conveniently manufactured, being scalable and utilizing conventional micro- or nanofabrication methods.

Although the disclosure encompasses "solid-phase" amplification methods in which only one amplification primer is immobilized (the other primer usually being present in free solution), in one embodiment the solid support is provided with both the forward and the reverse primers immobilized. In practice, there will be a 'plurality' of identical forward primers and/or a 'plurality' of identical reverse primers immobilized on the solid support, since the amplification process requires an excess of primers to sustain amplification. References herein to forward and reverse primers are to be interpreted accordingly as encompassing a 'plurality' of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may include template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the disclosure. Other embodiments may use forward and reverse primers which contain identical template-specific sequences but which differ in some other structural features. For example, one type of primer may contain a non-nucleotide modification which is not present in the other.

Primers for solid-phase amplification are preferably immobilized by single point covalent attachment to the solid support at or near the 5' end of the primer, leaving the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatization or functionalization applied to it. The primer itself may include a moiety, which may be a non-nucleotide chemical modification, to facilitate attachment. In a particular embodiment, the primer may include a sulphur-containing nucleophile, such as phosphorothioate or thiophosphate, at the 5' end. In the case of solid-supported polyacrylamide hydrogels, this nucleophile will bind to a bromoacetamide group present in the hydrogel. A more particular means of attaching primers and templates to a solid support is via 5' phosphorothioate attachment to a hydrogel comprised of polymerized acrylamide and N-(5-bromoacetamidylpentyl) acrylamide (BRAPA), as described in Int. Pub. No. WO 05/065814.

Certain embodiments of the disclosure may make use of solid supports that include an inert substrate or matrix (e.g. glass slides, polymer beads, etc.) which has been "functionalized," for example by application of a layer or coating of an intermediate material including reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement.

The pooled samples may be amplified on beads wherein each bead contains a forward and reverse amplification primer. In a particular embodiment, the library of triple-index fragments is used to prepare clustered arrays of nucleic acid colonies, analogous to those described in U.S. Pub. No. 2005/0100900, U.S. Pat. No. 7,115,400, WO 00/18957 and WO 98/44151 by solid-phase amplification and more particularly solid phase isothermal amplification. The terms ' cluster' and 'colony' are used interchangeably herein to refer to a discrete site on a solid support including a plurality of identical immobilized nucleic acid strands and a plurality of identical immobilized complementary nucleic acid strands. The term "clustered array" refers to an array formed from such clusters or colonies. In this context, the term "array" is not to be understood as requiring an ordered arrangement of clusters.

The term "solid phase" or "surface" is used to mean either a planar array wherein primers are attached to a flat surface, for example, glass, silica or plastic microscope slides or similar flow cell devices; beads, wherein either one or two primers are attached to the beads and the beads are amplified; or an array of beads on a surface after the beads have been amplified.

Clustered arrays can be prepared using either a process of thermocycling, as described in WO 98/44151, or a process whereby the temperature is maintained as a constant, and the cycles of extension and denaturing are performed using changes of reagents. Such isothermal amplification methods are described in patent application numbers WO 02/46456 and U.S. Pub. No. 2008/0009420. Due to the lower temperatures useful in the isothermal process, this is particularly preferred in some embodiments.

It will be appreciated that any of the amplification methodologies described herein or generally known in the art may be used with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence-based amplification (NASBA), as described in U.S. Pat. No. 8,003,354. The above amplification methods may be employed to amplify one or more nucleic acids of interest. For example, PCR, including multiplex PCR, SDA, TMA, NASBA and the like may be utilized to amplify immobilized DNA fragments. In some embodiments, primers directed specifically to the polynucleotide of interest are included in the amplification reaction.

Other suitable methods for amplification of polynucleotides may include oligonucleotide extension and ligation, rolling circle amplification (RCA) (Lizardi et al., Nat. Genet. 19:225-232 (1998)) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835) technologies. It will be appreciated that these amplification methodologies may be designed to amplify immobilized DNA fragments. For example, in some embodiments, the amplification method may include ligation probe amplification or oligonucleotide ligation assay (OLA) reactions that contain primers directed specifically to the nucleic acid of interest. In some embodiments, the amplification method may include a primer extension-ligation reaction that contains primers directed specifically to the nucleic acid of interest. As a non-limiting example of primer extension and ligation primers that may be specifically designed to amplify a nucleic acid of interest, the amplification may include primers used for the GoldenGate assay (Illumina, Inc., San Diego, California) as exemplified by U.S. Pat. Nos. 7,582,420 and 7,611,869.

DNA nanoballs can also be used in combination with methods and compositions as described herein. Methods for creating and using DNA nanoballs for genomic sequencing can be found at, for example, US patents and publications U.S. Pat. No. 7,910,354, 2009/0264299, 2009/0011943, 2009/0005252, 2009/0155781, 2009/0118488 and as described in, for example, Drmanac et al. (2010, Science 327(5961): 78-81). Briefly, following genomic library DNA fragmentation, adaptors are ligated to the fragments, the adapter ligated fragments are circularized by ligation with a circle ligase and rolling circle amplification is carried out (as described in Lizardi et al., 1998. Nat. Genet. 19:225-232 and US 2007/0099208 A1). The extended concatameric structure of the amplicons promotes coiling thereby creating compact DNA nanoballs. The DNA nanoballs can be captured on substrates, preferably to create an ordered or patterned array such that distance between each nanoball is maintained thereby allowing sequencing of the separate DNA nanoballs. In some embodiments such as those used by Complete Genomics (Mountain View, California), consecutive rounds of adapter ligation, amplification and digestion are carried out prior to circularization to produce head to tail constructs having several genomic DNA fragments separated by adapter sequences.

Exemplary isothermal amplification methods that may be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587. Other non-PCR-based methods that may be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyper-branched strand displacement amplification which is described in, for example Lage et al., Genome Res. 13:294-307 (2003). Isothermal amplification methods may be used with, for instance, the strand-displacing Phi 29 polymerase or Bst DNA polymerase large fragment, 5'→3' exo- for random primer amplification of genomic DNA. The use of these polymerases takes advantage of their high processivity and strand displacing activity. High processivity allows the polymerases to produce fragments that are 10-20 kb in length. As set forth above, smaller fragments may be produced under isothermal conditions using polymerases having low processivity and strand-displacing activity such as Klenow polymerase. Additional description of amplification reactions, conditions and components are set forth in detail in the disclosure of U.S. Pat. No. 7,670,810.

Another polynucleotide amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993). The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers may be removed and further replication may take place using primers complementary to the constant 5' region.

In some embodiments, isothermal amplification can be performed using kinetic exclusion amplification (KEA), also referred to as exclusion amplification (ExAmp). A nucleic acid library of the present disclosure can be made using a method that includes a step of reacting an amplification reagent to produce a plurality of amplification sites that each includes a substantially clonal population of amplicons from an individual target nucleic acid that has seeded the site. In some embodiments, the amplification reaction proceeds until a sufficient number of amplicons are generated to fill the capacity of the respective amplification site. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example, in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

In some embodiments, amplification sites in an array can be, but need not be, entirely clonal. Rather, for some applications, an individual amplification site can be predominantly populated with amplicons from a first triple-indexed fragment and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons. It will be understood that in an array or other collection of sites, at least 50%, 75%, 80%, 85%, 90%, 95% or 99% or more of the sites can be clonal or apparently clonal.

In some embodiments, kinetic exclusion can occur when a process occurs at a sufficiently rapid rate to effectively exclude another event or process from occurring. Take for example the making of a nucleic acid array where sites of the array are randomly seeded with triple-indexed fragments from a solution and copies of the triple-indexed fragments are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of U.S. Pat. Appl. Pub. No. 2013/0338042.

Kinetic exclusion can exploit a relatively slow rate for initiating amplification (e.g. a slow rate of making a first copy of a triple-index fragment) vs. a relatively rapid rate for making subsequent copies of the triple-indexed fragment (or of the first copy of the triple-indexed fragment). In the example of the previous paragraph, kinetic exclusion occurs due to the relatively slow rate of triple-indexed fragment seeding (e.g. relatively slow diffusion or transport) vs. the relatively rapid rate at which amplification occurs to fill the site with copies of the triple-indexed fragment seed. In another exemplary embodiment, kinetic exclusion can occur due to a delay in the formation of a first copy of a triple-indexed fragment that has seeded a site (e.g. delayed or slow activation) vs. the relatively rapid rate at which subsequent copies are made to fill the site. In this example, an individual site may have been seeded with several different triple-indexed fragments (e.g. several triple-indexed fragments can be present at each site prior to amplification). However, first copy formation for any given triple-indexed fragment can be activated randomly such that the average rate of first copy formation is relatively slow compared to the rate at which subsequent copies are generated. In this case, although an individual site may have been seeded with several different triple-indexed fragments, kinetic exclusion will allow only one of those triple-indexed fragments to be amplified. More specifically, once a first triple-indexed fragment has been activated for amplification, the site will rapidly fill to capacity with its copies, thereby preventing copies of a second triple-indexed fragment from being made at the site.

In one embodiment, the method is carried out to simultaneously (i) triple-index fragments to amplification sites at an average transport rate, and (ii) amplify the triple-index fragments that are at the amplification sites at an average amplification rate, wherein the average amplification rate exceeds the average transport rate (U.S. Pat. No. 9,169,513). Accordingly, kinetic exclusion can be achieved in such embodiments by using a relatively slow rate of transport. For example, a sufficiently low concentration of triple-index fragments can be selected to achieve a desired average transport rate, lower concentrations resulting in slower average rates of transport. Alternatively or additionally, a high viscosity solution and/or presence of molecular crowding reagents in the solution can be used to reduce transport rates. Examples of useful molecular crowding reagents include, but are not limited to, polyethylene glycol (PEG), ficoll, dextran, or polyvinyl alcohol. Exemplary molecular crowding reagents and formulations are set forth in U.S. Pat. No. 7,399,590, which is incorporated herein by reference. Another factor that can be adjusted to achieve a desired transport rate is the average size of the target nucleic acids.

An amplification reagent can include further components that facilitate amplicon formation and in some cases increase the rate of amplicon formation. An example is a recombinase. Recombinase can facilitate amplicon formation by allowing repeated invasion/extension. More specifically, recombinase can facilitate invasion of a triple-index fragment by the polymerase and extension of a primer by the polymerase using the triple-indexed fragment as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, MA). Further, examples of useful formulations that include a helicase protein are described in U.S. Pat. Nos. 7,399,590 and 7,829,284.

Yet another example of a component that can be included in an amplification reagent to facilitate amplicon formation and in some cases increase the rate of amplicon formation is an origin binding protein.

Use in Sequencing/Methods of Sequencing

Following attachment of triple-indexed fragments to a surface, the sequence of the immobilized and amplified triple-indexed fragments is determined. Sequencing can be carried out using any suitable sequencing technique, and methods for determining the sequence of immobilized and amplified triple-indexed fragments, including strand re-synthesis, are known in the art and are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a triple-index fragment can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

In one embodiment, a nucleotide monomer includes locked nucleic acids (LNAs) or bridged nucleic acids (BNAs). The use of LNAs or BNAs in a nucleotide monomer increases hybridization strength between a nucleotide monomer and a sequencing primer sequence present on an immobilized triple-index fragment.

SBS can use nucleotide monomers that have a terminator moiety or those that lack any terminator moieties. Methods using nucleotide monomers lacking terminators include, for example, pyrosequencing and sequencing using γ-phosphate-labeled nucleotides, as set forth in further detail herein. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can use nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments where two or more different nucleotides are present in a sequencing reagent, the different nucleotides can be distinguishable from each other, or alternatively the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320). In pyrosequencing, released PPi can be detected by being immediately converted to adenosine triphosphate (ATP) by ATP sulfurase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026. This approach is being commercialized by Solexa (now Illumina Inc.), and is also described in WO 91/06678 and WO 07/123,744. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In some reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments, each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth herein.

In particular embodiments some or all of the nucleotide monomers can include reversible terminators. In such embodiments, reversible terminators/cleavable fluorophores can include fluorophores linked to the ribose moiety via a 3' ester linkage (Metzker, Genome Res. 15:1767-1776 (2005)). Other approaches have separated the terminator chemistry from the cleavage of the fluorescence label (Ruparel et al., Proc Natl Acad Sci USA 102: 5932-7 (2005)). Ruparel et al. described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluorophore and effectively reverses the termination. Examples of modified nucleotides are also described in U.S. Pat. Nos. 7,427,673, and 7,057,026.

Additional exemplary SBS systems and methods which can be utilized with the methods and systems described herein are described in U.S. Pub. Nos. 2007/0166705, 2006/0188901, 2006/0240439, 2006/0281109, 2012/0270305, and 2013/0260372, U.S. Pat. No. 7,057,026, PCT Publication No. WO 05/065814, U.S. Patent Application Publication No. 2005/0100900, and PCT Publication Nos. WO 06/064199 and WO 07/010,251.

Some embodiments can use detection of four different nucleotides using fewer than four different labels. For example, SBS can be performed using methods and systems described in the incorporated materials of U.S. Pub. No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can use sequencing by ligation techniques. Such techniques use DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597.

Some embodiments can use nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis", Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003)). In such embodiments, the triple-index fragment passes through a nanopore. The nanopore can be a synthetic pore or biological membrane protein, such as α-hemolysin. As the triple-index fragment passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008)). Data obtained from nanopore sequencing can be stored, processed and analyzed as set forth herein. In particular, the data can be treated as an image in accordance with the exemplary treatment of optical images and other images that is set forth herein.

Some embodiments can use methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414, or nucleotide incorporations can be detected with zero-mode waveguides as described, for example, in U.S. Pat. No. 7,315,019, and using fluorescent nucleotide analogs and engineered polymerases as described, for example, in U.S. Pat. No. 7,405,281 and U.S. Pub. No. 2008/0108082. The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008)). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in U.S. Pub. Nos. 2009/0026082; 2009/0127589; 2010/0137143; and 2010/0282617. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different triple-index fragments are manipulated simultaneously. In particular embodiments, different triple-index fragments can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the triple-index fragments can be in an array format. In an array format, the triple-index fragments can be typically bound to a surface in a spatially distinguishable manner. The triple-index fragments can be bound by direct covalent attachment, attachment to a bead or other particle or binding to a polymerase or other molecule that is attached to the surface. The array can include a single copy of a triple-index fragment at each site (also referred to as a feature) or multiple copies having the same sequence can be present at each site or feature. Multiple copies can be produced by amplification methods such as, bridge amplification or emulsion PCR as described in further detail herein.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of cm$^2$, in parallel. Accordingly, the present disclosure provides integrated systems capable of preparing and detecting nucleic acids using techniques known in the art such as those exemplified herein. Thus, an integrated system of the present disclosure can include fluidic components capable of delivering amplification reagents and/or sequencing reagents to one or more immobilized triple-index fragments, the system including components such as pumps, valves, reservoirs, fluidic lines and the like. A flow cell can be configured and/or used in an integrated system for detection of target nucleic acids. Exemplary flow cells are described, for example, in U.S. Pat. Nos. 8,241,573 and 8,951,781. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, CA) and devices described in U.S. Pat. No. 8,951,781.

Compositions

Also provided herein are compositions. During the practice of the methods described herein various compositions can result. For example, a composition including cells or nuclei having a hashing oligo non-specifically or specifically attached can result. Other compositions include those having multiple populations of normalization oligos as described herein. A composition including a plurality of compartments where each compartment includes multiple populations of normalization oligos can result, or a composition including a plurality of nuclei or cells where the nuclei or cells are associated with multiple populations of normalization oligos can result.

Exemplary Embodiments

Embodiment 1. A method of preparing a sequencing library comprising nucleic acids from a plurality of single nuclei or single cells, the method comprising:
(a) providing a plurality of cells in a first plurality of compartments;
(b) exposing the plurality of cells of each compartment to a predetermined condition;
(c) contacting nuclei isolated from the cells of each compartment or the cells of each compartment with a hashing oligo,
wherein at least one copy of the hashing oligo is associated with isolated nuclei or cells, wherein the hashing oligo comprises a hashing index, wherein the hashing index in each compartment comprises an index sequence that is different from index sequences in the other compartments to generate hashed nuclei or hashed cells; and (d) combining the hashed nuclei or hashed cells of different compartments to generate pooled hashed nuclei or pooled hashed cells.

Embodiment 2. The method of Embodiment 1, further comprising exposing the cells or nuclei to a cross-linking compound to fix hashing oligos cells or to isolated nuclei.

Embodiment 3. The method of any of Embodiments 1-2, wherein the cross-linking compound comprises paraformaldehyde, formalin, or methanol.

Embodiment 4. The method of any of Embodiments 1-3, wherein the predetermined condition comprises exposure to an agent.

Embodiment 5. The method of any of Embodiments 1-4, wherein the agent comprises a protein, a non-ribosomal protein, a polyketide, an organic molecule, an inorganic molecule, an RNA or RNAi molecule, a carbohydrate, a glycoprotein, a nucleic acid, a drug, or a combination thereof Embodiment 6. The method of any of Embodiments 1-5, wherein the hashing oligo comprises a single stranded nucleic acid.

Embodiment 7. The method of any of Embodiments 1-6, wherein the hashing oligo consists of a single stranded nucleic acid.

Embodiment 8. The method of any of Embodiments 1-7, wherein the nucleic acid of the hashing oligo comprises DNA, RNA, or a combination thereof.

Embodiment 9. The method of any of Embodiments 1-8, wherein the hashing oligo comprises a domain that mediates specific binding of the hashing oligo to the surface of cells or nuclei.

Embodiment 10. The method of any of Embodiments 1-9, wherein the domain comprises a ligand, an antibody, or an aptamer.

Embodiment 11. The method of any of Embodiments 1-10, wherein the association between the hashing oligo and the cells or isolated nuclei is non-specific.

Embodiment 12. The method of any of Embodiments 1-11, wherein the non-specific association between the hashing oligo and the cells or isolated nuclei is by absorption.

Embodiment 13. The method of any of Embodiments 1-12, further comprising processing the pooled hashed cells or pooled hashed nuclei using a single-cell combinatorial indexing method to result in a sequencing library comprising nucleic acids from the plurality of single nuclei, wherein the nucleic acids comprise a plurality of indexes.

Embodiment 14. The method of any of Embodiments 1-13, wherein the single-cell combinatorial indexing method is single-nuclei transcriptome sequencing, single-cell transcriptome sequencing, single-cell transcriptome and transposon-accessible chromatin sequencing, whole genome sequencing of single nuclei, single nuclei sequencing of transposon accessible chromatin, sci-HiC, DRUG-seq, sci-CAR, sci-MET, sci-Crop, sci-perturb, or sci-Crispr.

Embodiment 15. The method of any of Embodiments 1-14, the method further comprising (e) distributing subsets of the pooled hashed cells or hashed nuclei into a second plurality of compartments and contacting each subset with reverse transcriptase or DNA polymerase and a primer, wherein the primer in each compartment comprises a first index sequence that is different from first index sequences in the other compartments to generate indexed nuclei comprising indexed nucleic acid fragments;

(f) combining the indexed cells or indexed nuclei to generate pooled indexed cells or pooled indexed nuclei;

(g) distributing subsets of the pooled indexed cells or pooled indexed nuclei into a third plurality of compartments and introducing a second index sequence to indexed nucleic acid fragments to generate dual-indexed cells or dual-indexed nuclei comprising dual-indexed nucleic acid fragments, wherein the introducing comprises ligation, primer extension, amplification, or transposition;

(h) combining the dual-indexed cells or dual-indexed nuclei to generate pooled dual-indexed nuclei or cells;

(i) distributing subsets of dual-indexed cells or the pooled dual-indexed nuclei into a fourth plurality of compartments and introducing a third index sequence to dual-indexed nucleic acid fragments to generate triple-indexed cells or triple-indexed nuclei comprising triple-indexed nucleic acid fragments, wherein the introducing comprises ligation, primer extension, amplification, or transposition;

(j) combining the triple-indexed fragments, thereby producing a sequencing library comprising transcriptome nucleic acids from the plurality of single nuclei.

Embodiment 16. The method of any of Embodiments 1-15, wherein (g) comprises contacting each subset with a transposome complex, wherein the transposome complex in each compartment comprises a transposase and a second index sequence under conditions suitable for ligation of the second index sequence to the ends of indexed nucleic acid fragments comprising a first index sequence to generate dual-indexed nuclei comprising dual-indexed nucleic acid fragments, wherein the second index sequence is different from second index sequences in the other compartments.

Embodiment 17. The method of any of Embodiments 1-16, wherein (i) comprises contacting each subset with a primer comprising a third index sequence and a universal primer sequence, wherein the contacting comprises conditions suitable for amplification and incorporation of the third index sequence to the ends of the dual-indexed nucleic acid fragments, wherein the third index sequence is different from third index sequences in the other compartments.

Embodiment 18. The method of any of Embodiments 1-17, wherein the compartments comprise a well or a droplet.

Embodiment 19. The method of any of Embodiments 1-18, further comprising:

providing a surface comprising a plurality of amplification sites, wherein the amplification sites comprise at least two populations of attached single stranded capture oligonucleotides having a free 3' end, and contacting the surface comprising amplification sites with the triple-indexed fragments under conditions suitable to produce a plurality of amplification sites that each comprise a clonal population of amplicons from an individual fragment comprising a plurality of indexes.

Embodiment 20. A composition comprising the hashed cells or hashed nuclei of Embodiment 1.

Embodiment 21. A composition comprising the pooled hashed cells or pooled hashed nuclei of Embodiment 1.

Embodiment 22. A multi-well plate, wherein compartments of the multi-well plate comprise the composition of any of Embodiments 20 or 21.

Embodiment 23. The multi-well plate of Embodiment 22, wherein a compartment of the multi-well plate comprises from 50 to 100,000,000 cells or nuclei.

Embodiment 24. A droplet, wherein the droplet comprises the composition of any of Embodiments 20 or 21.

Embodiment 25. The droplet of Embodiment 24, wherein the droplet comprises from 50 to 100,000,000 cells or nuclei.

Embodiment 26. A method of preparing a sequencing library comprising nucleic acids from a plurality of single nuclei or single cells, the method comprising:

(a) providing a first plurality of compartments comprising isolated nuclei or cells and contacting the isolated nuclei or cells of each compartment with a hashing oligo, wherein at least one copy of the hashing oligo is associated with isolated nuclei or cells, wherein the hashing oligo comprises a nucleic acid and a hashing index, wherein the hashing index in each compartment comprises an index sequence that is different from index sequences in the other compartments to generate hashed nuclei or hashed cells; and (b) combining the hashed nuclei or hashed cells of different compartments to generate pooled hashed nuclei or pooled hashed cells.

Embodiment 27. A method of preparing a sequencing library comprising nucleic acids from a plurality of single nuclei or single cells, the method comprising:

(a) providing a first plurality of compartments comprising isolated nuclei or cells and contacting the isolated nuclei or cells of each compartment with a hashing oligo, wherein at least one copy of the hashing oligo is associated with isolated nuclei or cells by absorption, wherein the hashing oligo comprises a nucleic acid and a hashing index, wherein the hashing index in each compartment comprises an index sequence that is different from index sequences in the other compartments to generate hashed nuclei or hashed cells; and (b) combining the hashed nuclei or hashed cells of different compartments to generate pooled hashed nuclei or pooled hashed cells.

Embodiment 28. A method of preparing a sequencing library comprising nucleic acids from a plurality of nuclei or cells, the method comprising:

(a) providing a plurality of compartments comprising nuclei or cells, wherein the nuclei or cells comprise a hashing oligo that comprises a compartment specific index;

(b) combining the nuclei or cells from different compartments into a second compartment to generate pooled hashed nuclei or pooled hashed cells.

Embodiment 29. The method of any of Embodiments 26-28, further comprising exposing the cells of each compartment to a predetermined condition or exposing the cells of each compartment to a predetermined condition and then isolating nuclei from a plurality of cells prior to step (a).

Embodiment 30. The method of any of Embodiments 28-29, wherein the predetermined condition comprises exposure to an agent.

Embodiment 31. The method of any of Embodiments 28-30, wherein the agent comprises a protein, a non-ribosomal protein, a polyketide, an organic molecule, an inorganic molecule, an RNA or RNAi molecule, a carbohydrate, a glycoprotein, a nucleic acid, a drug, or a combination thereof.

Embodiment 32. A composition comprising multiple populations of normalization oligos, wherein the composition comprises a first population of normalization oligos comprising a first index sequence and other populations of normalization oligos each comprising a unique index sequence that is different from the index sequences of the other populations, and wherein the concentration of each population is the same.

Embodiment 33. A composition comprising multiple populations of normalization oligos, wherein the composition comprises a first population of normalization oligos comprising a first index sequence and other populations of normalization oligos each comprising a unique index sequence that is different from the index sequences of the other populations, and wherein the concentrations of at least two of the populations are different.

Embodiment 34. A composition comprising multiple populations of normalization oligos, wherein the composition comprises a first population of normalization oligos comprising a set of first index sequences and other populations of normalization oligos each comprise a set of unique index sequences that is different from the sets of index sequences of the other populations, and wherein the concentration of each population is the same.

Embodiment 35. A composition comprising multiple populations of normalization oligos, wherein the composition comprises a first population of normalization oligos comprising a set of first index sequences and other populations of normalization oligos each comprise a set of unique index sequences that is different from the sets of index sequences of the other populations, and wherein the concentrations of at least two of the populations are different.

Embodiment 36. The composition of any one of Embodiments 32-35, wherein the composition comprises from 2 to 100 populations of normalization oligos.

Embodiment 37. The composition of any one of Embodiments 32-36, wherein the normalization oligos comprise single-stranded DNA.

Embodiment 38. The composition of any one of Embodiments 32-37, wherein the normalization oligos comprise a unique molecular identifier.

Embodiment 39. The composition of any one of Embodiments 32-38, wherein the normalization oligos comprise a universal sequence.

Embodiment 40. The composition of any one of Embodiments 32-39, wherein the normalization oligos comprise a non-nucleic acid component Embodiment 41. The composition of any of Embodiments 32-40, wherein the non-nucleic acid component comprises protein.

Embodiment 42. The composition of any of Embodiments 32-41, wherein the non-nucleic acid component comprises protein.

Embodiment 43. The composition of any one of Embodiments 32-42, wherein the first population is present in the composition at a lowest concentration of normalization oligos and one of the other populations is present in the composition at a highest concentration of normalization oligos, and wherein the lowest and highest concentrations differ by a factor of from 1 to 10,000.

Embodiment 44. A plurality of compartments, wherein each compartment comprises the composition of any one of Embodiments 32-43.

Embodiment 45. The plurality of compartments of Embodiment 44, wherein the compartments comprise wells or droplets.

Embodiment 46. The plurality of compartments of any of Embodiments 44-45, wherein each compartment further comprises nuclei or cells, and wherein the multiple populations of normalization oligos are associated with the nuclei or cells.

Embodiment 47. The plurality of compartments of any of Embodiments 44-46, wherein the concentration of normalization oligos of each of the populations is selected from at least 0.001 zeptomoles to no greater than 100 attomoles.

Embodiment 48. A population of nuclei or cells, wherein the nuclei or cells comprise the composition of any one of Embodiments 32-47, and wherein members of each population of normalization oligos are associated with the nuclei or the cells.

Embodiment 49. The population of Embodiment 48, wherein the association between nuclei or cells and normalization oligos is non-specific.

Embodiment 50. A method for normalizing a sequencing library comprising nucleic acids from a plurality of single nuclei or single cells, the method comprising:

(a) providing a first plurality of compartments comprising isolated nuclei or cells;

(b) contacting the isolated nuclei or cells of each compartment with the composition of any one of Embodiments 32-35, wherein members of each population of normalization oligos are associated with isolated nuclei or cells; and (c) combining the labeled nuclei or labeled cells of different compartments to generate pooled labeled nuclei or pooled labeled cells.

Embodiment 51. The method of Embodiment 50, further comprising exposing the cells of each compartment to a predetermined condition, or exposing the cells of each compartment to a predetermined condition and then isolating nuclei from a plurality of cells prior to step (a).

Embodiment 52. The method of any of Embodiments 50-51, wherein the predetermined condition comprises exposure to an agent.

Embodiment 53. The method of any of Embodiments 50-52, wherein the agent comprises a protein, a non-ribosomal protein, a polyketide, an organic molecule, an inorganic molecule, an RNA or RNAi molecule, a carbohydrate, a glycoprotein, a nucleic acid, a drug, or a combination thereof Embodiment 54. The method of any of Embodiments 50-53, further comprising prior to step (b) contacting the isolated nuclei or cells of each compartment with a hashing oligo, wherein at least one copy of the hashing oligo is associated with isolated nuclei or cells, wherein the hashing oligo comprises a nucleic acid and a hashing index, wherein the hashing index in each compartment comprises an index sequence that is different from index sequences in the other compartments and different from index sequences of normalization oligos present in the compartment to generate labeled hashed nuclei or labeled hashed cells; and combining the labeled hashed nuclei or labeled hashed cells of different compartments to generate pooled labeled hashed nuclei or pooled labeled hashed cells.

Embodiment 55. The method of any of Embodiments 50-54, further comprising exposing the cells or nuclei to a cross-linking compound to fix normalization oligos cells or to isolated nuclei.

Embodiment 56. The method of any of Embodiments 50-55, wherein the cross-linking compound comprises paraformaldehyde, formalin, or methanol.

Embodiment 57. The method of any of Embodiments 50-56, wherein the association between the normalization oligo and the cells or isolated nuclei is non-specific.

Embodiment 58. The method of any of Embodiments 50-57, wherein the non-specific association between the normalization oligo and the cells or isolated nuclei is by absorption.

Embodiment 59. The method of any of Embodiments 50-58, further comprising processing the pooled labeled hashed cells or pooled labeled hashed nuclei using a single-cell combinatorial indexing method to result in a sequencing library comprising nucleic acids from the plurality of single nuclei or single cells, wherein the nucleic acids comprise a plurality of indexes.

Embodiment 60. The method of any of Embodiments 50-59, wherein the single-cell combinatorial indexing method is single-nuclei transcriptome sequencing, single-cell transcriptome sequencing, single-cell transcriptome and transposon-accessible chromatin sequencing, whole genome sequencing of single nuclei, single nuclei sequencing of transposon accessible chromatin, sci-HiC, DRUG-seq, sci-CAR, sci-MET, sci-Crop, sci-perturb, or sci-Crispr.

Embodiment 61. A method for normalizing a sequencing library comprising nucleic acids from a plurality of single nuclei or single cells, the method comprising:

(a) providing isolated nuclei or cells;

(b) contacting the isolated nuclei or cells with the composition of any one of Embodiments 32-35, wherein members of each population of normalization oligos are associated with isolated nuclei or cells; and (c) distributing subsets of the labeled nuclei or labeled cells into a plurality of compartments.

Embodiment 62. The method of Embodiment 61, further comprising exposing the cells to a predetermined condition, or exposing the cells to a predetermined condition and then isolating nuclei from a plurality of cells prior to step (a).

Embodiment 63. The method of any of Embodiments 61-62, wherein the predetermined condition comprises exposure to an agent.

Embodiment 64. The method of any of Embodiments 61-63, wherein the agent comprises a protein, a non-ribosomal protein, a polyketide, an organic molecule, an inorganic molecule, an RNA or RNAi molecule, a carbohydrate, a glycoprotein, a nucleic acid, a drug, or a combination thereof Embodiment 65. The method of any of Embodiments 61-64, further comprising after step (c) contacting the isolated nuclei or cells of each compartment with a hashing oligo, wherein at least one copy of the hashing oligo is associated with isolated nuclei or cells, wherein the hashing oligo comprises a nucleic acid and a hashing index, wherein the hashing index in each compartment comprises an index sequence that is different from index sequences in the other compartments and different from index sequences of normalization oligos present in the compartment to generate labeled hashed nuclei or labeled hashed cells; and combining the labeled hashed nuclei or labeled hashed cells of different compartments to generate pooled labeled hashed nuclei or pooled labeled hashed cells.

Embodiment 66. The method of any of Embodiments 61-65, further comprising exposing the cells or nuclei to a cross-linking compound to fix normalization oligos cells or to isolated nuclei.

Embodiment 67. The method of any of Embodiments 61-66, wherein the cross-linking compound comprises paraformaldehyde, formalin, or methanol.

Embodiment 68. The method of any of Embodiments 61-67, wherein the association between the normalization oligo and the cells or isolated nuclei is non-specific.

Embodiment 69. The method of any of Embodiments 61-68, wherein the non-specific association between the normalization oligo and the cells or isolated nuclei is by absorption.

Embodiment 70. The method of Embodiment any of Embodiments 61-69, further comprising processing the pooled labeled hashed cells or pooled labeled hashed nuclei using a single-cell combinatorial indexing method to result in a sequencing library comprising nucleic acids from the plurality of single nuclei or single cells, wherein the nucleic acids comprise a plurality of indexes.

Embodiment 71. The method of any of Embodiments 61-70, wherein the single-cell combinatorial indexing method is single-nuclei transcriptome sequencing, single-cell transcriptome sequencing, single-cell transcriptome and transposon-accessible chromatin sequencing, whole genome sequencing of single nuclei, single nuclei sequencing of transposon accessible chromatin, sci-HiC, DRUG-seq, sci-CAR, sci-MET, sci-Crop, sci-perturb, or sci-Crispr.

EXAMPLES

Example 1

Massively Multiplex Chemical Transcriptomics at Single-Cell Resolution

High-throughput chemical screens typically use coarse assays such as cell survival, limiting what can be learned about mechanisms of action, off-target effects, and heterogeneous responses. Here, we introduce "sci-Plex," which uses "nuclear hashing" to quantify global transcriptional responses to thousands of independent perturbations at single-cell resolution. As a proof of concept, we applied sci-Plex to screen three cancer cell lines exposed to 188 compounds. In total, we profiled ~650,000 single-cell transcriptomes across 5000 independent samples in one experiment. Our results reveal substantial intercellular heterogeneity in response to specific compounds, commonalities in response to families of compounds, and insight into differential properties within families. In particular, our results with histone deacetylase inhibitors support the view that chromatin acts as an important reservoir of acetate in cancer cells. This Example is also available as Srivatsan et al., 2020, Science, 367:45-51).

To enable cost-effective high-throughput screens (HTSs) with single-cell transcriptome sequencing (scRNAseq)-based phenotyping, we describe a new sample labeling (hashing) strategy that relies on labeling nuclei with unmodified single stranded DNA oligos. Recent improvements in single-cell combinatorial indexing (sci-RNA-seq3) have lowered the cost of scRNAseq library preparation to <$0.01 per cell, with millions of cells profiled per experiment (21). Here, we combine nuclear hashing and sci-RNA-seq into a single workflow for multiplex transcriptomics in a process called "sci-Plex." As a proof of concept, we use sci-Plex to perform HTS on three cancer cell lines, profiling thousands of independent perturbations in a single experiment. We further explore how chemical transcriptomics at single-cell resolution can shed light on mechanisms of action. Most notably, we find that gene-regulatory changes consequent to treatment with histone deacetylase (HDAC) inhibitors are consistent with the model that they interfere with proliferation by restricting a cell's ability to draw acetate from chromatin (22, 23).

Results

Nuclear Hashing Enables Multisample Sci-RNA-Seq

Single-cell combinatorial indexing (sci-) methods use split-pool barcoding to specifically label the molecular contents of large numbers of single cells or nuclei (24). Samples can be barcoded by these same indices, e.g., by placing each sample in its own well during reverse transcription in sci-RNA-seq (21, 25), but such enzymatic labeling at the scale of thousands of samples is operationally infeasible and cost prohibitive. To enable single-cell molecular profiling of a large number of independent samples within a single sci-experiment, we set out to develop a low-cost labeling procedure.

Figure 4B:
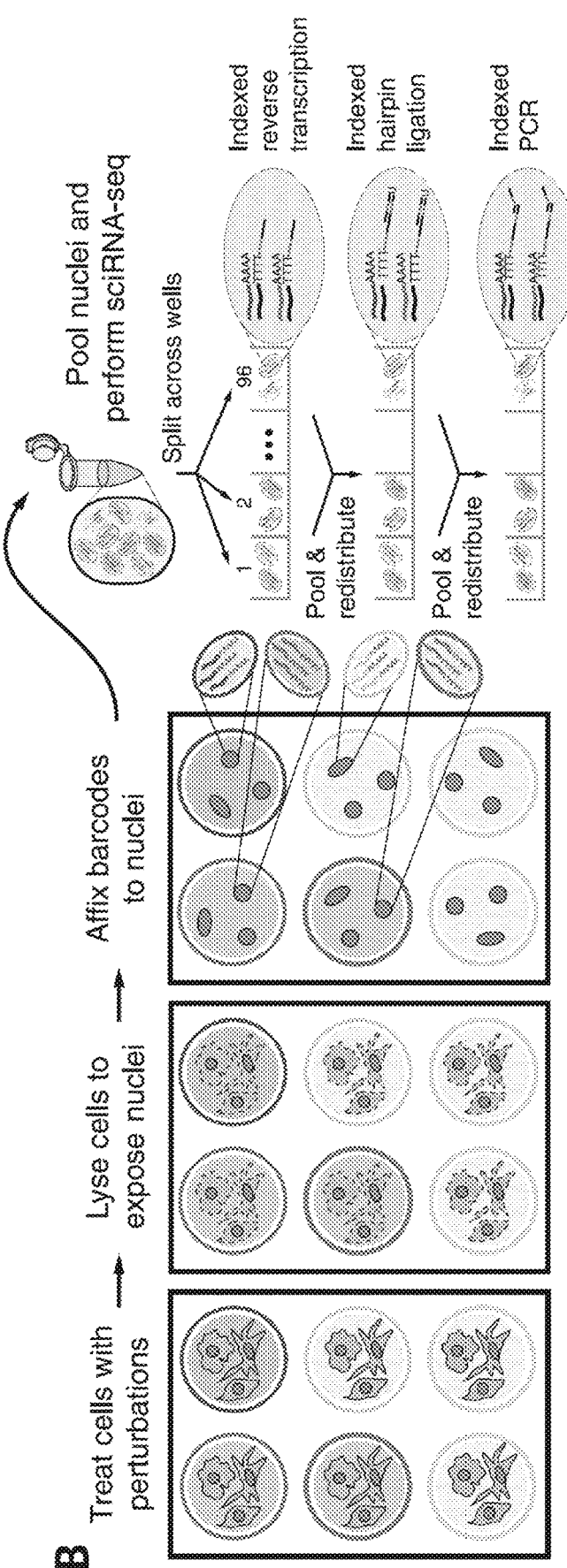
FIG. 4 shows sci-PLEX uses polyadenylated single-stranded oligonucleotides to label nuclei, enabling cell hashing and doublet detection. (A) Flourescent images of permeabilized nuclei after incubation with DAP1 (top) and an Alexa Fluor-647-conjugated single-stranded digonucleotide (bottom). (B) Overview of sci-Plex. Cells corresponding to different perturbations are lysed in well, their nuclei labeled with well specific "hash" oligos, followed by fixation, pooling, and sci-RNA-seq. (C) Scatter plot depicting the number of UMIs from single-cell transcriptomes derived from a mixture of hashed human HEK293T cells and murine NIH3T3 cells. Points are colored on the basis of hash oligo assignment. (D) Boxplot depicting the number of mRNA UMIs recovered per cell for fresh versus frozen human and mouse cell lines. (E) Scatter plot of overloading experiment; axes are as in (C). Identified has oligo collisions (red) identify cellular collisions with high sensitivity.
Figures 5E, 5F:
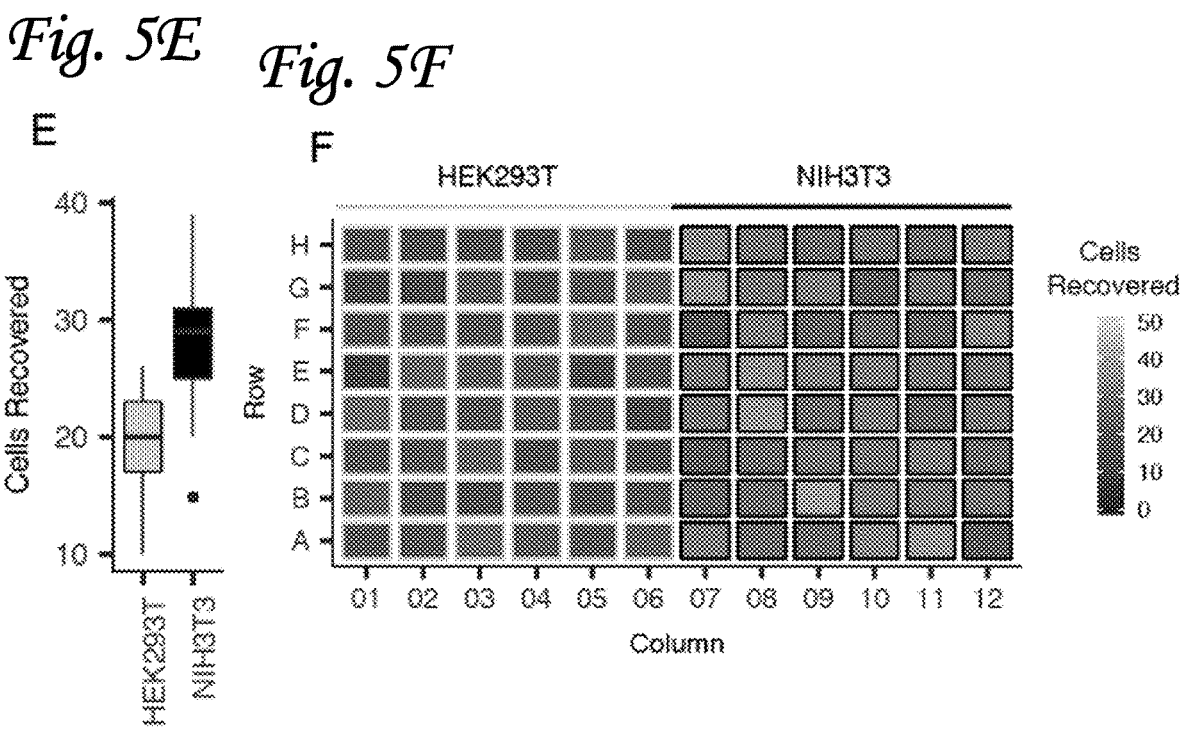
FIG. 5 shows hashing with short, polyadenylated single-stranded oligonucleotides enables stable, low-cost labeling of nuclei for sci-RNA-seq and subsequent doublet detection. A) Fluorescent microscopy images demonstrating lack of Alexa 647-conjugated oligo staining (right) of unpermabilized H3-GFP+NIH3T3 cells (left). B) Design of polyadenylated hash oligos (top) and indexed primer used for reverse transcription (bottom). C) Number of hash UMIs detected per cell. Cells with fewer than 10 hash UMIs (red line) were excluded from further analysis. D) Distribution of enrichment ratios for cells. Enrichment ratios were calculated as the UMI count ratio of the most abundant vs. the second most abundant hash oligo. An enrichment ratio cutoff of 15 (red line) was used to distinguish doublets vs. singlets. E) Boxplot of the number of cells recovered per well for each cell line. F) Layout of culture plate wells with color indicating number of cells recovered and outline indicating cell line. Note that although more NIH3T3 cells were recovered per well, similar numbers of cells were recovered across wells of each cell type. G) Log-scale per-gene aggregated, size-factor normalized UMI counts recovered from sci-RNA-seq on fresh vs. frozen preparations. Size factors are calculated as the log counts observed in a single cell divided by the geometric mean of log counts from all measured cells. Black line indicates y=x. Red line is the fit with Pearson correlation shown. H) Log-scale boxplot of number of hash UMIs recovered from sci-RNA-seq of HEK293T (human) or NIH3T3 (mouse cells) from fresh vs. frozen preparations. I) Theoretical (red bars) vs. observed (black dots for individual wells and blue bars for means) doublet rate as a function of the number of nuclei sorted into the final plate during sci-RNA-seq. J) Barnyard plot from FIG. 1E after removal of doublets detected by hashing. K) Log-scale boxplot of number of RNA UMIs in singlet vs. doublet cells, as called based on the purity of hash UMIs. Of note, these are 'within species' doublets, i.e. human-human or mouse-mouse, which are not readily detected by conventional barnyard experiments.

We noticed that single-stranded DNA (ssDNA) specifically stained the nuclei of permeabilized cells but not intact cells (FIG. 4A and FIG. 5A). We therefore postulated that a polyadenylated ssDNA oligonucleotide could be used to label populations of nuclei in a manner compatible with sci-RNA-seq (FIG. 4B and FIG. 5B). To test this concept, we performed a "barnyard" experiment. We separately seeded human (HEK293T) and mouse (NIH3T3) cells to 48 wells of a 96-well culture plate. We then performed nuclear lysis in the presence of 96 well-specific polyadenylated ssDNA oligos ("hash oligos") and fixed the resulting nuclear suspensions with paraformaldehyde. Having labeled or "hashed" the nuclei with a molecular barcode, we pooled nuclei and performed a two-level sci-RNA-seq experiment. Because the hash oligos were polyadenylated, they had the potential to be combinatorially indexed identically to endogenous mRNAs. As intended, we recovered reads corresponding to both endogenous mRNAs [median 4740 unique molecular identifiers (UMIs) per cell] and hash oligos (median 270 UMIs per cell).

Figures 4C, 4D, 4E:
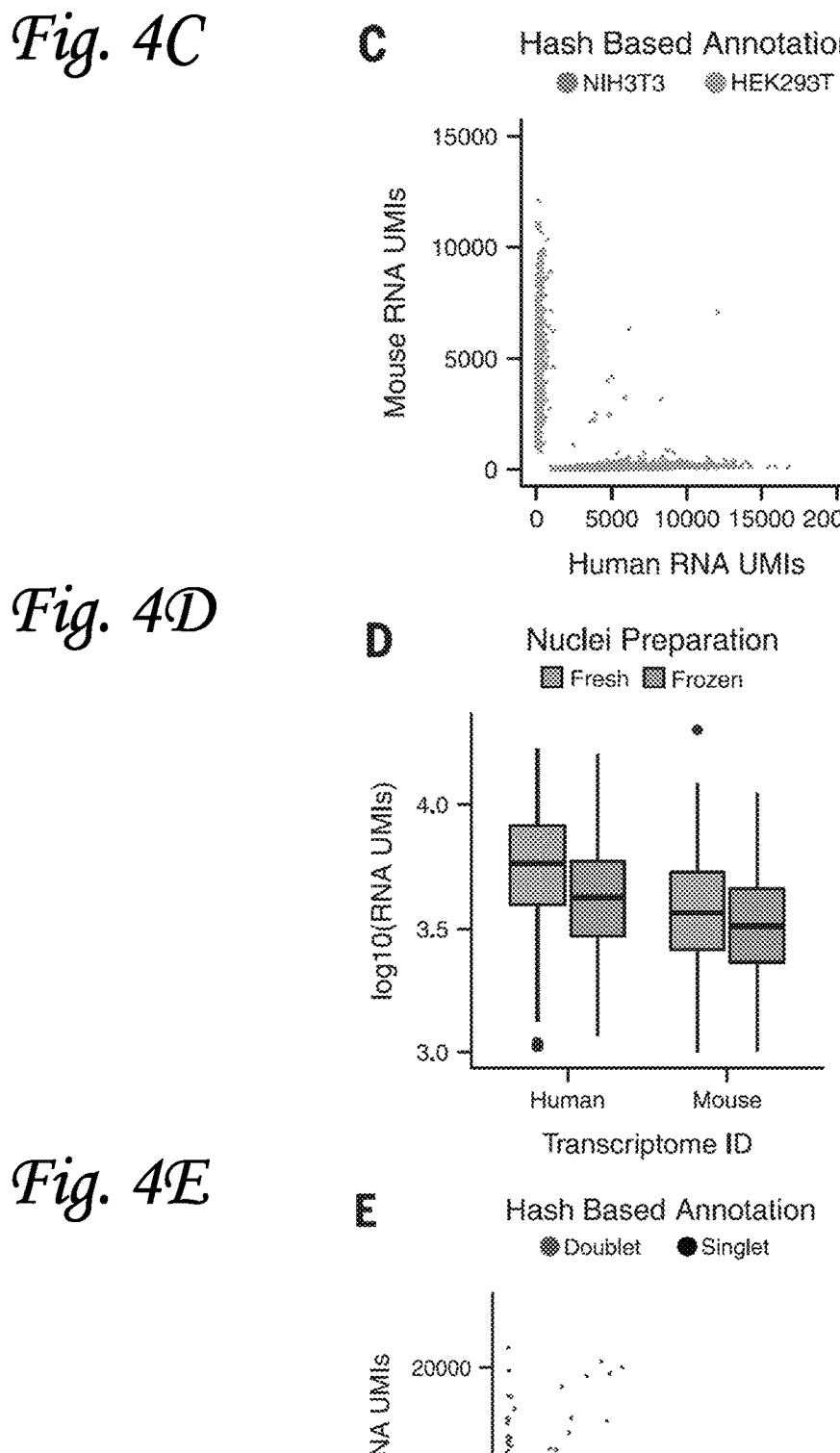
Figure 5G:
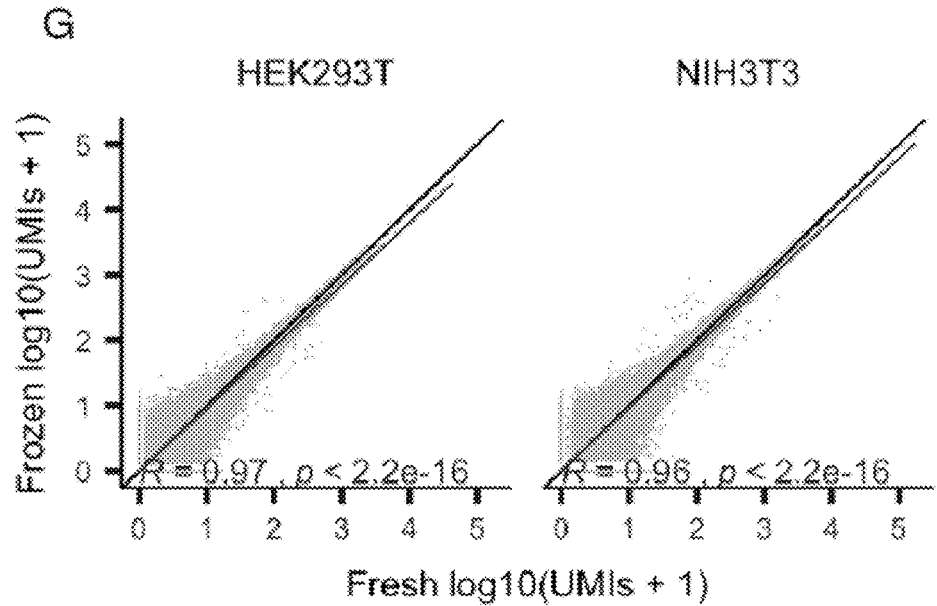

We devised a statistical framework to identify the hash oligos associated with each cell at a frequency exceeding background (Table S1). We observed 99.1% concordance between species assignments on the basis of hash oligos versus endogenous cellular transcriptomes (FIG. 4C and FIG. 5, C to F). Additionally, the association of hash oligos and nuclei was stable to a freeze-thaw cycle, highlighting the opportunity to label and store samples (FIG. 4D and FIG. 5, G and H). These results demonstrate that hash oligos stably label nuclei in a manner that is compatible with sci-RNA-seq.

57

TABLE 1

| Experiment | sci-RNA-seq protocol used | Cells Profiled | RNA Treshold (# UMIs) | Hash Oligo Treshold (# UMIs) | Hash Oligo Enrichment Ratio (UMIs Top Rank Oligo / UMIs Second Rank Oligo) |
|---|---|---|---|---|---|
| Barnyard | 2-level | 3024 | 1000 | 10 | 15 |
| Proof-of-concept Screen | 2-level | 12,435 | 1000 | 30 | 10 |
| Large Screen | 3-level | 649,220 | 500 | S/S (Well Oligo and Plate | S/S (Well Oligo and Plate Oligo) |
| HDACi phenocopy/ rescue | 3-level | 72,966 | 500 | 5 | 5 |

Figures 5H, 5I, 5J, 5K:
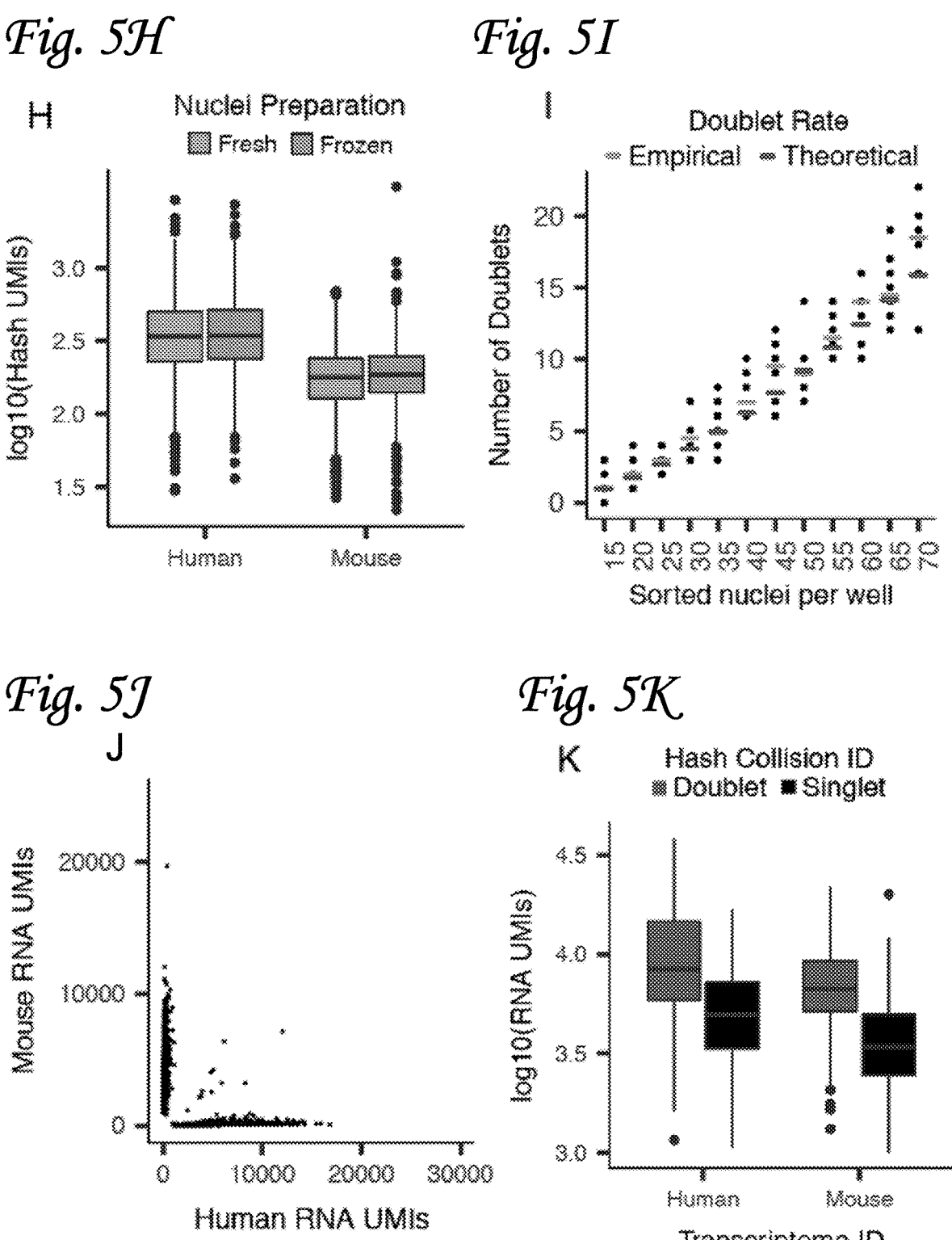

In sci-experiments, "collisions" are instances in which two or more cells are labeled with the same combination of barcodes by chance (24). To evaluate hashing as a means of detecting doublets resulting from collisions, we varied the number of nuclei loaded per polymerase chain reaction well, resulting in a range of predicted collision rates (7 to 23%) that was well matched by observation (FIG. 5I). Hash oligos facilitated the identification of the vast majority of interspecies doublets (95.5%) and otherwise undetectable within-species doublets (FIG. 4E and FIG. 5, J and K).

Sci-Plex Enables Multiplex Chemical Transcriptomics at Single-Cell Resolution

Figure 6A:
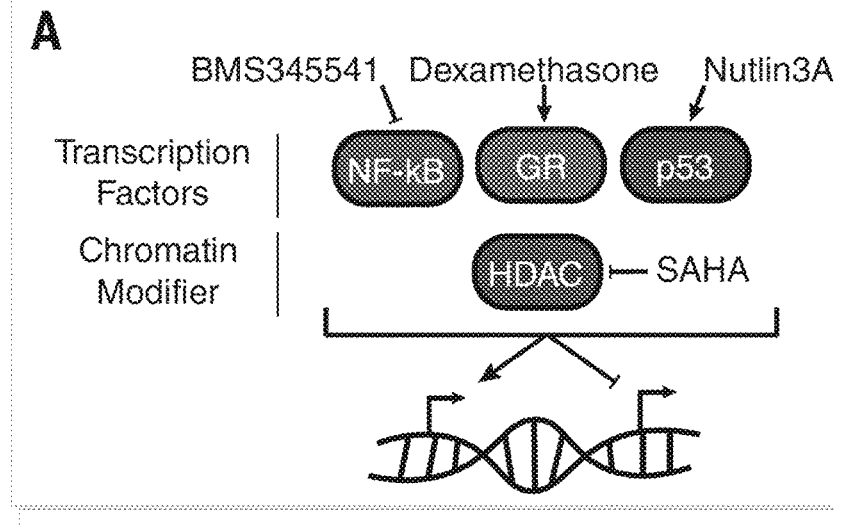
FIG. 6 shows sci-Plex enables multiplex chemical tran-scriptomics at single-cell resolution. (A) Diagram depicting compounds and corresponding targets assayed within the pilot sci-Plex experiment. A549 lung adenocarcinoma cells were treated with either vehicle [dimethylsulfoxide (DMSO) or ethanol] or one of four compounds (BMS345541, dexamethasone, nutlin-3a, or SAHA). (B) UMAP embedding of chemically perturbed A549 cells colored by drug treatment. (C) UMAP embedding of chemically perturbed A549 cells faceted by treatment with cells colored by dose. (D and E) Expression of a canonical (D) glucocorticoid receptor activated (ANGPTL4) and repressed (GDF15) target genes as a function of dexamethasone dose or (E) p53 target genes as a function of nutlin-3a dose. y-axes indicate the percentage of cells with at least one read corresponding to the transcript. (F) Dose-response viability estimates for BMS345541-, dexamethasone-, nutlin-3a-, and SAHA-treated A549 cells on the basis of the relative number of cells recovered at each dose.
Figure 6B:
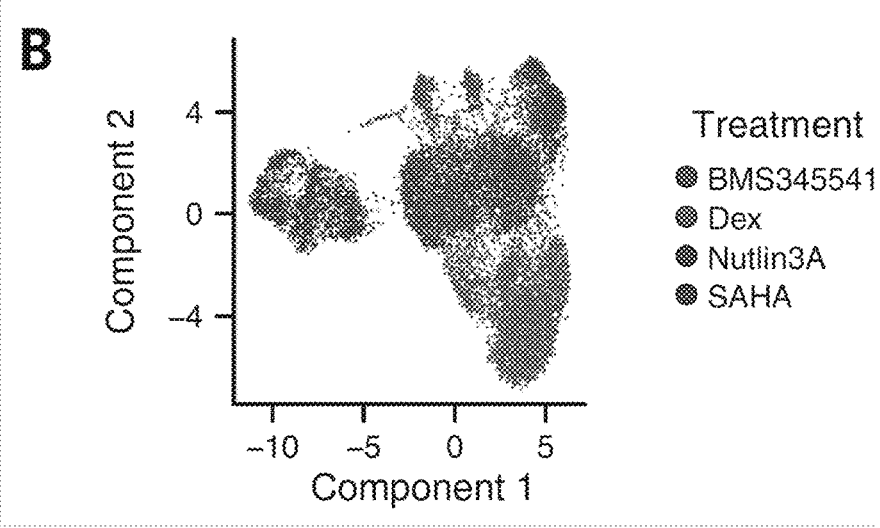
Figure 6C:
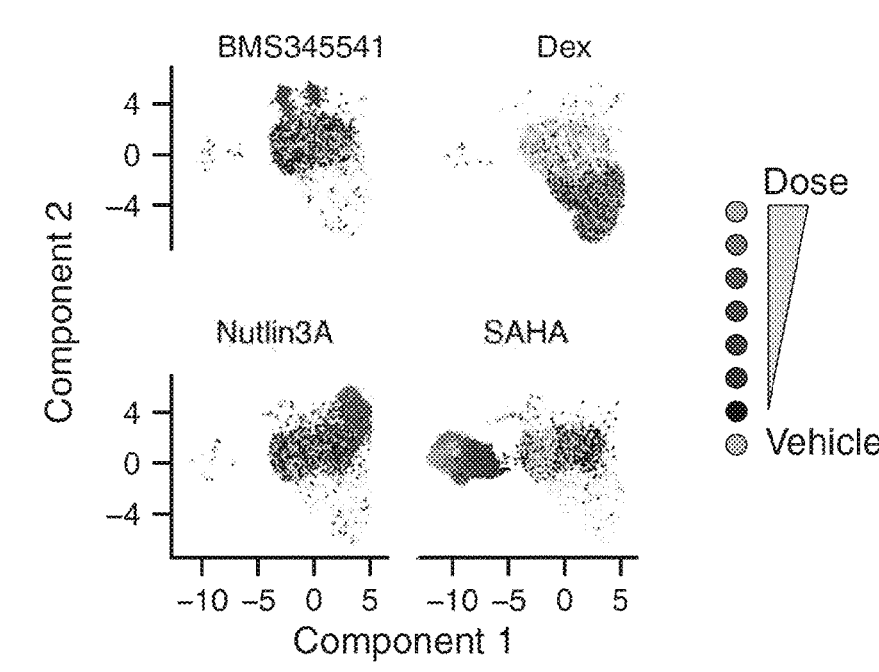
Figure 6D:
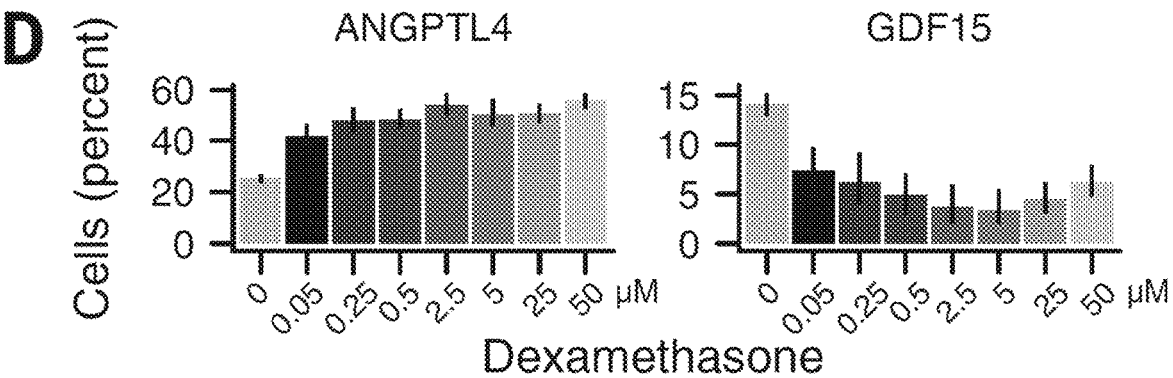
Figure 6E:
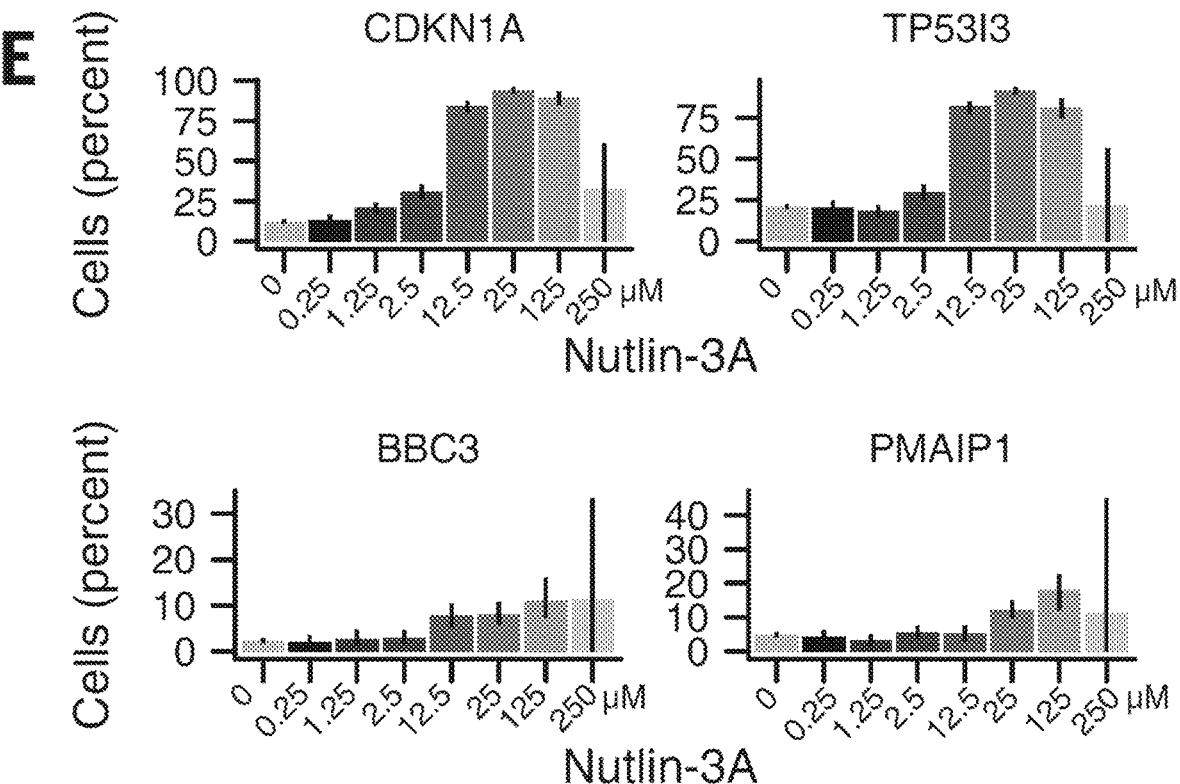
Figure 6F:
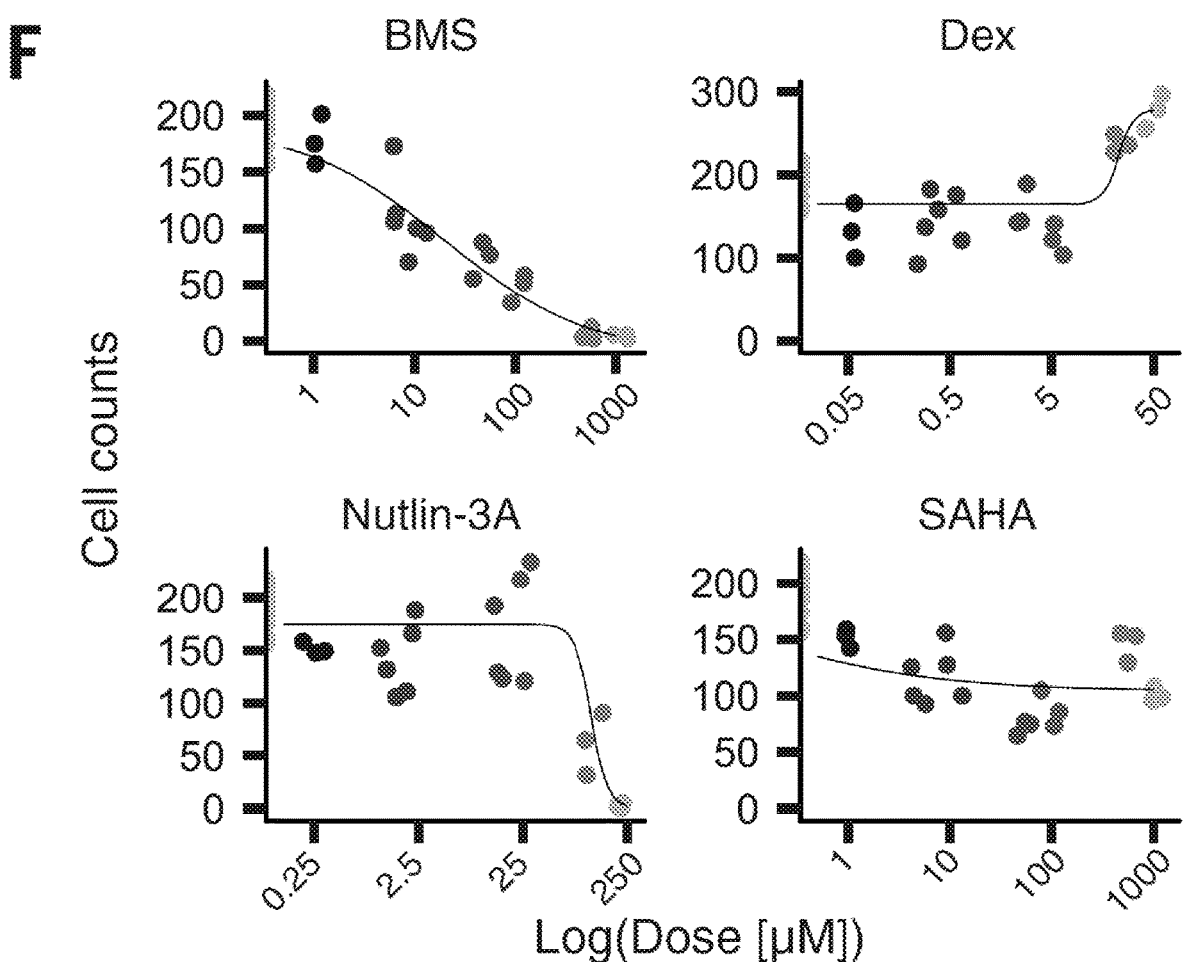
Figures 7A, 7B, 7C, 7D:
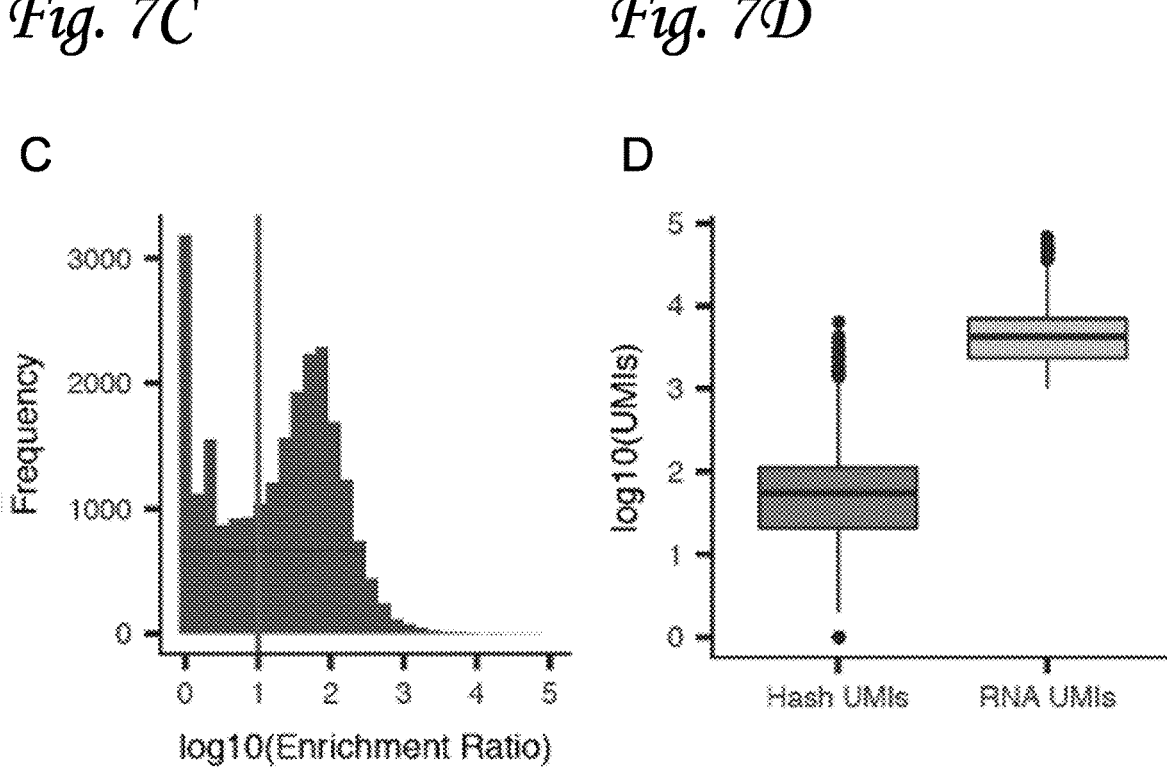
FIG. 7 shows sci-Plex distinguishes transcriptional responses of A549 cells to four small molecules and recovers dose-response estimates similar to established assays. A) Experimental layout of A549 cells in 96 well plates. Cells were treated for 24 hours in two 96 well plates using 7 doses (or vehicle) arrayed along each column. B) Cells that contained more than 30 hash oligo UMIs and C) had an enrichment ratio of greater than 10 were retained. D) Retained cells had a median hash UMI count of 78 and median RNA UMI count of 4,681. E) UMAP embedding of chemically perturbed A549 cells, equivalent to FIG. 2B but with cells colored by whether they were treated with vehicle or one of the four small molecules. F) UMAP embedding of chemically perturbed A549 cells, equivalent to FIG. 2B but with cells colored by cluster as defined using the density peak algorithm in Monocle 3. G) Cartoon depicting how pooling of barcoded nuclei preserves relative cell counts. H) Viability estimates from counting the proportion of recovered hashed nuclei (grey) vs. CellTiter-Glo (red, n=6). I) Scatter plot of inferred cell counts (x-axis) and CellTiter-Glo viability estimates (y-axis) across all treatments and doses tested (Pearson correlation and chi square test).
Figure 7E:
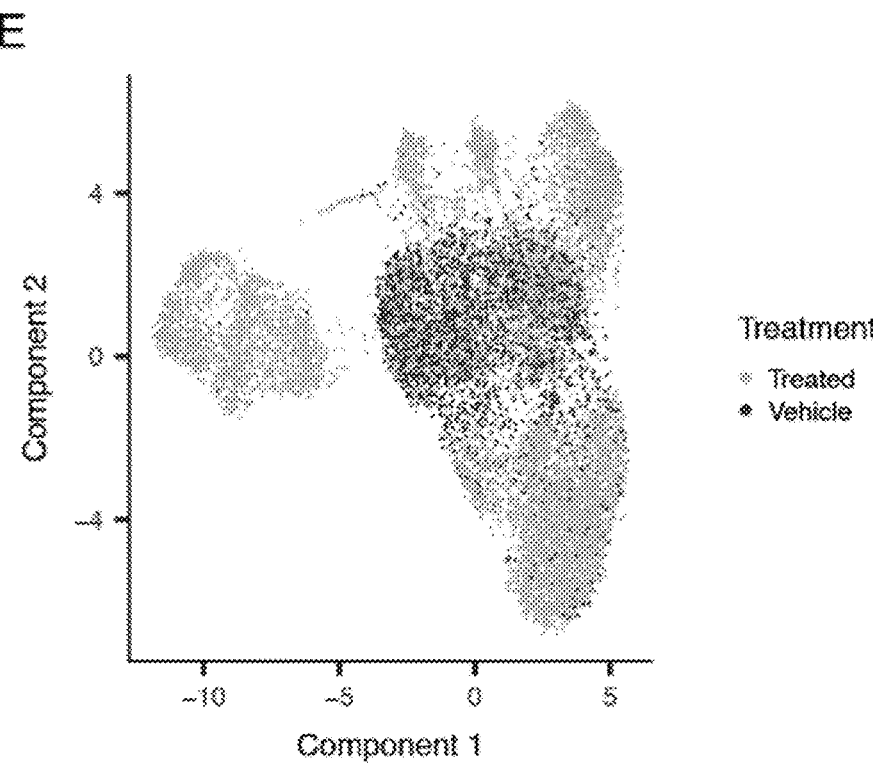
Figure 7F:
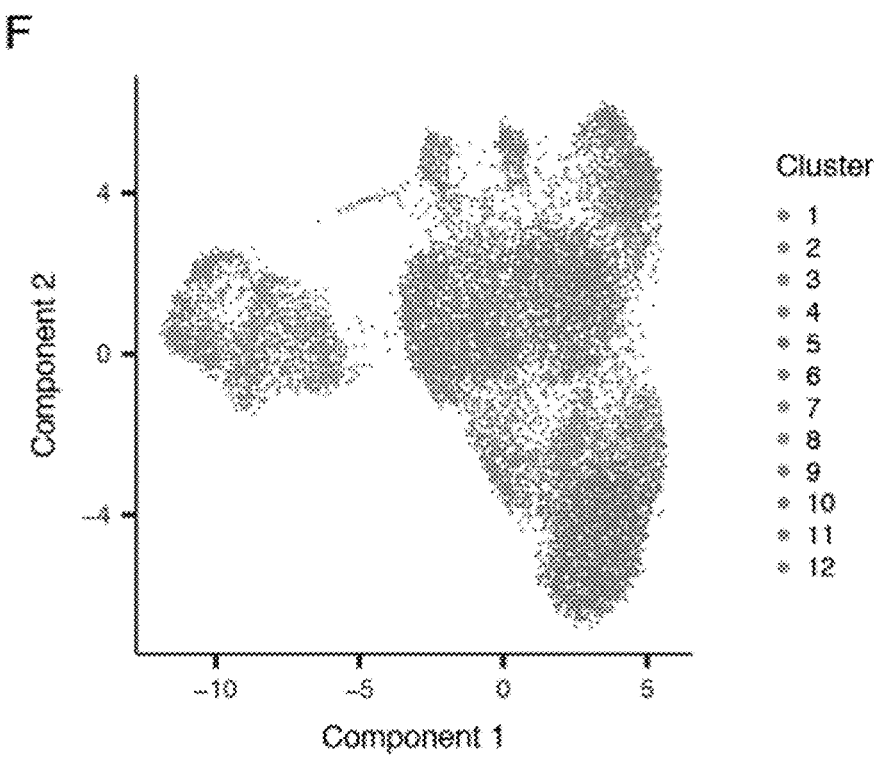
Figure 7G:
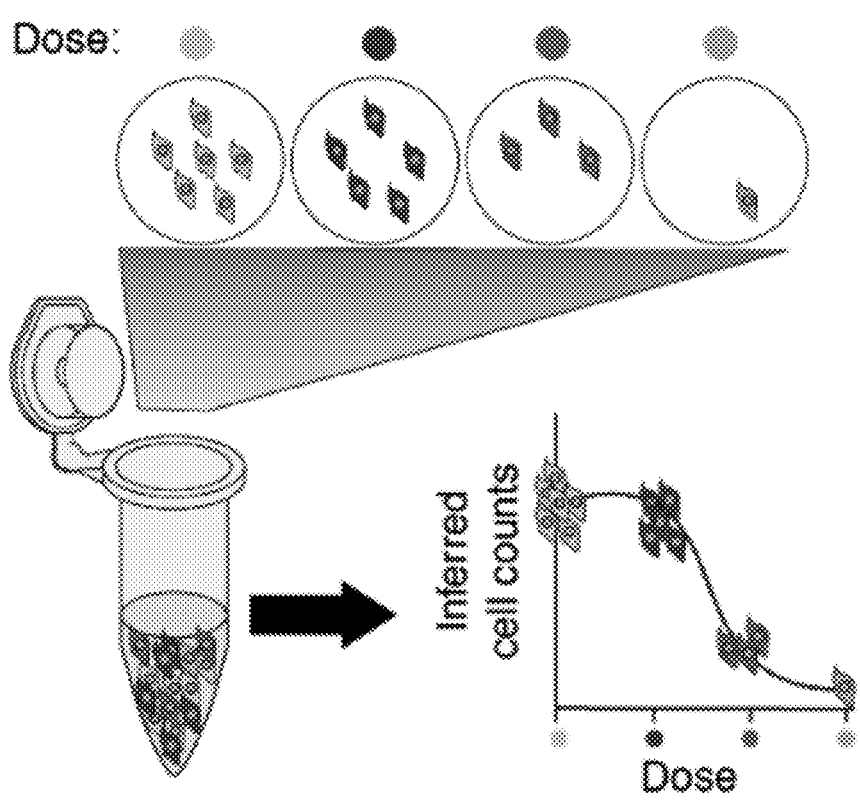

We next evaluated whether nuclear hashing could enable chemical screens by labeling cells that had undergone a specific perturbation, followed by single-cell transcriptional profiling as a high-content phenotypic assay. We exposed A549, a human lung adenocarcinoma cell line, to one of four compounds: dexamethasone (a corticosteroid agonist), nutlin-3a (a p53-Mdm2 antagonist), BMS-345541 (an inhibitor of nuclear factor kB-dependent transcription), or vorinostat [suberoylanilide hydroxamic acid (SAHA), an HDAC inhibitor], for 24 hours across seven doses in triplicate for a total of 84 drug-dose-replicate combinations and additional vehicle controls (FIG. 6A and FIG. 7A). We labeled nuclei from each well and subjected them to sci-RNA-seq2 (FIG. 7, B to D, and Table 1).

Figure 8A:
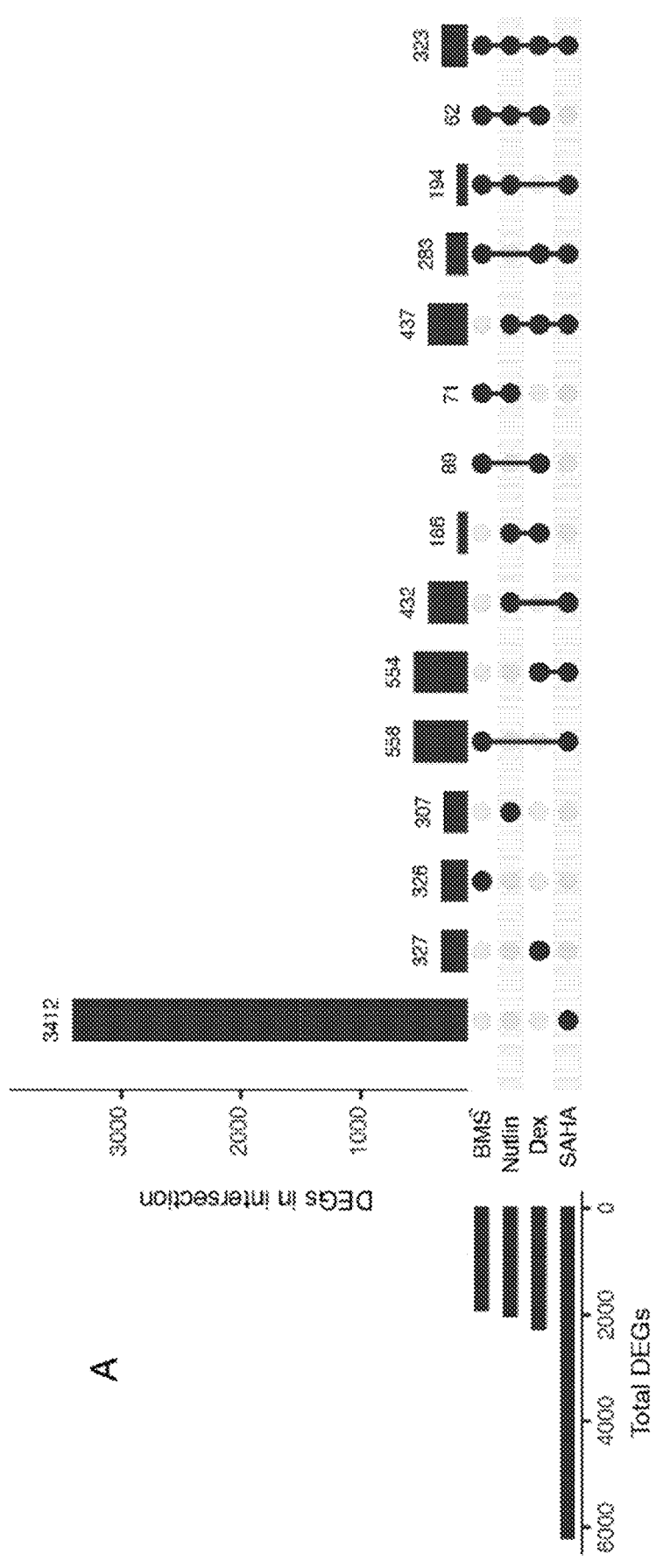
FIG. 8 shows dose-dependent differentially expressed genes (DEG) recover expected transcriptional modules. A) Upset plot displaying the intersections of dose-dependent DEGs between treatments (vertical bars) as well as the total number of dose-dependent DEGs per treatment (horizontal bars). A gene is defined as a dose-dependent DEG if the quasi-poisson regression model relating its expression in a given cell to the dose of drug that cell received shows a significant dose effect (Wald test) after Benjamini-Hochberg correction (FDR<0.05). See Methods for full details on regression modeling. The four leftmost vertical bars correspond to drug-specific dose-dependent DEGs, while the rightmost vertical bar corresponds to dosedependent DEGs shared by all four drugs. B) Gene set analysis (GSA) performed with dosedependent DEGs using the runGSA( ) function from the piano package and the Hallmarks gene set from MSigDB (45). Heatmap color indicates the value of the directional GSA enrichment statistic with values that were capped at either −10 or +10 for visualization.
Figure 8B:
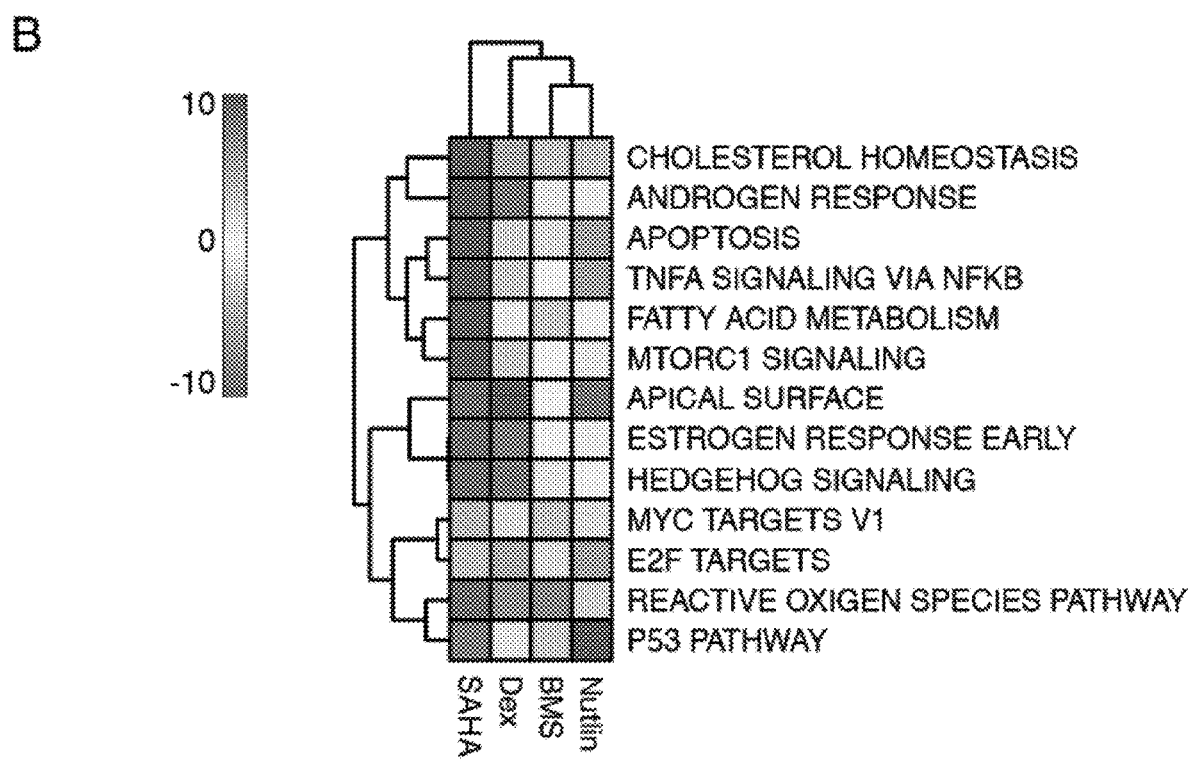

We used Monocle 3 (21) to visualize these data using Uniform Manifold Approximation and Projection (26) (UMAP) and Louvain community detection to identify compound specific clusters of cells, which were distributed in a dose-dependent manner (FIG. 6, B and C, and FIG. 7, E and F). To quantify the "population average" transcriptional response of A549 cells to each of the four drugs, we modeled each gene's expression as a function of dose through generalized linear regression. A total of 7561 genes were sensitive to at least one drug, and 3189 genes were differentially expressed in response to multiple drugs (FIG. 8A and data not shown). These included canonical targets of dexamethasone (FIG. 6D) and nutlin-3a (FIG. 6E). Gene ontology analysis of differentially expressed genes revealed the involvement of drug-specific pathways (e.g., hormone signaling for dexamethasone; p53 signaling for nutlin-3a; FIG. 8B). Additionally, we evaluated whether the number of cells recovered at each concentration could be used to infer toxicity akin to traditional screens. After fitting a response curve to the recovered cellular counts, we inferred a "viability score" from sci-plex data, a metric that was concordant with "gold standard" measurements (FIG. 6F and FIG. 7, G to I).

58

Sci-Plex Scales to Thousands of Samples and Enables HTS

Figure 9A:
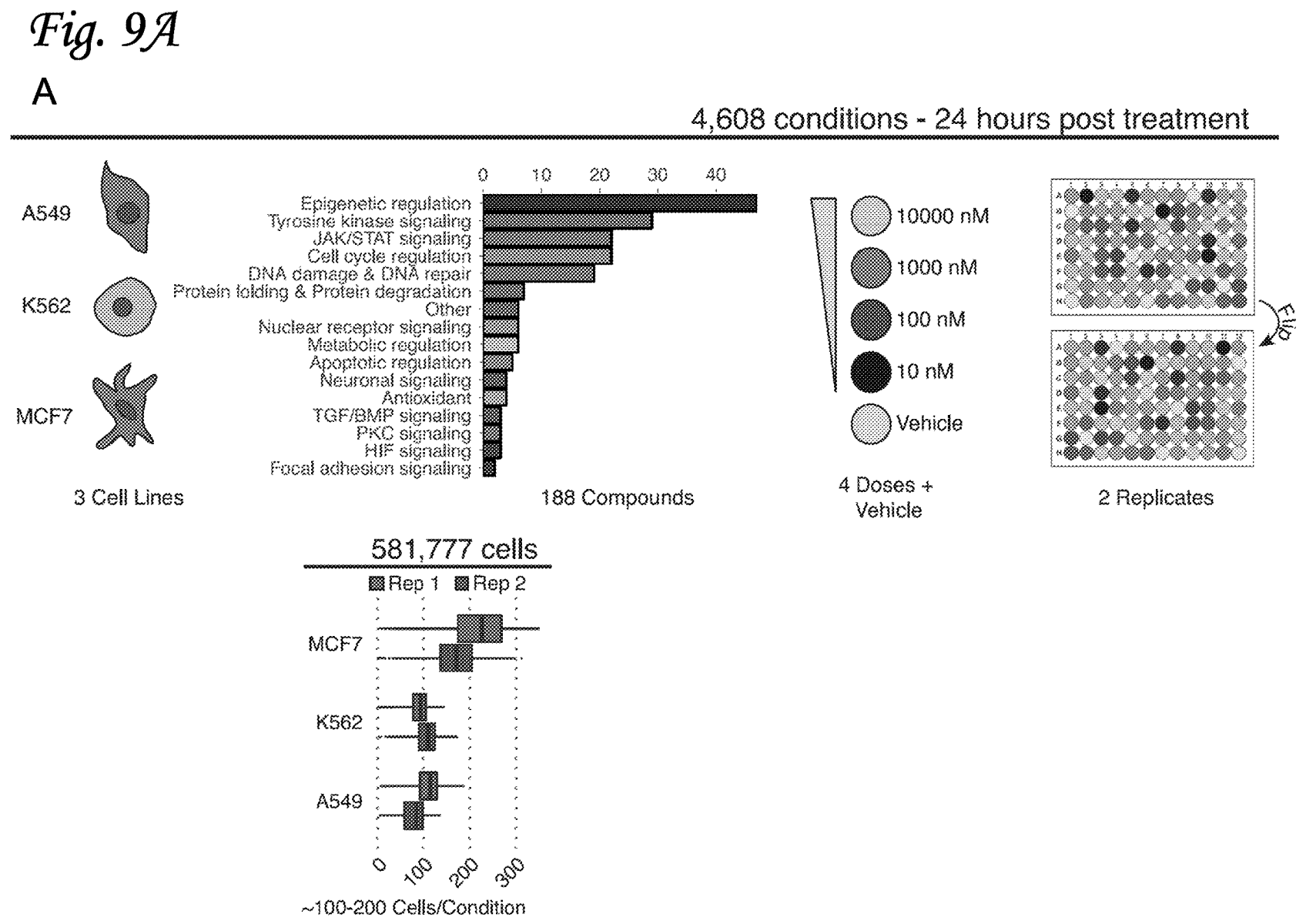
Figure 10B:
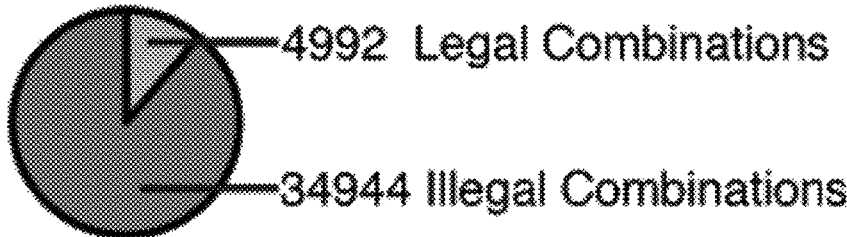
FIG. 10 shows hash-based cell labeling in large-scale sci-Plex experiment. A) Hashing design for sci-Plex with 188 compounds. The experiment used 52×96-well plates where each well was marked by a combination of two oligos, one specific to a single 96-well culture plate and another specific to a well within that culture plate. B) Although this could theoretically be implemented with just 96 well hash oligos, we instead used 768, which meant that out of the 39,936 possible pairings of plate and well hash oligos, only a minority (12.5%) of combinations were expected ('legal'), while most were unexpected ('illegal') C) Observed pairings of plate and well hash oligos were strongly enriched for 'legal' combinations. D) Scatter plot of HEK293T and NIH3T3 cells seeded in a single RT well of the large-scale sci-Plex experiment. E-H) Hash UMI (panels E & G) and enrichment ratio (panels F & H) cutoffs used for well hash oligos (panels E & F) and plate hash oligos (panels G & H). Enrichment ratio cutoffs corresponds to greater than 5-fold enrichment. Hash UMI cutoffs correspond to >5.
Figure 10C:
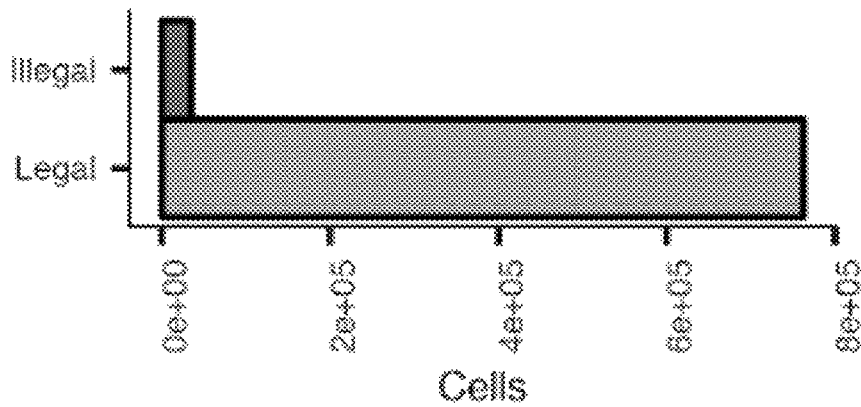
Figure 10D:
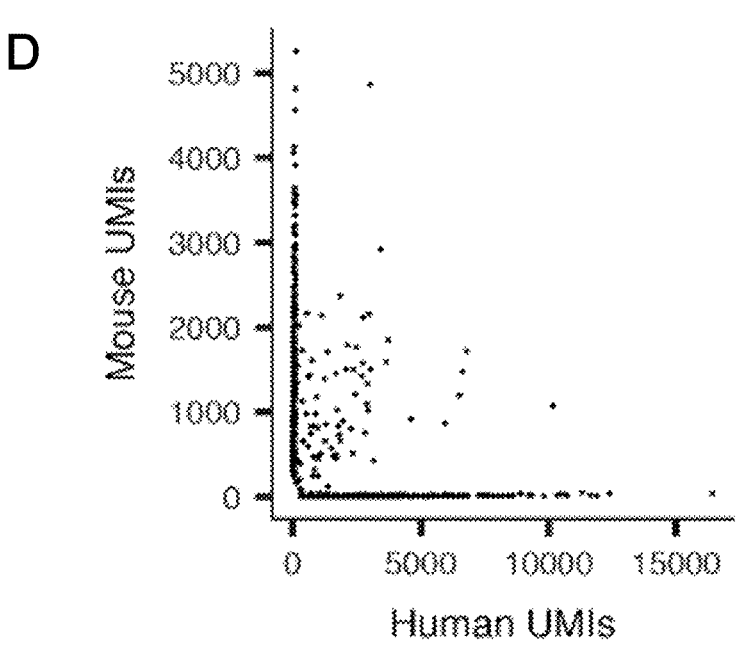
Figure 10E:
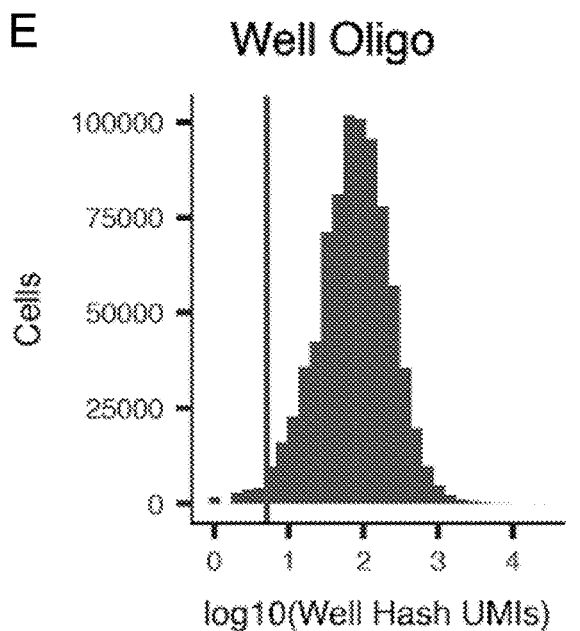
Figure 10F:
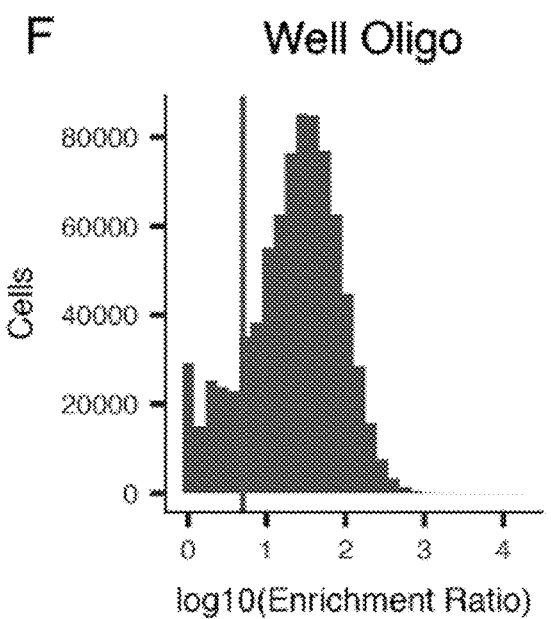
Figure 10G:
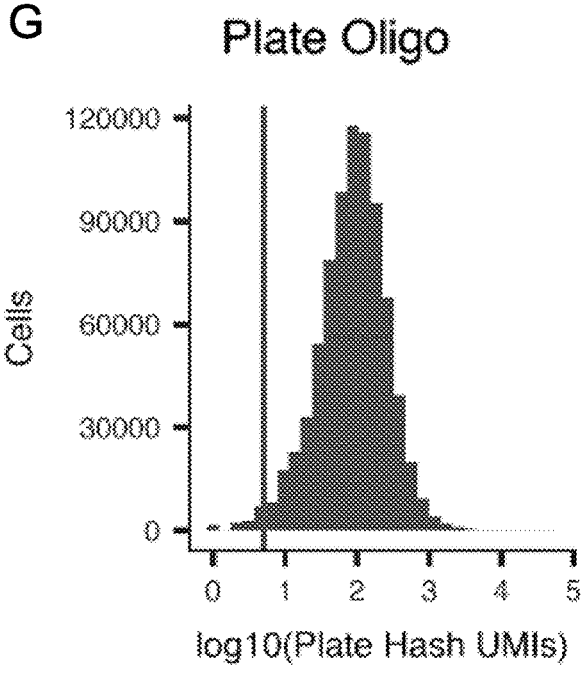
Figure 10H:
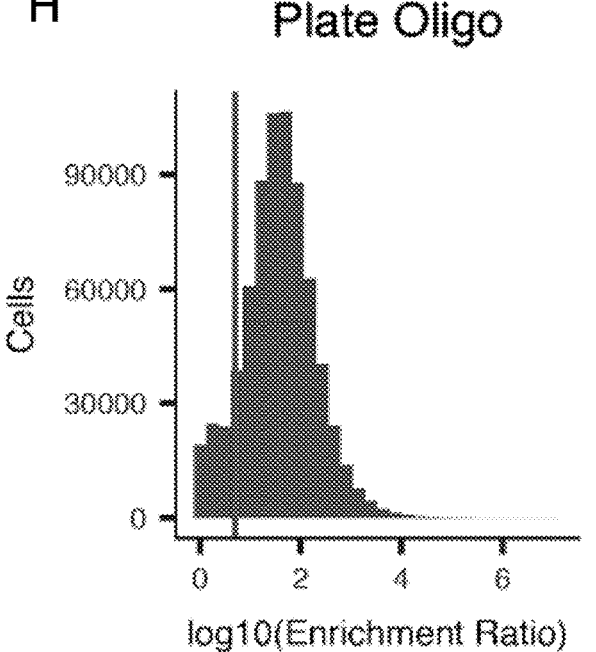
Figures 11A, 11B, 11C:
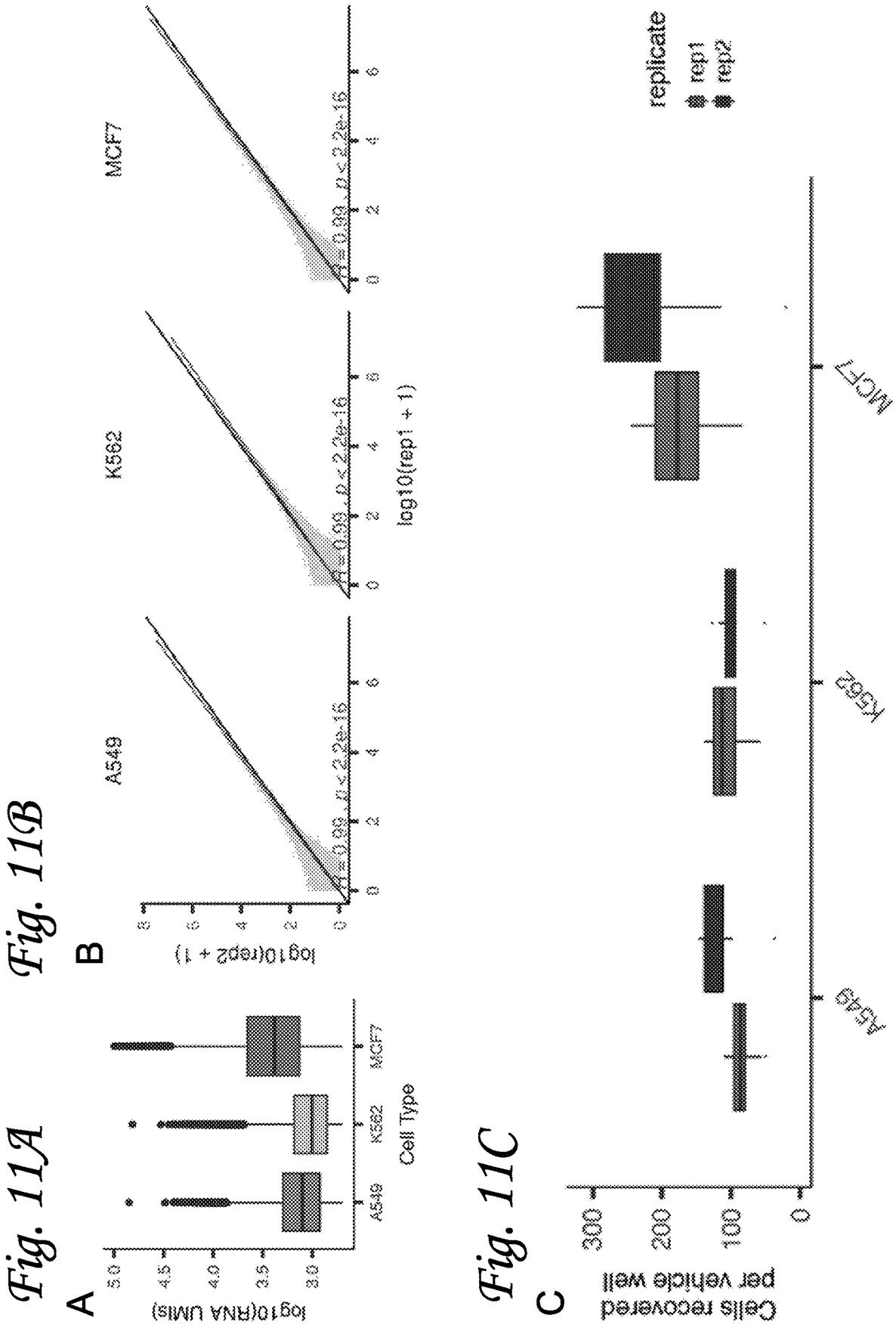
FIG. 11 shows quality control metrics for large-scale sci-Plex experiment. A) Log-scale boxplot of number of RNA UMIs for cells that passed hash and RNA UMI cutoff filters for each of three cell lines. B) Correlation of size factor-normalized counts for genes between replicates for each of the three cell lines. Black line indicates y=x. Red line is the fit with Pearson correlation shown. C) Boxplots showing the number of vehicle cells recovered from each of 8 vehicle control wells within each replicate for A549, K562 and MCF7 cells.
Figure 12A:
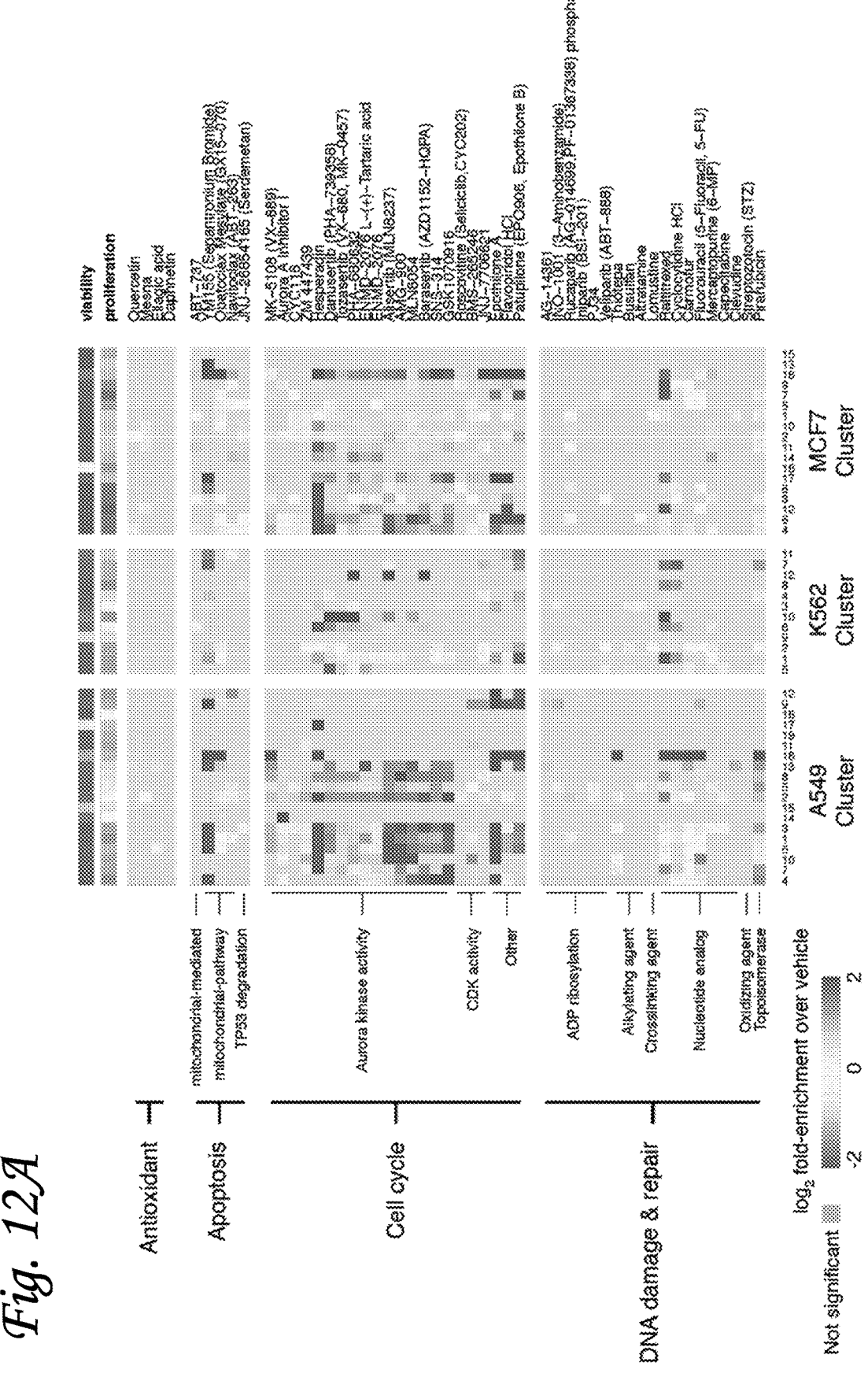
FIG. 12 shows exposing cells to compounds alters their distribution across cell clusters. Heatmap showing the log-transformed ratio of cells treated with a particular drug compared to vehicle control cells in each Louvain community. Columns correspond to clusters in PCA space (see FIG. 13A-C) and rows correspond to compounds, annotated by pathway and target. A gray entry denotes a compound that is not significantly enriched or depleted relative to vehicle in the corresponding cluster (Fisher's exact test, FDR<1%).
Figure 12B:
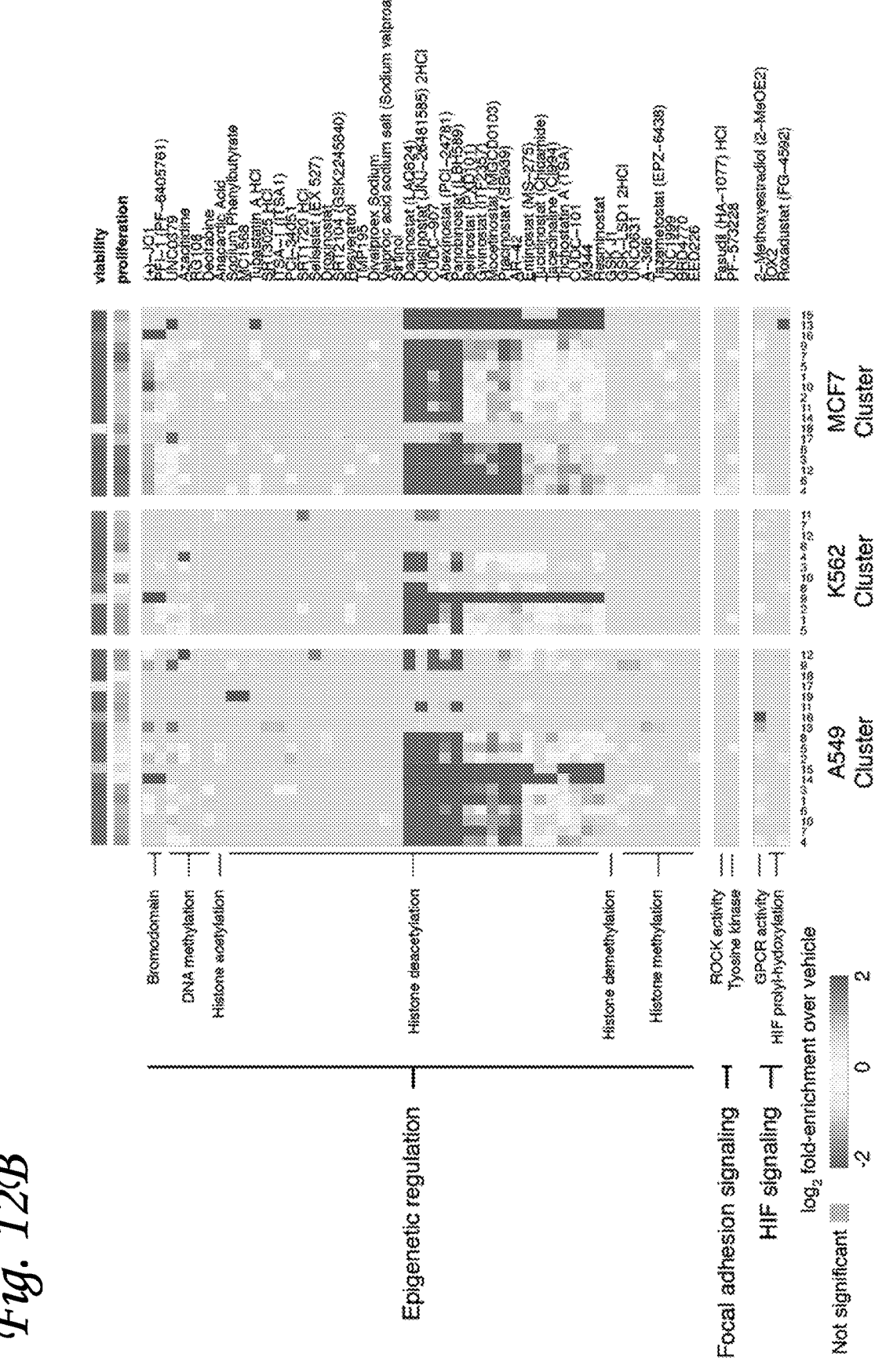
Figure 12C:
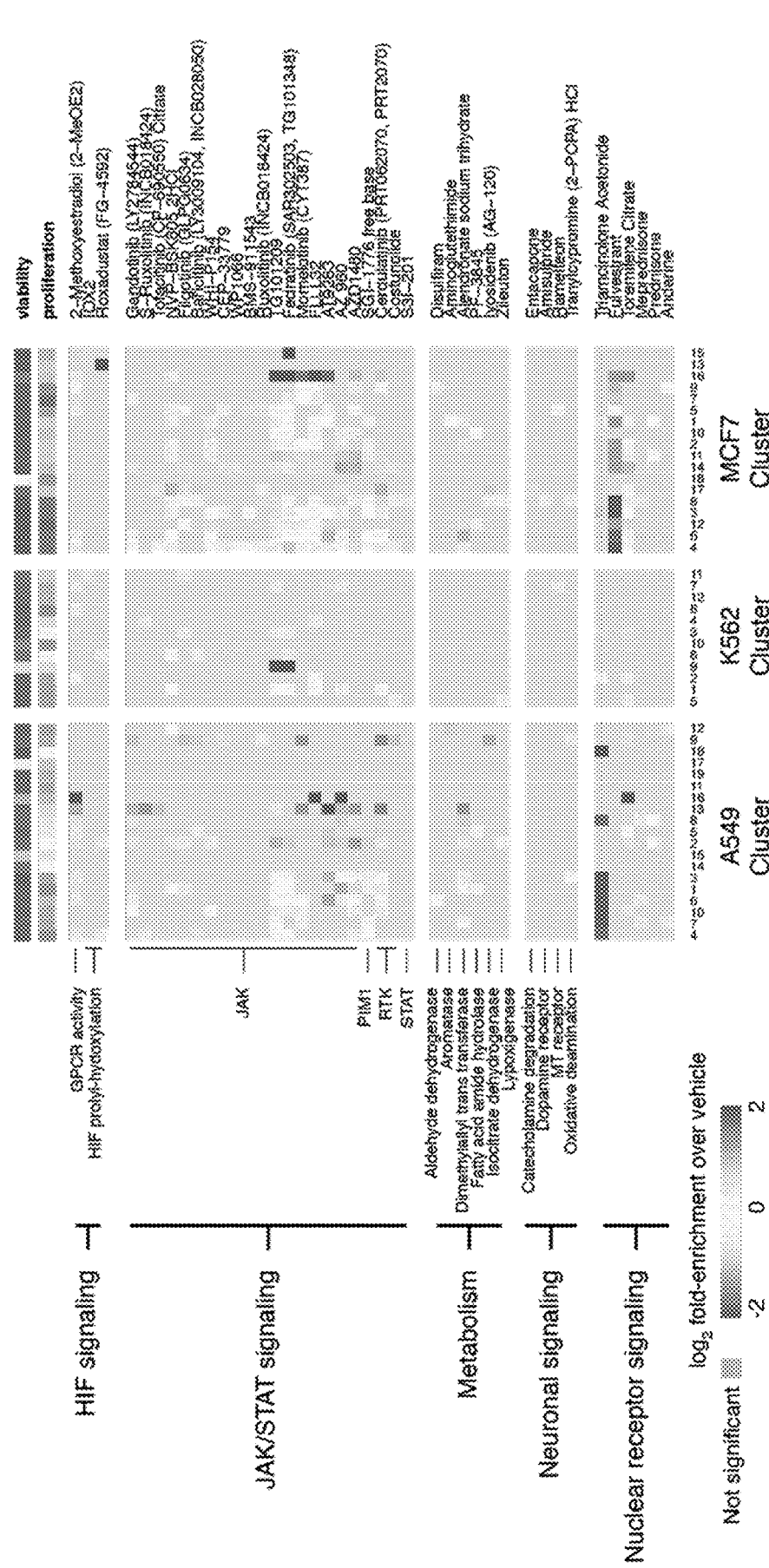
Figure 12D:
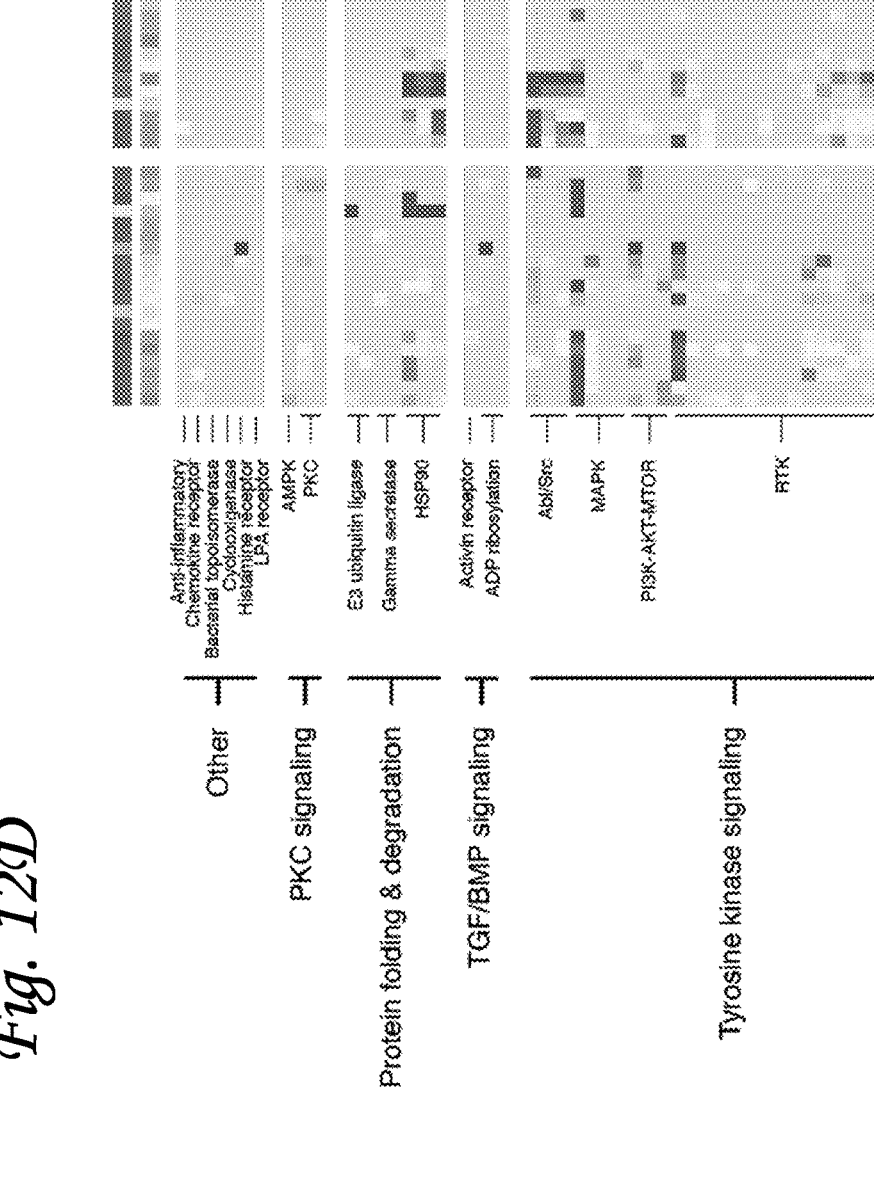

To assess how sci-Plex scales for HTS, we performed a screen of 188 compounds targeting a diverse range of enzymes and molecular pathways (FIG. 9A). Half of this panel was chosen to target transcriptional and epigenetic regulators. The other half was chosen to sample diverse mechanisms of action. We exposed three well-characterized human cancer cell lines, A549 (lung adenocarcinoma), K562 (chronic myelogenous leukemia), and MCF7 (mammary adenocarcinoma), to each of these 188 compounds at four doses (10 nM, 100 nM, 1 mM, and 10 mM) in duplicate, randomizing compounds and doses across well positions in replicate culture plates (data not shown). These conditions, together with vehicle controls, accounted for 4608 of 4992 independently treated cell populations in this experiment. After treatment, we lysed cells to expose nuclei, hashed them with a specific combination of two oligos (FIG. 10A), and performed sci-RNA-seq3 (21). After sequencing and filtering based on hash purity (FIG. 10, B to F), we obtained transcriptomes for 649,340 single cells, with median mRNA UMI counts of 1271, 1071, and 2407 for A549, K562, and MCF7, respectively (FIG. 11A). The aggregate expression profiles for each cell type were highly concordant between replicate wells (Pearson correlation=0.99) (FIG. 11B).

Figures 13A, 13B, 13C:
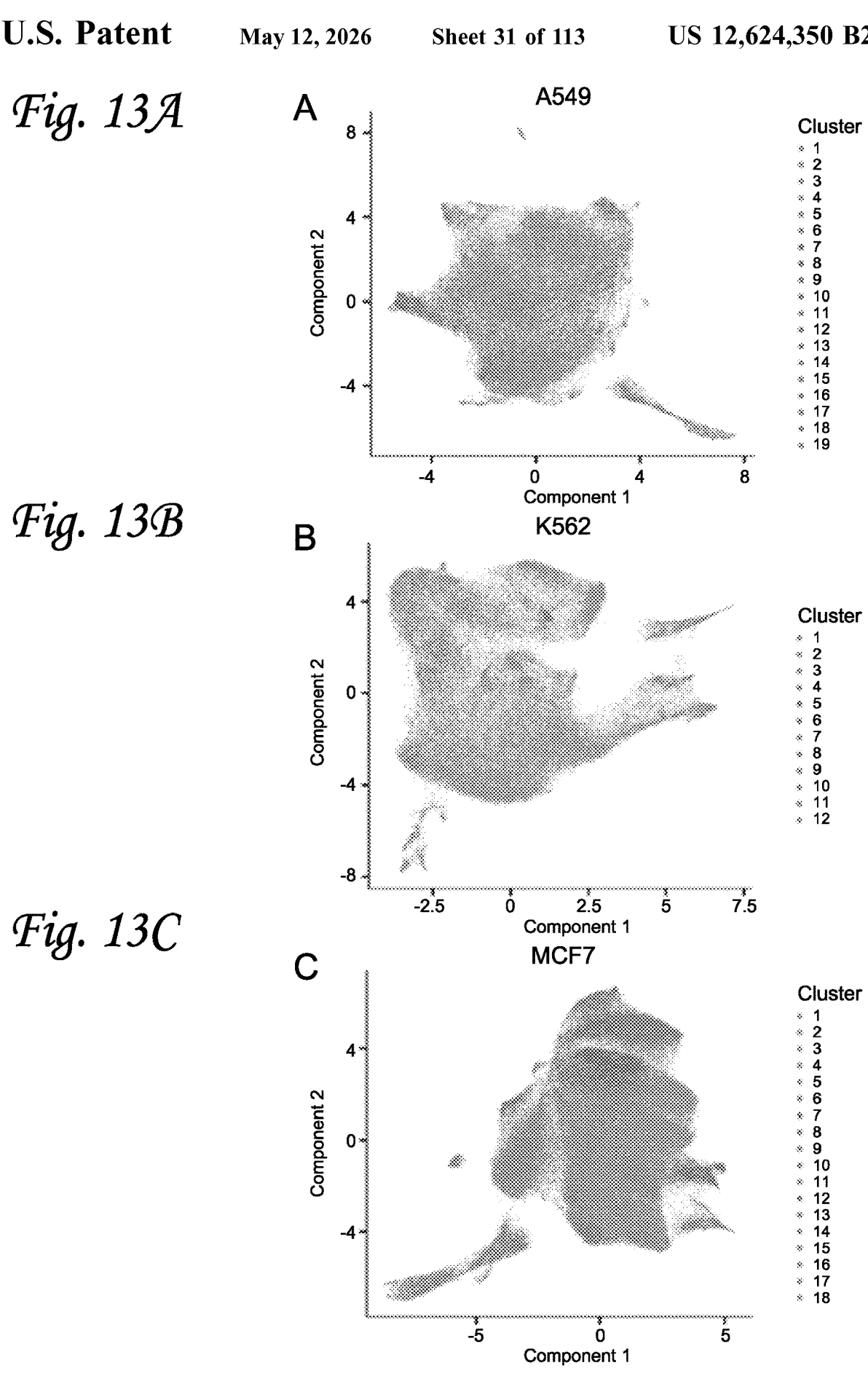
FIG. 13 shows sci-Plex identifies pathway-specific enrichment of compounds across UMAP clusters. A-C) UMAP embedding from FIG. 3B colored by cells' assignment to Louvain communities across PCA space for A549 (panel A), K562 (panel B) and MCF7 (panel C) cells. D) UMAP embedding of A549 cells from FIG. 3B. Cells treated with the glucocorticoid receptor (GR) agonist triamcinolone acetonide are highlighted in green while all other cells are colored grey. These cells comprise the vast majority (95%) of the cells in cluster 18 from panel A. E) Percent of A549 cells expressing the GR target genes ANGPTL4 and GDF15, as a function of increasing doses of the synthetic GR agonist triamcinolone acetonide. F-H) UMAP embedding of A549 cells colored by cells treated with varying doses of epothilone A (F), epothilone B (G), or colored by proliferation index (H). Insets display magnified views of distinct foci induced upon treatment. The treatments with the highest number of cells in each bounding box are indicated in panel H with the number of cells in parentheses.
Figure 13D:
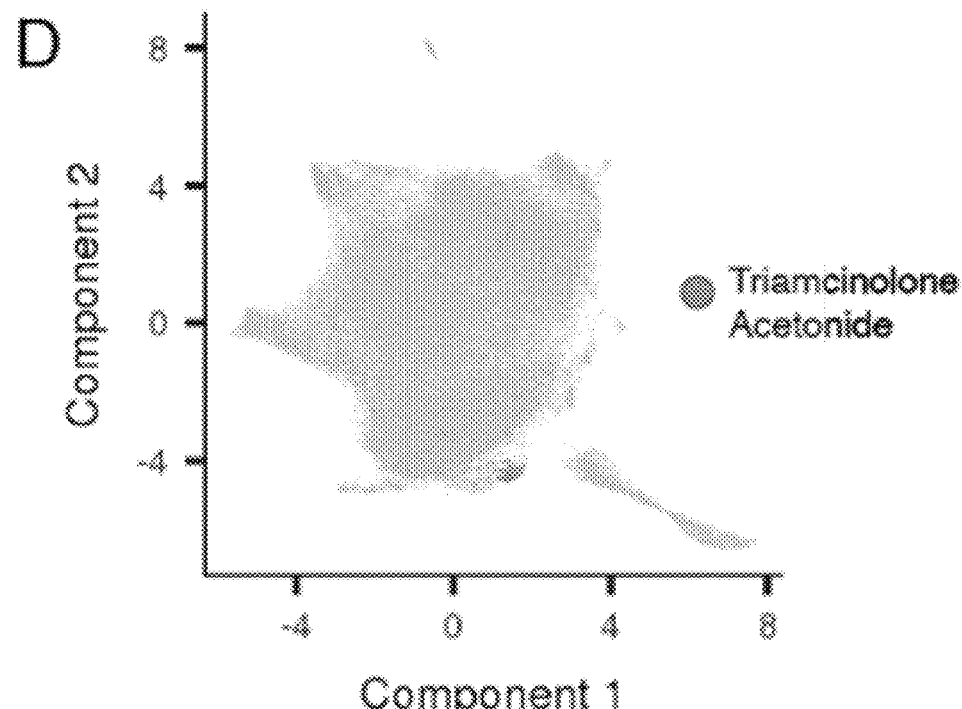
Figure 13E:
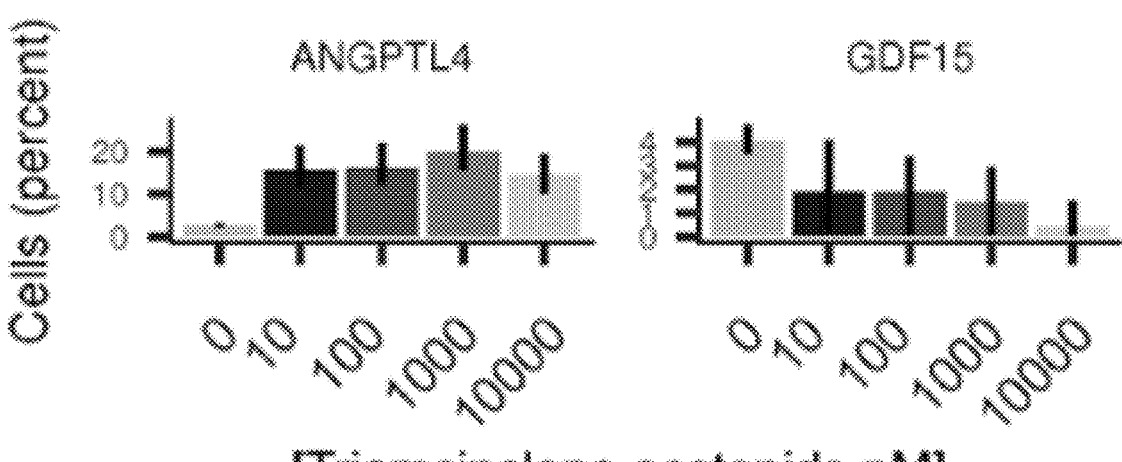
Figure 13F:
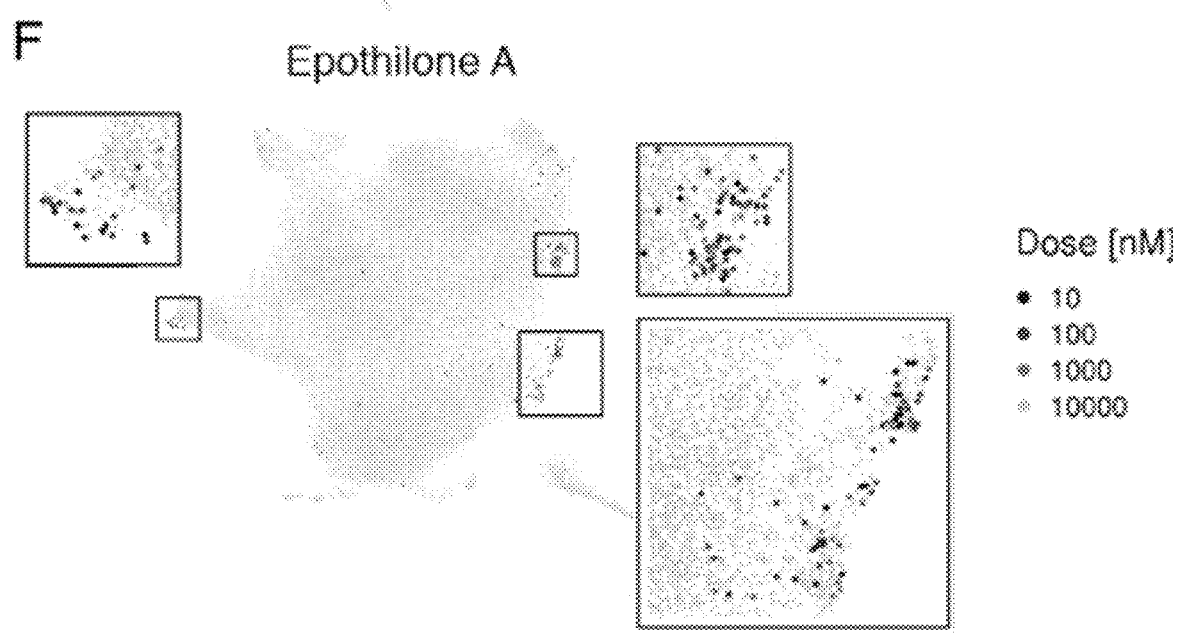
Figure 13G:
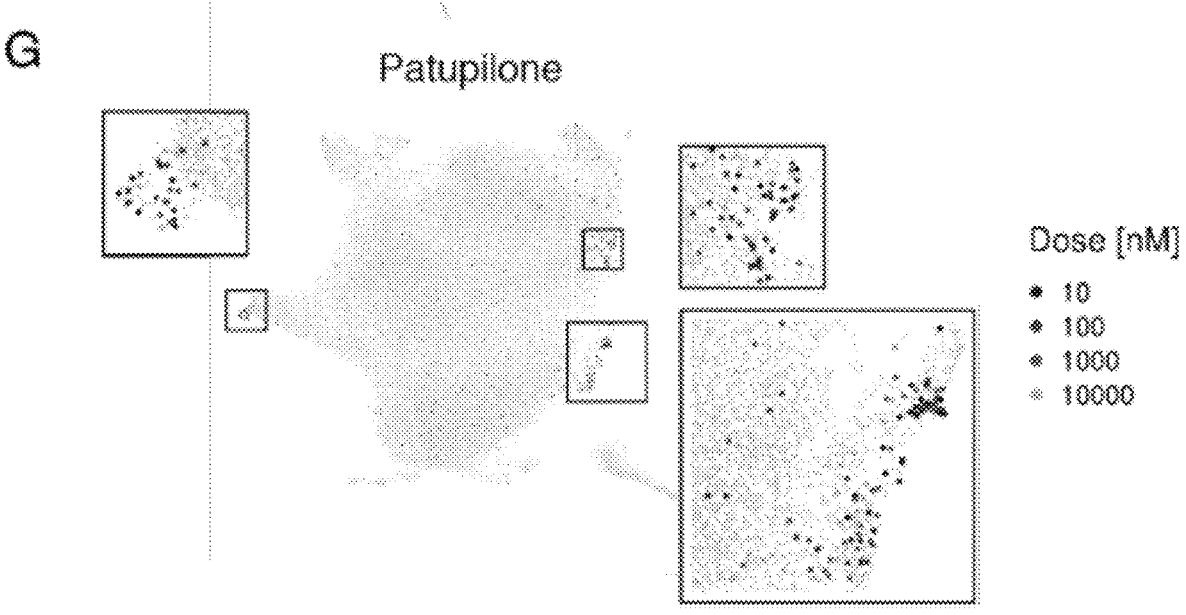
Figure 13H:
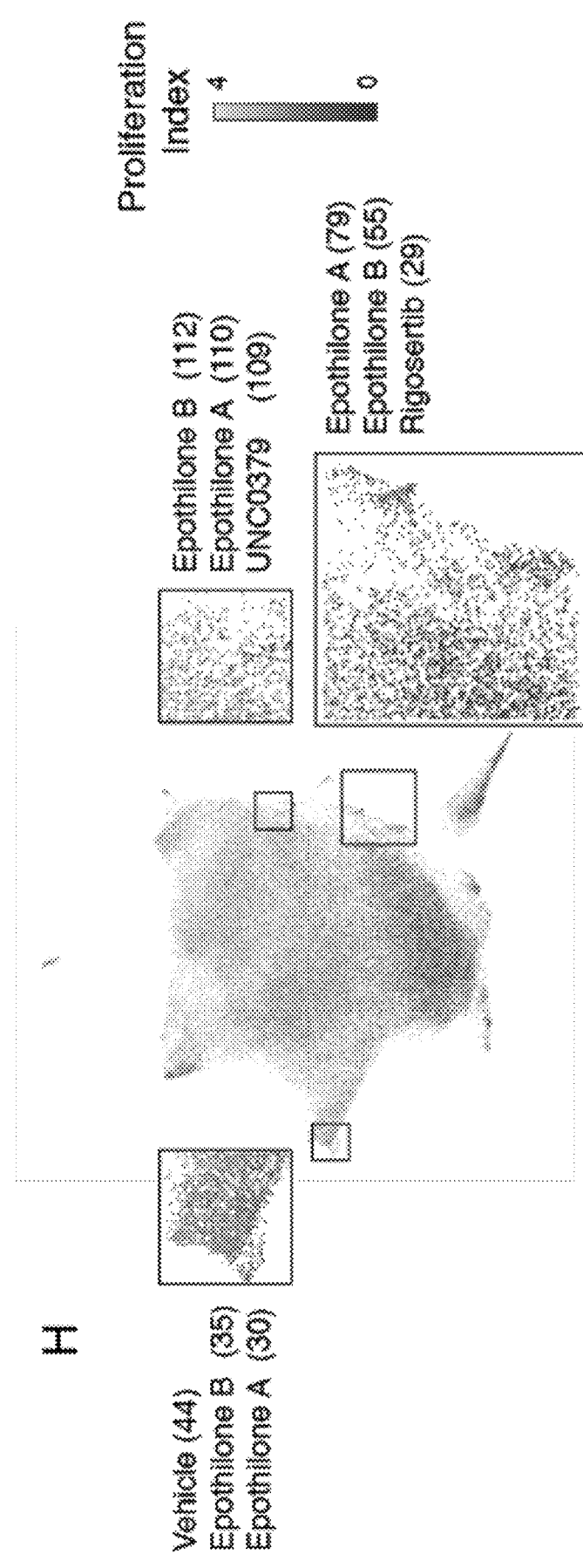

Visualizing sci-RNA-seq profiles separately for each cell line revealed compound-specific transcriptional responses and patterns that were common to multiple compounds. For each of the cell lines, UMAP projected most cells into a central mass, flanked by smaller clusters (FIG. 9B). These smaller clusters were largely composed of cells treated with compounds from only one or two compound classes (FIGS. 12 and 13, A to C). For example, A549 cells treated with triamcinolone acetonide, a synthetic glucocorticoid receptor agonist, were markedly enriched in one such small cluster, comprising 95% of its cells [Fisher's exact test, false discovery rate (FDR)<1%; FIG. 13, D and E]. Although many drugs were associated with a seemingly homogeneous transcriptional response, we also identified cases in which distinct transcriptional states were induced by the same drug. For example, in A549, the microtubule-stabilizing compounds epothilone A and epothilone B were associated with three such focal enrichments, each composed of cells from both compounds at all four doses (FIG. 13, F and G). The cells in each focus were distinct from one another, but transcriptionally similar to other treatments: a recently identified microtubule destabilizer, rigosertib (27); the SETD8 inhibitor UNC0397; or untreated proliferating cells (FIG. 13H).

Figure 14:
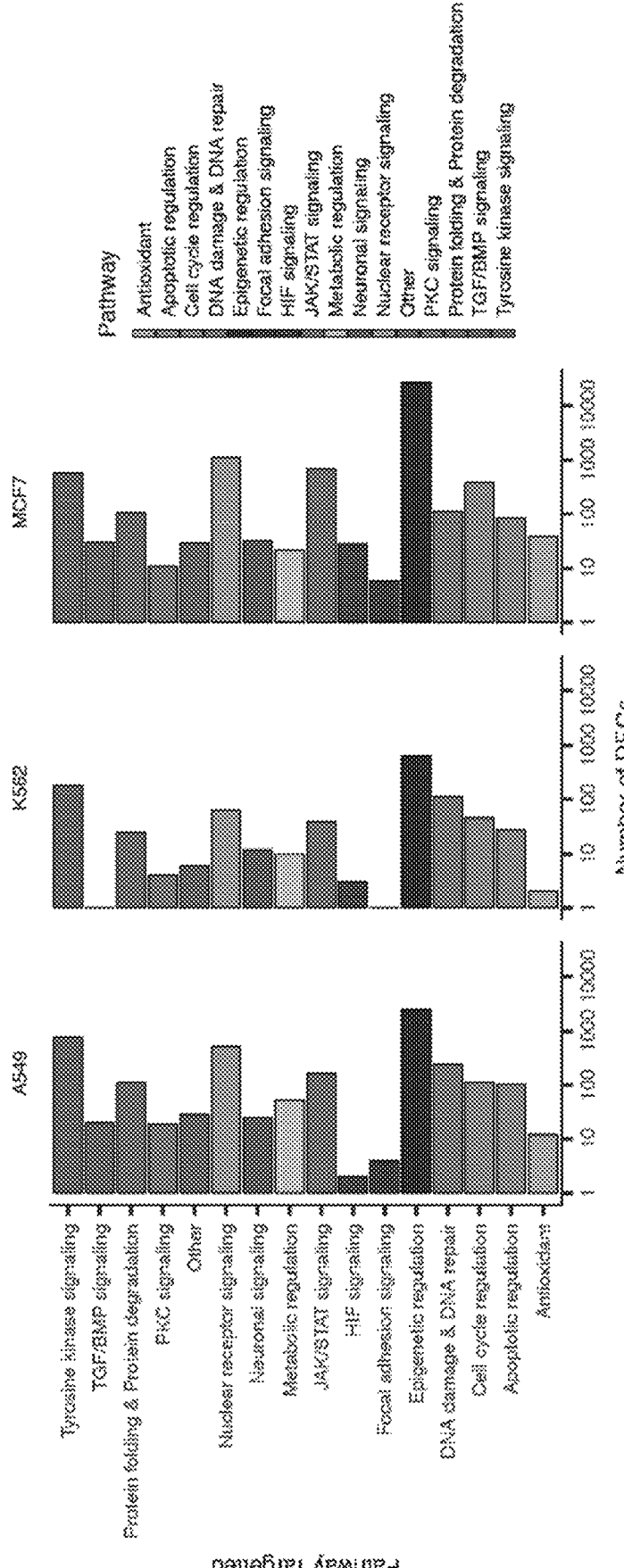
FIG. 14 shows number of dose-dependent differentially expressed genes detected per compound category. Significant dose-dependent differentially expressed genes (FDR<0.05) are grouped by cell line and colored by targeted pathway.
Figures 15A, 15B:
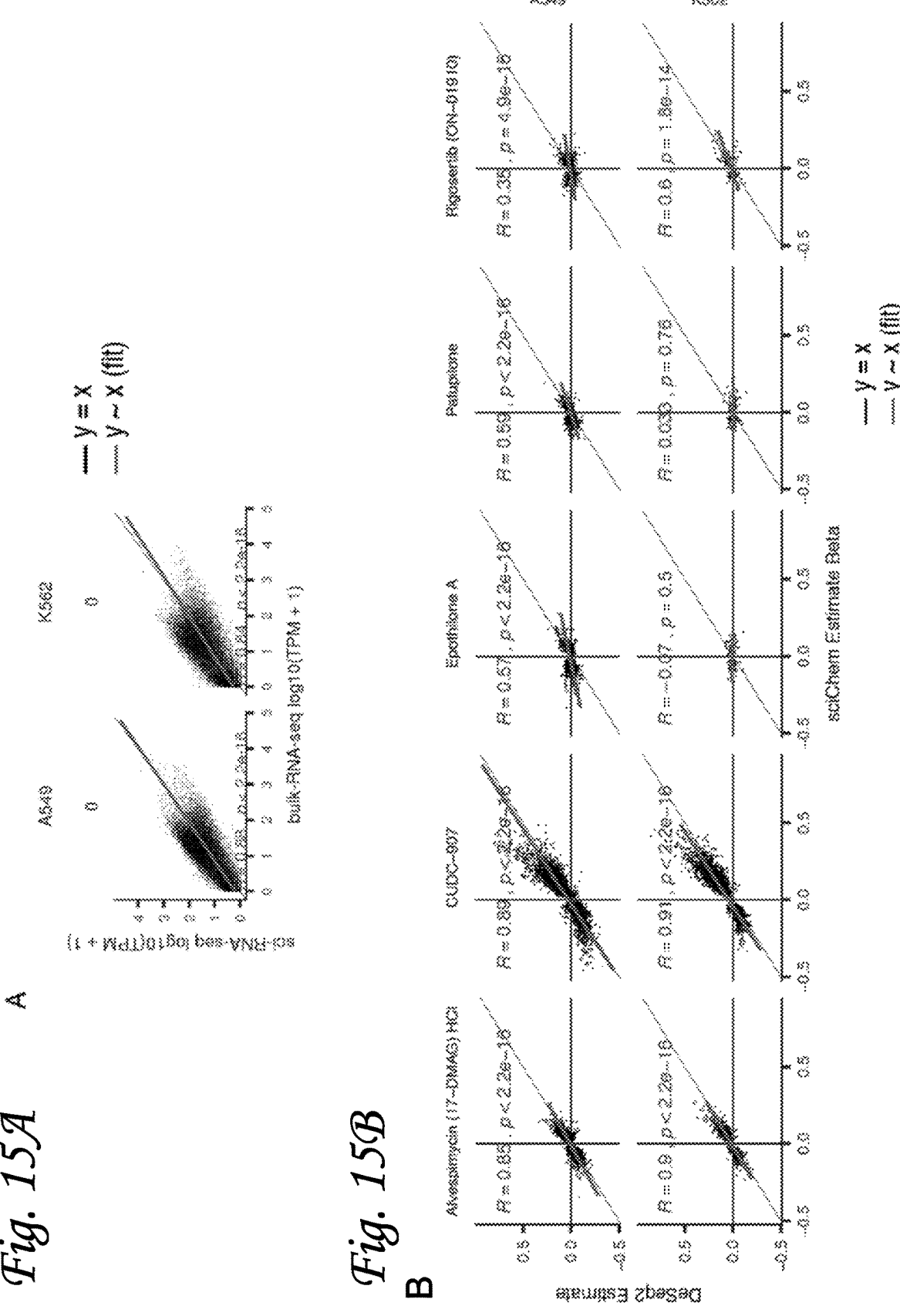
FIG. 15 shows correlation of "pseudobulk" sci-Plex with bulk-RNA-seq. A) Log 10 transcripts per million (TPM) for protein-coding genes measured by bulk RNA-seq (xaxes) vs. size factor-normalized, aggregated single cell profiles for vehicle treated cells from sci-Plex (y-axis). Results are shown for both A549 and K562 cells. Black line indicates the line y=x, while the blue line shows the linear fit with Pearson correlation shown. B) Scatter plots, for selected compounds, comparing statistically significant estimates derived from linear models fit to single cell data (x-axes) vs. estimates derived from bulk RNA-seq using DESeq2 (y-axes). Black line indicates y=x. Blue line is the fit with Pearson correlation shown.
Figure 16A:
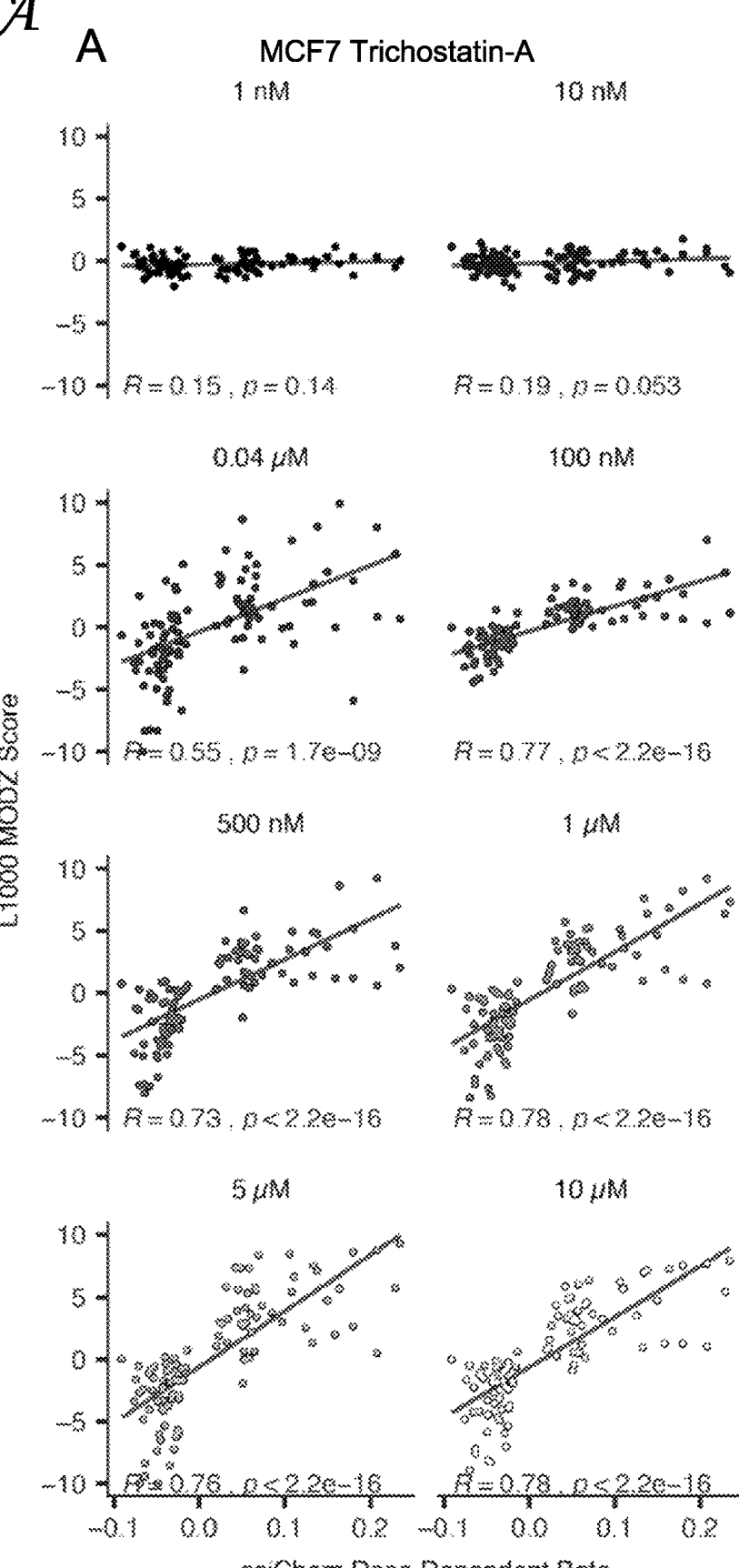
FIG. 16 shows moderated Z scores from the L1000 assay correlate with dosedependent betas from sci-Plex. A) For a selected compound-cell line combination (trichostatin A in MCF7 cells), we plot moderated Z scores from the L1000 assay with treatment for 24 hrs at each of eight doses (y-axes) (11) vs. dose-dependent betas from sci-Plex data (x-axes). All genes that are part of the L1000 assay and significant for dose-dependent effects with sci-Plex (p-value <0.01) are shown. Line is the fit with Spearman correlation shown. B) Boxplot of Spearman correlations between significant sci-Plex computed dose-dependent betas and L1000 moderated Z-score values from LINCS L1000 data for measured genes at the highest dose in MCF7 cells. Compounds are presented as grouped by the pathway they target. Red point corresponds to fluvestrant. C) Similar to panel A, but for fluvestrant in MCF7 cells and at the highest dose (10 μM). D) Similar to panel B, but for A549 cells. Red point corresponds to triamcinolone acetonide. E) Similar to panel A, but for triamcinalone acetonide in A549 cells and at the highest dose (10 μM).
Figures 16B, 16C:
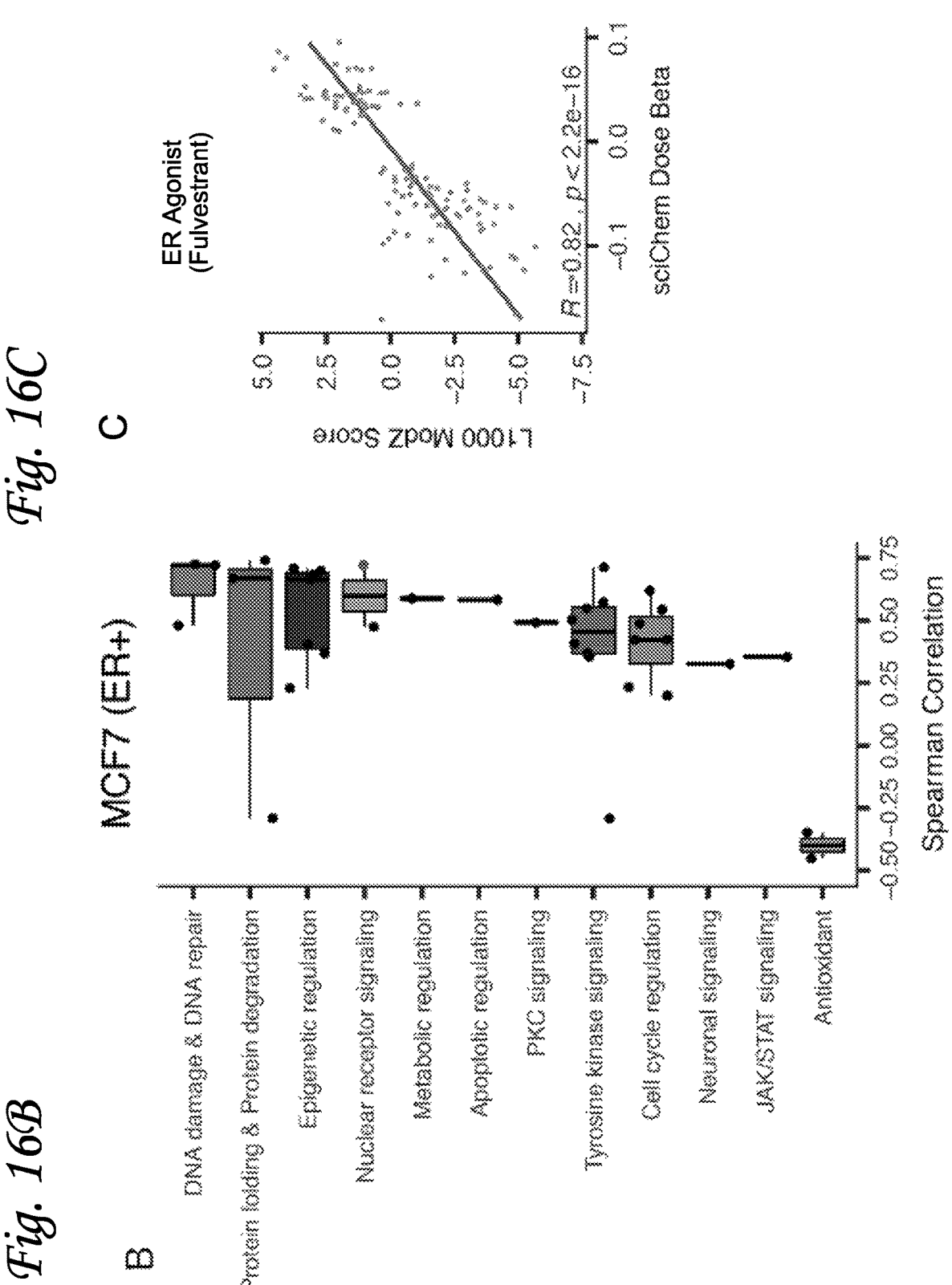
Figures 16D, 16E:
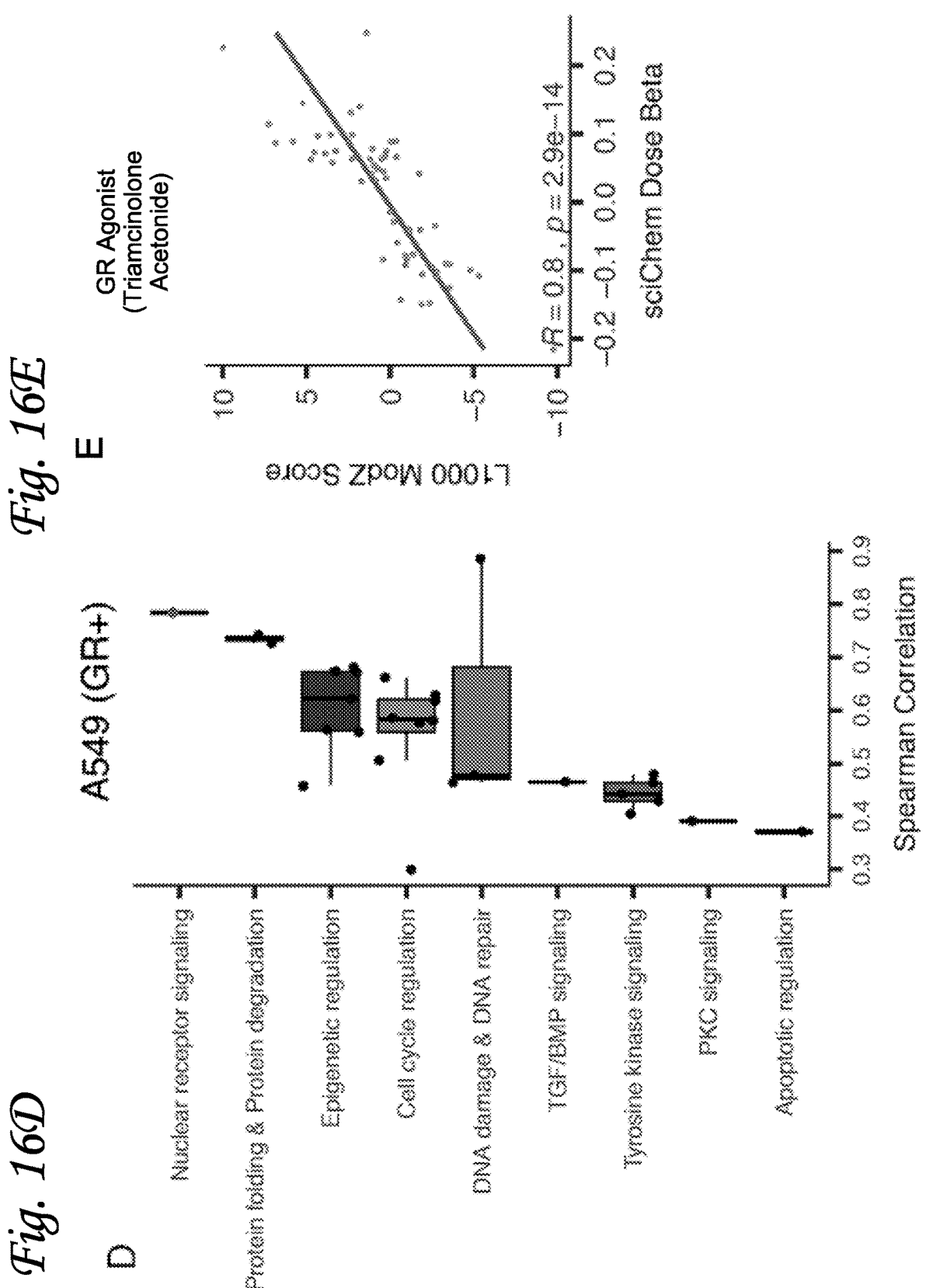
Figure 17G:
FIG. 17 shows single cell measurements reveal variation in proliferation status in vehicle treated cell and across each dose of each drug. A-C) UMAP projection of A549(A), K562 (B) and MCF7 (C) colored by proliferation index. High proliferation index indicates an increase in the aggregate expression of transcripts that are markers for G1/S phase or G2/M phase (43). (D-F) Density plot of cell cycle distribution for compound-treated cells (blue fill) or vehicle-treated cells (red line). Grey line indicates cutoff used to distinguish proliferating cells (greater than cutoff) vs. non-proliferating cells (less than cutoff). G-I) Relationship between the percentage of cells designated as low proliferation at each dose of each drug (x-axis) versus the median estimated viability of that combination (y-axis). Each black point corresponds to cells treated with the same dose of a given drug. Red points correspond to vehicle treatment. J) Volcano plot depicting the log 2 fold change for significant (q value <0.01) differentially expressed genes between high and low fractions of vehicle treated cells.
Figure 17H:
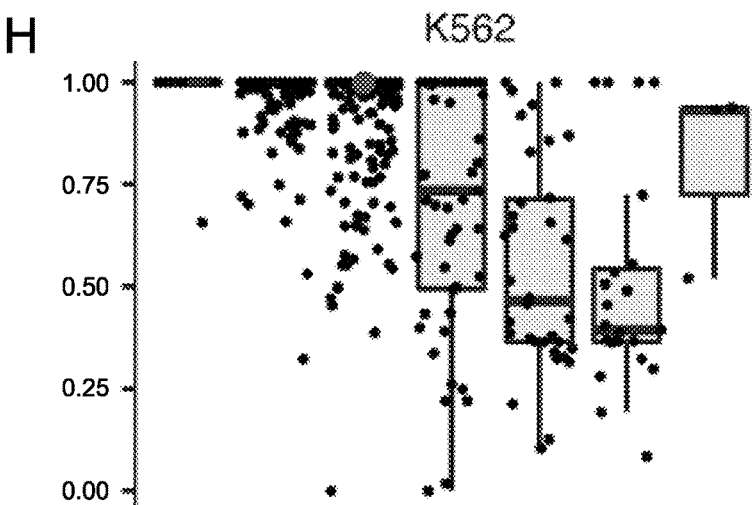
Figure 17I:
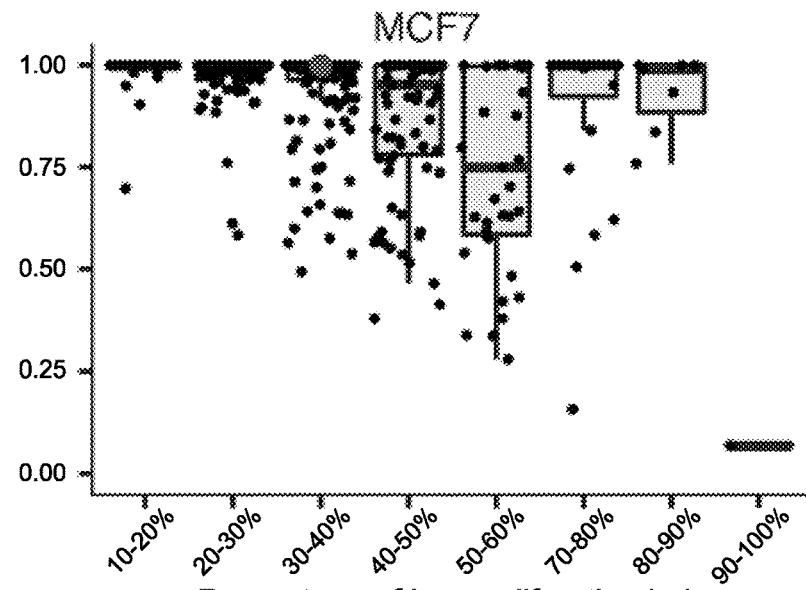
Figure 17J:
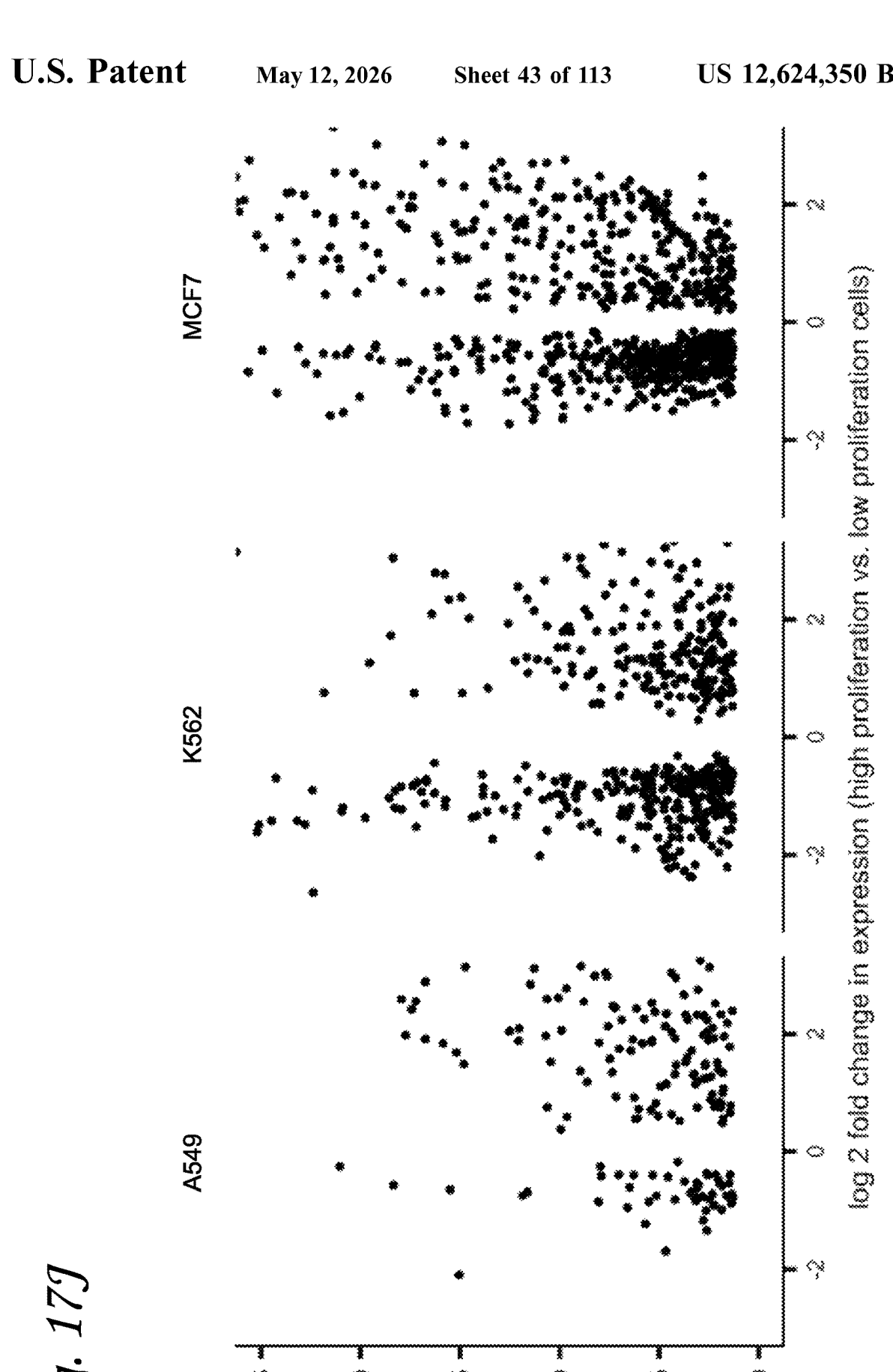

We next assessed the effects of each drug on the "population average" transcriptome of each cell line. In total, 6238 genes were differentially expressed in a dose-dependent manner in at least one cell line (FDR<5%; FIG. 14 and data not shown). Bulk RNA-seq measurements collected for five compounds across four doses and vehicle agreed with averaged gene expression values and estimated effect sizes across identically treated single cells, although correlations between small effect sizes were diminished (FIG. 15). Moreover, sci-Plex dose-dependent effect profiles correlated with compound-matched L1000 measurements (11) (FIG. 16).

Figure 9C:
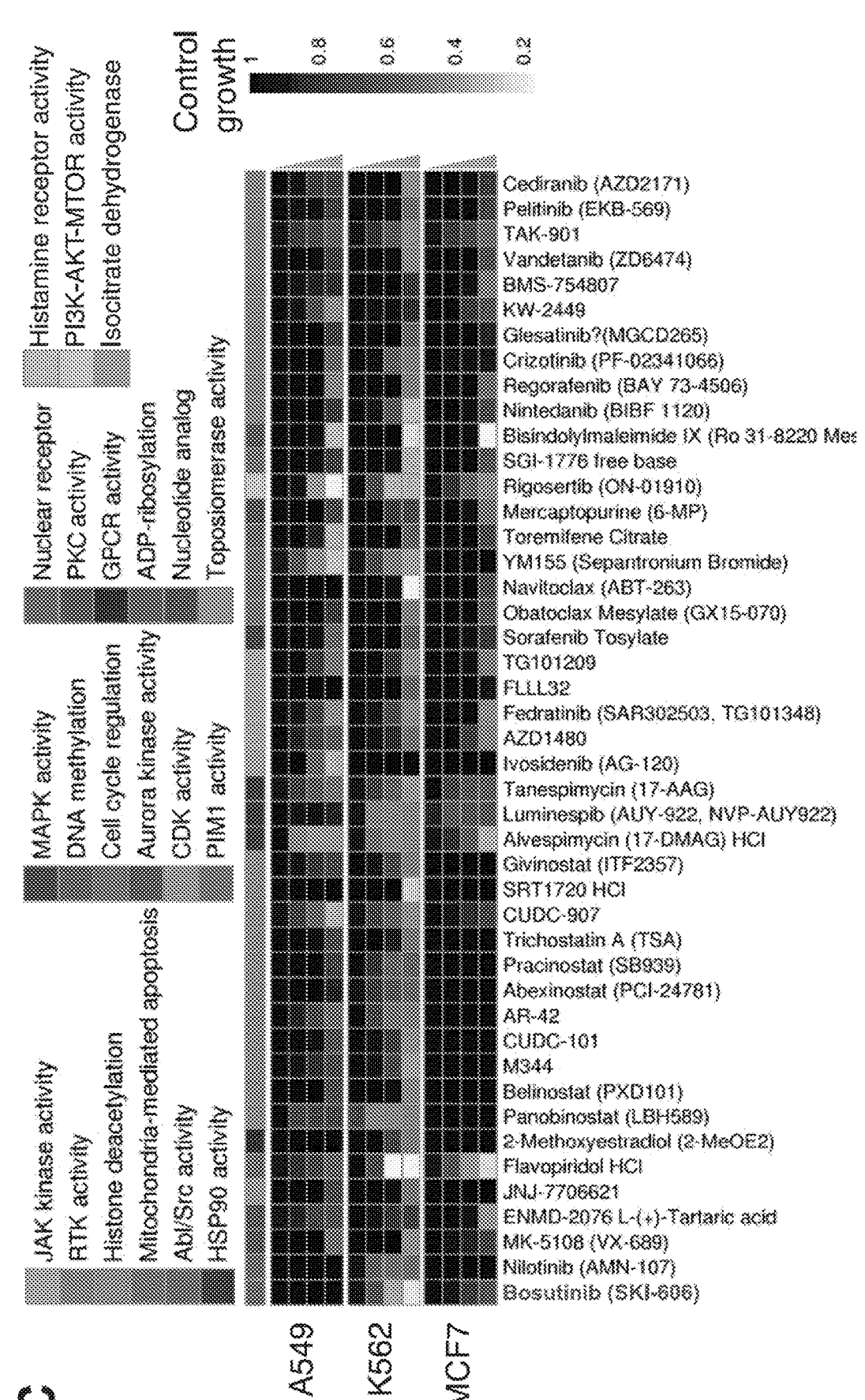
FIG. 9 shows sci-Plex enables global transcriptional profiling of thousands of chemical perturbations in a single experiment. (A) Schematic of the largescale sci-Plex experiment (sci-RNA-seq3). A total of 188 small molecules were tested for their effects on A549, K562, and MCF7 human cell lines, each at four doses and in biological replicate, after 24 hours of treatment. The plate positions of doses and drugs were varied between replicates, and a median of 100 to 200 cells were recovered per condition. Colors demarcate cell line, compound pathway, and dose. (B) UMAP embeddings of A549, K562, and MCF7 cells in our screen with each cell colored by the pathway targeted by the compound to which a given cell was exposed. To facilitate visualization of significant molecular phenotypes, we added transparency to cells treated with compound or dose combinations that did not appreciably alter the corresponding cells' distribution in UMAP space compared with vehicle controls (Fisher's exact test, FDR<1%). (C) Viability estimates obtained from hash-based counts of nuclei at each dose of selected compounds (bosutinib is highlighted in red text). Rows represent compound doses increasing from top to bottom, and columns represent individual compounds. Annotation bar at top depicts the broad cellular activity targeted by each compound. (D) UMAP embeddings highlighted by treatment with the MEK inhibitor trametinib (red), an HSP90 inhibitor (purple), or vehicle control (gray). (E) HSP90AA1 expression levels in cells exposed to increasing doses of trametinib. y-axes indicate the percentage of cells with at least one read corresponding to the transcript.
Figure 18B:
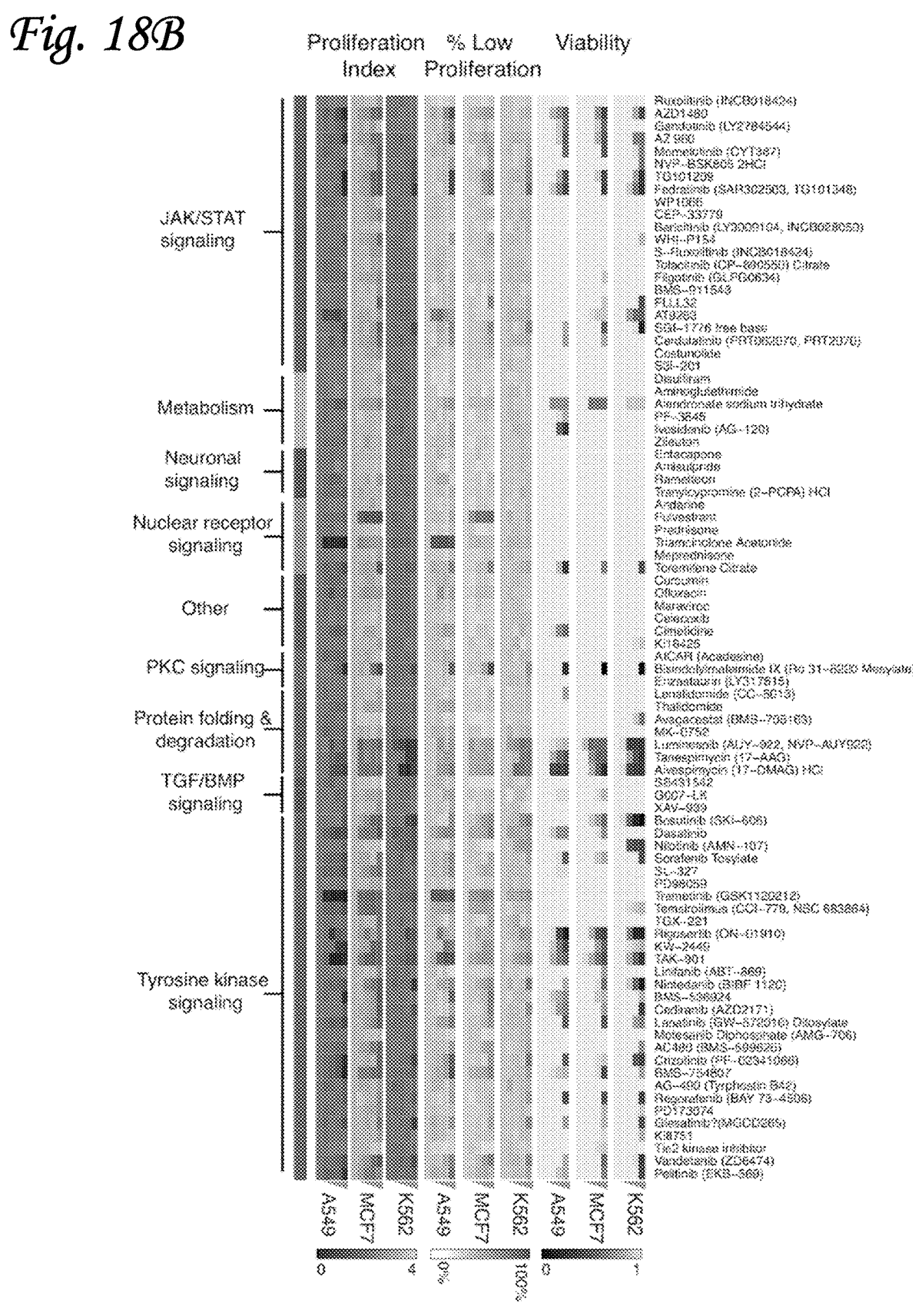
Figure 19A:
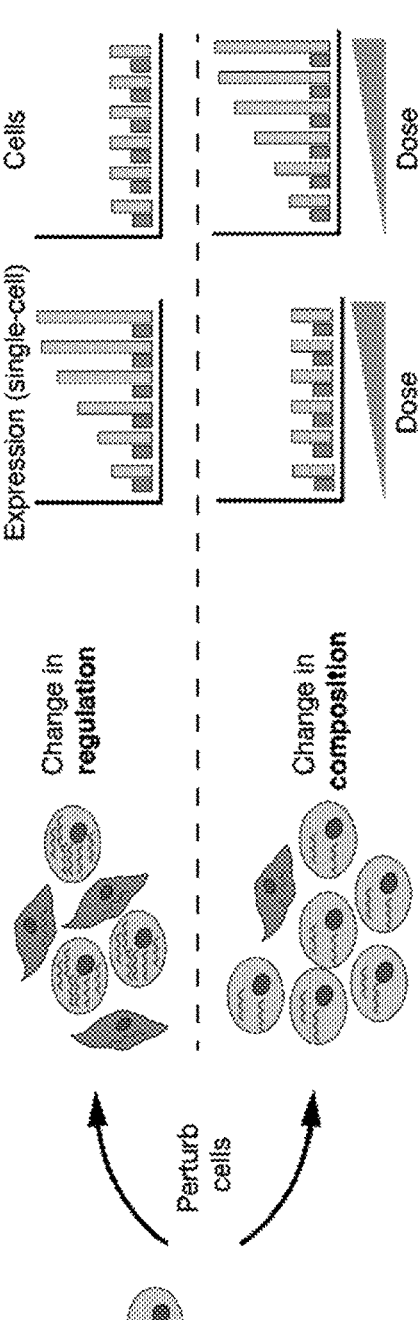
FIG. 19 shows sci-Plex enables the dissection of proliferating and nonproliferating cell populations. A) Schematic depicting how changes in cellular state (top) and changes in the relative frequency of subpopulations (bottom) look identical upon subjecting the sample to aggregate measures such as bulk RNA-seq. Adapted from ref (14). B,C) Pearson correlations between dose-dependent effect sizes estimated from high vs. low proliferation index cells for each cell line (panel B) and drug class (panel C). D) Per-gene effect sizes estimated from high ($\beta_{dh}$) vs. low ($\beta_{dl}$) proliferation index cells for 4 selected compounds. Effect sizes are expressed as log 2 transformed fold changes over intercept. Four classes of genes are shown: those significant in only high proliferation index cells (green); only low proliferation index cells (purple); both high and low cells, and with concordant effect estimates (red); both high and low cells, but with discordant effect estimates (blue). A drug had concordant dose-dependent effects on gene h in high cells ($\beta_{dh}$) and low cells ($\beta_{dh}$) when $|\beta_{dh}-\beta_{dl}|$ was less than 10 percent of $\frac{1}{2}(|\beta_{dh}+\beta_{dl}|)$. Black line indicates y=x.
Figures 19B, 19C:
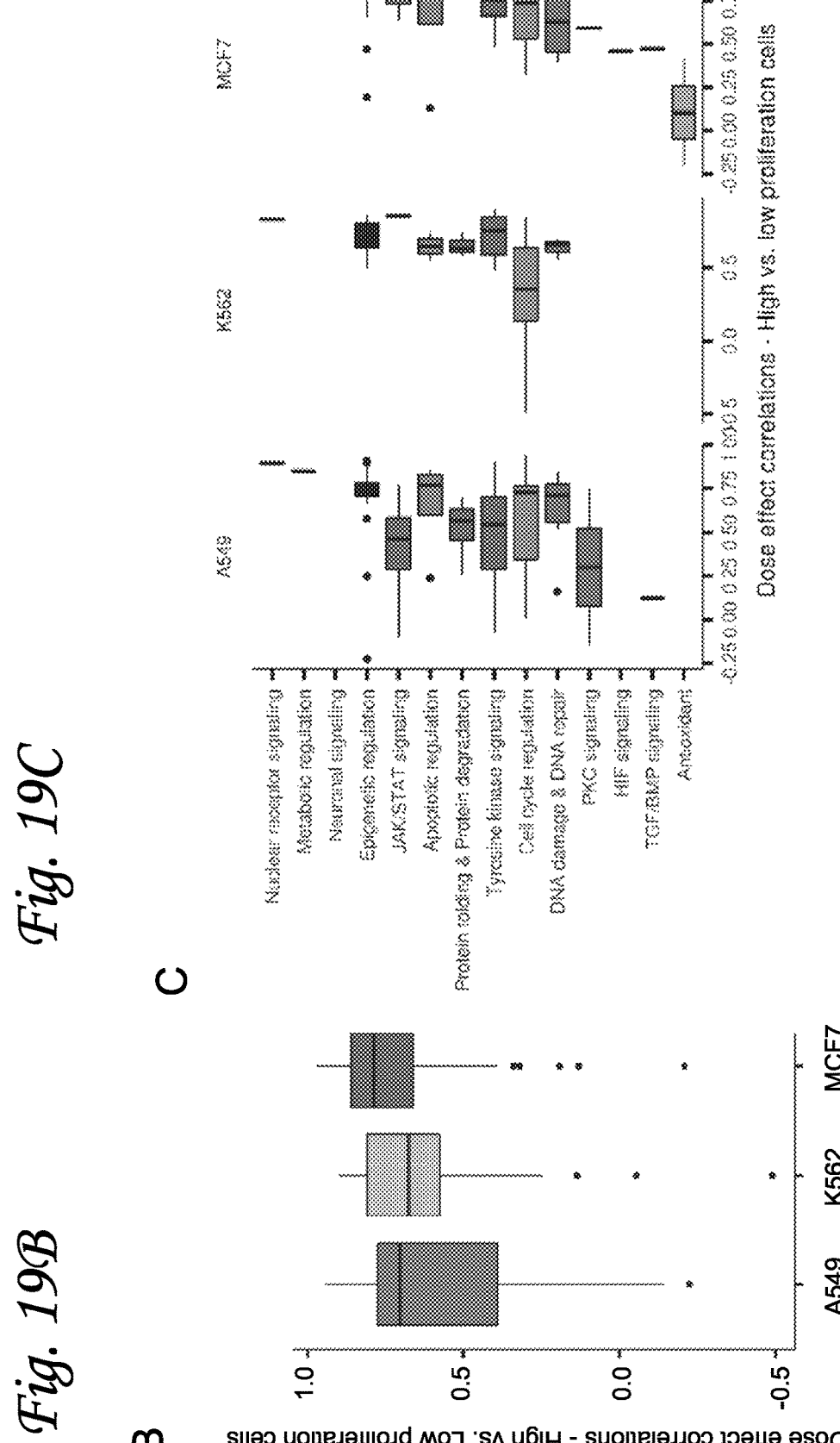
Figure 19D:
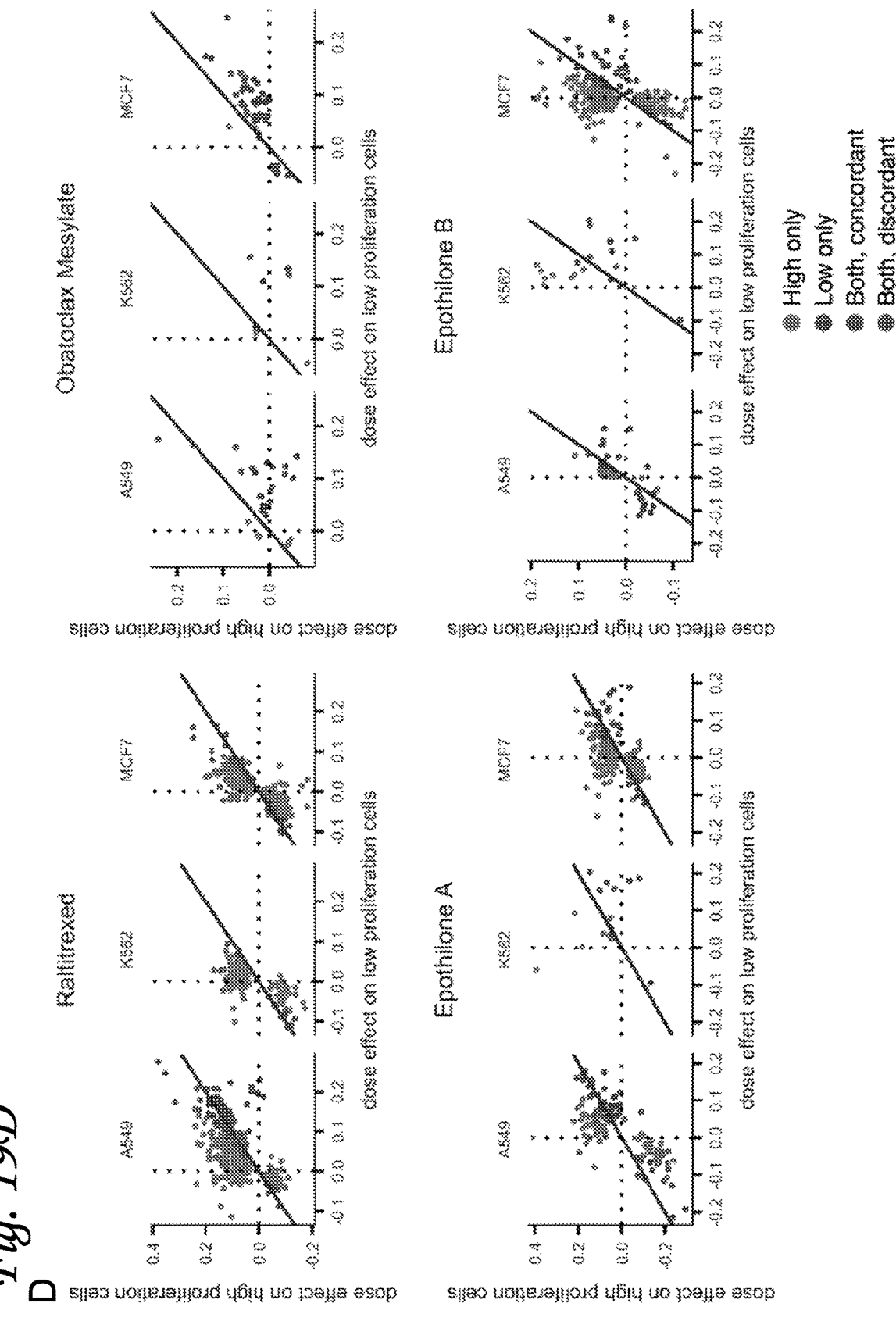
Figures 20A, 20B:
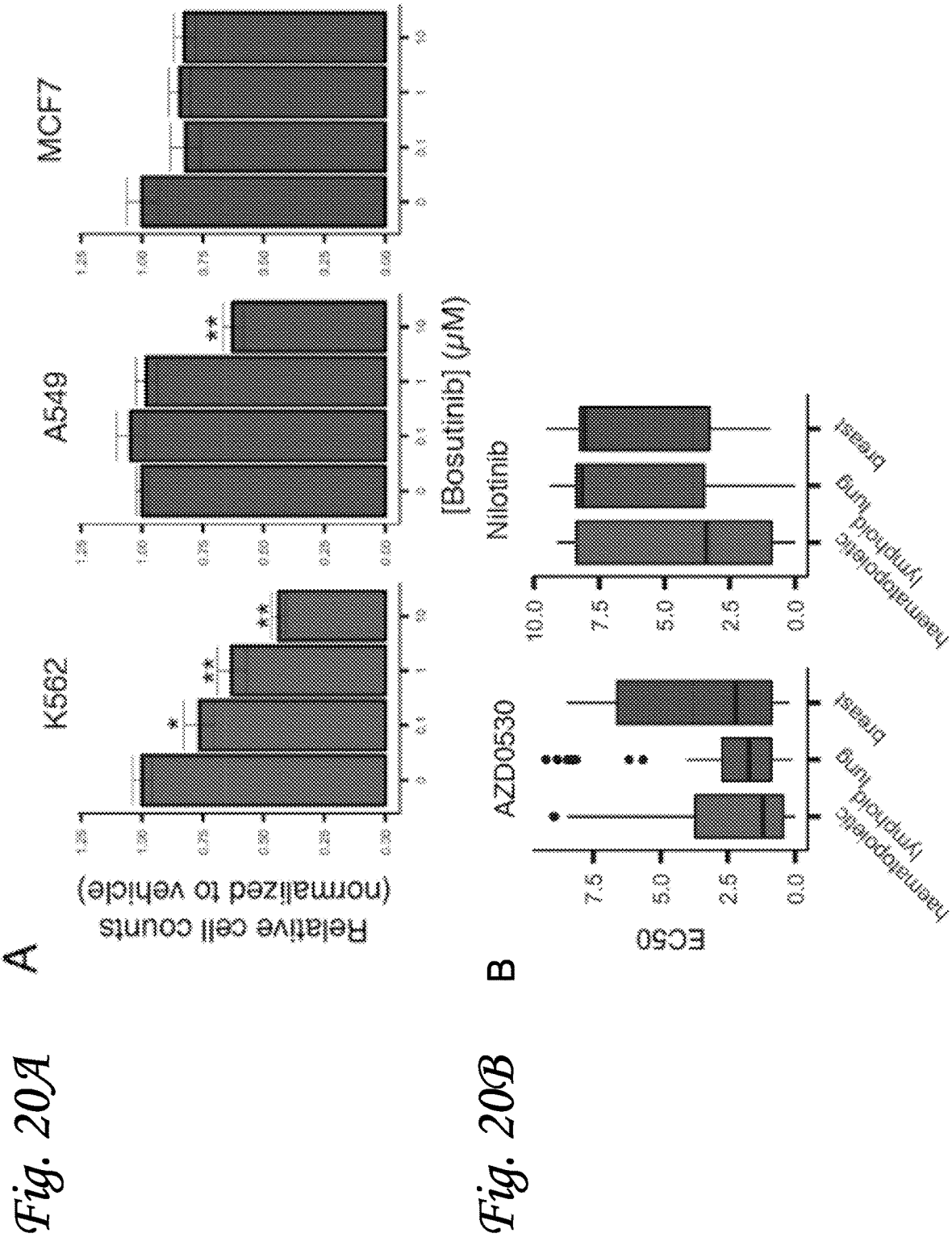
FIG. 20 shows sci-Plex screen identifies viability and expression signatures that are reproducible across validation experiments and orthogonal datasets. A) Cell count viability estimates for K562 (red), A549 (blue) and MCF7 (green) cells exposed to vehicle or increasing doses of the Src/Abl inhibitor bosutinib (n=6 culture replicates, Wilcoxon rank sum test). For each cell line, cell count values were normalized to the mean cell counts value of vehicle control treated cells. Error bars denote standard error of the mean, n=8. B) EC50 values for cell lines of hematopoietic and lymphoid, lung and breast tissue origin, for which viability estimates are available from the Cancer Cell Line Encyclopedia (CCLE), exposed to the Abl inhibitors AZD0530 (left panel) or nilotinib (right panel). C-E) Top connectivity scores (a measure that summarizes similarities between transcriptional signatures induced by different drugs (11, 12)) for MEK and HSP inhibitors from the CMAP database across all cell lines (summary, panel C) or for A549 (panel D) and MCF7 (panel E) cells individually. A connectivity score cutoff of +/−90 was applied as in (11).
Figure 20C:
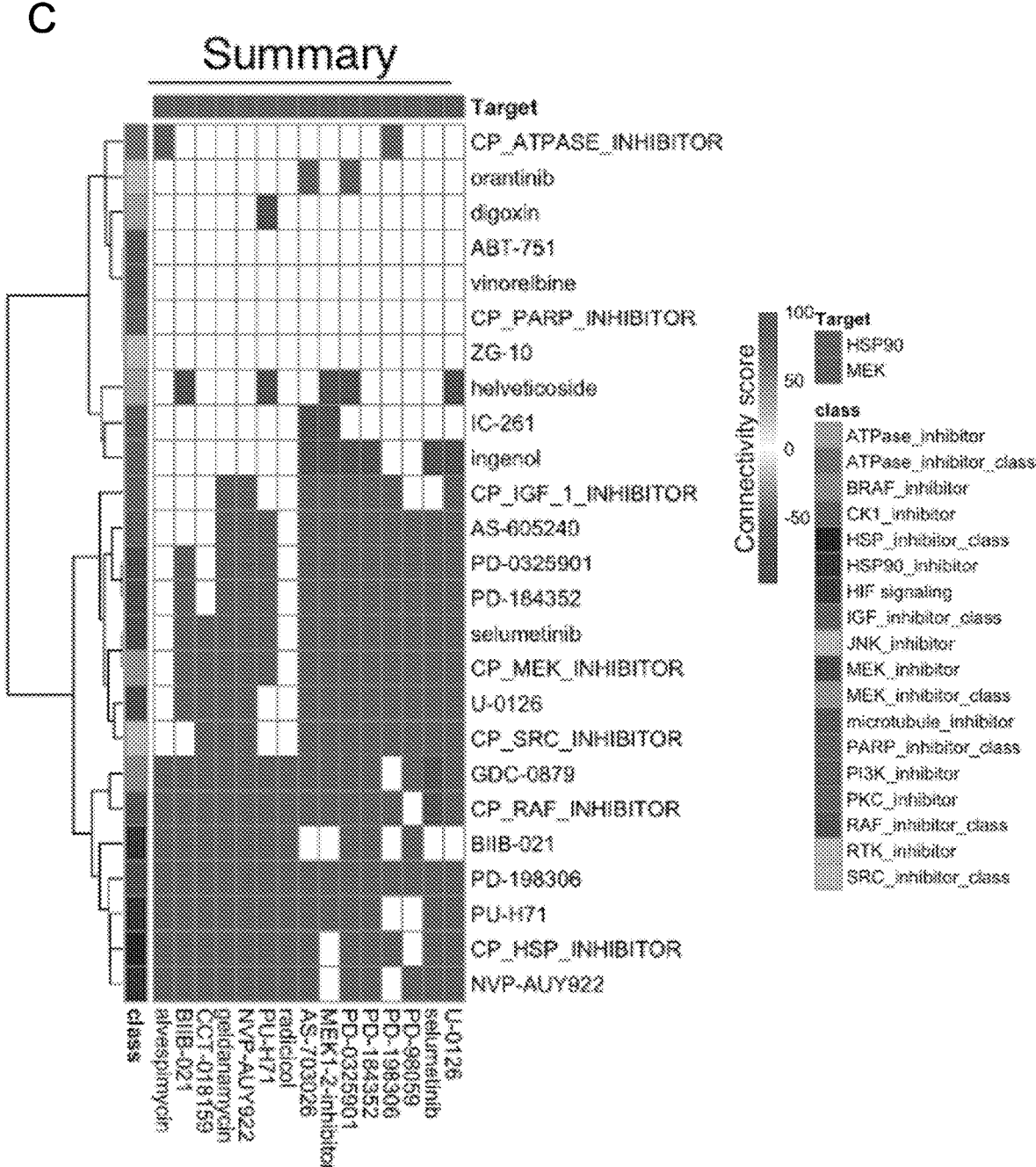
Figure 20D:
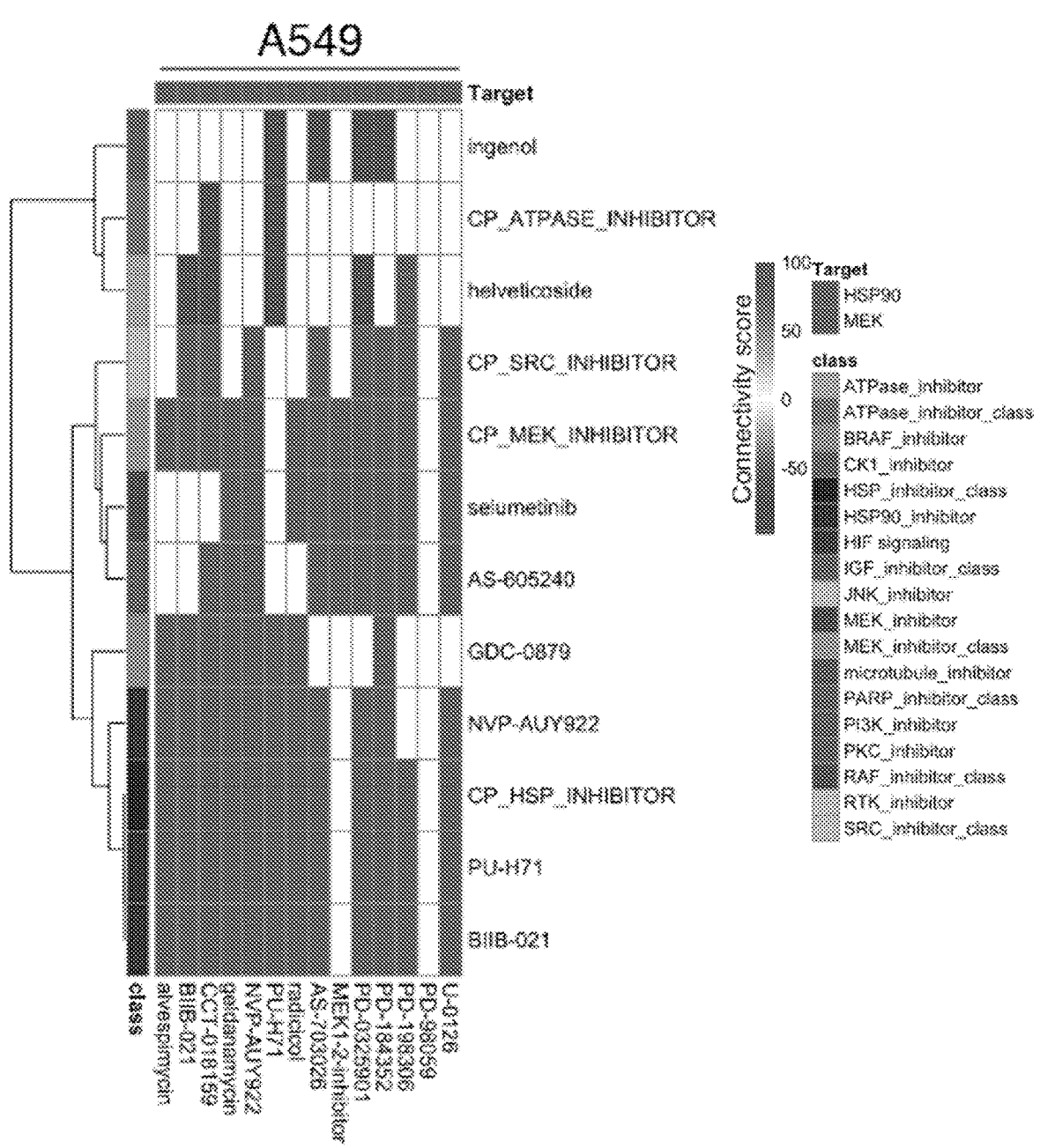
Figure 20E:
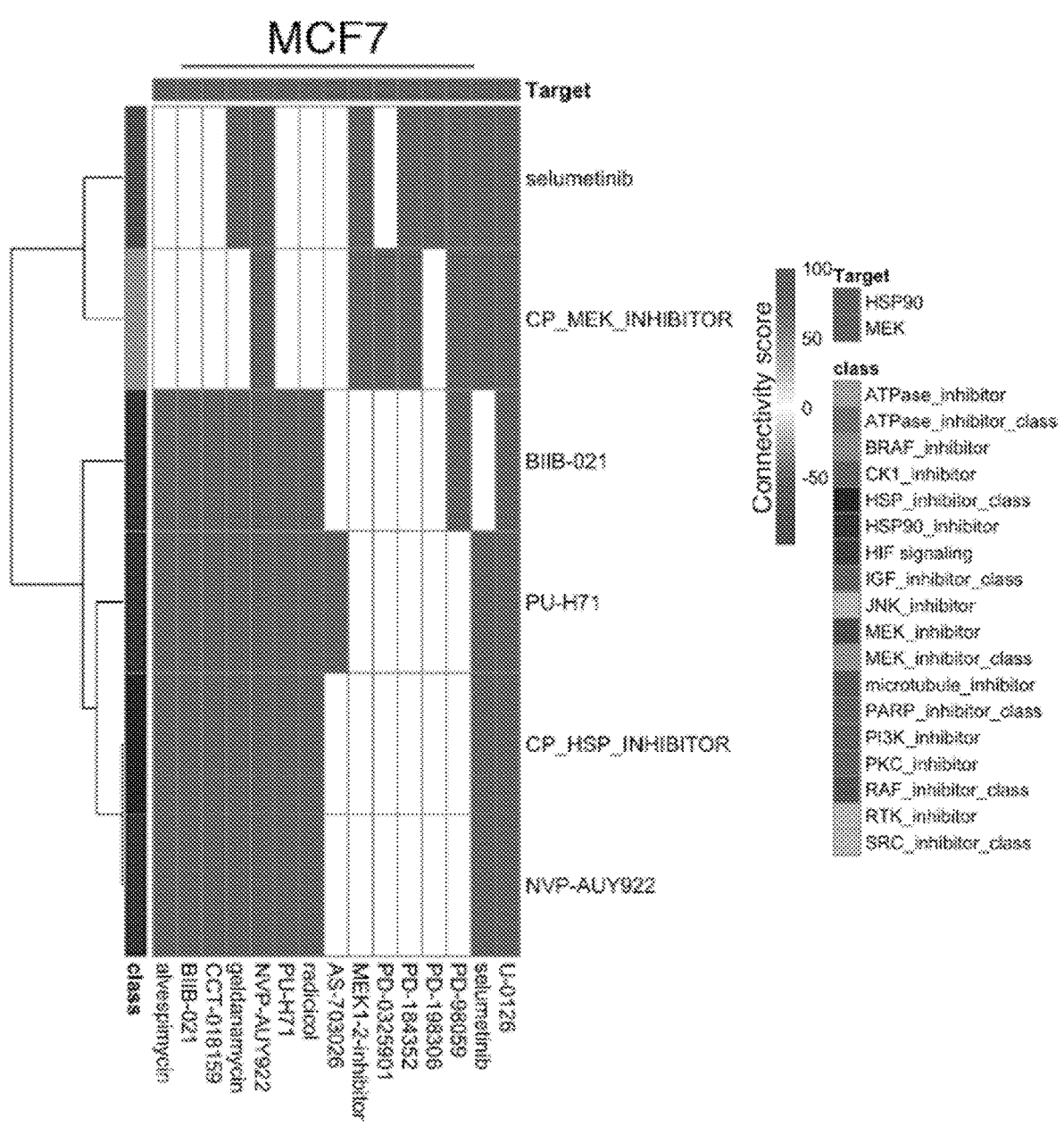
Figure 21:
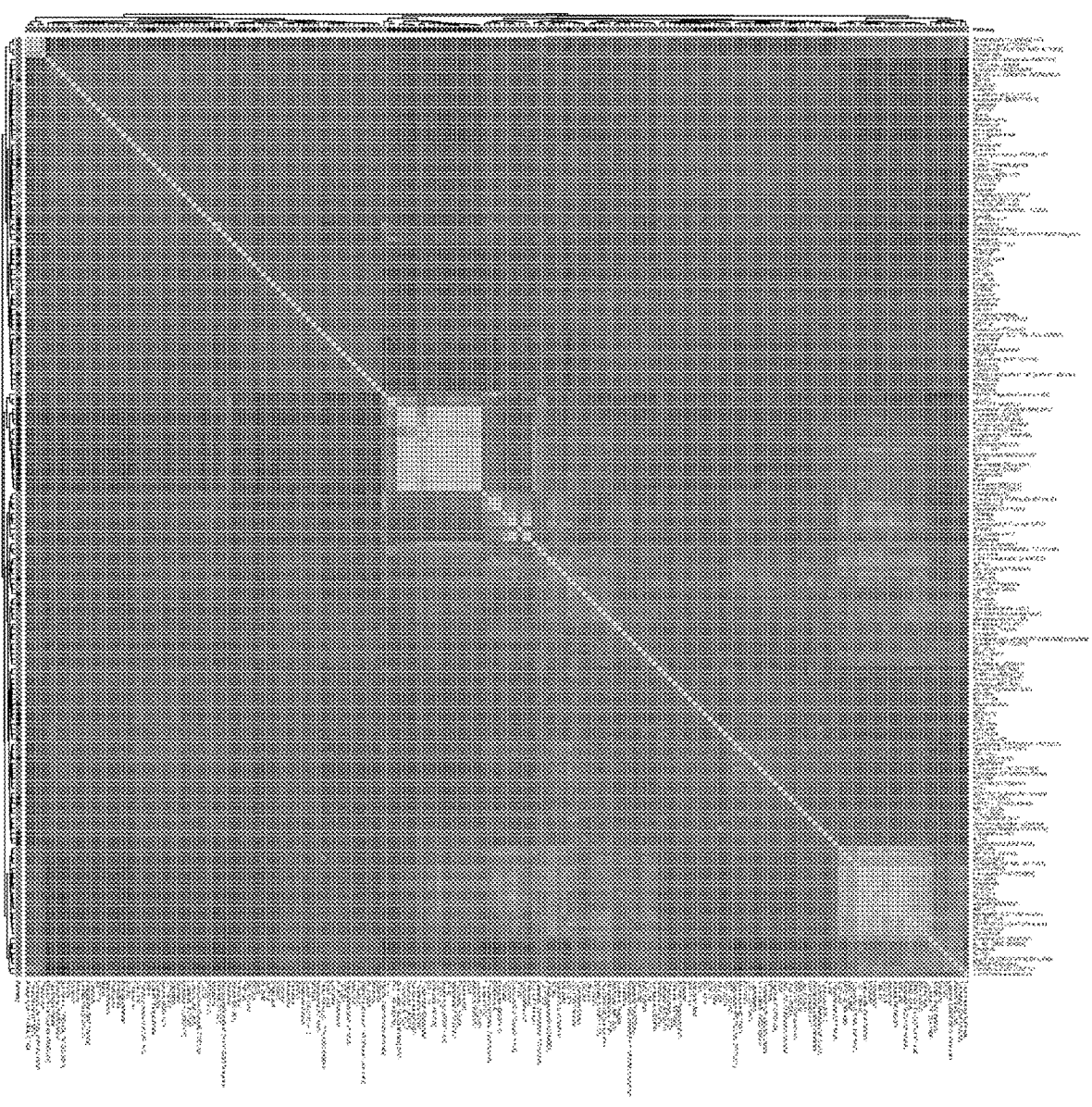
FIG. 21 shows correlation of compound-driven molecular signatures for A549 cells identified in sci-Plex screen. Heatmap depicts the Pearson correlation of beta coefficients across dose-dependent differentially expressed genes for every pairwise combination of compounds screened. To aid in visualization Pearson correlations were capped at 0.6.
Figure 22:
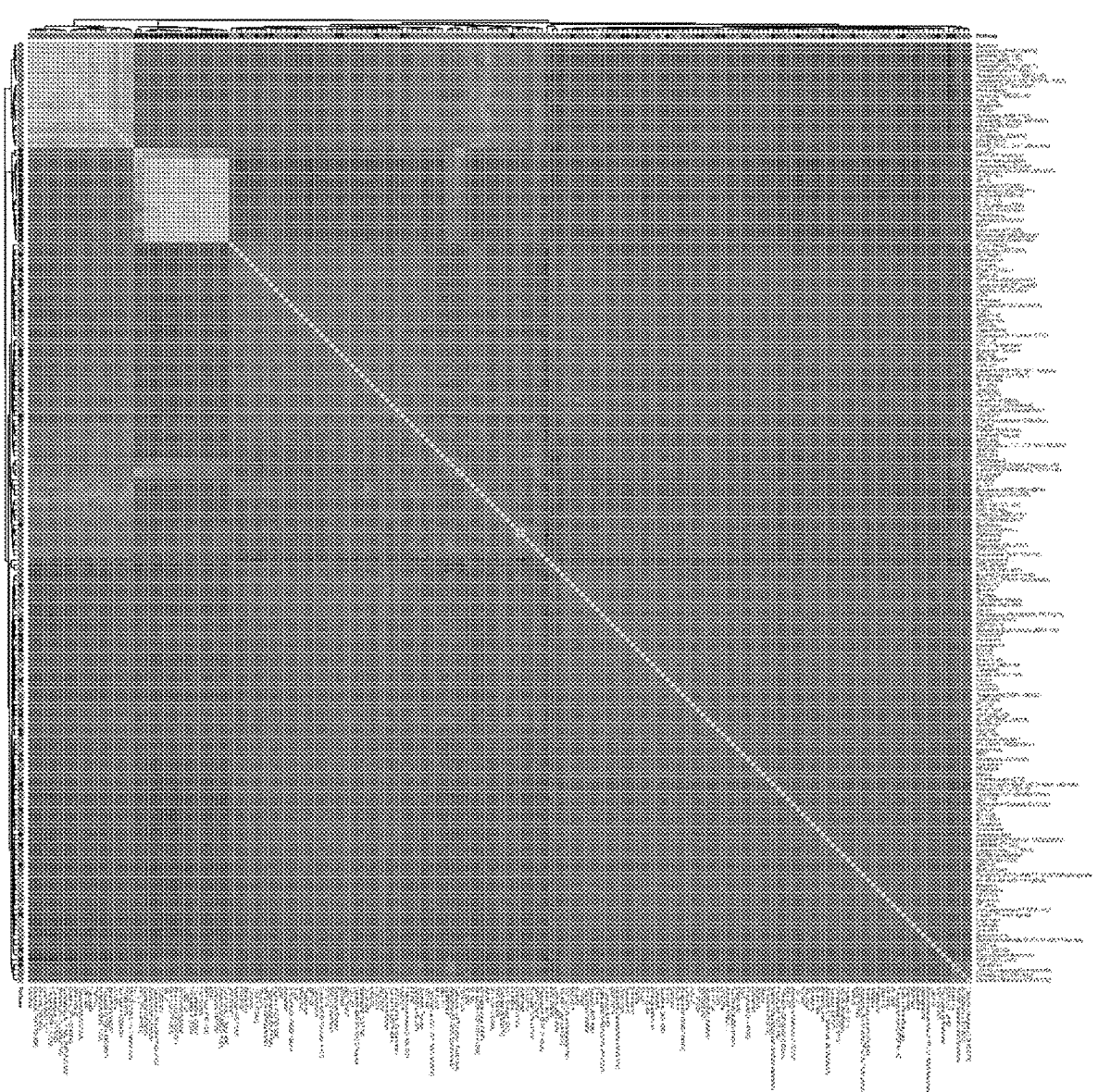
FIG. 22 shows correlation of compound-driven molecular signatures for K562 cells identified in sci-Plex screen. Heatmap depicts the Pearson correlation of beta coefficients across dose-dependent differentially expressed genes for every pairwise combination of compounds screened. To aid in visualization Pearson correlations were capped at 0.6.
Figure 23:
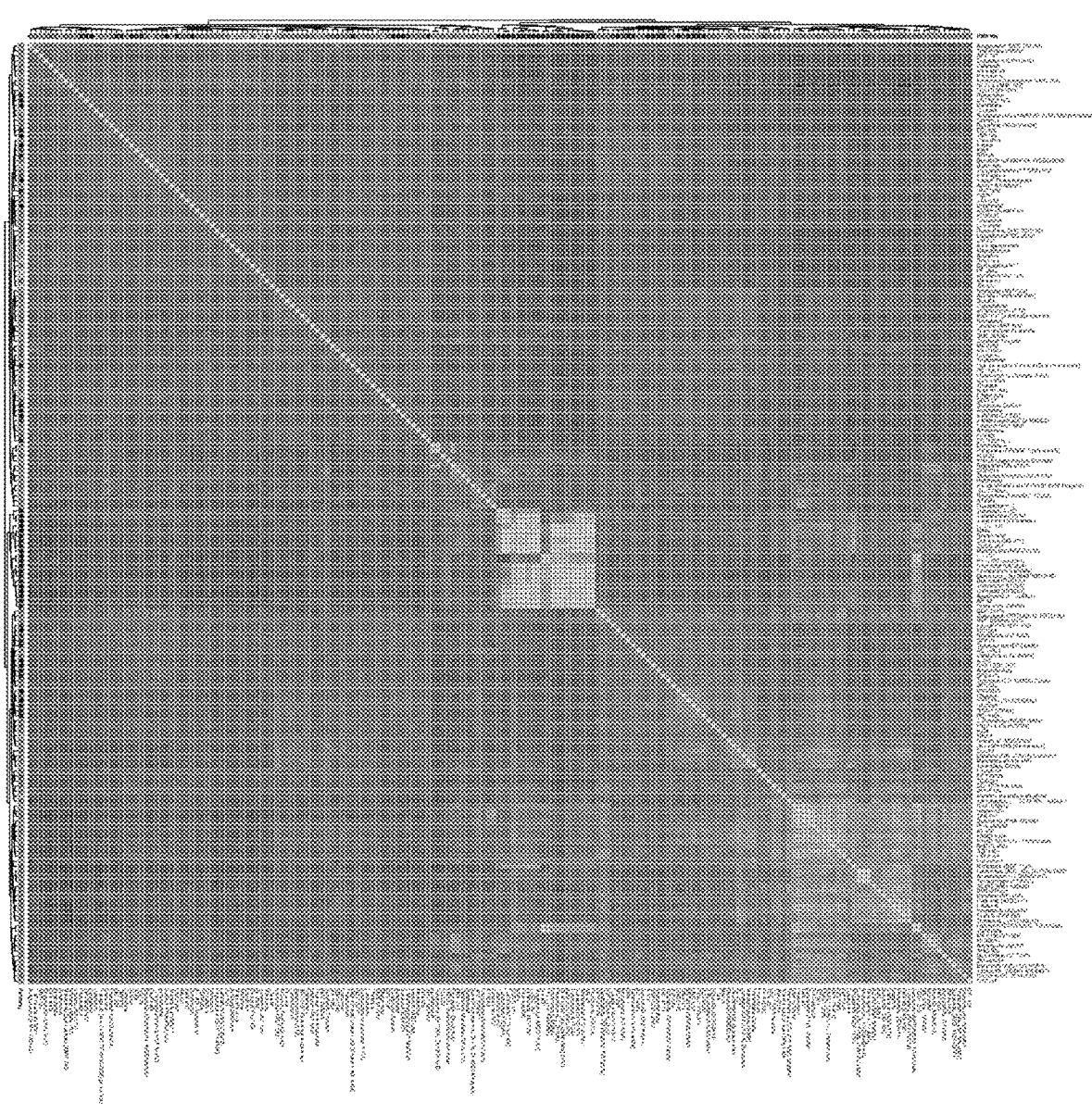
FIG. 23 shows correlation of compound-driven molecular signatures for MCF7 cells identified in sci-Plex screen. Heatmap depicts the Pearson correlation of beta coefficients across dose-dependent differentially expressed genes for every pairwise combination of compounds screened. To aid in visualization Pearson correlations were capped at 0.6.
Figures 26A, 26B:
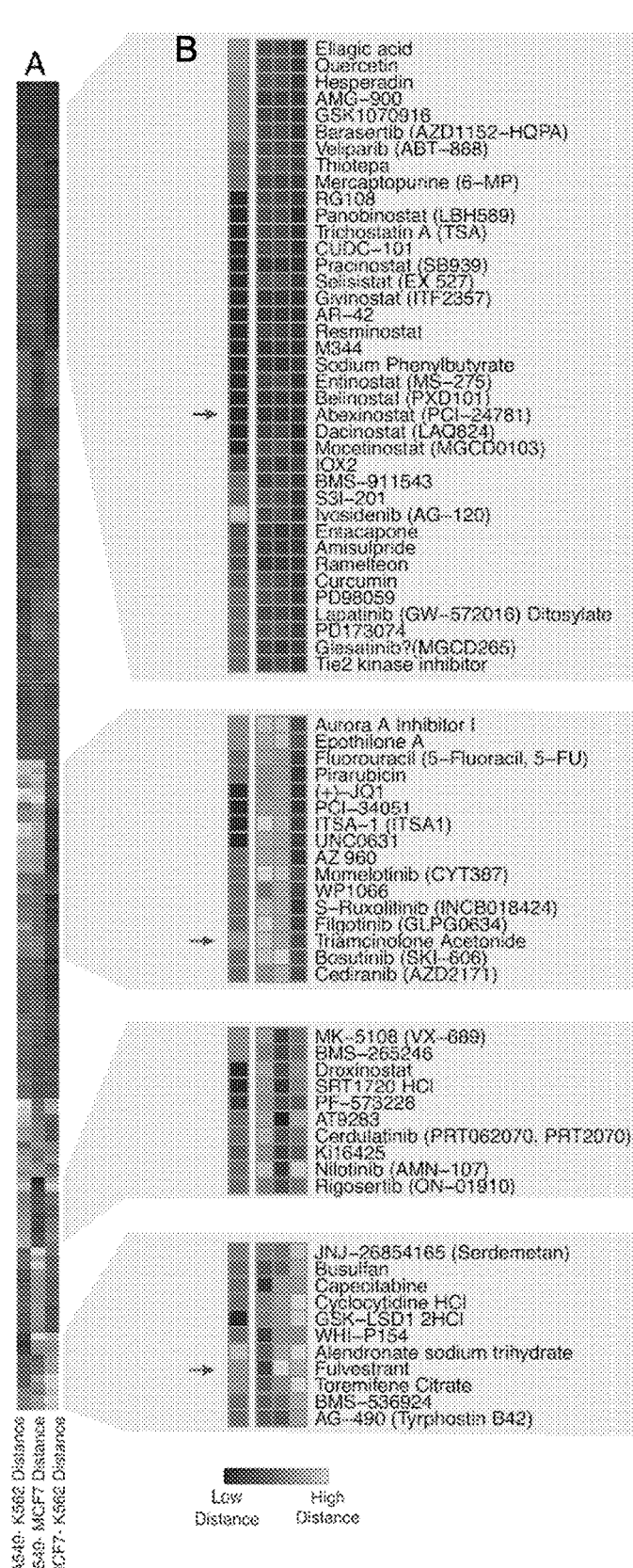
FIG. 26 shows pairwise distances between PCA embeddings of drugs based on their dose-dependent effects. A)
Figures 26C, 26D:
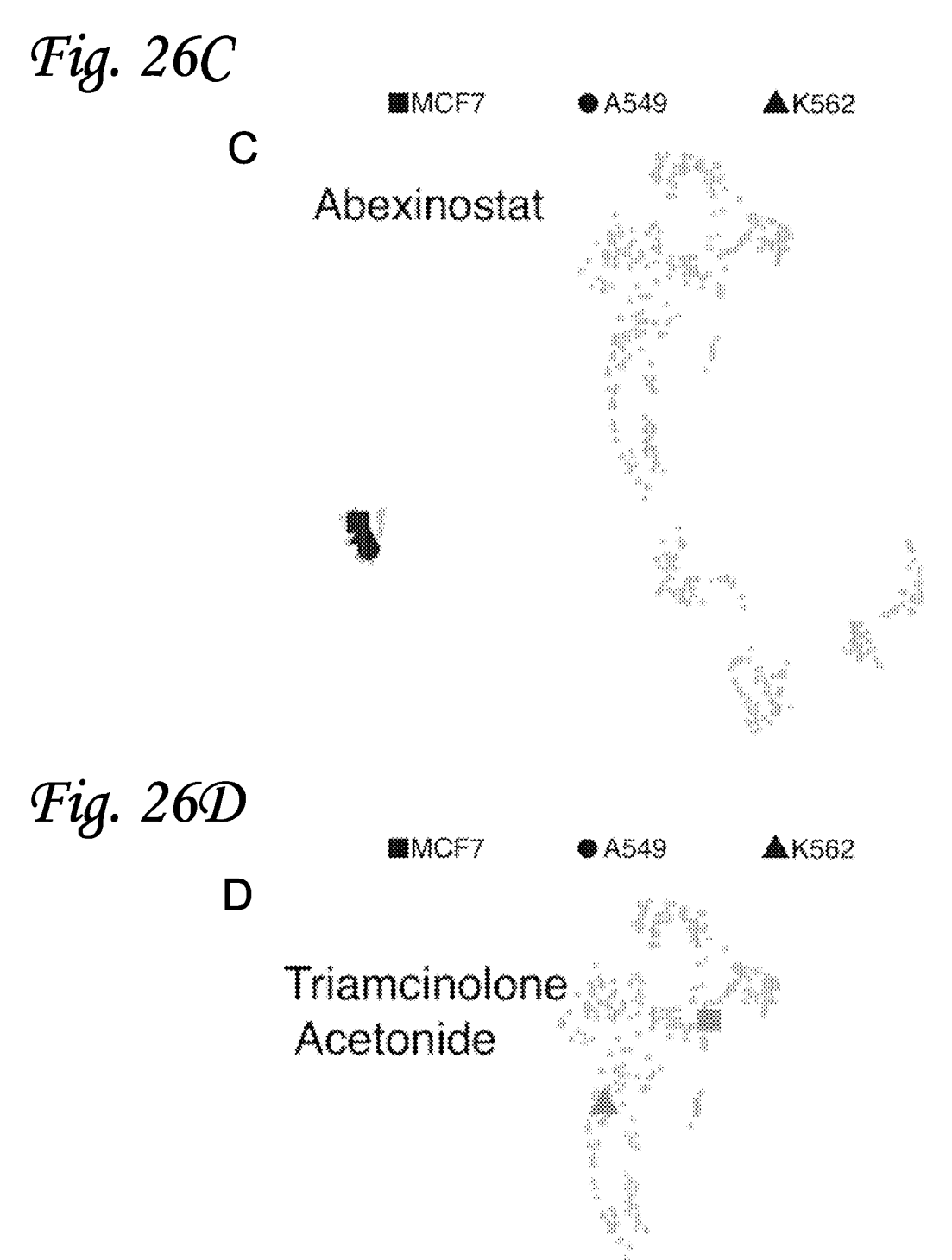
Figure 26E:
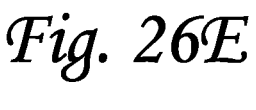
Figure 26F:
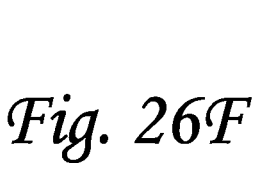

Genes associated with the cell cycle were highly variable across individual cells, and many drugs reduced the fraction of cells that expressed proliferation marker genes (FIGS. 17 and 18). In principle, scRNA-seq should be able to distinguish shifts in the proportion of cells in distinct transcriptional states from gene-regulatory changes within those states. By contrast, bulk transcriptome profiling would confound these two signals (FIG. 19A) (14). We therefore tested for dose-dependent differential expression on subsets of cells corresponding to the same drug but expressing high versus low levels of proliferation marker genes (FIG. 19B). Correlation between the dose dependent effects on the two fractions of each cell type varied across drug classes (FIG. 19C), with some frankly discordant effects for individual compounds (FIG. 19D). Viability analysis performed as in the pilot experiment revealed that after drug exposure at the highest dose, only 52 (27%) compounds caused a decrease in viability of 50% or more (FIG. 9C and FIG. 11C). Among the drugs that reduced viability, we observed a higher sensitivity of K562 to the Src and Abl inhibitor bosutinib (FIG. 9C), a result that we confirmed by cell counting (FIG. 20A). This result is consistent with K562 cells harboring a constitutively active BCR-ABL fusion kinase (28) and an observed increased sensitivity of hematopoietic and lymphoid cancer cell lines to Abl inhibitors (29) (FIG. 20B).

Figures 9D, 9E:
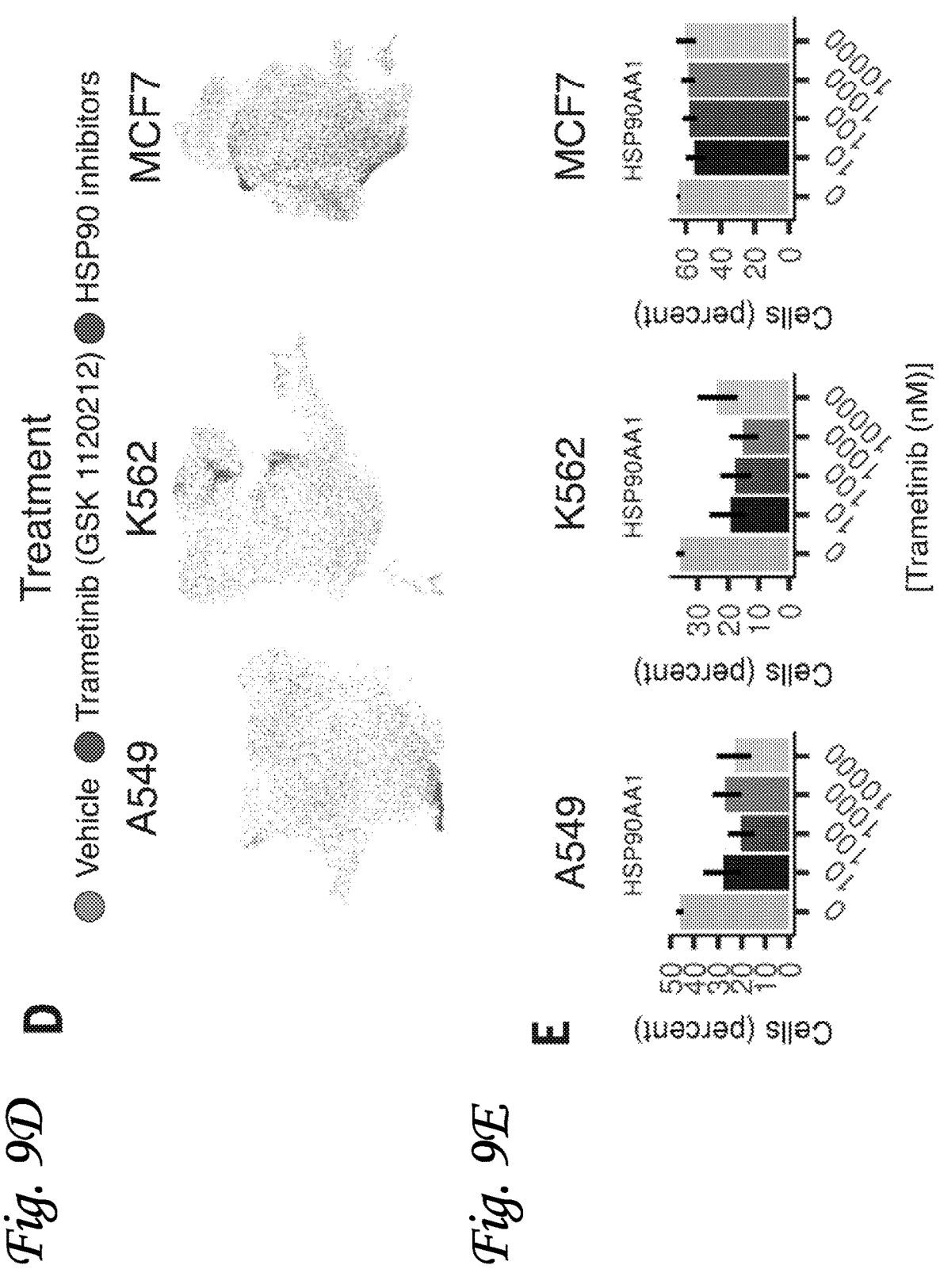

To assess whether each compound elicited similar responses across the three cell lines, we clustered compounds using the effect sizes for dose-dependent genes as loadings in each cell line (FIGS. 21 to 24). Joint analysis of the three cell lines revealed common and cell type-specific responses to different compounds (FIGS. 25 and 26). For example, trametinib, a mitogen-activated protein kinase kinase (MEK) inhibitor, induced a transcriptionally distinct response in MCF7 cells. Inspection of UMAP projections revealed trametinib-treated MCF7 cells interspersed among vehicle controls, reflecting limited effects. By contrast, trametinib treated A549 and K562 cells, which harbor activating KRAS and ABL mutations (30), respectively, were tightly clustered, consistent with a strong, specific transcriptional response to inhibition of MEK signaling by trametenib (FIG. 9D). Further, we observed that these A549 and K562 cells appeared proximal to clusters enriched with inhibitors of HSP90, a key chaperone for protein folding (FIG. 9D). This observation was corroborated by concordant changes in HSP90AA1 expression in trametinib-treated cells (FIG. 9E). Analysis of Connectivity Map data (11, 12) revealed further evidence that MEK inhibitors do indeed induce highly similar gene expression signatures to HSP90 perturbations (FIG. 20C), especially in A549 but not in MCF7 (FIG. 20, D and E). These results are concordant with previous observations of the regulation of HSP90AA1 downstream of MEK signaling (31) and suggest that similarity in single-cell transcriptomes treated with distinct compounds can highlight drugs that target convergent molecular pathways.

Inference of Chemical and Mechanistic Properties of HDAC Inhibitors

Figures 27A, 27B, 27C:
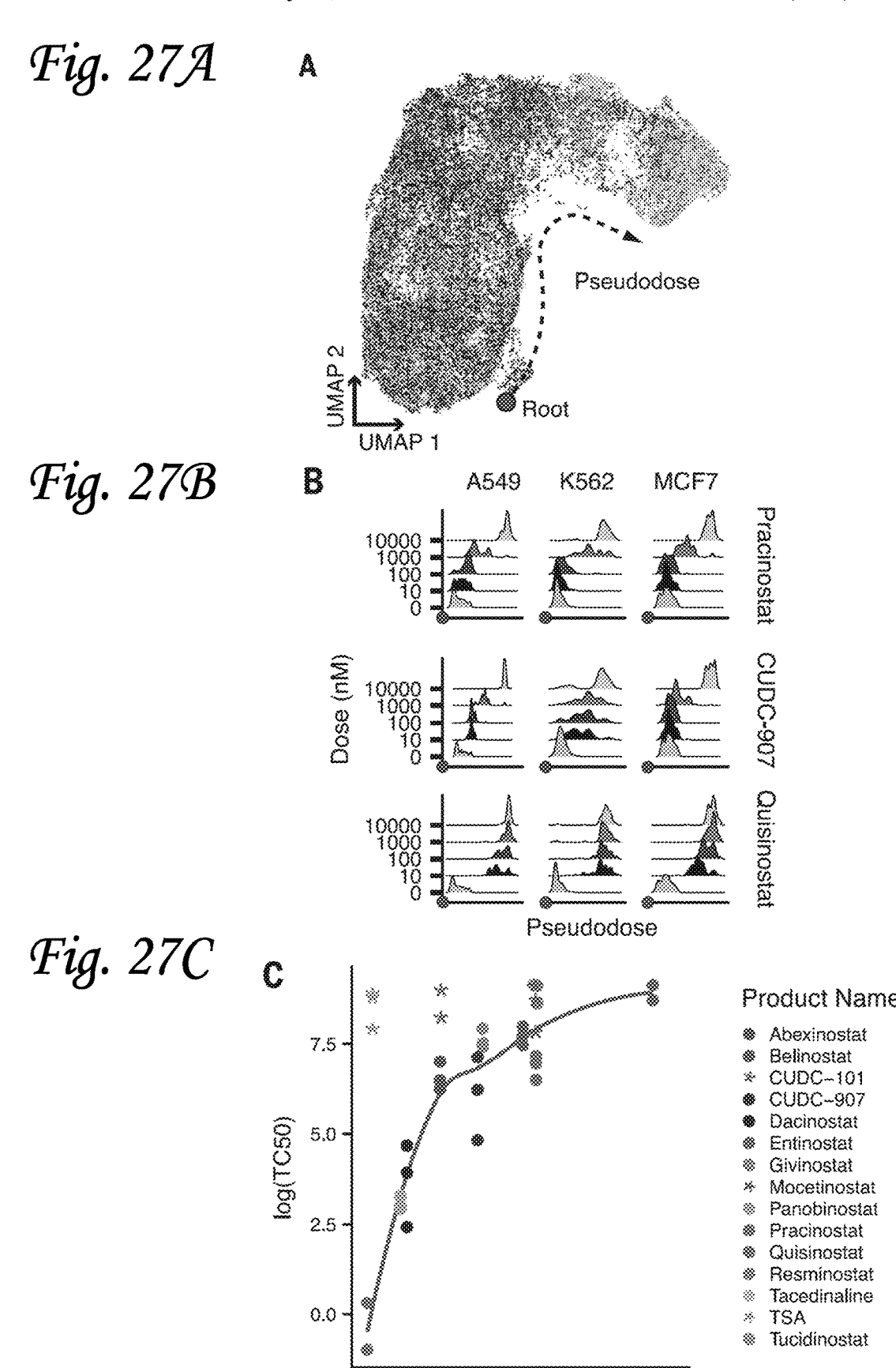

For each of the three cell lines, the most prominent compound response was composed of cells treated with one of 17 HDAC inhibitors (FIG. 9B, dark blue, and data not shown). To assess the similarity of the dose-response trajectories between cell lines, we aligned HDAC-treated cells and vehicle-treated cells from all three cell lines using a mutual-nearest neighbor (MNN) matching approach (32) to produce a consensus HDAC inhibitor trajectory, which we call "pseudodose" [analogous to "pseudotime" (33)] (FIG. 27A and FIG. 28). We observed that some HDAC inhibitors induced homogeneous responses, with nearly all cells localized to a relatively narrow range of the HDAC inhibitor trajectory at each dose (e.g., pracinostat in A549), whereas other drugs induced much greater cellular heterogeneity (FIG. 27B and FIG. 29).

Such heterogeneity could be explained by cells executing a defined transcriptional program asynchronously, with the dose of drug that the cells are exposed to modulating the rates of their progression through it. To test this hypothesis, we sequenced the transcriptomes of 64,440 A549 cells that were treated for 72 hours with one of 48 compounds, including many of the HDAC inhibitors from the large sci-Plex screen. Upon accounting for confluency-dependent cell-cycle effects and MNN alignment (FIGS. 30 and 31), the coembedded UMAP projection revealed new focal concentrations of cells at 72 hours that were not evident at the 24-hour time point, e.g., SRT1024 (FIG. 32). However, for the majority of HDAC inhibitors tested, we did not observe that cells at a given dose moved farther along an aligned HDAC trajectory at 72 hours (FIG. 33). This suggests that the dose of many HDAC inhibitors governs the magnitude of a cell's response rather than its rate of progression and that any observed heterogeneity cannot be attributed solely to asynchrony (FIG. 33).

Next, we assessed whether a given HDAC inhibitor's target affinity explained its global transcriptional response to the compound. We used dose-response models to estimate each compound's transcriptional median effective concentration ($TC_{50}$), i.e., the concentration needed to drive a cell halfway across the HDAC inhibitor pseudodose trajectory (FIG. 34A and data not shown). To compare the transcriptionally derived measures of potency with the biochemical properties of each compound, we collected published median inhibitory concentration (IC50) values for each compound from in vitro assays performed on eight purified HDAC isoforms (data not shown). With the exception of two relatively insoluble compounds, our calculated $TC_{50}$ values increased as a function of compound IC50 values (FIG. 27C and FIG. 34, B and C).

Figure 35C:
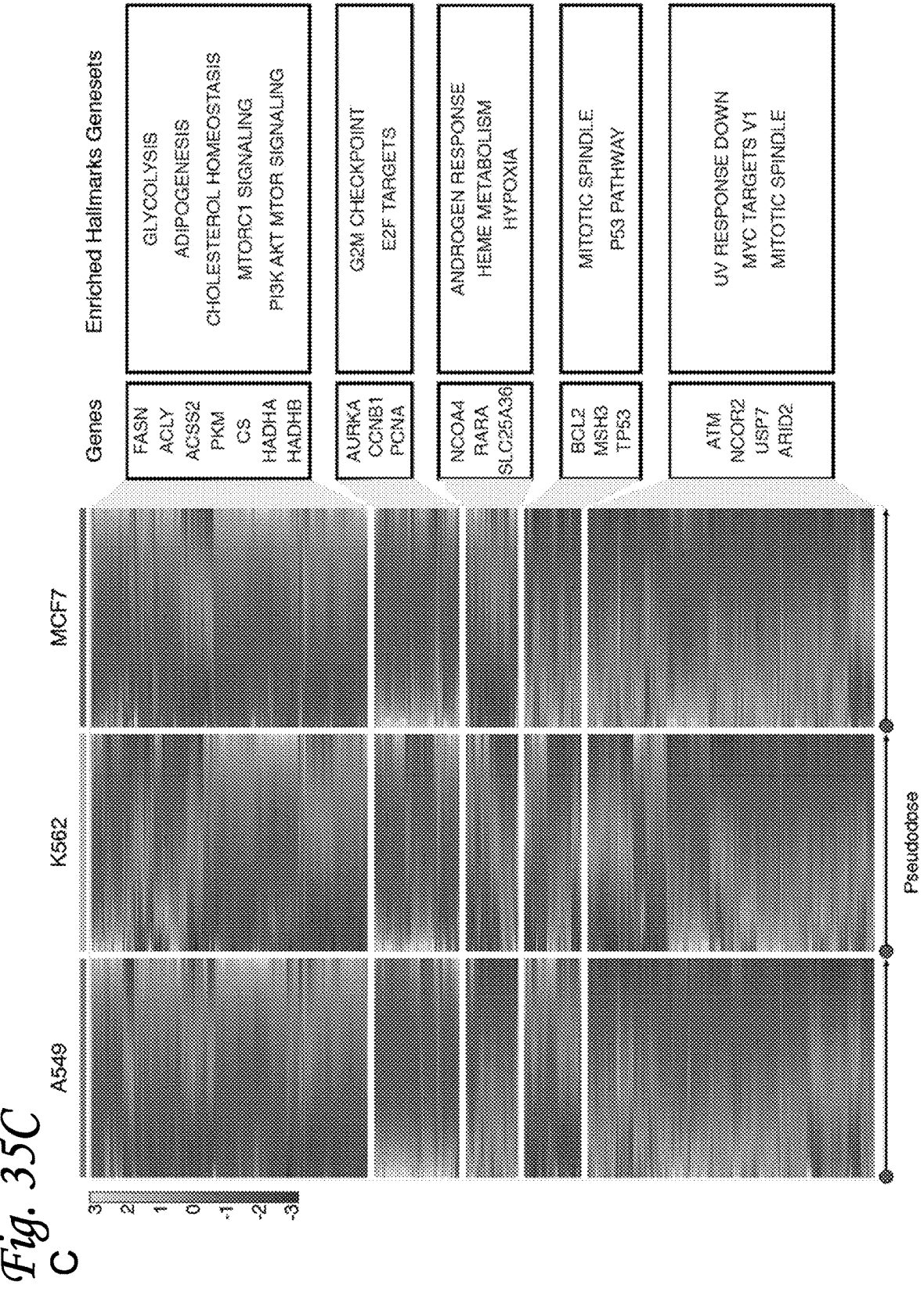
Figure 36A:
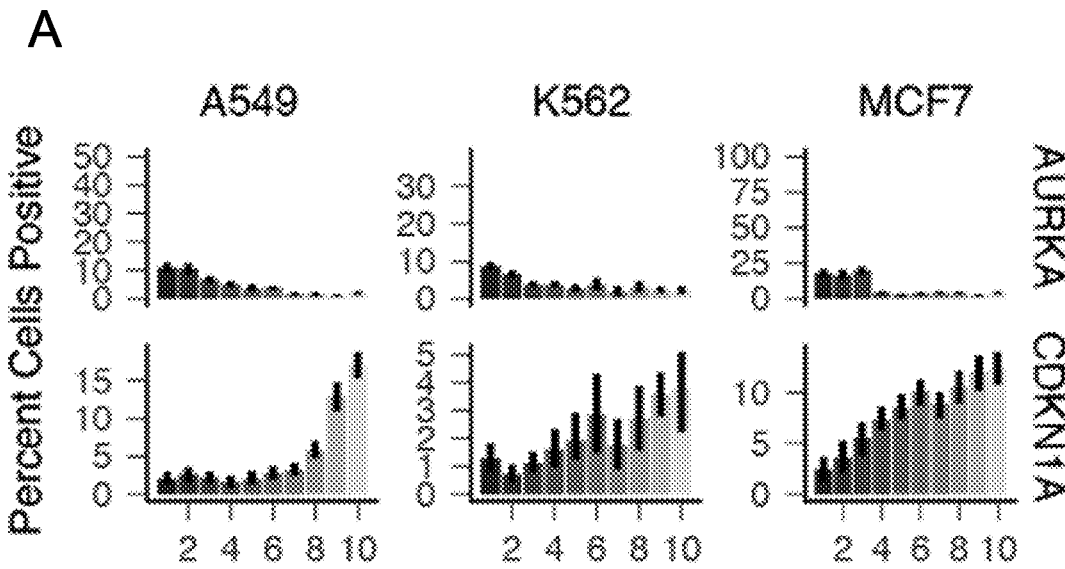
Figure 36B:
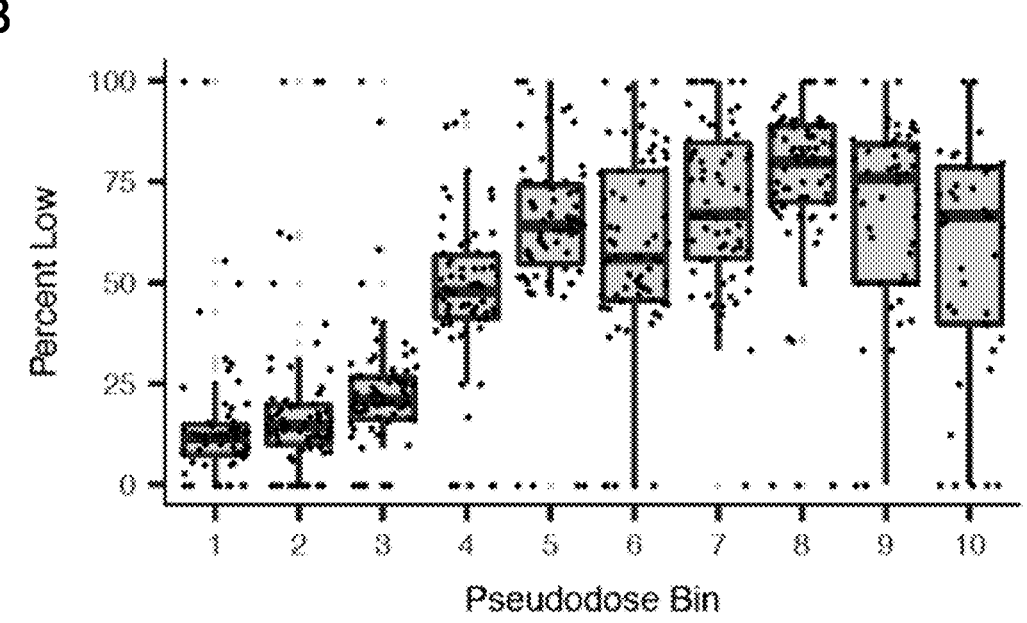
Figure 36C:
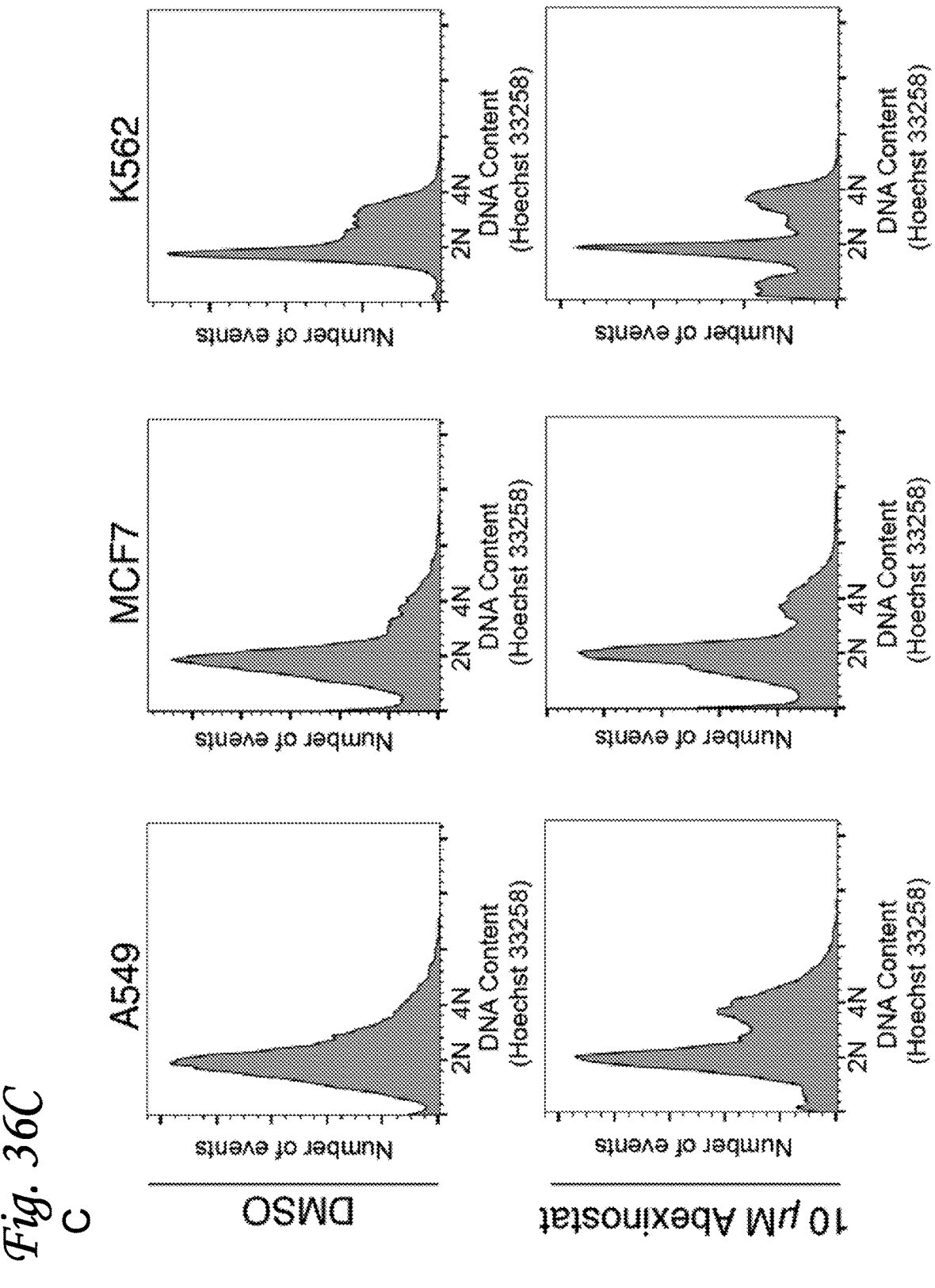
Figure 36D:
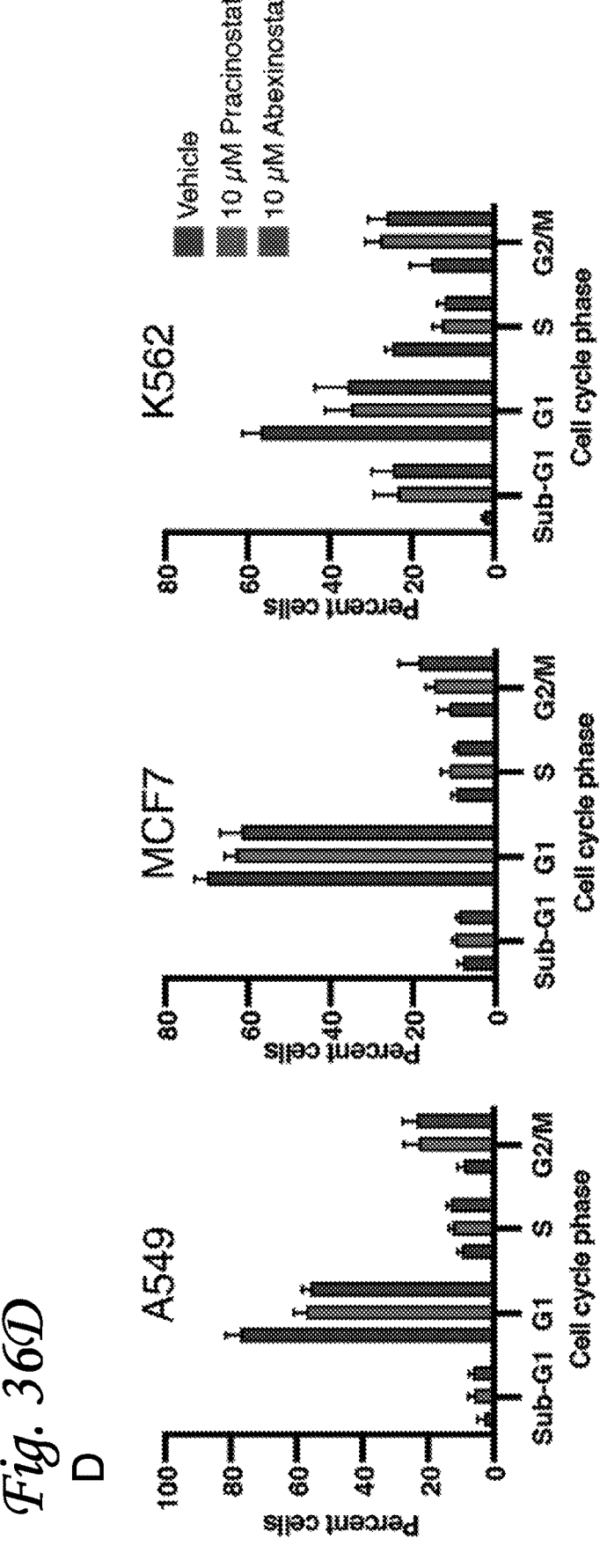

To assess the components of the HDAC inhibitor trajectory, we performed differential expression analysis using pseudodose as a continuous covariate. Of the 4308 genes that were significantly differentially expressed over this consensus trajectory, 2081 (48%) responded in a cell-type-dependent manner and 942 (22%) exhibited the same pattern in all three cell lines (FIG. 35, A and B and data not shown). One prominent pattern shared by the three cell lines was an enrichment for genes and pathways indicative of progression toward cell-cycle arrest (FIGS. 35C and 36, A and B). DNA content staining and flow cytometry confirmed that HDAC inhibition resulted in the accumulation of cells in the G2/M phase of the cell cycle (34) (FIG. 36, C and D).

The shared response to HDAC inhibition included not only cell-cycle arrest but also the altered expression of genes involved in cellular metabolism (FIG. 35C). Histone acetyltransferases and deacetylases regulate chromatin accessibility and transcription factor activity through the addition or removal of charged acetyl groups (35-37). Acetate, the product of HDAC class I-, II-, and IV-mediated histone deacetylation and a precursor to acetylcoenzyme A(acetyl-CoA), is required for histone acetylation but also has important roles in metabolic homeostasis (23, 38, 39). Inhibition of nuclear deacetylation limits recycling of chromatin-bound acetyl groups for both catabolic and anabolic processes (39). Accordingly, we observed that HDAC inhibition led to sequestration of acetate in the form of markedly increased acetylated lysine levels after exposure to a 10 mM dose of the HDAC inhibitors pracinostat and abexinostat (FIG. 37).

Figure 38A:
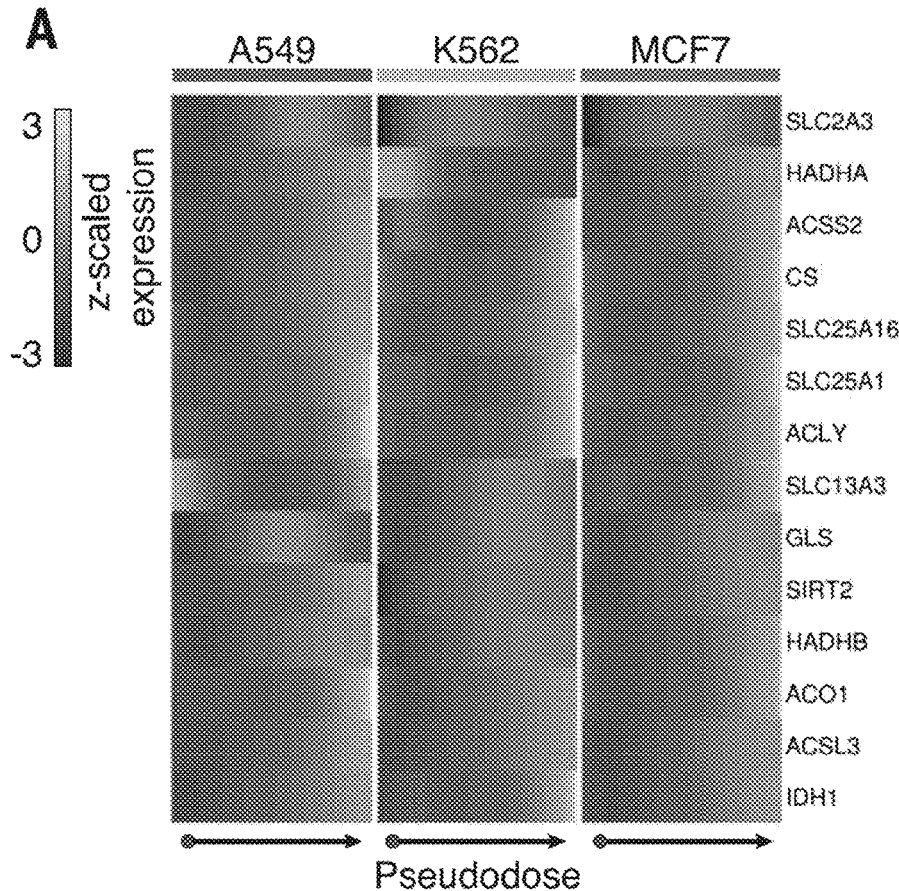

Upon further inspection of pseudodose dependent genes, we observed that enzymes critical for cytoplasmic acetyl-CoA synthesis from either citrate (ACLY) or acetate (ACSS2) were up-regulated (FIG. 38A). Genes involved in cytoplasmic citrate homeostasis (GLS, IDHL and ACO1), citrate cellular import (SLC13A3), and mitochondrial citrate production and export (CS, SLC25A1) were also up-regulated. Up-regulation of SIRT2, which deacetylates tubulin, was also observed in response to HDAC inhibition.

Figure 38B:
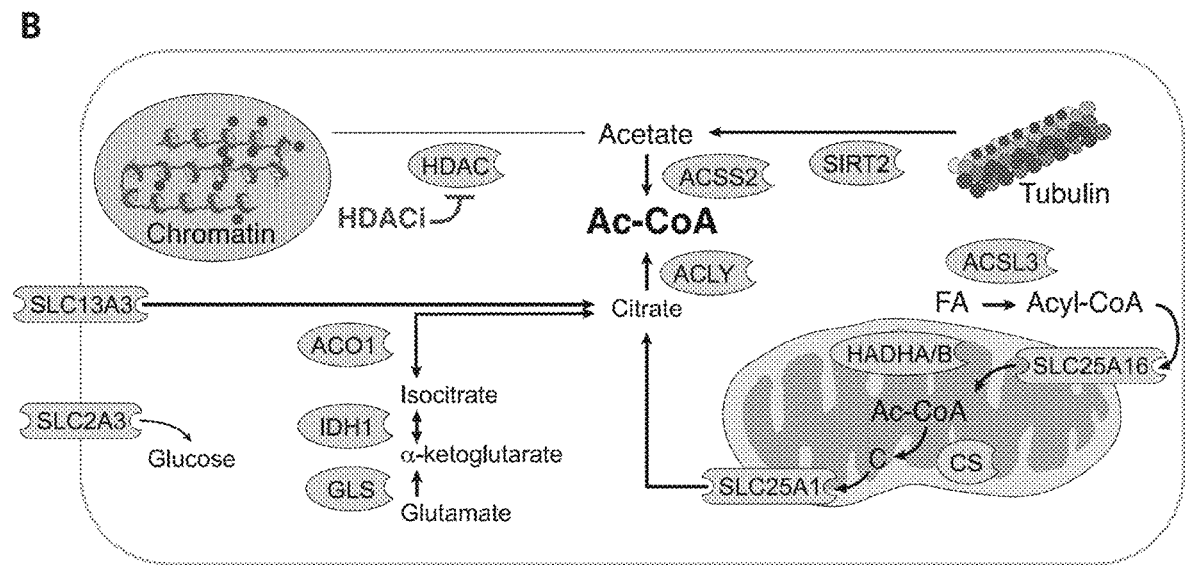
Figures 39A, 39B, 39C, 39D:
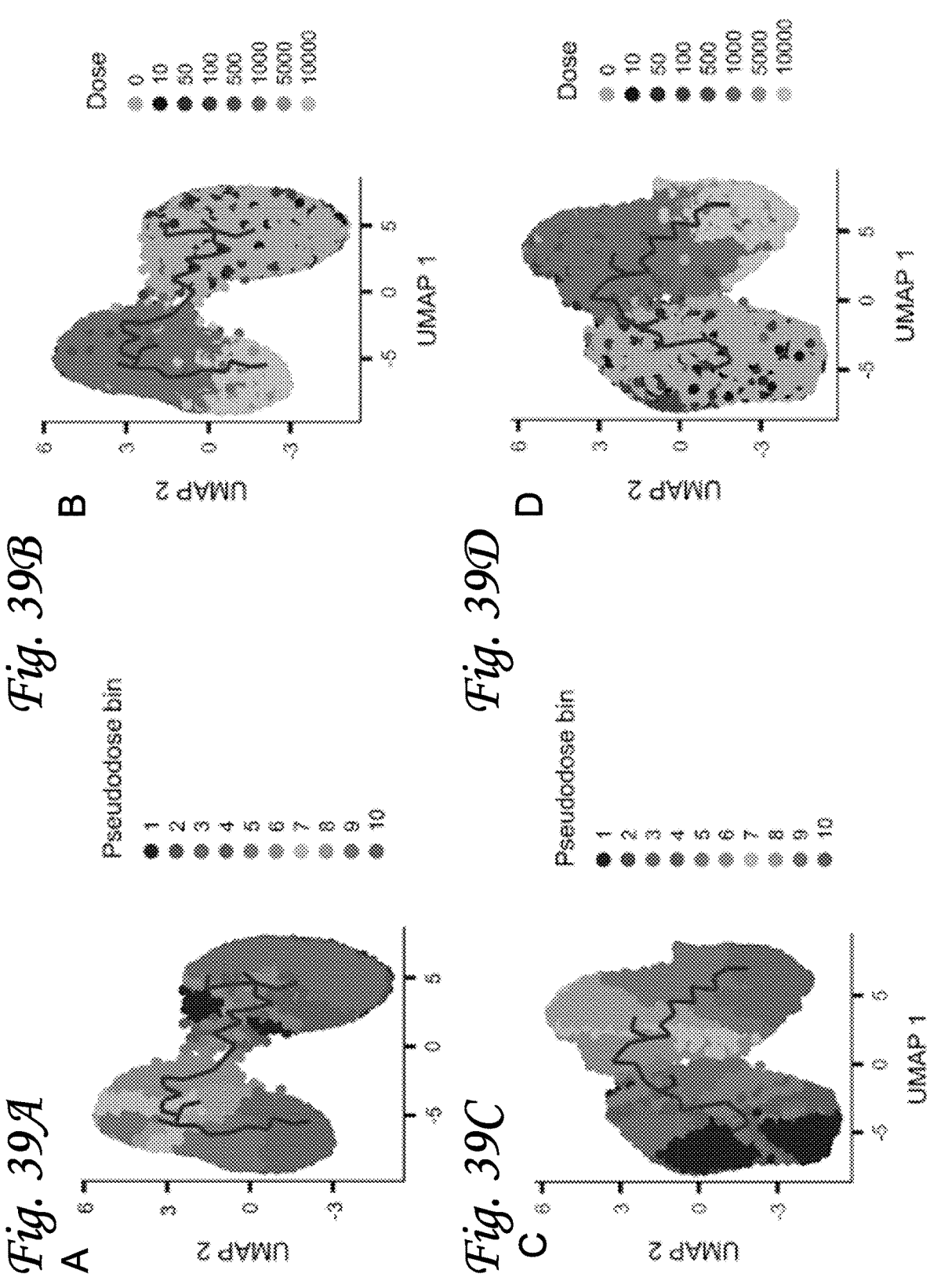
Figure 39E:
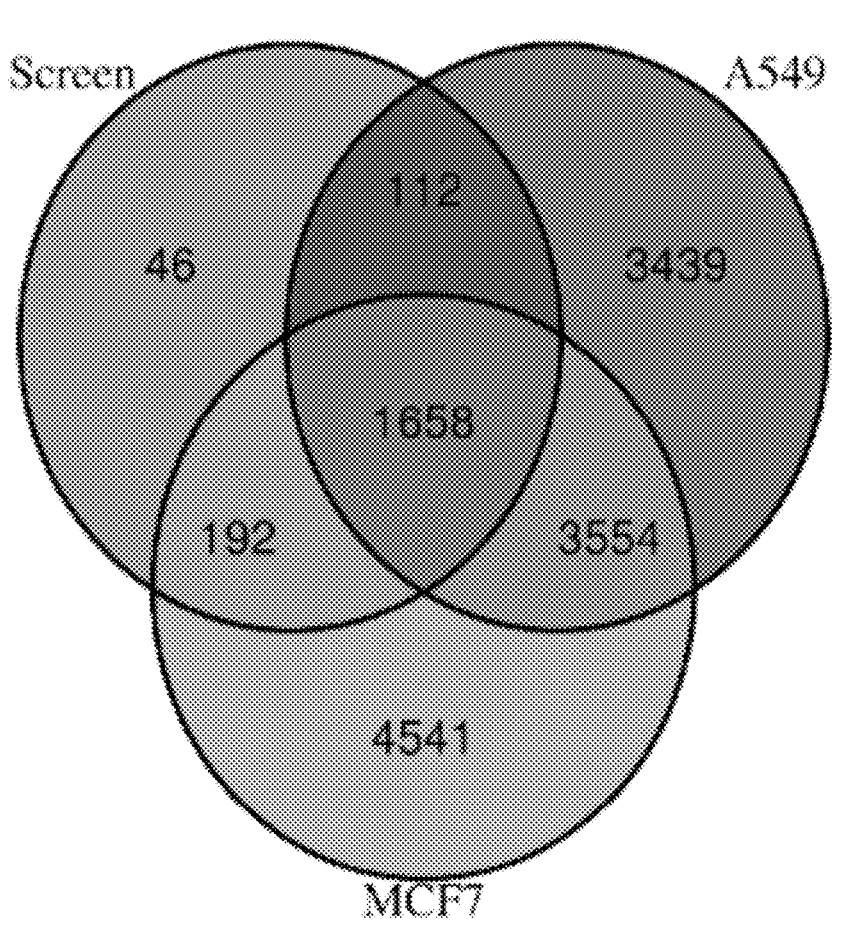
Figure 39F:
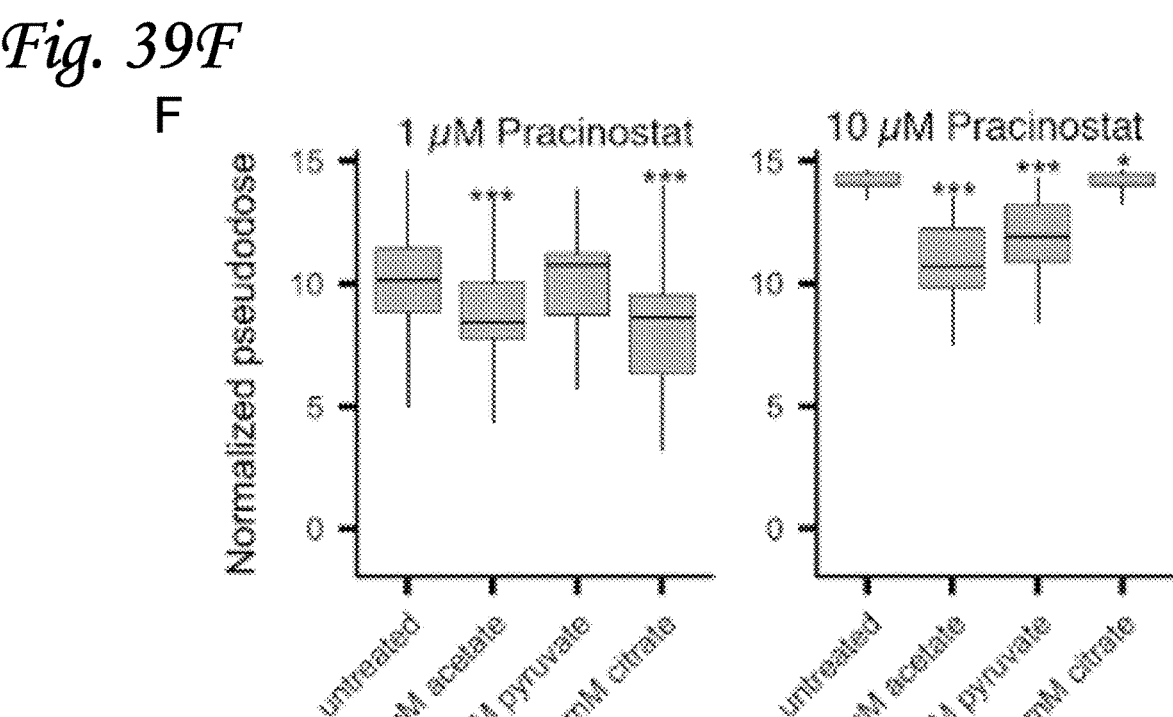
Figure 39G:
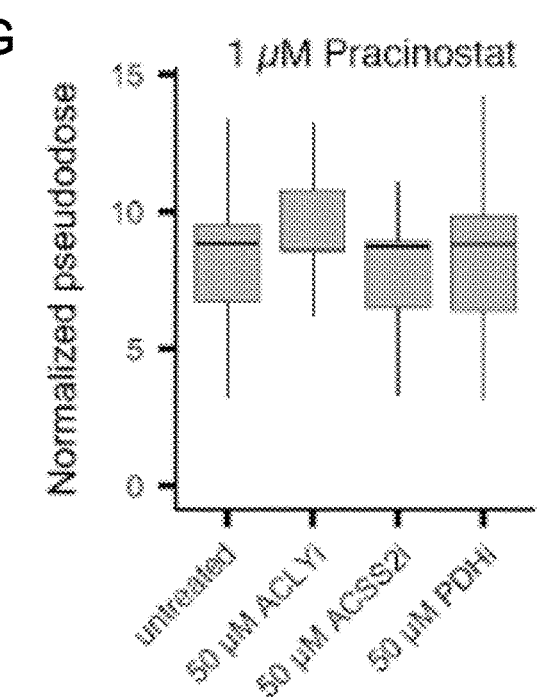
Figure 39H:
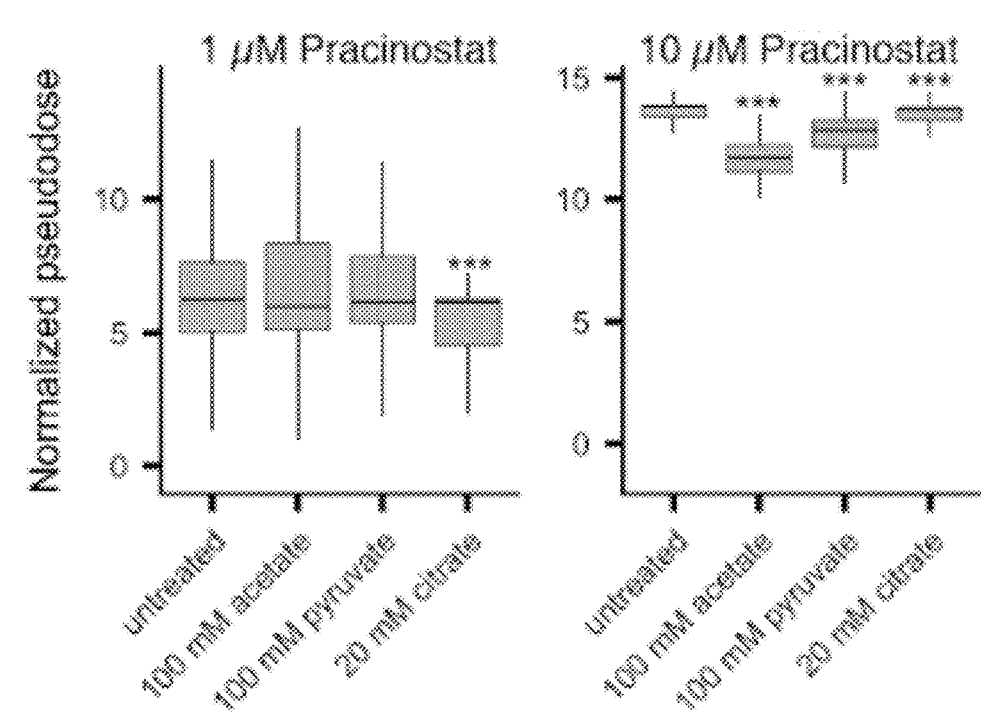
Figure 39I:
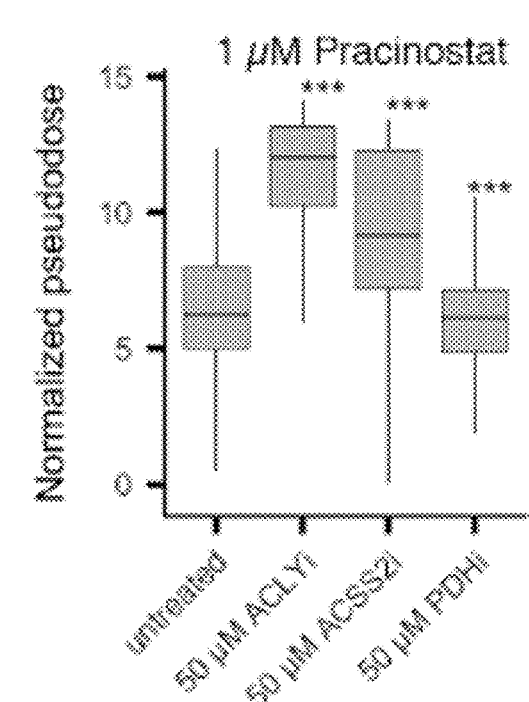
Figure 39J:
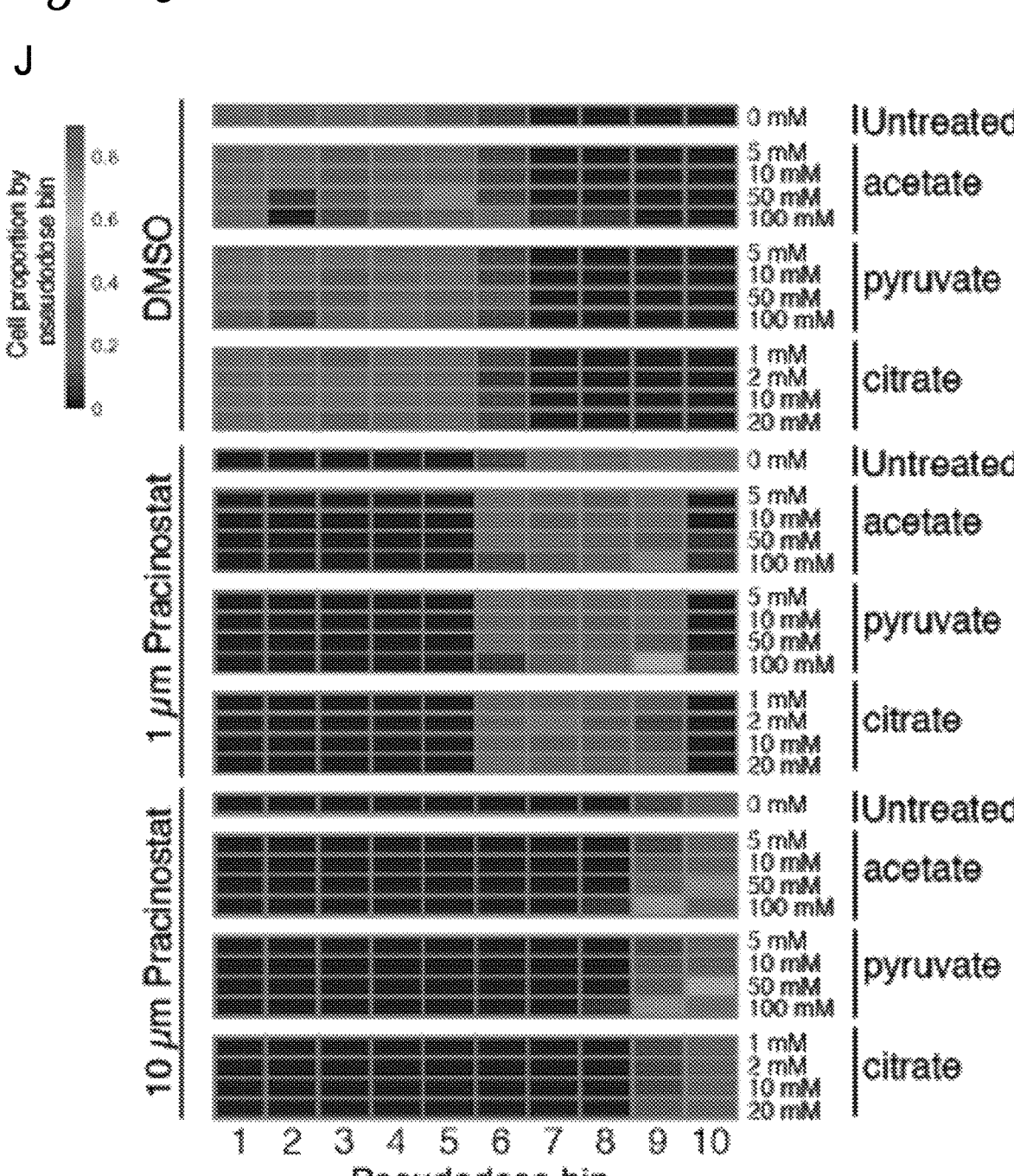
Figure 39K:
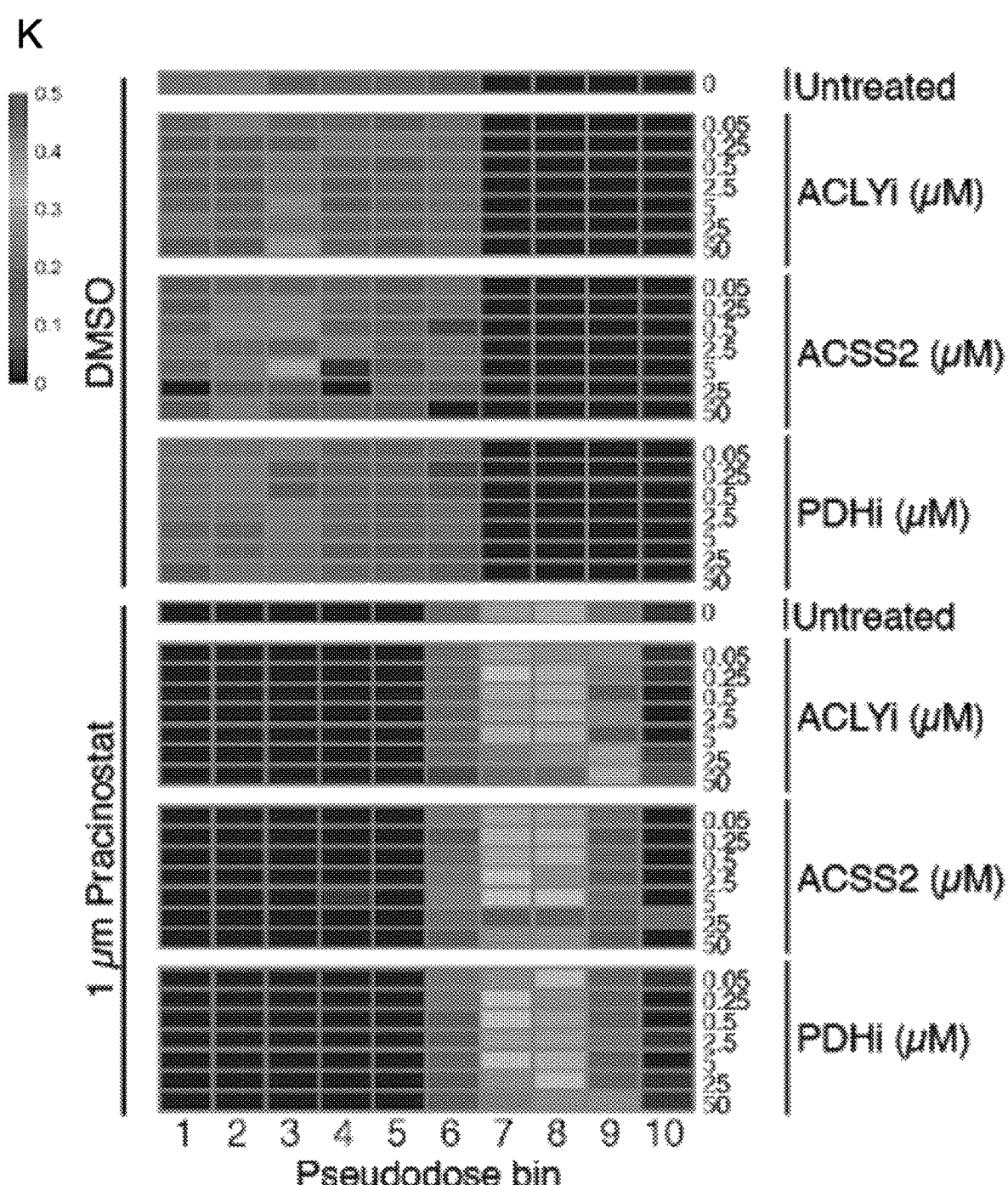
Figure 39L:
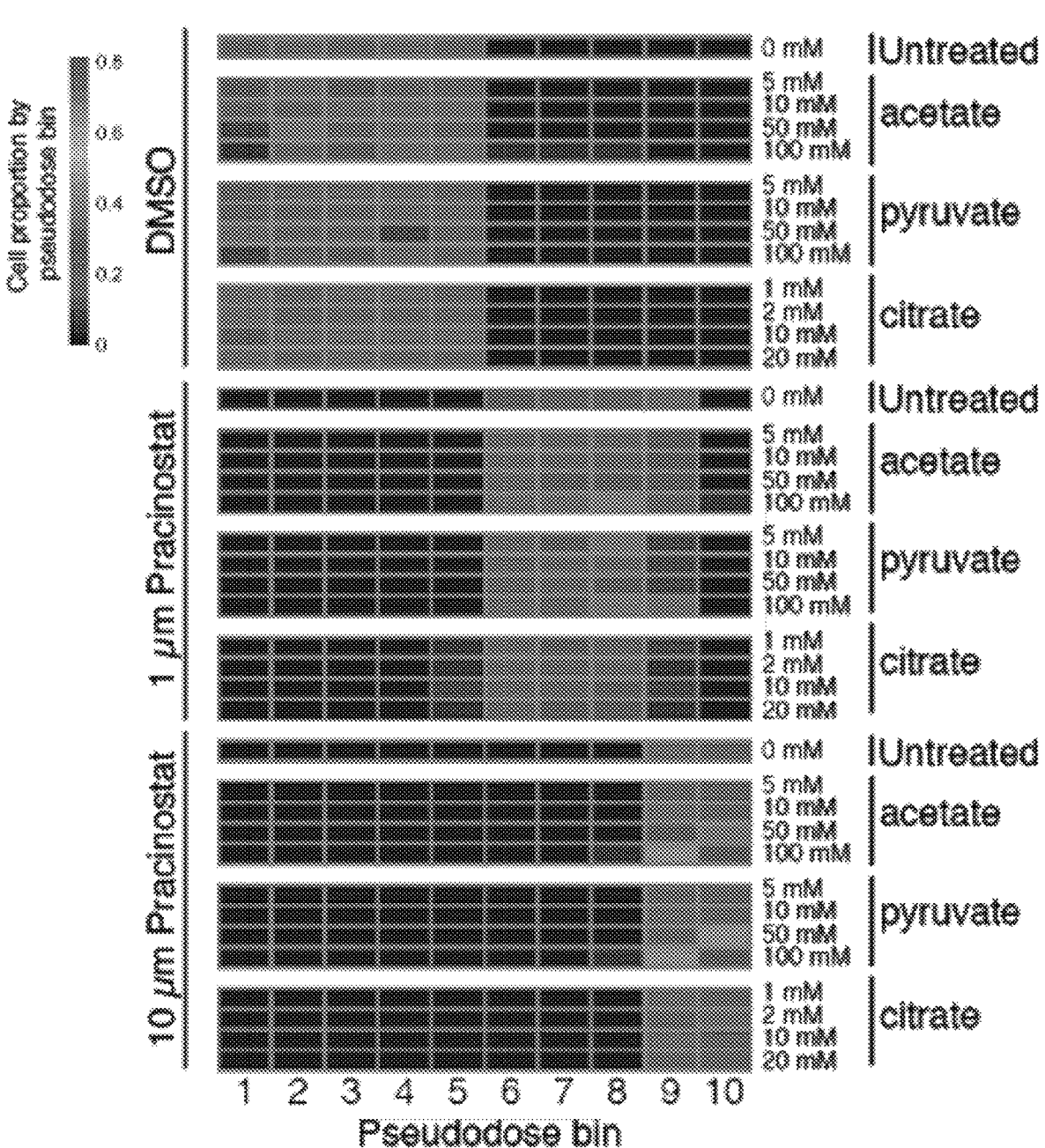

Together with increases in chromatin-bound acetate, these transcriptional responses suggest a metabolically consequential depletion of cellular acetyl-CoA reserves in HDAC-inhibited cells (FIG. 38B). To validate this further, we sought to shift the distribution of cells along the HDAC inhibitor trajectory by modulating cellular acetyl-CoA levels. We treated A549 and MCF7 cells with pracinostat in the presence and absence of acetyl-CoA precursors (acetate, pyruvate, or citrate) or inhibitors of enzymes (ACLY, ACSS2, or PDH) involved in replenishing acetyl-CoA pools. After treatment, cells were harvested and processed using sci-Plex and trajectories constructed for each cell line (FIGS. 39 and 40). In both A549 and MCF7 cells, acetate, pyruvate, and citrate supplementation was capable of blocking pracinostat treated cells from reaching the end of the HDAC inhibitor trajectory (FIG. 39, F, J, H, and L). In MCF7 cells, both ACLY and ACSS2 inhibition shifted cells farther along the HDAC inhibitor trajectory, although no such shift was observed in A549 (FIG. 39, G, K, I, and M). Taken together, these results suggest that a major feature of the response of cells to HDAC inhibitors, and possibly their associated toxicity, is the induction of an acetyl-CoA-deprived state.

Discussion

Here, we present sci-Plex, a massively multiplex platform for single-cell transcriptomics. sci-Plex uses chemical fixation to cost-effectively and irreversibly label nuclei with short, unmodified ssDNA oligos. In the proof-of-concept experiment described here, we applied sci-Plex to quantify the dose-dependent responses of cancer cells to 188 compounds through an assay that is both high content (global transcription) and high resolution (single cell). By profiling several distinct cancer cell lines, we distinguished between shared and cell-line-specific molecular responses to each compound.

sci-Plex offers some distinctive advantages over conventional HTS: it can distinguish a compound's distinct effects on cellular subsets (including complex in vitro systems such as cellular reprogramming, organoids, and synthetic embryos); it can unmask heterogeneity in cellular response to a perturbation; and it can measure how drugs shift the relative proportions of transcriptionally distinct subsets of cells. Highlighting these features, our study provides insight into the mechanism of action of HDAC inhibitors. Specifically, we find that the main transcriptional responses to HDAC inhibitors involve cell-cycle arrest and marked shifts in genes related to acetyl-CoA metabolism. For some HDAC inhibitors, we observed clear heterogeneity in responses observed at the single-cell level. Although HDAC inhibition is conventionally thought to act through mechanisms directly involving chromatin regulation, our data support an alternative model, albeit not a mutually exclusive one, in which HDAC inhibitors impair growth and proliferation by interfering with a cancer cell's ability to draw acetate from chromatin (22, 23, 39). As such, variation in cells' acetate reservoirs is a potential explanation for their heterogeneous responses to HDAC inhibitors.

As the cost of single-cell sequencing continues to fall, the opportunities for leveraging sci-Plex for basic and applied goals in biomedicine may be substantial. The proof-of-concept experiments described here, consisting of nearly 5000 independent treatments with transcriptional profiling of >100 single cells per treatment, can potentially be scaled toward a comprehensive, high-resolution atlas of cellular responses to pharmacologic perturbations (e.g., hundreds of cell lines or genetic backgrounds, thousands of compounds, multichannel single-cell profiling, etc.). The ease and low cost of oligo hashing, coupled with the flexibility and exponential scalability of single-cell combinatorial indexing, would facilitate this goal.

CITATIONS

1. J. R. Broach, J. Thorner, Nature 384 (Suppl), 14-16 (1996).
2. D. A. Pereira, J. A. Williams, Br. J. Pharmacol. 152, 53-61 (2007).
3. D. Shum et al., J. Enzyme Inhib. Med. Chem. 23, 931-945 (2008).
4. C. Yu et al., Nat. Biotechnol. 34, 419-423 (2016).
5. Z. E. Perlman et al., Science 306, 1194-1198 (2004).
6. Y. Futamura et al., Chem. Biol. 19, 1620-1630 (2012).
7. J. Kang et al., Nat. Biotechnol. 34, 70-77 (2016).
8. K. L. Huss, P. E. Blonigen, R. M. Campbell, J. Biomol. Screen. 12, 578-584 (2007).
9. C. Ye et al., Nat. Commun. 9, 4307 (2018).
10. E. C. Bush et al., Nat. Commun. 8, 105 (2017).
11. A. Subramanian et al., Cell 171, 1437-1452.e17 (2017).
12. J. Lamb et al., Science 313, 1929-1935 (2006).
13. M. B. Elowitz, A. J. Levine, E. D. Siggia, P. S. Swain, Science 297, 1183-1186 (2002).
14. C. Trapnell, Genome Res. 25, 1491-1498 (2015).
15. S. M. Shaffer et al., Nature 546, 431-435 (2017).
16. S. L. Spencer, S. Gaudet, J. G. Albeck, J. M. Burke, P. K. Sorger, Nature 459, 428-432 (2009).
17. M. Stoeckius et al., Genome Biol. 19, 224 (2018).
18. J. Gehring, J. H. Park, S. Chen, M. Thomson, L. Pachter, Highly multiplexed single-cell RNA-seq for defining cell population and transcriptional spaces. bioRxiv 315333 [Preprint] 5 May 2018. doi.org/10.1101/315333.
19. C. S. McGinnis et al., Nat. Methods 16, 619-626 (2019).
20. D. Shin, W. Lee, J. H. Lee, D. Bang, Sci. Adv. 5, eaav2249 (2019).
21. J. Cao et al., Nature 566, 496-502 (2019).
22. M. A. McBrian et al., Mol. Cell 49, 310-321 (2013).
23. S. A. Comerford et al., Cell 159, 1591-1602 (2014).
24. D. A. Cusanovich et al., Science 348, 910-914 (2015).
25. J. Cao et al., Science 357, 661-667 (2017).
26. L. McInnes, J. Healy, UMAP: Uniform Manifold Approximation and Projection for Dimension Reduction. arXiv:1802.03426 [stat.ML] (9 Feb. 2018).
27. M. Jost et al., Mol. Cell 68, 210-223.e6 (2017).
28. G. Grosveld et al., Mol. Cell. Biol. 6, 607-616 (1986).
29. E. K. Greuber, P. Smith-Pearson, J. Wang, A. M. Pendergast, Nat. Rev. Cancer 13, 559-571 (2013).
30. J. Barretina et al., Nature 483, 603-607 (2012).
31. C. Dai et al., J. Clin. Invest. 122, 3742-3754 (2012).
32. L. Haghverdi, A. T. L. Lun, M. D. Morgan, J. C. Marioni, Nat. Biotechnol. 36, 421-427 (2018).
33. C. Trapnell et al., Nat. Biotechnol. 32, 381-386 (2014).
34. W. Brazelle et al., PLOS ONE 5, e14335 (2010).
35. J.-S. Roe, F. Mercan, K. Rivera, D. J. Pappin, C. R. Vakoc, Mol. Cell 58, 1028-1039 (2015).

36. J. E. Brownell et al., Cell 84, 843-851 (1996).
37. J. Taunton, C. A. Hassig, S. L. Schreiber, Science 272, 408-411 (1996).
38. S. K. Kurdistani, Curr. Opin. Genet. Dev. 26, 53-58 (2014).
39. K. E. Wellen et al., Science 324, 1076-1080 (2009).

Materials and Methods

Cell Culture

A549 cells and K562 cells were a kind gift from Dr. Robert Bradley (UW) and Dr. David Hawkins (UW), respectively. MCF7 (cat no. HTB-22), NIH3T3 (cat no. CRL-1658) and HEK293T (cat no. CRL-11268) cells were purchased from ATCC. A549 and MCF7 cells were cultured in DMEM (ThermoFisher, 11995073) media supplemented with 10% FBS (ThermoFisher, cat no. 26140079) and 1% penicillin-streptomycin (ThermoFisher, 15140122). K562 cells were cultured in RPMI 1640 (Fisher Scientific, cat no. 11-875-119) supplemented with 10% FBS and 1% penicillin-streptomycin and maintained between $0.2$-$1 \times 10^6$ cells/ml. All cells were cultured at 37 C with 5% $CO_2$. Adherents cells were split when they reached 90% confluence by washing with DPBS (Life Technologies, cat no. 14190-250), trypsinizing using TryPLE (Fisher Scientific, cat no. 12-604-039) and split at either 1:4 (MCF7) or 1:10 (A549, NIH3T3 and HEK293T).

Compound Preparation

Dexamethasone was purchased from Sigma-Aldrich and resuspended in molecular biology grade ethanol (Fisher Scientific). BMS-345541 (S8044), Vorinostat (S1047), and Nutlin-3a (S8059) were acquired from Selleck Chemicals and resuspended in DMSO (VWR Scientific, 97063-136). Cherry-picked 96-well compound screens were acquired from Selleck Chemicals resuspended to 10 mM in DMSO (data not shown). Compounds were diluted in their respective vehicle to 1000× of their desired treatment concentration and stored at −80 C until use.

Drug Treatment

For 96-well experiments, adherent cells were trypsinized, washed with PBS and plated in tissue culture treated 96 well flat bottom plates (Thermo Fisher Scientific, cat no. 12-656-66) at 25,000 cells per well in 100 μL of media. Suspension cells were washed with PBS and plated in 96 well V-bottom tissue culture plates (Thermo Fisher Scientific, cat no. 549935) at 25,000 cells per well in 100 μL of media. Cells were allowed to recover for 24 hours before treatment with 1 μL of a 1:10 dilution of the appropriate compound or vehicle in PBS to maintain a vehicle concentration of 0.1% for all wells. Cells were then exposed to small molecules at the specified concentration for either 24 or 72 hours. For experiments where cells were co-treated with HDAC inhibitors and either acetate, pyruvate, citrate, ACSS2 inhibitor (EMD Millipore Inc., Cat No. 533756), ACLY inhibitor (Cayman Chemicals, BMS-303141 Cat No. 943962-47-8) or PDH inhibitor (Cayman Chemicals, Cat No. 504817), cells were treated 24 hours after plating and harvested after 24 hours. In this set of experiments, all wells contained a final concentration of 0.2% DMSO to match treatment with both the HDAC inhibitor and inhibitors of metabolic processes.

CellTiter Glo

A549, MCF7 and K562 cells were seeded in 96 well plates, allowed to attach for 24 hours and treated with BMS345541, dexamethasone, nutlin-3A, SAHA, as described above. 24 hours post treatment, plates were allowed to reach room temperature and viability estimated using the CellTiter-Glo viability assay (Promega) according to manufacturer's instructions. Luminescence was recorded using a BioTek synergy plate reader. For each drug treatment luminescence readings were normalized to the average luminescence intensities of vehicle DMSO treated wells.

Cell Counts of Bosutinib Exposed Cells

A549, MCF7 and K562 cells were seeded in 12 well plates at $2.8 \times 10^5$ cells per well. After 24 hours to allow for A549 and MCF7 attachment, cells were exposed for 24 hours to 0.1, 1 and 10 μM bosutinib or DMSO vehicle control. After treatment, adherent cells were detached using TrypLE or directly resuspended in 1 mL of media and cells counted on a Countess II FL automated cell counter (ThermoFisher).

Cancer Cell Line Encyclopedia and Connectivity Map Data and Analysis

Pharmacological profiling data was downloaded from the Cancer cell line encyclopedia (CCLE) data portal (available on the world wide web at portals.broadinstitute.org/ccle/data). Data was isolated and plotted for cell line of haematopoietic and lymphoid, lung and breast tissue origin exposed to the Abl inhibitors AZD0530 and nilotinib. Connectivity map (CMAP) data was downloaded from the CLUE command app in the CMAP data portal (available on the world wide web at clue.io/command?q=/home). Top connections and connectivity scores (obtained using the /conn command) were exported between the MEK inhibitor perturbagen class (CP_MEK_INHIBITOR) and HSP inhibitor perturbagen class (CP_HSP_INHIBITOR) across all cell lines (Summary) or individual cell lines that overlap with our study (A549 and MCF7). Results were then filtered for data from inhibitor exposure. To determine how connectivities change across all vs. individual cell lines, we filtered for the top connections that overlap with the connectivity summary in data from individual cell lines. Connectivity scores were subjected to a threshold value of 90 as in the associated CMAP study (11).

Flow Cytometry

A549 and MCF7 cells were seeded in 6 cm dishes at $1.6 \times 10^6$ cells per plate. K562 cells were seeded in T25 cm2 flasks at $1.6 \times 10^6$ cells per flask. After 24 hours to allow for A549 and MCF7 attachment cells were exposed for 24 hours to 10 μM abexinostat, 10 μM pracinostat or DMSO as a vehicle control. After treatment cells were harvested as described above, pellets washed twice in PBS, resuspended in 500 μL of cold PBS and fixed by the addition of 5 mL of ice-cold ethanol while vortexing at low speed. Cells were stored at −20 C prior to processing for flow cytometry analysis. For flow cytometry, ethanol was removed and fixed cells washed twice with PBS containing 1% BSA (PBS-B) and blocked for 1 hour at room temperature. Then, blocking buffer was removed and cells were incubated in PBS containing 1% BSA and 0.1% tryton X-100 (PBS-BT) as well as a 1:500 dilution of mouse anti-acetyl-lysine antibody (cat no. ICP0390, ImmuneChem Pharmaceuticals Inc) for 2 hours at room temperature. After incubation, cells were washed twice with PBS-BT and incubated with goat anti-mouse Alexa-647 in PBS-BT for 1 hour at room temperature. Lastly, cells were washed twice with PBS-BT, once with PBS-B and resuspended in PBS-B containing 5 μg/ml Hoechst 33258 (Life Sciences Technologies) to stain the DNA. Then the levels of total acetylated-lysine and DNA content was analyzed by flow cytometry on an LSRII flow cytometer (BD Biosciences). Quantification and downstream analysis was performed using FlowJo10 (FlowJo.LLC).

Cell Harvest, Nuclei Isolation and Sample Hashing

For the harvest of adherent cells, media was removed, and cells were rinsed with 100 µL of DPBS and tryspinized with 50 µL of Tryp-LE for 15 minutes at 37 C. Once cells had detached from the culture plate, the reaction was quenched with 150 µl of ice-cold DMEM containing 10% FBS. Cell suspensions were generated by pipetting and the entire volume was transferred to a 96 well V-bottom plate. Cells were then pelleted by centrifugation at 300×g for 6 minutes, washed with 100 µL of ice-cold DPBS and re-pelleted at 300×g for 6 minutes.

Lysis was conducted in the 96 well V-bottom plate. Following removal of PBS, cell suspensions were lysed and labeled with 50 µL of cold lysis buffer (10 mM Tris-HCl, pH 7.4, 10 mM NaCl, 3 mM $MgCl_2$, 0.1% IGEPAL CA-630) (24) supplemented with 1% Superase RNA Inhibitor and 400 femtomoles of hashing oligo of the form 5'-GTCTCGTGGGCTCGGAGATGTGTATAAGA-GACAG-[10 bp-barcode]-BAAAAAAAAAAAAAAAAAAAAAAAAAAAAAAAA-3' (SEQ ID NO:1) where B is G, C or T (IDT). For the large compound screen, 500 femtomoles of an additional oligo was used to uniquely index each 96 well treatment plate. After lysis with 3 strokes of multichannel pipette, cells were fixed by addition of 200 µL of fixation buffer (5% Paraform-aldehyde, 1.25×PBS). Nuclei were then fixed on ice for 15 minutes before pooling into a trough. Nuclei were pooled by plate into a 50 mL conical tube and pelleted by centrifuga-tion at 500×g for 5 minutes. Subsequently, cells were resuspended in 500 µL of nuclei suspension buffer (NSB; (10 mM Tris-HCl, pH 7.4, 10 mM NaCl, 3 mM $MgCl_2$, 1% Superase RNA Inhibitor, 1% 0.2 mg/mL Ultrapure BSA)). Finally, nuclei from all plates were pooled into a single conical tube and nuclei were pelleted by centrifugation at 500×g for 5 minutes. Nuclei were then resuspended in 1 mL of NSB and flash frozen into liquid nitrogen in 100 µL aliquots. Nuclei were then stored at −80 C until further processing with sci-RNA-seq.

Preparation of Sci-RNA-Seq2 Libraries

Frozen nuclei were thawed over ice and spun down at 500 g for 5 minutes. Cells were then permeabilized in permea-bilization buffer (NSB+0.25% Triton-X) for 3 minutes and then spun down. Following another a wash in NSB, two-level sci-RNA-seq libraries prepared as previously described (25). Briefly, nuclei were pelleted at 500×g for 5 minutes, and resuspended in 100 µL of NSB. Cell counts were obtained by staining nuclei with 0.4% trypan blue (Sigma-Aldrich) and counted using a hemocytometer. 5000 nuclei in 2 µL of NSB and 0.25 µL of 10 mM dNTP mix (Thermo Fisher Scientific, cat no. R0193) were then distrib-uted onto a skirted twin.tec 96 well LoBind plate (Fisher Scientific, cat no. 0030129512) after which 1 µL of uniquely indexed oligo-dT (25 µM)(25) was added to every well, incubated at 55 C for 5 minutes and placed on ice. 1.75 µL of reverse transcription mix (1 µL of Superscript IV first-strand buffer, 0.25 µL of 100 mM DTT, 0.25 µL of Super-script IV and 0.25 µL of RNAseOUT recombinant ribonu-clease inhibitor) was then added to every well and plates incubated at 55 C for 10 minutes and placed on ice. 5 µL of stop solution (40 mM EDTA, 1 mM spermidine and 0.5% BSA) were added to each well to stop the reaction. Wells were pooled using wide bore tips, and nuclei transferred to a flow cytometry tube through a 0.35 µm filter cap and DAPI added to a final concentration of 3 µM. Pooled nuclei were then sorted on a FACS Aria II cell sorter (BD) at 150 cells per well into 96 well LoBind plates containing 5 µL of EB buffer (Qiagen). After sorting, 0.75 µL of second strand mix (0.5 µL of mRNA second strand synthesis buffer and 0.25 µL of mRNA second strand synthesis enzyme, New England Biolabs) were added to each well, second strand synthesis performed at 16 C for 150 minutes. Tagmentation was performed by addition of 5.75 µL of tagmentation mix (0.01 µL of a custom TDE1 enzyme in 5.74 µL 2× Nextera TD buffer, Illumina) and plates incubated for 5 minutes at 55 C. Reaction was terminated by addition of 12 µL of DNA binding buffer (Zymo) and incubated for 5 minutes at room temperature. 36 µL of Ampure XP beads were added to every well, DNA purified using the standard Ampure XP protocol (Beckman Coulter) eluting with 17 µL of EB buffer and DNA transferred to a new 96 well LoBind plate. For PCR, 2 µL of indexed P5, 2 µL of indexed P7 (25) and 20 µL of NEBNext High-Fidelity master mix (New England Biolabs) were added to each well and PCR performed as follows: 75 C for 3 minutes, 98 C for 30 seconds and 18 cycles of 98 C for 10 seconds, 66 C for 30 seconds and 72 C for 1 minute followed by a final extension at 72 C for 5 minutes. After PCR, all wells were pooled, concentrated using a DNA clean and concentrator kit (Zymo) and purified via a 0.8× Ampure XP cleanup. Final library concentrations were determined by Qubit (Invitrogen), libraries visualized using a TapeStation D1000 DNA Screen tape (Agilent) and libraries sequenced on a Nextseq 500 (Illumina) using a high output 75 cycle kit (Read 1: 18 cycles, Read 2: 52 cycles, Index 1: 10 cycles and Index 2: 10 cycles).

Preparation of Sci-RNA-Seq3 Libraries

Frozen nuclei were thawed as before and three-level sci-RNA-seq libraries prepared as described in (21). Nuclei were pelleted at 500×g for 5 minutes, washed three times with NSB and a small aliquot of nuclei stained with 0.4% trypan blue (Sigma-Aldrich) and nuclei counted using a hemocytometer. 80000 nuclei in 22 µL of NSB, 2 µL of 10 mM dNTP mix and were then distributed into a skirted 2 µL of ligation compatible indexed oligo-dT primers were dis-tributed into each well of 96 well LoBind plates, incubated at 55 C for 5 minutes and placed on ice. 14 µL of reverse transcription mix (8 µL of Superscript IV first-strand buffer, 2 µL of 100 mM DTT, 2 µL of Superscript IV and 2 µL of RNAseOUT recombinant ribonuclease inhibitor) was then added to every well and RT performed on a thermocycler using the following program: 4 C for 2 minutes, 10 C for 2 minutes, 20 C for 2 minutes, 30 C for 2 minutes, 40 C for 2 minutes, 50 for 2 minutes and 55 C for 15 minutes. After RT, 60 µL of nuclei buffer containing BSA (NBB, 10 mM Tris-HCl, pH 7.4, 10 mM NaCl, 3 mM $MgCl_2$ and 1% BSA) were added to each well, nuclei pooled using a wide bore tip, nuclei pelleted by centrifugation at 500×g for 10 minutes and the supernatant removed. A second round of combina-torial indexing was performed by ligation of indexed prim-ers onto the 5' end of RT indexed cDNA. Nuclei were resuspended in NSB and 10 µL added to each well of 96 well LoBind plates after which 8 µL of indexed ligation primers were added to each well along with 22 µL of ligation mix (20 µL of Quick ligase buffer and 2 µL of Quick ligase, New England Biolabs). Ligation was then performed at 25 C for 10 minutes. After ligation, 60 µL of NBB were added to each well, nuclei pooled using a wide bore tip, another 40 mL of NBB added to the nuclei and nuclei pelleted by centrifuga-tion at 600×g for 10 minutes and the supernatant removed. Nuclei were then washed once with 5 mL of NBB, resus-pended in 4 mL of NBB, multiplets removed by filtering using a 40 µm Flowmi cell strainer (Sigma-Aldrich), nuclei counted and 5000 nuclei were distributed per well into 96 well LoBind plates in a 5 µL volume. Plates containing nuclei were frozen and stored at −80 C until further processing. After thawing the frozen plate 5 μL of second strand synthesis mix (3 μL of elution buffer, 1.33 μL mRNA second strand synthesis buffer and 0.66 μL of mRNA second strand synthesis enzyme) were added to each well and incubated at 16 C for 3 hours. Tagmentation was performed by addition of 10 μL of tagmentation mix (0.01 μL of a custom TDE1 enzyme in 9.99 μL of 2×Nextera TD buffer, Illumina) and plates incubated for 5 minutes at 55 C. After tagmentation, 20 μL of DNA binding buffer was added to every well and plates incubated at room temperature for 5 minutes. 40 μL of Ampure XP beads were then added to each well and plates incubated for 5 minutes at room temperature. Upon isolation of beads using a magnetic stand, supernatant was removed and beads were washed twice with 80% ethanol. 10 μL of USER reaction mix (1 μL of 10×USER buffer and 1 μL of USeR enzyme in nuclease-free water, New England Biolabs) was then added to each well and beads resuspended and incubated at 37 C for 15 minutes. After incubation, 7 μL of elution buffer were added to each well and supernatant transferred to a new 96 well LoBind plate after binding beads on a magnetic stand. After incubation at 85 C for 10 minutes, libraries were generated with 15 cycles of PCR. Following PCR amplification, sequencing library was purified by first concentrating 1 mL of PCR library using a 1× Ampure cleanup and then running the resulting product on a 2% agarose gel containing ethidium bromide. Gel was cut to isolate 2 fragments, hash molecules (220 bp-250 bp) and RNA library (250 bp-1000 bp). Following gel extraction and an additional 1× Ampure cleanup RNA libraries were sequenced on a NovaSeq 6000 (Illumina) (Read 1: 34 bp, Read 2: 100 bp, Index 1: 10 bp and Index 2: 10 bp) and hash libraries were sequenced on a 75 cycle NextSeq (Read 1: 34 bp, Read 2: 38 bp, Index 1: 10 bp and Index 2: 10 bp).

Preparation of Bulk RNA Sequencing Libraries

Compound treated cells were first trypsinized and harvested as described previously. Cells were then lysed in V-bottom plates using 26 μL of NSB. 2 μL of 25 μM indexed RT primers were added and annealed at 65 C for 5 minutes. Subsequently, RT reaction was performed using the SuperScript IV system, with 8 μL of 5× SuperScript Buffer, 2 μL of SuperScript IV, 2 μL 10 mM dNTP mix, 2 μL of 100 mM DTT and 2 μL of RNAseOUT recombinant ribonuclease inhibitor per well. Reaction was performed for 10 minutes at 55 C and subsequently stopped via heat inactivation (80 C for 10 minutes). Libraries were then pooled and excess RT primer was removed through either two 0.7×SPRI clean-ups or a single 0.7×SPRI cleanup followed by Exo-1 treatment and inactivation. Double stranded DNA was produced through incubation at 16 C for 3 hours with second strand synthesis mix containing 0.5 μL of enzyme and 2 μL of second strand reaction buffer in a final volume of 20 μL. Following second strand synthesis, libraries were tagmented with 1 μL of commercial Nextera reagent with 20.5 μL of 2×TD buffer. Reactions were stopped with 40 μL of Zymo Clean and Concentrate buffer and incubated at room temperature for 5 minutes. Libraries were subsequently purified with a 1×SPRI cleanup and eluted in 16 μL of elution buffer. Sequencing libraries were generated through PCR with 2 μL of index P7 and P5 primers each and 20 μL of 2×NEB Next Master Mix. Finally, libraries were pooled, purified with a 1×SPRI cleanup and quantified. Libraries were sequenced on a Nextseq 500 (Illumina) using a high output 75 cycle kit (Read 1: 18 cycles, Read 2: 52 cycles, Index 1: 10 cycles and Index 2: 10 cycles).

Pre-Processing of Sequencing Data

Sequencing runs were first demultiplexed using bcl2fastq v.2.18. Only barcodes that matched reverse transcription indices within an edit distance of 2 bp were retained. For sci-RNA-seq3 libraries, barcodes which matched both provided reverse transcription indices and ligation indices within an edit distance of 2 bp were retained. Following assignment of indices, polyA tails were trimmed using trim-galore, and reads were mapped to a human transcriptome (hg-38) or human-mouse transcriptome (hg-38 and mm-10) using the STAR aligner. Following alignment, reads were filtered for alignment quality, and duplicates were removed. Reads were considered duplicates if they (1) mapped to the same gene, (2) mapped to the same cell barcode and (3) contained the same unique molecular identifier (UMI). Reads that met the first two criteria, and differed by an edit distance of 1 from a previously observed UMI were also marked as duplicates and discarded. Non-duplicate reads were assigned to genes using bedtools (40) to intersect with an annotated gene model. All 3' UTRs in the gene model were extended by 100 bp to account for the possibility that some gene 3' UTR annotations may be too short, causing genic reads to improperly be annotated as intergenic. Cell barcodes were considered to correspond to a bona fide cell if the number of unique reads associated with the barcode was greater than an interactively defined threshold on a knee plot. Reads from cells that passed this UMI count threshold were first aggregated into a sparse matrix format and then loaded and saved as a CDS object for analysis with Monocle 3.

Assigning Sample Labels from Hash Reads

Demultiplexed reads that matched combinatorial indexing barcodes were examined to identify hash reads. Reads were considered hash reads when they met two criteria: (1) the first 10 bp of read 2 matched a hash barcode in the experiment within an edit distance of two and (2) contained a polyA track between base pairs 12 to 16 of read 2. These reads were then deduplicated by cell barcode and collapsed by UMIs to create a vector $h_i$ of hash oligo UMI counts for each nucleus i in the experiment.

To assign each nucleus i to the culture well from which it came, we test whether its sci-RNA-seq library is enriched for a particular hash barcode. We compare a nucleus's hash UMIs against a 'background distribution', which under ideal circumstances, would be the uniform distribution. In practice, minor variation in concentrations of hash oligos added to each well of liberated nuclei may necessitate empirically estimating the background. To do so, we simply average the relative hash UMIs from cell indices for which fewer than <mRNA UMIs were collected, reasoning that these reflect library contributions from RT well supernatant, debris fragments, etc. We then compare the hash UMIs $h_i$ for nucleus i to this background by a chi-squared test. After correcting the resulting p values for multiple testing by Benjamini-Hochberg, we reject the null hypothesis that $h_i$ originates from the background distribution at specified FDR (5% FDR was used in this study). Those nuclei with hash counts deemed different than background are then evaluated for enrichment for a single hash sequence. Enrichment ratios were calculated as the UMI count ratio of the most abundant vs. the second most abundant hash oligo. Specifically, if the UMI count for the most abundant hash in nucleus i is α-fold higher than the second most abundant, i is marked as a singleton. α was determined on a per-experiment basis by examining the distribution of these ratios and choosing a value that separated unlabeled cells and singularly labeled cells. Cells that fell below α-fold enrichment of a unique hash oligo were flagged as a multiplet or debris and discarded.

Dose-Response Analysis

Dose-response analysis was conducted in R using the drc package (41) by fitting a four-parameter log-logistic model for each drug to the number of cells recovered in the single-cell RNA-seq data at each dose. Cells that survived doublet analysis and QC were grouped by their culture well of origin and counted. These counts were then adjusted to account for variation in recovery as a function of cell type and culture plate as follows. The vector x of cell counts across wells were fit with the model $$\ln(x_i) = \beta_0 + \beta_{t_1} t_1 + \ldots + \beta_{t_m} t_m + \beta_{w_1} w_1 + \ldots + \beta_{w_n} w_n$$

Where $t_i$ and $w_j$ are binary indicator variables encoding the cell type and culture plate, respectively. The adjusted cell counts for a given well from culture plate of cells of type are then computed as $$\bar{x}_j = x_j - \exp(\beta_{t_k} t_k + \beta_{w_p} w_p)$$

Next, adjusted per-well cell counts were grouped by type and drug and passed as input to the drm( ) function of the drc package with a model formula 'cell_count~log_dose' and the LL.4( ) model family function. This procedure fits the model:

$$f(x; b, c, d, e) = c + \frac{d - c}{1 + \exp(b(\ln x - \ln e))}$$

In the above model, the parameters and correspond to the lower and upper asymptotic limits of the response, respectively. The steepness of the response curve is reflected in b, and e is a parameter that encodes the half-maximal 'effective dose' (ED50).

The dose response curves enable cells to be annotated according to the impact of their culture conditions on viability. Each cell is assigned a 'viability score' which is simply the expected fraction of vehicle cells remaining after exposure to a given dose of a compound. These cell counts are generated via the predict( ) function of the drc package and then normalized relative to the corresponding vehicle control.

Dimensionality Reduction and Trajectory Analysis

Gene expression profiles were visualized with Monocle 3, which uses UMAP to project them into a two or three dimensional space. Briefly, Monocle 3 first calculates size factors for every cell. Size factors were calculated as the log UMI counts observed in a single cell divided by the geometric mean of log UMI counts from all measured cells. After scaling each nucleus' UMI counts by its library size factor, Monocle3 adds a pseudocount of 1, and log transforms the counts. Next, these log-transformed profiles are projected onto the top 25 principal components. These PCA coordinates were transformed by Monocle 3 (using an approach similar to the removeBatchEffect( ) function in the limma package (42)) according to the model '~log(UMIs)+replicate' (FIG. 9) or 'log(UMIs)+viability+proliferation index+replicate'. Adjusted PCA coordinates for each cell are used to initialize UMAP. Unless otherwise noted, UMAP was run with the following parameters: 50 nearest neighbors, min_dist=0.1, inter-cell distance assessed by cosine similarity. UMAP projection of cells after dual HDAC inhibition and acetyl-COA precursor supplementation or acetyl-CoA generating enzyme inhibition was performed as described with the exception that PCA initialization was performed on the top 1000 most overdispersed genes. Louvain community detection was then performed on this UMAP space using the python package 'louvain'. Trajectory reconstruction was then performed as described in (21).

To determine whether cells exposed to a particular compound/dose combination displayed an enrichment along UMAP space we created contingency tables of the number of compound or vehicle treated cells within and outside clusters and used the stats R package implementation of Fisher's exact test to test for enrichment. For visualization of drug enrichment in FIG. 9B, cells opacity was added to cells under the minimum compound/dose that passed meet an enrichment cutoff of FDR<1% and a log 2 of the odds ratio >2.5. Cells that passed these filters were used to generate the heatmap of the fraction of enriched cells by cluster in FIG. 12.

Estimation of Proliferation Index To obtain an estimate of proliferation index for a single cell, size factor normalized expression of cell cycle marker genes (from Table S5 in (43)) were summed for each cell and logged. Scores were calculated in this way for both G1S and G2M. "Proliferation Index" refers to overall proliferative state of a cell and is calculated as the logged sum of the aggregated G1S and G2M gene expression.

Differential Expression Analysis

To test whether a gene is differentially expressed by a cell line in a dose-dependent manner when exposed to a compound, we fit its (library size-factor adjusted) UMI count recorded from each nucleus with a generalized linear model:

$$\ln(y_i) = \beta_0 + \beta_d d$$

Where $Y_i$ is a quasipoisson-valued random variable, d is the log-transformed dose of the compound being evaluated. We fit these models with Monocle 3, which uses the speed-glm package. To fit the regression model for each drug's effect on each gene, we first identify the subset of cells that are relevant for the model. To determine the effects on gene G in cells of type C when treated with drug D, we include all cells of type C that were treated with any dose of D. To these, we add cells of type C that were treated with the vehicle control. We then fit a model defined above relating the expression level of G across all of these cells. Genes are deemed to be dose-dependent differentially expressed genes (DEGs) if their fitted models include a term $\beta_d$ that is significantly different from zero as assessed by a Wald test (Benjamini-Hochberg adjusted p<0.05). P values for $\beta_d$ terms are pooled across all compounds and all genes prior to correction for multiple testing.

To assess a gene for differential expression as a function of 'pseudodose' in the consensus HDAC inhibition trajectory, we fit a model $$\ln(y_i) = \beta_{\psi}\psi + \beta_c c + \beta_{c\psi}\psi c + \beta_{d_1} d_1 + \ldots + \beta_{d_k} d_k$$

Where $Y_i$ is a quasipoisson variable capturing the gene's UMI counts, $\psi$ encodes the pseudodose values smoothed via a natural spline, c is a factor encoding the cell type, and $\beta\psi$ captures the interaction between cell type and pseudodose. The term $\beta d_j d_j$ encodes the (log) dose dependent effects of compound.

Pairwise Correlation of Screened Compounds

To identify compounds that result in similar dose-dependent changes to cellular transcriptomes we calculated the Pearson correlation between every pairwise set of compounds. We created a gene by compound matrix for the union of dose-dependent genes across all compounds where each entry is the beta coefficient for the dose dependence term $\beta_d$ and ten calculated the Pearson correlation for every drug pair using the cor.test( ) function in the R stats package specifying to use complete observations. The resulting correlation matrix was then hierarchically clustered using the pheatmap package in R. The significance of every pairwise correlation was determined using the corr.test( ) function from the psych package in R specifying Benjamini-Hochberg as the method for adjusting for multiple hypothesis testing.

Geneset Enrichment Analysis

After fitting a generalized linear model, genes that had significant coefficients (5% FDR threshold) were used for gene set enrichment analysis with the R package piano (44). Briefly, gene sets were ranked according to the set-wide average Wald test statistic corresponding to the generalized linear model term being evaluated with piano's runGSA( ) function. Genes were randomized across sets to establish a null distribution for each set's rank. After 10000 permutations, runGSA( ) computed p values using the 'mixed' directional enrichment policy. The top gene sets, corresponding to those with the largest magnitude enrichment statistic, were chosen for visualization.

Alignment of HDAC Inhibitor Treated Cells

To organize cells treated with HDAC inhibitors into a trajectory cells were sampled to equalize the number of cells represented between the three cell lines or between treatments at 24 and 72 hrs. Next, PCA coordinates were computed jointly, and then aligned using the mnnCorrect function from the package scran (32). These adjusted coordinates were used to initialize UMAP in Monocle 3. We then fit a principal graph to the data via lean_graph( ). To define the origin of the trajectory, we mapped each cell to its nearest principal graph node, and then selected all principal graph nodes for which a majority of mapped cells were treated with vehicle. All other cells' pseudodoses was measured as the geodesic distance between their nearest principal graph node to an origin node.

To quantify the potency of each HDAC inhibitor, we first grouped all cells from each replicate according to treatment and dose, and then computed the mean pseudodose for each cell. We then fit mean pseudodose values as a function of compound concentration using the drc package (41). We used a four-parameter log-logistic model, with the maximal response fixed at the highest pseudodose value achieved across all compounds and doses. We then take the model parameter e as described in the 'dose response analysis' section above as the transcriptional EC50 (TC50) for each compound.

Example 2

Massively Multiplexed Chromatin Accessibility Profiling within Single Cells

Cells undergo gene expression rewiring in response to numerous environmental, developmental and therapeutic stimuli and the specific responses vary greatly among individual cell types. Such genomic reprogramming is established through DNA-binding transcription factors (TFs), which direct a dynamic system of changes to the state of the chromatin near promoters and enhancers (Takahashi and Yamanaka 2016). However, measuring and interpreting such genomic choreography remains extremely challenging in heterogeneous cell populations or tissue samples. To address this issue, a novel approach was developed, sciPlex-ATAC-seq, which enables the simultaneous profiling of the accessible genome within thousands of individual cells from virtually unlimited experimental conditions.

Technology Overview

Highly scalable methods for single-cell transcriptome sequencing (sci-RNA-seq) and chromatin accessibility profiling via combinatorial indexing (sci-ATAC-seq), which do not require the physical isolation of single cells (Cusanovich et al. 2015; Cao et al. 2017), have been developed. These methods employ a combinatorial molecular indexing strategy that profiles exponentially more cells with each round of barcoding, driving down the cost of the experiment dramatically.

Figure 41A:
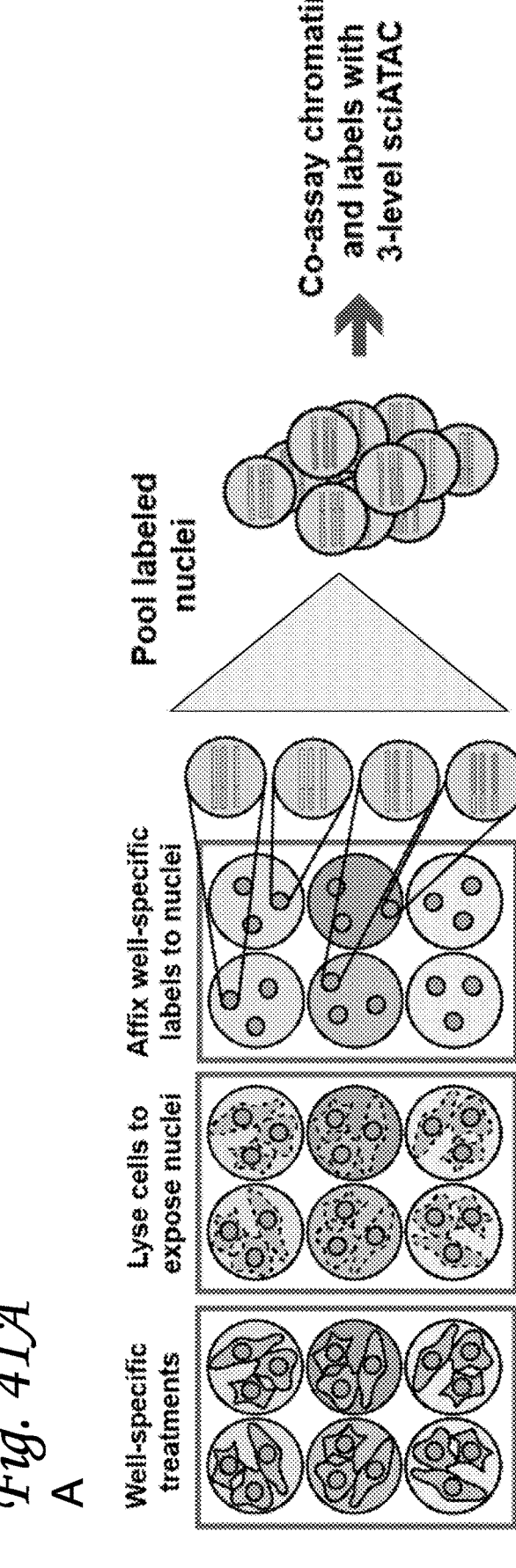
Figure 41B:
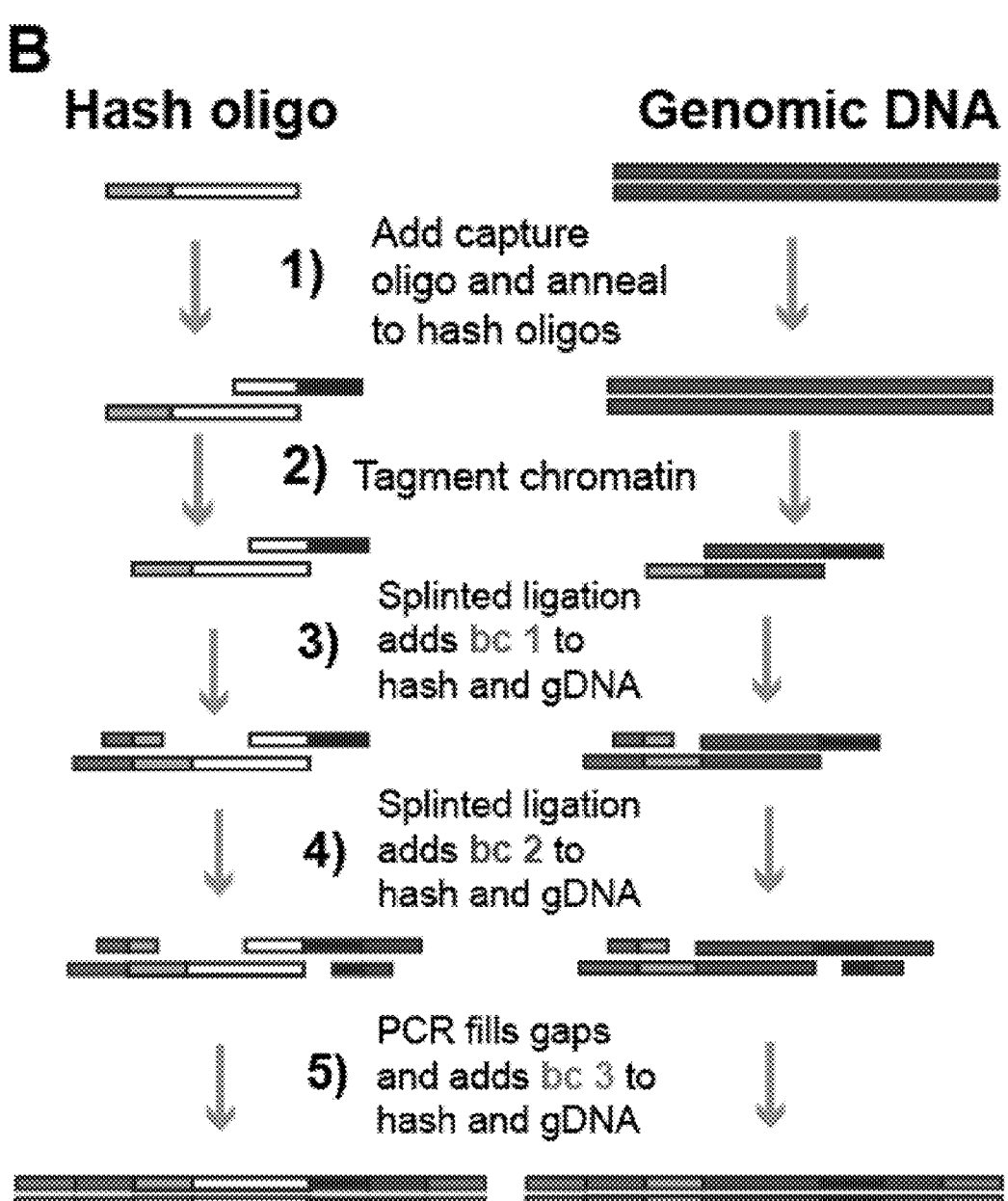

Here, in order to enable processing of multiple samples simultaneously, we have devised a system for labeling cells, such that by sequencing the accessible chromatin, one also co-assays the labels within each nucleus. The labeling approach exploits a propensity for isolated nuclei to absorb single stranded DNA oligos (labels), which can then be trapped via mild fixation (Srivatsan et al. 2020). As nuclei undergo multiple rounds of indexing, sequenceable barcodes are added to labels and chromatin within each nucleus, ultimately producing a unique barcode combination for material from each cell. Thus, all sequenced chromatin fragments and labels sharing an identical barcode combination will have come from the same cell. With this labeling strategy, we are able to obtain accessible chromatin profiles within thousands of individual cells from virtually any number of uniquely labeled samples simultaneously (FIG. 41A, 41B).

Results

Single Stranded DNA Oligos Label Nuclei, Enabling Parallel Processing of Multiple Samples for Single Cell Chromatin Accessibility Profiling To test whether our labeling approach could accurately recall the sample origin of individual cells, we performed a species mixing experiment in which human and mouse cell lines were separately labeled with species-identifying oligos (hashes), before pooling and preparing single-cell chromatin accessibility profiles through combinatorial indexing. Mouse cells (NIH-3T3) and Human cell lines (A549) were each split into three samples each and separately labelled with one of six oligos. Briefly, from each of the six samples, nuclei were isolated, incubated briefly with a distinct oligo label and then fixed with 1% formaldehyde (FIG. 41A). Following fixation all cells were pooled and nuclear labels were annealed to a common capture oligo, producing a structure resembling tagmented DNA, thus enabling the future co-assay with genomic DNA. Pooled nuclei were then tagmented in bulk by Tn5 with Nextera adaptors and 5' ends were phosphorylated with T4PNK. Combinatorial indexing was then performed on both the nuclear DNA and captured label oligos through the following steps: 1) distributing nuclei evenly between 96 wells, ligating well-specific barcode 1 to the N7 ends, 2) pooling all wells and redistributing nuclei evenly between 96 wells, ligating well-specific barcode 2 to the N5 ends, and 3) pooling all wells and redistributing nuclei to a final 96-well plate for PCR-based addition of barcode 3 (FIG. 41B). Because it is exceedingly unlikely that material from two nuclei will receive the same combination of barcodes, all chromatin fragments and label molecules with matching barcodes are expected to have come from the same cell.

Figure 41D:
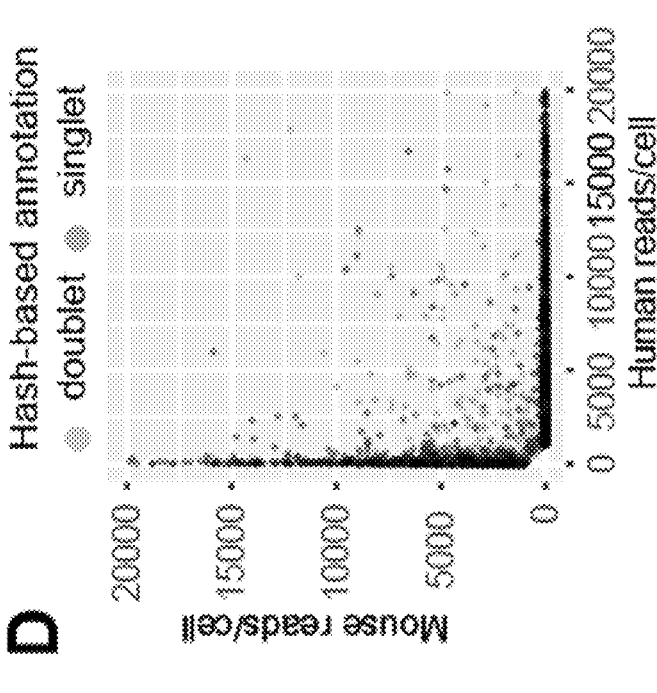
Figure 41C:
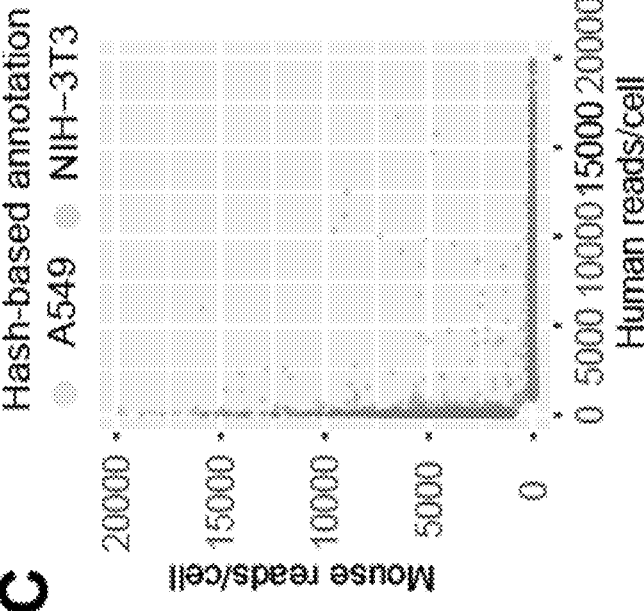
Figures 41E, 41F:
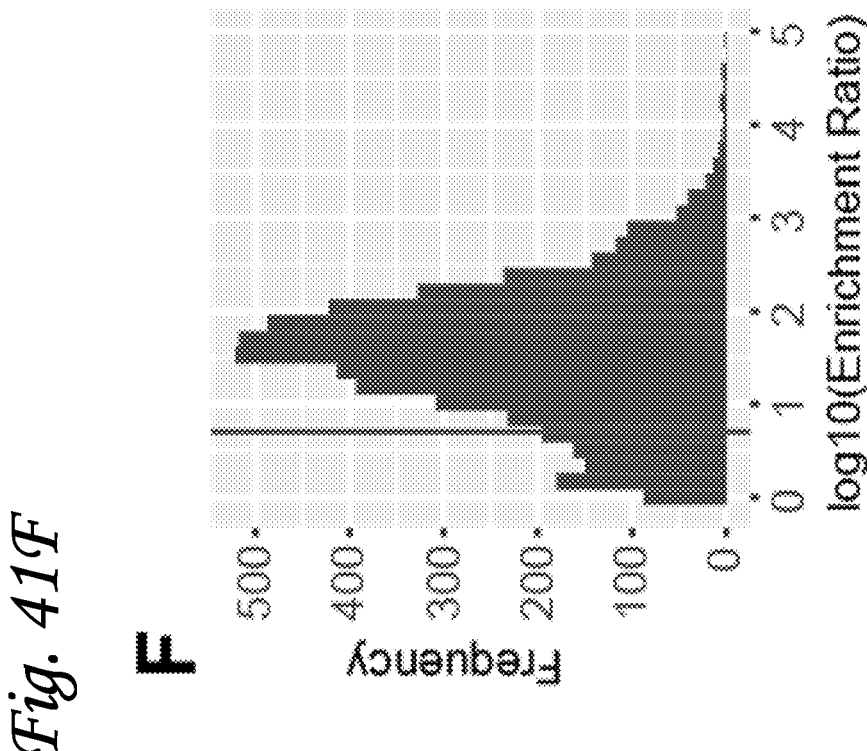

If added labels faithfully remain inside fixed nuclei throughout the described library preparation, we would expect to recover labels used on human samples strictly from human cells, and mouse labels from mouse cells. Indeed, the species of a cell could be determined solely based on the label molecules recovered from each nucleus (FIG. 411C). Moreover, cells found to have a mixture of human and mouse specific labels also had a mixture of chromatin fragments from both species, suggestive of doublets (FIG. 41D). In this experiment, we recovered more than 100 label molecules from the majority of cells (FIG. 41E) and the most common label within a nucleus was typically at least 5-fold more abundant than any other label molecule (FIG. 41F), suggesting very little background due to label mixing.

Figure 42A:
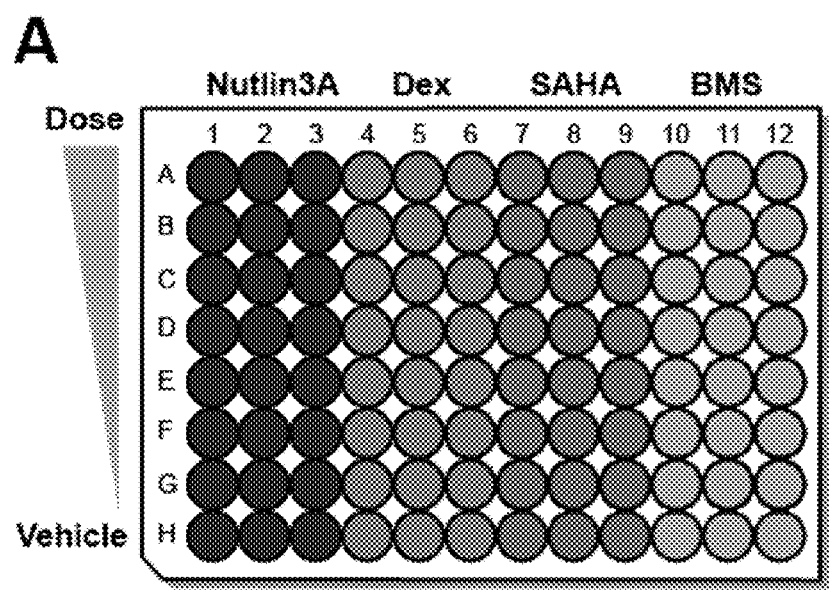

SciPlex-ATAC Enables Multiplexed Single-Cell Chromatin Profiling in Chemical Screens To demonstrate the ability to multiplex many samples with our approach, we performed a chemical screen on lung adenocarcinoma-derived (A549) cells to explore how the chromatin landscape is altered in response to four compounds, known to impact global gene regulation. Each well of a 96-well culture dish was treated for 24 hours with Nutlin-3A (p53 agonist), SAHA (broad spectrum histone deacetylase inhibitor), BMS345541 (NF-kB inhibitor), Dexamethasone (glucocorticoid receptor agonist) or a vehicle control. Moreover, we varied the dose of drug added to each well, such that the effects of each compound could be evaluated at seven different concentrations. Finally, all treatments were performed in biological triplicate (FIG. 42A). After applying unique labels to each well, cells from all conditions were pooled for parallel preparation of single cell accessible chromatin profiles.

Figure 42B:
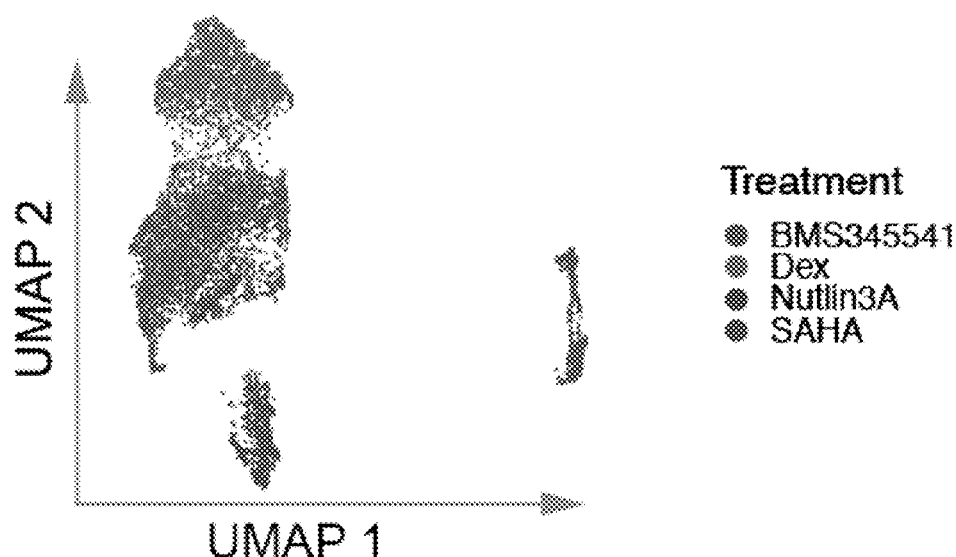
Figure 42C:
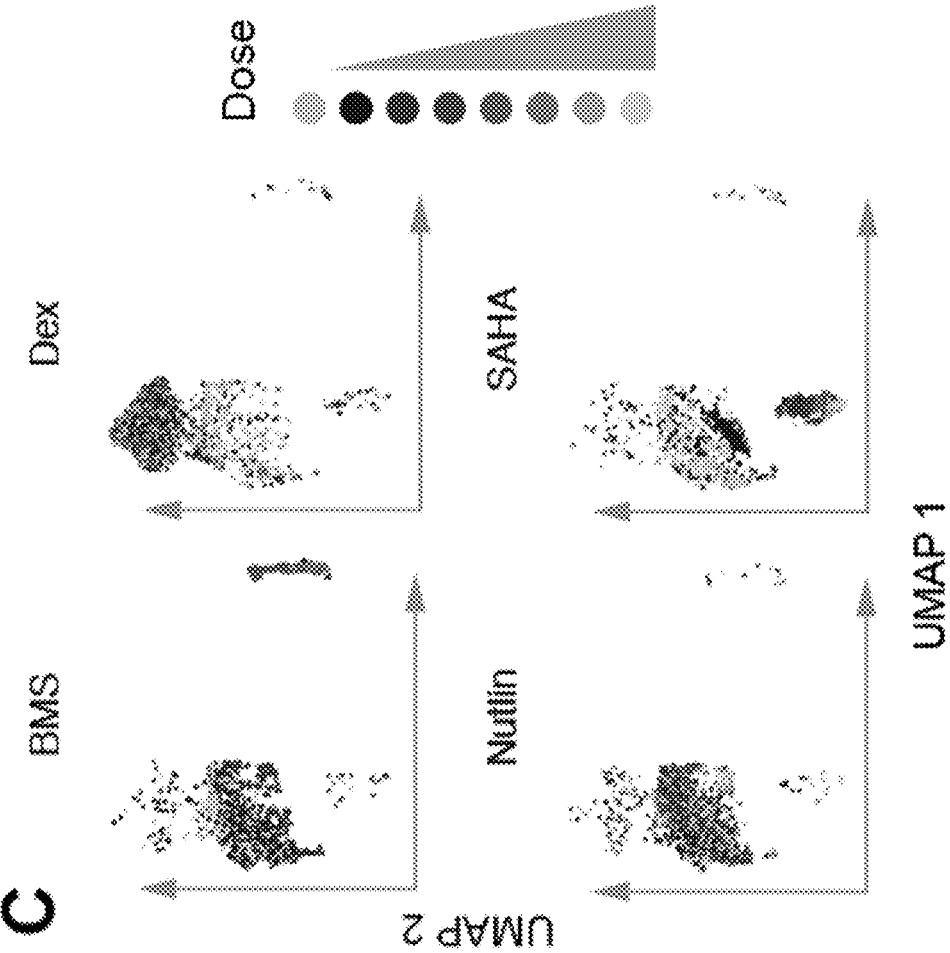
Figure 42D:
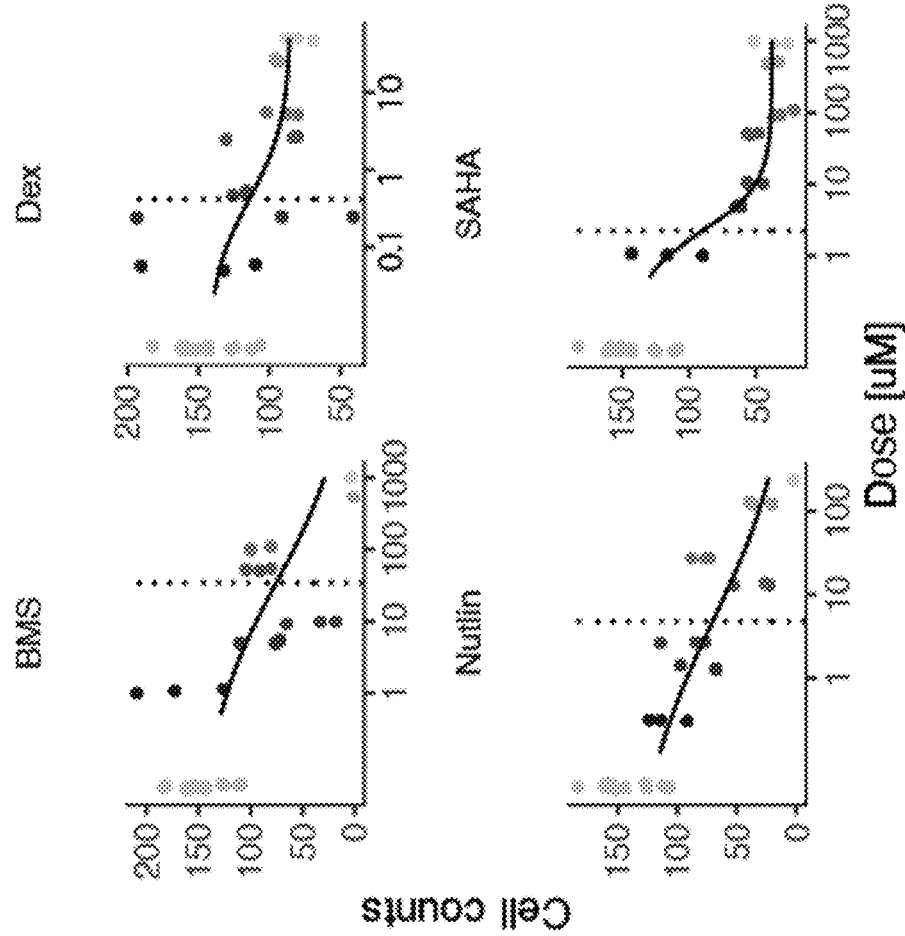
Figure 42E:
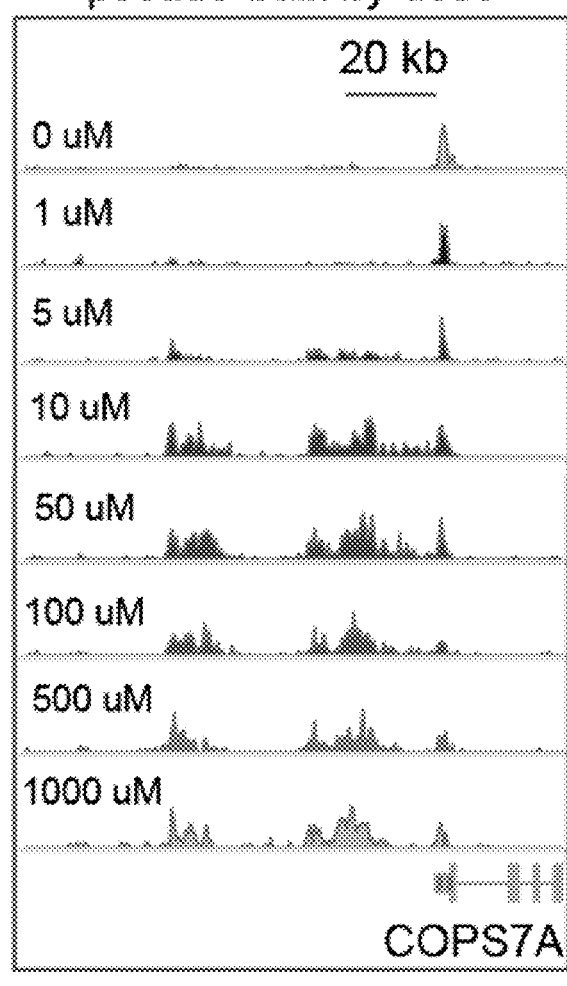

From this pilot experiment, we obtained high quality chromatin profiles from 7,770 cells, which diverged into discrete populations of chromatin organization. Importantly, using sequenced labels to identify treatment conditions for each cell, it was apparent that population structure was largely driven by drug-specific impacts on chromatin profiles (FIG. 42B). Moreover, dosage-dependent trends showed increasingly altered regulatory landscapes with higher doses, particularly upon broad inhibition of histone deacetylases (SAHA) (FIG. 42C, bottom right panel). Interestingly, from this data alone we were also able to determine thresholds beyond which specific drugs become toxic to cells (FIG. 42D). This experiment demonstrates the ability to assay chromatin accessibility of individual cells from nearly 100 samples simultaneously. Ongoing analysis of these data aims to investigate differentially accessible sites across the genome responding to drug treatments. For example, non-coding sites upstream of the COPS7A locus showed dose dependent accessibility in response to SAHA (FIG. 42E).

Methods

Hash Labeling Nuclei

Adherent cells grown in 96 well format were prepared by first aspirating the existing media. 504 of TrypLE (Termo-Fisher) was then added per well and the plate was incubated at 37 C for 15 minutes for A549. After incubation, 1504 of 1×DMEM (Gibco)+10% FBS (Gibco) was added to quench the TrypLE reaction. The 2004 volume cell suspension in each well was then transferred into a V-bottom 96 well plate, preserving the well orientations. Cells were then spun for 5 minutes at 300 g to pellet cells before aspirating media. Cell pellets were washed with 100 μL 1×DPBS and then pelleted at 300 g for 5 minutes. For suspension cells, well contents were first transferred to a v-bottom plate and then pelleted at 300 g for 5 minutes. Cells were then washed in 200 μL 1×DPBS and spun down again and removing the DPBS. To isolate nuclei from cells, pellets were then resuspended and gently pipetted up and down several times in 50 μL of either cold lysis buffer (10 mM TrisHCl, 10 mM NaCl, 3 mM MgCl$_2$, 0.1% Igepal, 0.1% Tween20), or OMNI lysis buffer (10 mM TrisHCl, 10 mM NaCl, 3 mM MgCl$_2$, 0.1% Igepal, 0.1% Tween20, 0.01% Digitonin (Promega), 1× Protease inhibitor (Thermo Pierce Protease Inhibitor Tablets, EDTA-free)). Single stranded DNA oligo labels (hashes) were then added to the nuclei (aiming for approximately 1 nMol hash molecules per 25,000 cells) in lysis buffer and incubated on ice for 5 minutes. Ice-cold fixation buffer (1.5% Formaldehyde, 1.25×DPBS (gibco)) was then added to samples to achieve a final formaldehyde concentration of 1% and mixed gently. Fixation was allowed to occur for 15 minutes on ice. At this point nuclei from different samples (i.e. different wells) were combined and further steps performed on this single pool. First the fixative was removed by spinning the pooled samples at 500×g for 5 minutes. The pellet was then resuspended in nuclei suspension buffer (10 mM TrisHCl, 10 mM NaCl, 3 mM MgCl2)+0.1% tween20. Nuclei were pelleted again before being resuspended in freezing buffer (50 mM Tris pH 8.0, 25% glycerol, 5 mM Mg(OAc)2, 0.1 mM EDTA, 5 mM DTT, 1× Protease inhibitor (Thermo Pierce)) at a final concentration of 2.5 million nuclei/mL (two-level), or 5 million nuclei/mL (three-level). Pooled samples were then flash frozen in liquid nitrogen and stored at −80 C.

Co-Capture of Hash Oligo and ATAC Profiles with Two-Level Sci-ATAC

Pooled, hash-labeled nuclei were thawed on ice, inspected for nuclei integrity, counted and further adjusted to 2.5 million nuclei/mL if necessary. 2 μL nuclei were then distributed to all wells of a 96-well deep-bind plate. To capture hash molecules within each nucleus, 1 μL of 25 μM single-stranded DNA oligos (5'-TCGTCGGCAGCGTCA-GATGTGTATAAGAGACAG-NNNNNNNNNXXXXXXXXXXT TTTTTTTTTTTTTTTTTTTTTTTTTTTTTTTVN-3' (SEQ ID NO:2)) were added to each well ('X's represent a well specific barcode while 'N's reflect the unique molecular index (UMI)). The plate was then incubated at 55 C for 5 minutes and immediately returned to ice for 5 minutes. Capture oligos annealed to hash molecules were then extended by adding 3 μL of NEBNext High-Fidelity 2×PCR Master Mix to each well and incubating at 55° C. for 10 minutes. After extension 12 μL 2× tagmentation buffer (20 mM Tris pH 7.3, 10 mM MgCl$_2$, 20% DMF) and 4 μL (40 mM TrisHCl, 40 mM NaCl, 12 mM MgCl$_2$, 0.4% NP40, 0.4% Tween20) was added to all wells. Finally, 1 μL of indexed Tn5 (Cusanovich et al. 2015) was added to each well and tagmentation was carried out at 55° C. for 15 minutes before returning to ice. Tagmentation was stopped by adding 25 μL of ice cold 40 mM EDTA+1 mM spermidine to all wells and then incubating at 37 C for 15 minutes. All wells were then pooled and DAPI was added to a final concentration of 3 μM for fluorescence-activated cell sorting (FACS). Using fluorescence based sorting, a limited number of cells (varied by experiment based on desired, expected doublet rate) were distributed to each well of a new 96-well deep-bind plate containing 12 μL reverse cross-linking buffer (11 μL EB (Qiagen), 0.5 μL 1% SDS, 0.5 μL 20 mg/mL Proteinase K (Promega)) within each well. Cross-links were reversed by incubating plates at 65° C. for 13.5 hrs on a PCR block. PCR was then used to add a second round of well specific barcodes to both the hash labels as well as tagmented chromatin. To each well we added 3.65 μL Tween-20, 1.25 μL indexed Nextera P5 primer, 1.25 indexed Nextera P7 primer, and 18.125 μL NEBNext High-Fidelity 2×PCR Master Mix. PCR conditions were as follows: 72° C. for 5 min, 98° C. for 30 s, (repeat the following three steps 23 times: 98° C. for 10 s, 63° C. for 30 s, 72° C. for 1 min), 72° C. for 5 min, hold at 4° C.

Amplified libraries from each well were then pooled and concentrated with Zymogen clean and concentrate kit (using 5×DNA binding buffer), before being eluted in 100 μL EB. To separate the hash library from the ATAC library, the concentrated, pooled library was run on a 1% agarose gel and gel purified. The hash library appears as a band of size 199 bp, while the ATAC library was cut from ~200-3000 bp. Gel extraction was performed with the Nucleospin PCR and Gel extraction kit and eluted in 50 μL (ATAC library), or 25 μL (hash library).

Co-Capture of Hash and ATAC Profiles with Three-Level Sci-ATAC

Hash-labeled nuclei were thawed on ice, inspected for nuclei integrity, counted and further adjusted to 5 million nuclei/mL if necessary. 10 μL nuclei were then distributed to wells of a 96-well deep-bind plate. To capture hash molecules within each nucleus, 2 μL of 25 μM of single-stranded DNA "capture" oligos (5'-TCGTCGGCAGCGTCA-GATGTGTATAAGAGACAGNNNNNNNNNTT+TTT+TTT+TT T+TTT+TTT+TTT+TTT+TTT+TTT+TVN-3') were added to each well ('N's reflect the unique molecular index (UMI), '+T' represents the presence of locked nucleic acids, which increase the melting temperature of the capture oligo annealed to hash oligo). The plate was then incubated at 55° C. for 5 minutes and immediately returned to ice for 5 minutes. 35.5 μL of Tn5 reaction mix (25 μL 2× tagmentation buffer, 8.25 μL 1×DPBS, 0.5 μL 1% digitonin, 0.5 μL 10% tween-20, 1.25 μL water) was then added to each well. Finally, 2.5 uL Nextera Tn5 enzyme was added to each well (final volume=50 μL). Plate was sealed with adhesive tape, and spun at 500×g for 30 sec. Tagmentation was then performed by incubating the plate at 55° C. for 30 min. Tagmentation was stopped by adding 50 μL of ice cold 40 mM EDTA+1 mM spermidine to all wells and then incubating at 37° C. for 15 minutes. Using wide bore tips, all wells were pooled and tagmented nuclei were pelleted for 5 minutes 4° C. at 500×g and supernatant was removed. Nuclei were carefully resuspended in 500 μL 40 mM TrisHCl, 40 mM NaCl, 12 mM MgCl₂, +0.1% Tween-20 and spun again at 500×g for 5 minutes at 4° C. Supernatant was aspirated and the pellet was resuspended in 110 μL 40 mM TrisHCl, 40 mM NaCl, 12 mM MgCl₂, +0.1% Tween-20.

5' ends of tagmented chromatin and captured hash oligos within fixed nuclei were then phosphorylated via a polynucleotide kinase (PNK) mediated reaction. 110 μL of resuspended nuclei was mixed with 55 μL 10×T4PNK Buffer (NEB), 55 μL rATP (NEB), 110 μL nuclease-free water, 220 μL T4PNK (NEB), and 5 uL of the reaction mix was distributed to each well of a 96-well plate. The plate was then sealed, spun at 500×g for 30 seconds, and then incubated at 37° C. for 30 minutes.

Following kinase reactions, the first level of indexing was achieved by attaching indexed oligos specifically to the 'N7-tagged' side of tagmented chromatin and captured hash molecules. N7-specific ligations were performed by adding 10 μL 2× T7 ligase buffer, 0.18 μL 1000 μM N7 splint oligo (5'-CACGAGACGACAAGT-3' (SEQ ID NO:3)), 1.12 μL nuclease-free water, 2.5 μL T7 DNA ligase, 1.2 μL 50 μM N7 oligo (5'-CAGCACGGCGA-GACTNNNNNNNNNNGACTTGTC-3' (SEQ ID NO:4), where 'N's represent a well specific index) directly to all wells containing the kinase reaction mixture (final well volume=204). The plate was then sealed, spun at 500×G for 30 sec, and ligation was carried out at 25° C. for 1 hr. Ligations were stopped by adding 20 μL ice cold 40 mM EDTA+1 mM spermidine to each well and incubating at 37° C. for 15 min. Using wide bore tips, all wells were pooled into a 15 ml conical tube and volume was increased by adding three volumes of 40 mM TrisHCl, 40 mM NaCl, 12 mM MgCl₂, +0.1% Tween-20. Nuclei were pelleted for 10 min at 500×G and 4° C., and resuspended in 550 μL 40 mM TrisHCl, 40 mM NaCl, 12 mM MgCl₂, +0.1% Tween-20.

The second level of indexing was performed by ligating indexed oligos to the phosphorylated 'N5-tagged' side of tagmented chromatin and captured hash molecules. 54 of pooled, resuspended nuclei were thus distributed to all wells of a new 96-well plate. The second ligation reaction was then performed by adding 10 μL 2× T7 ligase buffer, 0.18 μL 1000 μM N5 splint oligo (5'-GCCGACGACTGATTA-3' (SEQ ID NO:5)), 1.12 μL nuclease-free water, 2.5 μL T7 DNA ligase, 1.2 μL 50 μM N5 oligo (5'-CACCGCACGAGAGGTNNNNNNNNNNGTAATCAG-3' (SEQ ID NO:6), where 'N's represent a well specific index) to all wells (final well volume=20 μL). The plate was then sealed, spun at 500×G for 30 sec, and ligation was carried out at 25° C. for 1 hr. Ligations were stopped by adding 20 μL ice cold 40 mM EDTA+1 mM spermidine to each well and incubating at 37° C. for 15 min. Using wide bore tips, all wells were pooled into a 15 ml conical tube and volume was increased by adding three volumes of 40 mM TrisHCl, 40 mM NaCl, 12 mM MgCl₂, +0.1% Tween-20. Nuclei were pelleted for 10 min at 500×G and 4° C., and gently resuspended in 500 μL EB buffer (Qiagen). For distribution to PCR wells, nuclei were either stained with DAPI (3 μM final) and sorted into wells of a 96-well plate (185 nuclei/well) containing reverse cross-linking buffer (11 μL EB buffer (Qiagen) 0.5 μL Proteinase K (Roche), 0.5 μL % SDS), or counted and adjusted to a concentration of 1850/mL. 104 of diluted nuclei were distributed to all wells of a 96-well plate and 1 μL EB buffer (Qiagen) 0.5 μL Proteinase K (Qiagen), 0.5 μL 1% SDS was added to enable crosslink reversal. Plates were then sealed, spun at 500×g for 30 seconds and crosslinks were removed by incubating plates at 65° C. for 16 hours.

The third level of indexing is achieved through PCR. Therefore PCR mix containing 2.5 μL 25 μM P7 primer (5'-CAAGCAGAAGACGGCAT-ACGAGATNNNNNNNNNNNCAGCACGGCGAGACT-3' (SEQ ID NO:7)), 2.5 μL 25 μM P5 primer (5'-AATGA-TACGGCGACCACCGAGATCTACACNNNNNNNNNN-CACCGCACGAGAG GT-3' (SEQ ID NO:8), 254 NEB-Next High-Fidelity 2×PCR Master Mix, 74 Water, 1 μL 20 mg/mL BSA(NEB). Importantly, each well received a unique, well-specific, combination of P7 and P5 primers. PCR conditions were as follows: 72° C. for 5 min, 98° C. for 30 s (cycle through the following three steps 20 times: 98° C. for 10 s, 63° C. for 30 s, 72° C. for 1 min) 72° C. for 5 min, hold at 4° C.

Amplified libraries from each well were then pooled and concentrated with Zymogen clean and concentrate kit (using 5×DNA binding buffer), before being eluted in 1004 EB.

Citations for Example 2

Cao, Junyue, Jonathan S. Packer, Vijay Ramani, Darren A. Cusanovich, Chau Huynh, Riza Daza, Xiaojie Qiu, et al. 2017. "Comprehensive Single-Cell Transcriptional Profiling of a Multicellular Organism." Science 357 (6352): 661-67.

Cusanovich, Darren A., Riza Daza, Andrew Adey, Hannah A. Pliner, Lena Christiansen, Kevin L. Gunderson, Frank J. Steemers, Cole Trapnell, and Jay Shendure. 2015.

"Multiplex Single Cell Profiling of Chromatin Accessibility by Combinatorial Cellular Indexing." Science 348 (6237): 910-14.

Srivatsan, Sanjay R., José L. McFaline-Figueroa, Vijay Ramani, Lauren Saunders, Junyue Cao, Jonathan Packer, Hannah A. Pliner, et al. 2020. "Massively Multiplex Chemical Transcriptomics at Single-Cell Resolution." Science 367 (6473): 45-51.

Takahashi, Kazutoshi, and Shinya Yamanaka. 2016. "A Decade of Transcription Factor-Mediated Reprogramming to Pluripotency." Nature Reviews. Molecular Cell Biology 17 (3): 183-93.

Example 3

Nuclear labeling strategy provides an unbiased standard for the normalization of single cell transcriptomes Abstract Even though single cell RNA sequencing data has transformed our understanding of biology, they can suffer from sparsity and high levels of technical noise, often masking our ability to extract biologically meaningful information. Here we describe a simple yet versatile method for labeling individual nuclei with unmodified single stranded DNA oligos that are captured via single nuclei transcriptome sequencing. When nuclei are labeled with a "ladder" of distinct oligos, present at differing known concentrations, we were able to capture read counts from each oligo proportional to its concentration within the ladder along with the transcriptome within each nucleus. By using a ladder of oligo abundances covering three orders of magnitude, the drop-out rates of transcripts could be estimated. Moreover, we show that by using the ladder counts from each cell as an external standard, we are able to estimate and remove technical noise in cell to cell gene expression variation, vastly improving differential expression analysis. Finally, by chemically inhibiting transcription elongation, we show that normalizing transcriptome counts within each cell based on the corresponding oligo ladder counts enables detection of global directional changes in gene expression that would otherwise be missed.

Methods

Cell Culture

A549 and HEK293T cells were cultured in DMEM media containing 10% fetal bovine serum and 1% penicillin and streptomycin at 37 C with 5% CO2.

For the flavopiridol time course experiment, HEK293T cells were seeded onto a 6-well culture plate at a density of 4×105 cells per well. For the HDAC inhibitor time course and HDAC inhibitor and Dexamethasone co-treatment experiments, A549 cells were seeded onto a 96-well culture plate at a density of 2.5×104 cells per well.

Drug Treatment

The cells were grown for 24 hours after they were seeded onto the cell culture plates. For the flavopiridol time course experiment, 0.9 uL of 1 mM flavopiridol was added to each 6 well to attain final concentration of 300 nM. For the HDACi time course and HDACi and Dexamethasone co-treatment experiments, 1 uL of 1 mM of either Abexinostat or Pracinostat was added to each 96 well to attain final concentration of 10 uM. 1 uL of 100 uM Dexamethasone was added two hours before its HDACi treated time. DMSO was used as a vehicle for flavopiridol and HDACi treatments and ethanol was used as a vehicle for dexamethasone treatment.

Design of Hash Ladder

The capture of hash ladder by nuclei is determined by factors including, but not limited to, sample processing and sequencing depth. For mammalian cell lines, we found that the hash capture rate efficiency is very low. We empirically determined that the ladder should be constructed so that around 6 million hash molecules are captured per nuclei (assuming that each nucleus takes up equal amount of hash molecules in the solution) to obtain a median hash UMI count of 1,000-5,000. For the pilot experiment, we used a hash ladder consisting of 8 different hash oligos, covering from 0.1-12.8 attomoles per nucleus. For the rest of our experiments, we used a hash ladder consisting of 48 different hash oligos, ranging from 0.025 zeptomoles-2 attomoles per nucleus.

Cell Harvest, Nuclei Isolation, and Hash Ladder Capture

For the harvest of cells, media was removed and cells were washed with DPBS and dissociated off the plate using trypLE. Trypsinization from trypLE was quenched with an equal volume of ice-cold media. Cells were pelleted by centrifugation at 500 g for 5 minutes, washed with ice cold DPBS, and resuspended in ice cold DPBS. Cells were then counted with a hemocytometer using 0.4% Trypan Blue. Around 2 million cells were pelleted at 500 g for 5 minutes and resuspended in 1 mL of ice cold lysis buffer (10 mM Tris-HCl, pH 7.4, 10 mM NaCl, 3 mM MgCl2, 0.1% IGEPAL CA-630) supplemented with 1% Superase RNA Inhibitor and the appropriate amount of hash ladder. After lysis with gentle pipetting, cells were fixed by addition of 4 mL of fixation buffer (5% paraformaldehyde in 1.25×PBS) on ice for 20 min. After the cells were fixed, they were washed with 1 mL of nuclei suspension buffer (10 mM Tris-HCl, pH 7.4, 10 mM NaCl, 3 mM MgCl2, 1% Superase RNA Inhibitor, 1% 0.2 mg/mL NEBNext BSA) and resuspended in 100 uL of NSB.

Preparation of Sci-RNA-Seq2 Libraries

Isolated and hashed nuclei were then permeabilized in permeabilization buffer (0.25% Triton-X in NSB) for 3 minutes on ice and then spun down. Following another a wash in NSB, two-level sci-RNA-seq libraries prepared as described (Example 1, Cao et al., Nature, 2019, 566:496-502). Briefly, nuclei were pelleted at 500 g for 5 minutes, and resuspended in 100 μL of NSB. Cell counts were obtained by staining nuclei with 0.4% Trypan Blue (Sigma-Aldrich) and counted using a hemocytometer. 5000 nuclei in 2 μL of NSB and 0.25 μL of 10 mM dNTP mix (Thermo Fisher Scientific, cat no. R0193) were then distributed onto a skirted twin.tec 96 well LoBind plate (Fisher Scientific, cat no. 0030129512) after which 1 μL of uniquely indexed oligo-dT (25 μM) was added to every well, incubated at 55 C for 5 minutes and placed on ice. 1.75 μL of reverse transcription mix (1 μL of Superscript IV first-strand buffer, 0.25 μL of 100 mM DTT, 0.25 μL of Superscript IV and 0.25 μL of RNAseOUT recombinant ribonuclease inhibitor) was then added to every well incubated at 55 C for 10 minutes and placed on ice. 5 μL of stop solution (40 mM EDTA and 1 mM spermidine) were added to each well to stop the reaction. Wells were pooled using wide bore tips, and nuclei transferred to a flow cytometry tube through a 0.35 μm filter cap and DAPI added to a final concentration of 3 μM. Pooled nuclei were then sorted on a FACS Aria II cell sorter (BD) at 25-50 cells per well into 96 well LoBind plates containing 5 μL of EB buffer (Qiagen). After sorting, 0.75 μL of second strand mix (0.5 μL of mRNA second strand synthesis buffer and 0.25 μL of mRNA second strand synthesis enzyme, New England Biolabs) were added to each well, second strand synthesis performed at 16 C for 150 minutes. Tagmentation was performed by addition of 6 μL of tagmentation mix (0.02 μL of a custom TDE1 enzyme in 6 μL 2× Nextera TD buffer, Illumina) and plates incubated for 5 minutes at 55 C. Reaction was terminated by addition of 12 μL of DNA binding buffer (Zymo) and incubated for 5 minutes at room temperature. 36 μL of Ampure XP beads were added to every well, DNA purified using the standard Ampure XP protocol (Beckman Coulter) eluting with 17 μL of EB buffer and DNA transferred to a new 96 well LoBind plate. For PCR, 2 μL of indexed P5, 2 μL of indexed P7 and 20 μL of NEBNext High-Fidelity master mix (New England Biolabs) were added to each well and PCR performed as follows: 72 C for 5 minutes, 98 C for 30 seconds and 19 cycles of 98 C for 10 seconds, 66 C for 30 seconds and 72 C for 1 minute followed by a final extension at 72 C for 5 minutes. After PCR, all wells were pooled, concentrated using a DNA clean and concentrator kit (Zymo) and purified via a 0.8× Ampure XP cleanup. Final library concentrations were determined by Qubit (Invitrogen), libraries visualized using a TapeStation D1000 DNA Screen tape (Agilent) and libraries sequenced on a Nextseq 500 (Illumina) using a high output 75 cycle kit (Read 1: 18 cycles, Read 2: 52 cycles, Index 1: 10 cycles and Index 2: 10 cycles).

Results

Hash Ladders can be Used as Spike-in Controls in Sci-RNA-Seq Experiments

Figures 43A, 43B, 43C:
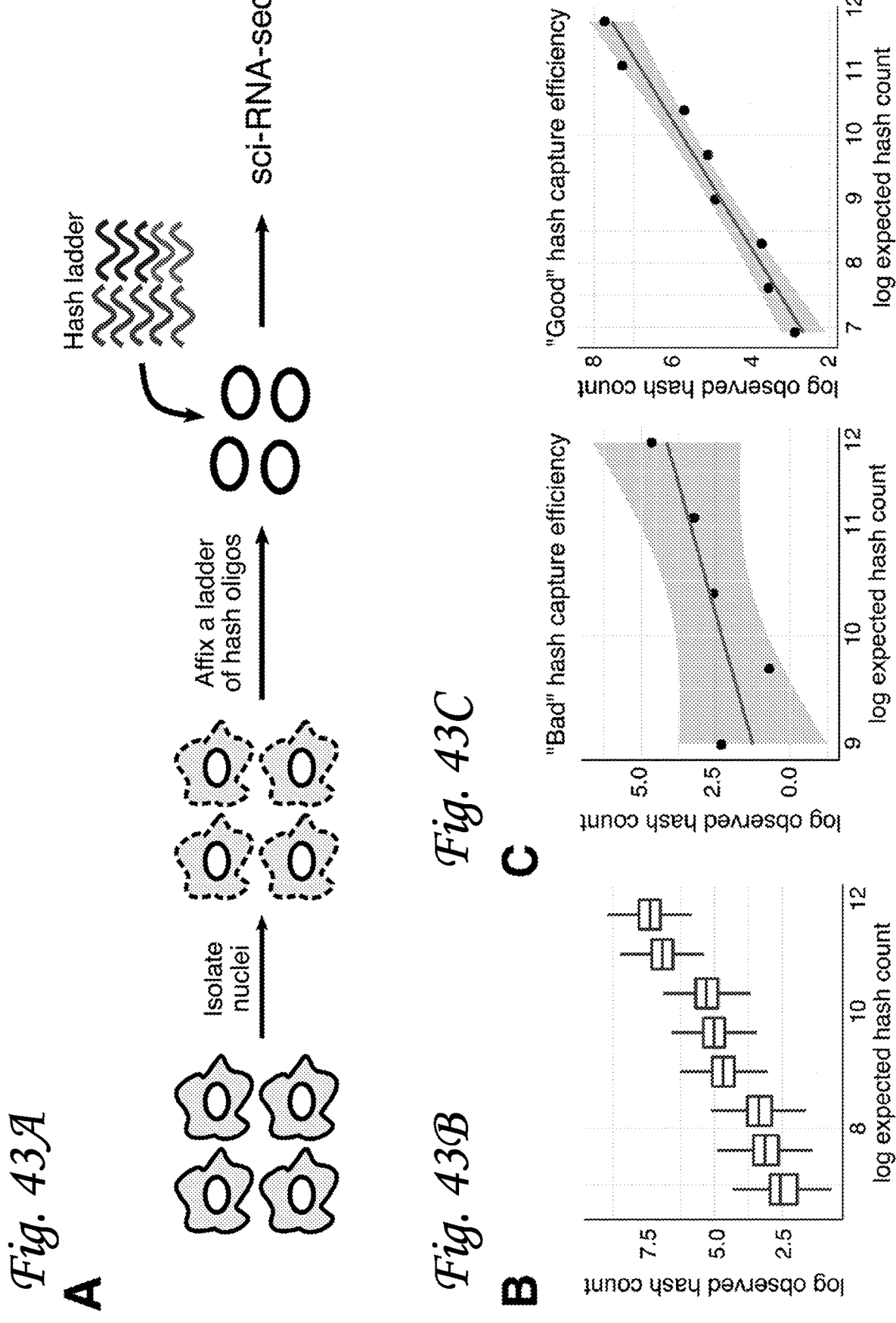

Based on our "hashing" technology [1], we asked whether a ladder of hash oligos covering a wide concentration range can be used to label nuclei and serve as external controls in sci-RNA-seq experiments (FIG. 43A). We reasoned that by labeling each nuclei with a mixture distinct hash oligos with concentration ranges reflecting the abundance of endogenous mRNA transcripts, we would be able to control for technical noise and use the ladder as a proxy for quantifying absolute transcript abundance in individual cells.

To test our hypothesis, we designed a ladder comprising eight different hash oligos, theoretical abundance ranging from 0.1-12.8 attomoles per nucleus, and introduced it to HEK293T cells during lysis step of sci-RNA-seq library preparation. As expected, we recovered reads from both the endogenous mRNAs and the hash ladder. The observed number of hash oligo unique molecular identifier (UMI) counts globally reflected the relative abundance of each hash oligos in the ladder (FIG. 43B). By looking at the UMI counts of hash ladder in individual cells, 1,806 out of 1,937 cells with reads from at least one hash molecule (93%) had reads from all eight hash molecules and showed strong correlation between the expected and observed number of hash counts (FIG. 43C, right plot). We also identified cells with low hash capture efficiency (FIG. 43C, left plot), likely reflecting variability in sample processing in sci-RNA-seq experiments.

Hash Ladder-Based Normalization Enables Detection of Global Changes within Transcript Levels in Single Cells Standard normalization approaches for scRNA-seq data scales a cell's gene expression values by a size factor proportional to the cell's total RNA count. Because the expression data is transformed to relative abundance measurements, it fails to capture potential global shifts transcript abundance, for example, in response to transcriptional repression. We therefore asked whether we could use our hash ladder to accurately detect global changes in transcription levels caused by treatment of CDK inhibitor flavopiridol.

Figure 44A:
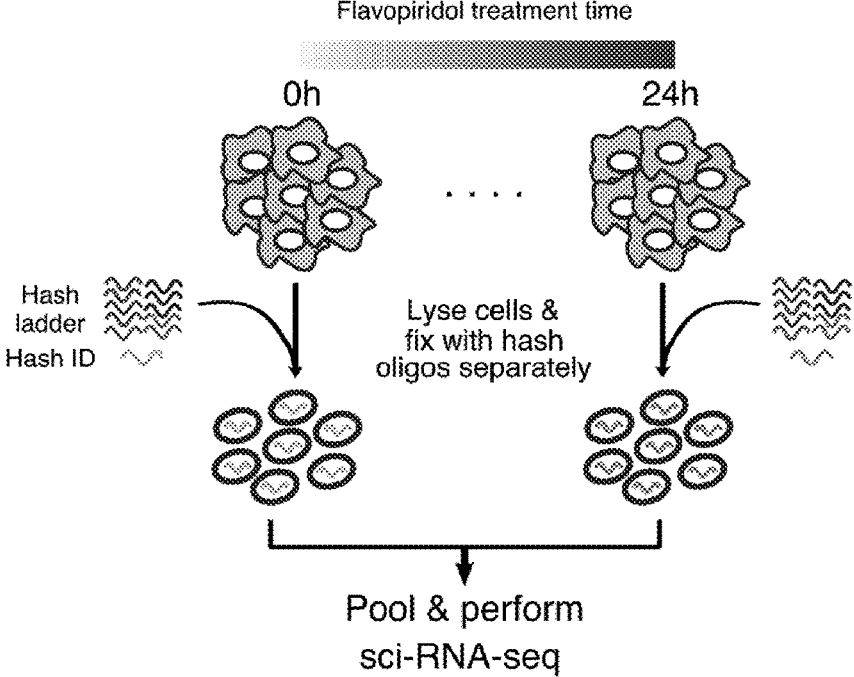
Figure 44B:
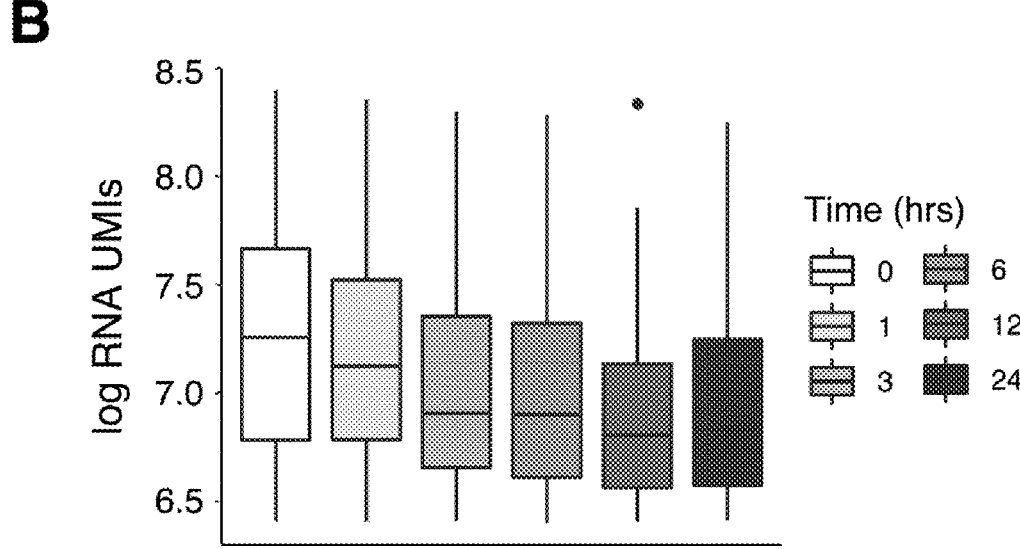

Flavopiridol is a cyclin-dependent kinase inhibitor known to cause a drastic reduction in global transcript levels [2]. Using the per-cell counts recovered from our ladder oligos as a normalization control for each cell, we sought to measure changes in gene expression as a result of treatment with flavopiridol for increasing amounts of time (FIG. 44A). As expected, cells exposed to the transcription elongation inhibitor for longest times showed the greatest reduction in RNA recovery per-cell (FIG. 44B).

Figure 44C:
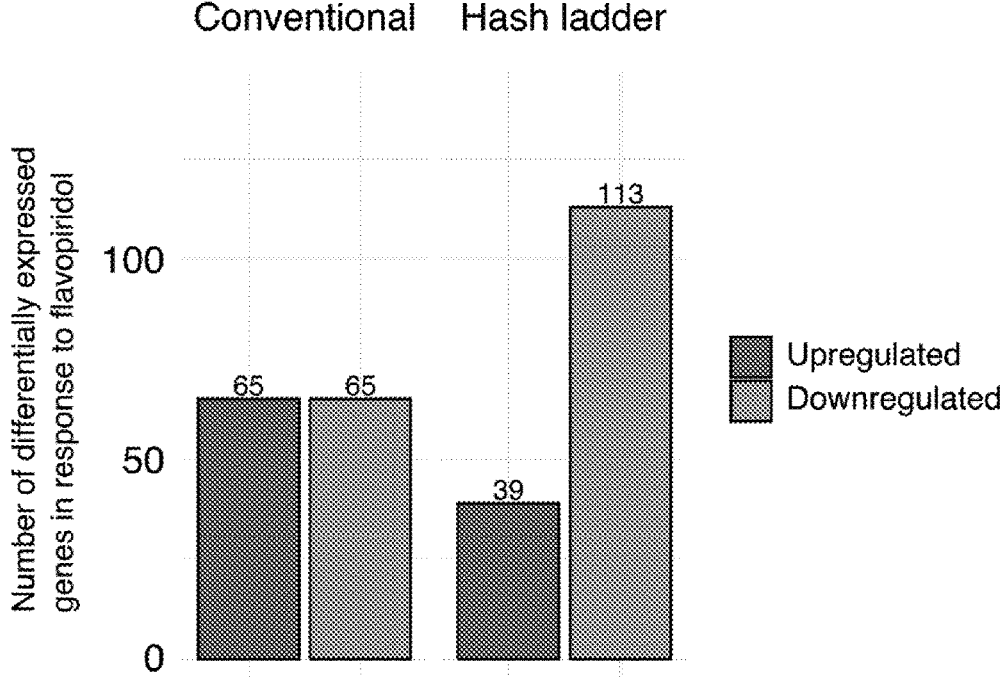
Figure 44D:
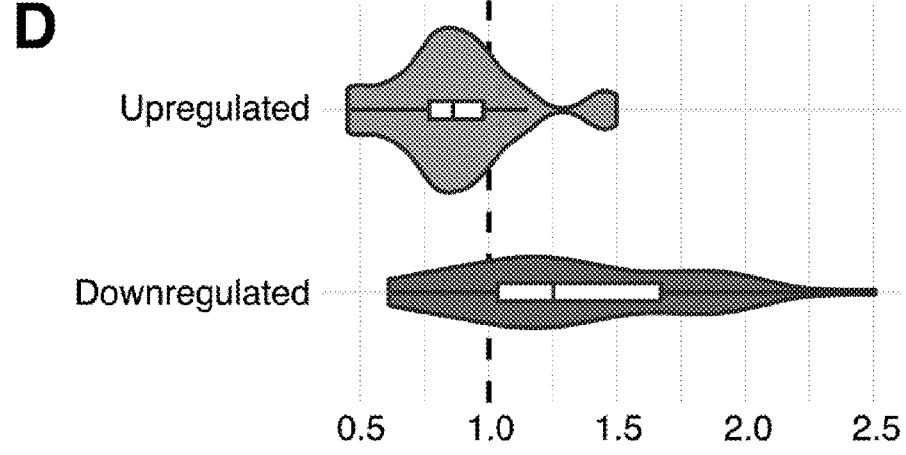

We then compared the effects of conventional and hash ladder-based normalization approaches on differential expression analyses. With the conventional, total RNA size-factor based normalization approach, the number of upregulated genes in response to flavopiridol treatment were equal to the number of downregulated genes, even though flavopiridol is known to shut down transcription, which is a characteristic of incorrect normalization [3] (FIG. 44C, left plot). However, by normalizing based on the cells' recovered hash ladder counts, we were able to successfully recover a higher number of downregulated genes that are known to have decreased expression upon flavopiridol treatment and reduce the number of falsely identified upregulated genes [4] (FIG. 44C, right plot). The effect size estimates computed from our hash ladder based approach were on average higher for downregulated genes and lower for upregulated genes compared to the conventional approach, further highlighting the hash ladder's ability to reveal global changes in transcription caused by flavopiridol.

Citations for Example 3

[1] Srivatsan et al. Massively multiplex chemical transcriptomics at single-cell resolution. *Science* 367, 6473, 45-51 (2020)
[2] Kelland, L. R. Flavopiridol, the first cyclin-dependent kinase inhibitor to enter the clinic: current status. *Expert Opin. Investig. Drugs* 12, 2903-2911 (2000)
[3] Athanasiadou et al. A complete statistical model for calibration of RNA-seq counts using external spike-ins and maximum likelihood theory. *PLoS Comput. Biol.* 15, 3 (2019)
[4] Lü et al. Transcriptional signature of flavopiridol-induced tumor cell death. *Mol. Cancer Ther.* 7, 861-872 (2004).

The present disclosure is illustrated by the following examples. It is to be understood that the particular examples, materials, amounts, and procedures are to be interpreted broadly in accordance with the scope and spirit of the disclosure as set forth herein.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

---

The invention claimed is:

1. A method of preparing a sequencing library comprising nucleic acids from a plurality of nuclei or cells, the method comprising:
   - (a) providing a plurality of compartments comprising nuclei or cells;
   - (b) contacting the nuclei or cells in the compartments with a hashing oligo that comprises a compartment specific index to result in absorption of the hashing oligo by the nuclei or cells; and
   - (c) exposing the nuclei or cells to a cross-linking compound to fix hashing oligos to cells or to isolated nuclei,
   - (d) combining the nuclei or cells from different compartments into a second compartment to generate pooled hashed nuclei or pooled hashed cells,
   wherein at least one copy of the hashing oligo is associated with nuclei or cells.

2. The method of claim 1, further comprising exposing the cells of each compartment of step (a) to a predetermined condition or, prior to step (a), providing a plurality of compartments comprising cells, exposing the cells of each compartment to a predetermined condition and then isolating nuclei from the cells.

3. The method of claim 2, wherein the predetermined condition comprises exposure to an agent.

4. The method of claim 3, wherein the agent comprises a protein, a non-ribosomal protein, a polyketide, an organic molecule, an inorganic molecule, an RNA or RNAi molecule, a carbohydrate, a glycoprotein, a nucleic acid, a drug, or a combination thereof.

5. The method of claim 1, wherein the providing further comprises:
   exposing the plurality of cells of each compartment to a predetermined condition.

6. The method of claim 5, wherein the predetermined condition comprises exposure to an agent.

7. The method of claim 1, wherein the hashing oligo comprises a single stranded nucleic acid.

8. The method of claim 1, further comprising processing the pooled hashed cells or pooled hashed nuclei using a single-cell combinatorial indexing method to result in a sequencing library comprising nucleic acids from the pooled hashed cells or pooled hashed nuclei, wherein the nucleic acids comprise a plurality of indexes.

9. The method of claim 8, wherein the single-cell combinatorial indexing comprises:
   distributing subsets of the pooled hashed cells or pooled hashed nuclei into a second plurality of compartments and contacting each subset with reverse transcriptase or DNA polymerase and a primer, wherein the primer in each compartment comprises a first index sequence that is different from first index sequences in the other compartments to generate indexed nuclei or indexed cells comprising indexed nucleic acid fragments;
   combining the indexed cells or indexed nuclei to generate pooled indexed cells or pooled indexed nuclei;
   distributing subsets of the pooled indexed cells or pooled indexed nuclei into a third plurality of compartments and introducing a second index sequence to the indexed nucleic acid fragments to generate dual-indexed cells or dual-indexed nuclei comprising dual-indexed nucleic acid fragments, wherein the introducing comprises ligation, primer extension, amplification, or transposition;

combining the dual-indexed cells or dual-indexed nuclei to generate pooled dual-indexed nuclei or pooled dual-indexed cells;
   distributing subsets of dual-indexed cells or the pooled dual-indexed nuclei into a fourth plurality of compartments and introducing a third index sequence to the dual-indexed nucleic acid fragments to generate triple-indexed cells or triple-indexed nuclei comprising triple-indexed nucleic acid fragments, wherein the introducing comprises ligation, primer extension, amplification, or transposition; and
   combining the triple-indexed fragments, thereby producing a sequencing library comprising nucleic acids from the pooled hashed cells or pooled hashed nuclei.

10. The method of claim 9, wherein distributing subsets of the pooled indexed cells or pooled indexed nuclei into a third plurality of compartments comprises contacting each subset with a transposome complex, wherein the transposome complex in each compartment comprises a transposase and a second index sequence under, conditions suitable for ligation of the second index sequence to the ends of the indexed nucleic acid fragments comprising a first index sequence to generate dual-indexed nuclei comprising dual-indexed nucleic acid fragments, wherein the second index sequence is different from second index sequences in the other compartments.

11. The method of claim 9, wherein distributing subsets of dual-indexed cells or the pooled dual-indexed nuclei into a fourth plurality of compartments comprises contacting each subset with a primer comprising a third index sequence and a universal primer sequence, wherein the contacting comprises conditions suitable for amplification and incorporation of the third index sequence to the ends of the dual-indexed nucleic acid fragments, wherein the third index sequence is different from third index sequences in the other compartments.

12. The method of claim 9, further comprising:
   providing a surface comprising a plurality of amplification sites, wherein the amplification sites comprise at least two populations of attached single stranded capture oligonucleotides having a free 3' end, and
   contacting the surface comprising amplification sites with the triple-indexed fragments under conditions suitable to produce a plurality of amplification sites that each comprise a clonal population of amplicons from an individual fragment comprising a plurality of indexes.

13. A composition comprising the hashed cells or hashed nuclei of claim 1.

14. A composition comprising the pooled hashed cells or pooled hashed nuclei of claim 1.

15. A multi-well plate, wherein compartments of the multi-well plate comprise the composition of claim 13.

16. A droplet, wherein the droplet comprises the composition of claim 13.

17. The method of claim 1, wherein
   the hashing oligo comprises a nucleic acid and a hashing index.

18. The method of claim 17, wherein the the hashing index in each compartment comprises an index sequence that is different from index sequences in the other compartments to generate hashed nuclei or hashed cells.

\* \* \* \* \*

SEQUENCE LISTING

```
<160> NUMBER OF SEQ ID NOS: 8

<210> SEQ ID NO 1
<211> LENGTH: 67
<212> TYPE: DNA
<213> ORGANISM: artificial
<220> FEATURE:
<223> OTHER INFORMATION: hashing oligo
<220> FEATURE:
<221> NAME/KEY: misc_feature
<222> LOCATION: (35)..(35)
<223> OTHER INFORMATION: B is G, C or T

<400> SEQUENCE: 1
gtctcgtggg ctcggagatg tgtataagag acagbaaaaa aaaaaaaaaa aaaaaaaaaa        60
aaaaaaa                                                                  67

<210> SEQ ID NO 2
<211> LENGTH: 83
<212> TYPE: DNA
<213> ORGANISM: artificial
<220> FEATURE:
<223> OTHER INFORMATION: single-stranded DNA oligo
<220> FEATURE:
<221> NAME/KEY: misc_feature
<222> LOCATION: (34)..(51)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t

<400> SEQUENCE: 2
tcgtcggcag cgtcagatgt gtataagaga cagnnnnnnn nnnnnnnnnn nttttttttt        60
tttttttttt tttttttttt tvn                                                83

<210> SEQ ID NO 3
<211> LENGTH: 15
<212> TYPE: DNA
<213> ORGANISM: artificial
<220> FEATURE:
<223> OTHER INFORMATION: splint oligo

<400> SEQUENCE: 3
cacgagacga caagt                                                         15

<210> SEQ ID NO 4
<211> LENGTH: 33
<212> TYPE: DNA
<213> ORGANISM: artificial
<220> FEATURE:
<223> OTHER INFORMATION: N7 oligo
<220> FEATURE:
```

-continued

```
<221> NAME/KEY: misc_feature
<222> LOCATION: (16)..(25)
<223> OTHER INFORMATION: n is a, c, g, or t

<400> SEQUENCE: 4
cagcacggcg agactnnnnn nnnnngactt gtc                                    33

<210> SEQ ID NO 5
<211> LENGTH: 15
<212> TYPE: DNA
<213> ORGANISM: artificial
<220> FEATURE:
<223> OTHER INFORMATION: splint oligo

<400> SEQUENCE: 5
gccgacgact gatta                                                       15

<210> SEQ ID NO 6
<211> LENGTH: 33
<212> TYPE: DNA
<213> ORGANISM: artificial
<220> FEATURE:
<223> OTHER INFORMATION: N5 oligo
<220> FEATURE:
<221> NAME/KEY: misc_feature
<222> LOCATION: (16)..(25)
<223> OTHER INFORMATION: n is a, c, g, or t

<400> SEQUENCE: 6
caccgcacga gaggtnnnnn nnnnngtaat cag                                    33

<210> SEQ ID NO 7
<211> LENGTH: 49
<212> TYPE: DNA
<213> ORGANISM: artificial
<220> FEATURE:
<223> OTHER INFORMATION: P7 primer
<220> FEATURE:
<221> NAME/KEY: misc_feature
<222> LOCATION: (25)..(34)
<223> OTHER INFORMATION: n is a, c, g, or t

<400> SEQUENCE: 7
caagcagaag acggcatacg agatnnnnnn nnnncagcac ggcgagact                   49

<210> SEQ ID NO 8
<211> LENGTH: 54
<212> TYPE: DNA
<213> ORGANISM: artificial
<220> FEATURE:
<223> OTHER INFORMATION: P5 primer
<220> FEATURE:
<221> NAME/KEY: misc_feature
<222> LOCATION: (30)..(39)
<223> OTHER INFORMATION: n is a, c, g, or t

<400> SEQUENCE: 8
aatgatacgg cgaccaccga gatctacacn nnnnnnnnnc accgcacgag aggt             54
```